US009434954B2

(12) United States Patent
Lessard et al.

(10) Patent No.: US 9,434,954 B2
(45) **Date of Patent: *Sep. 6, 2016**

(54) PLANTS WITH ALTERED LEVELS OF VEGETATIVE STARCH

(75) Inventors: Philip A. Lessard, Framingham, MA (US); Michael Lanahan, Cary, MA (US); Vladimir Samoylov, Sudbury, MA (US); Oleg Bougri, Boise, ID (US); Jonas Emery, Eugene, OR (US); R. Michael Raab, Arlington, MA (US)

(73) Assignee: Agrivida, Inc., Medford, MA (US)

( * ) Notice: Subject to any disclaimer, the term of this patent is extended or adjusted under 35 U.S.C. 154(b) by 617 days.

This patent is subject to a terminal disclaimer.

(21) Appl. No.: 13/806,654

(22) PCT Filed: Jun. 27, 2011

(86) PCT No.: PCT/US2011/041991

§ 371 (c)(1),
(2), (4) Date: Mar. 19, 2013

(87) PCT Pub. No.: WO2011/163659

PCT Pub. Date: Dec. 29, 2011

(65) Prior Publication Data

US 2013/0318656 A1 Nov. 28, 2013

Related U.S. Application Data

(60) Provisional application No. 61/358,720, filed on Jun. 25, 2010.

(51) Int. Cl.
*C12N 15/113* (2010.01)
*C12N 15/82* (2006.01)

(52) U.S. Cl.
CPC ....... *C12N 15/8245* (2013.01); *C12N 15/8218* (2013.01)

(58) Field of Classification Search
None
See application file for complete search history.

(56) References Cited

U.S. PATENT DOCUMENTS

| | | | | |
|---|---|---|---|---|
| 5,912,415 | A | 6/1999 | Olszewski et al. | |
| 6,521,816 | B1 * | 2/2003 | Frohberg | 800/284 |
| 7,186,898 | B1 | 3/2007 | Kossmann et al. | |
| 7,919,682 | B2 | 4/2011 | Frohberg et al. | |
| 8,257,502 | B2 | 9/2012 | Frohberg et al. | |
| 8,343,747 | B2 | 1/2013 | Burke et al. | |
| 8,420,387 | B2 * | 4/2013 | Shen | C12N 9/2437 435/183 |
| 2004/0123343 | A1 | 6/2004 | La Rosa et al. | |
| 2006/0150278 | A1 | 7/2006 | Frohberg et al. | |
| 2006/0272049 | A1 * | 11/2006 | Waterhouse et al. | 800/279 |
| 2007/0250961 | A1 | 10/2007 | Blaylock et al. | |
| 2009/0119800 | A1 * | 5/2009 | Lanahan et al. | 800/284 |
| 2009/0258930 | A1 | 10/2009 | Pachuk et al. | |
| 2012/0054915 | A1 | 3/2012 | Steffens | |
| 2013/0269061 | A1 * | 10/2013 | Lessard et al. | 800/284 |

FOREIGN PATENT DOCUMENTS

| | | | | |
|---|---|---|---|---|
| WO | 0011144 | | 3/2000 | |
| WO | 02086112 | | 10/2002 | |
| WO | 03071860 | | 9/2003 | |
| WO | 2005/030942 | | 4/2005 | |
| WO | 2005095618 | A2 | 10/2005 | |
| WO | 2005097999 | | 10/2005 | |
| WO | 2009067751 | A1 | 6/2009 | |
| WO | WO 2009067751 | A1 * | 6/2009 | C07K 14/415 |

OTHER PUBLICATIONS

Ritte et al, 2002, PNAS, 99:7166-7171.*

Hood, E.E., et al., "Commercial Production of Avidin from Transgenic Maize: Characterization of Transformant, Production, Processing, Extraction and Purification," Molecular Breeding, 1997, pp. 291-306.

Horsch, R.B., et al, "A Simple and General Method for Transferring Genes into Plants," Science, Mar. 1985, pp. 1229-1231.

Ingram, L.O., et al., "Enteric Bacterial Catalysts for Fuel Ethanol Production," Biotechnology Progress, 1999, pp. 856-866.

Kane, P.M., et. al., "Protein Splicing Converts the Yeast TFP1 Gene Product to the 69-kD Subunit of the Vacuolar H+-Adenosine Triphosphatase," Science, New Series, vol. 250, No. 4981, Nov. 2, 1990, pp. 651-657.

Klein, T.M., et al., "High-Velocity Microprojectiles for Delivering Nucleic Acids Into Living Cells," Nature, vol. 327, May 1987, pp. 70-73.

Lai et al., "Structural Characterization of Human Erythropoietin." The Journal of Biological Chemistry, vol. 261, pp. 3116-3121, Mar. 5, 1986.

Latif, F., et al., "Production of Ethanol and Xylitol from Corn Cobs by Yeasts," Bioresource Technology, vol. 77, 2001, pp. 57-63.

Lynd, L.R., et al., "Biocommodity Engineering," Biotechnology Progress, vol. 15, 1999, pp. 777-793.

Mansfield, S.D., et al., "Substrate and Enzyme Characteristics that Limit Cellulose Hydrolysis," Biotechnology Progress, vol. 15, 1999, pp. 804-816.

Montvalvo-Rodriguez, R., et al., "Autohydrolysis of Plant Polysaccharides Using Transgenic Hyperthermophilic Enzymes," Biotechnology and Bioengineering, vol. 2, 2000, pp. 151-159.

Matsumoto, S., et al., "Characterization of Human Glycoprotein (Erythropoietin) Produced in Cultured Tobacco Cells," Plant Molecular Biology, 1995, pp. 1163-1172.

Morassutti, et al., "Production of a Recombinant Antimicrobial Peptide in Transgenic Plants Using a Modified VMA Intein Expressing System," FEBS letters, vol. 519, Nos. 1-3, pp. 141-146 (Apr. 2002).

Murashige, T., et al., A Revised Medium for Rapid Growth and Bio Assays with Tobacco Tissue Cultures, Physiologia Plantarum, vol. 15, 1962, pp. 473-497.

(Continued)

*Primary Examiner* — Jason Deveau Rosen

(74) *Attorney, Agent, or Firm* — Volpe and Koenig, P.C.

(57) ABSTRACT

Vectors for altering the expression of one or more starch regulation enzymes are provided. Methods of transformation of plant tissues to express elements altering expression of one or more starch regulation enzymes, and resulting transgenic plants are provided. Methods of using the transgenic plants are provided.

5 Claims, 15 Drawing Sheets

(56) References Cited

OTHER PUBLICATIONS

Olsson, L., et al., "Fermentation of lignocellulosic Hydrolysates for Ethanol Production," Enzyme and Microbial Technology, vol. 18, 1996, pp. 312-331.
Parsons, T.J., et al., "Transformation of Poplar by Agrobacterium Tumefaciens," Biotechnology, vol. 4, Jun. 1986, pp. 533-536.
Perler, Francine B., "InBase: The Intein Database," Nucleic Acids Research, 2002, vol. 30, No. 1, pp. 383,384.
Perler, F.B., et al., "Protein Splicing Elements; Inteins and Exteins—A Definition of Terms and Recommended Nomenclature", Nucleic Acids Research, vol. 22, No. 7, Feb. 24, 1994, pp. 1125-1127.
Pietrokovski, Samuel, "Conserved Sequence Features of Inteins (Protein Introns) and Their Use in Indentifying New Inteins and Related Proteins," Protein Science, vol. 3, pp. 2340-2350, Aug. 10, 1994.
Poirier, Yves, "Green Chemistry Yields a Better Plastic," Nature Biotechnology, vol. 17, Oct. 1999, pp. 960-961.
Rocha-Sosa, M., et al., "Both Developmental and Metabolic Signals Activate the Promoter of a Class I Patatin Gene," The EMBO Journal, vol. 8, No. 1, 1989, pp. 23-29.
Wood, D.W., et al., "Optimized Single-Step Affinity Purification with a Self-Cleaving Intein Applied to Human Acidic Fibroblast Growth Factor," Biotechnology Progress, vol. 16, 2000, pp. 1055-1063.
Yukon Hiei and Toshihiko Komari, "Improved Protocols for Transformation of Indica Rice Mediated by Agrobacterium tumefaciens," 2006 Plant Cell Tissue and Organ Culture, 2006, 85: 271-283.
Toshihiko Komari, et al., "Vectors Carrying Two Separate T-DNAs for Co-transformation of Higher Plants Mediated by Agrobacterium tumefaciens and Segregations of Trsnformants Free From Selection Markers," The Plant Journal, 1996, 10(1): 165-174.
Ryan, A.J., et al., Genomic Sequence of a 12S Seed Storage Protein from Oilseed Rape, Nucleic Acids Research, vol. 17, No. 9, 1989, p. 3584.
Minesh Patel, et al., "Transgenic Barley Expressing a Fungal Xylanase Gene in the Endosperm of the Developing Grains," Molecular Breeding, 2000, 6:113-123.
Yang, Jianjun, et al., "Intein-mediated assembly of a functional β-glucuronidase in transgenic plants", PNAS, vol. 100, No. 6, pp. 3513-3518 (2003).
Thomas Ziegelhoffer, et al., "Expression of Bacterial Cellulase Genes in Transgenic Alfalfa (Medicago sativa L.), potato (Solanum tuberosum L) and tobacco (Nicotiana tabacum)," Molecular Breeding, 1999, 5: 309-318.
Thomas Ziegelhoffer, et al., "Dramatic Effects of Truncation and Sub-cellular Targeting on the Accumulation of recombinant Microbial Cellulase in Tobacco," Molecular Breeding, 2001, 8: 147-158.
Peilong Yang, et al., Expression of Xylanase with High Specific Activity from Streptomyces olivaceoviridis A1 in Transgenic Potato Plants (Solanum tuberosum L.), Biotechnology Letters, 2007, 29: 659-667.
Schreier, P.H., et al., The Use of Nuclear-Encoded Sequences to Direct the Light-Regulated Synthesis and Transport of a Foreign Protein into Plant Chloroplasts, The EMBO Journal, vol. 4, No. 1, 1985, pp. 25-32.
Goutami Banerjee and John S. Scott-Craig, "Improving Enzymes for Biomass Conversion: A Basic Research Perspective," BioEnergy Research, 2010, 3: 82-92.
Mariam B. Sticklen, "Plant Genetic Engineering for Biofuel Production: Towards Affordable Cellulosic Ethanol," Nature Reviews: Genetics, 2008, 9: 433-443.
Yuji Ishida, et al.,"High Efficiency Transformation of Maize (*Zea mays* L.) Mediated by Agrobacterium Transformation," Nature Biotechnology, 1996, 14: 745-750.
K. Herbers, et al., "A Thermostable Xylanase from Clostridium thermocellum Expressed at High Levels in the Apoplast of Transgenic Tobacco Has no. Detrimental Effects and Is Easily Purified," Nature Biotechnology, 1995, 13:63-66.
Manuel B. Sainz, "Commercial Cellulosic Ethanol: The Role of Plant-Expressed Enzymes," In Vitro Cellular and Developmental Biology, 2009, 45: 314-329.
Shimamoto, J., et al., Fertile Transgenic Rice Plants Regenerated from Transformed Protoplasts, Nature, vol. 338, Mar. 1989, pp. 274-276.
Hesham Oraby, et al., "Enhanced Conversion of Plant Biomass Into Glucose Using Transgenic Rice-Produced Endoglucanase for Cellulosic Ethanol," Transgenic Research, 2007, 16:739-749.
Tetsuya Kimura, et al., "Stable Expression of a Thermostable Xylanase of Clostridium thermocellum in Cultured Tobacco Cells," Journal of Bioscience and Bioengineering, 2003, 95(4): 397-400.
Bae Hyunjong, et al., Dual Targeting of Xylanase to Chloroplasts and Peroxisomes as a Means to Increase Protein Accumulation in Plant Cells, Journal of Experimental Botany, 2006, 57 (1): 161-169.
Gadab C. Ghosh Biswas, et al., "Expression of Biologically Active Acidothermus cellulolyticus Endoglucanase in Transgenic Maize Plants," Plant Science, 2006, 617-623.
Bernhard Borkhardt, et al., "Autohydrolysis of Plant Xylans by Apoplastic Expression of Thermophilic Bacterial Endo-Xylanases," Plant Biotechnology Journal, 2010, 8: 363-374.
Yuji Ishida, et al., "Agrobacterium—Mediated Transformation of Maize," Nature Protocols, 2007, 2(7):1614-1621.
Yong Woo Park, et al., "Enhancement of Growth and Cellulose Accumulation by Overexpression of Xyloglucanase in Poplar," FEBS Letters, 2004, 564: 183-187.
Daniel D. Morris, et al., "Cloning of the xynB Gene from Dictyoglomus thermophilum Rt46B.1 and Action of the Gene Product on Kraft Pulp," Applied and Envoronmental Microbiology, 1998, 64(5):1759-1765.
Ingrid Lindh, et al., "Production of the p24 Capsid Protein from HIV-1 Subtype C in *Arabidopsis thaliana* and Daucus carota Using an Endoplasmic Recticulum-Directing SEKDEL sequence in Protein Expression Constructs," Protein Expression and Purification, 2009, 66(1): 46-51.
Elizabeth E. Hood et al., "Subcellular Targeting is a Key Condition for High-Level Accumulation of Cellulase Protein in Transgenic Maize Seed," Plant Biotechnology Journal, 2007, 5: 709-719.
Dylan Dodd and Isaac K. O. Cann, "Enzymatic Deconstruction of Xylan for Biofuel Production," Global Change Biology Bioenergy, 2009, 1(1):2-17.
Shingledecker, et al., "Reactivity of the Cysteine Residues in the Protein Splicing Active Center of the *Mycobacterium tuberculosis* RecA Intein", Mar. 1, 2000, Archives of Biochemistry and Biophysics, vol. 375, No. 1, pp. 138-144.
Sijmons, P.C., et al., Production of Correctly Processed Human Serum Albumin in Transgenic Plants, Biotechnology, vol. 8, Mar. 1990, pp. 217-221.
Matsuoka et al., "The promoters of two carboxylases in a C4 plant (maize) direct cell-specific, light-regulated expression in a C3 plant (rice)," The Plant Journal (1994) 6(3), 311-319.
Echeverria and Boyer, "Localization of Starch Biosynthetic and Degradative Enzymes in Maize Leaves," American Journal of Botany, vol. 73 (2), 167-171, Feb. 1986.
Grennan Aleel K., "Regulation of starch metabolism in *Arabidopsis* leaves," Plant Physiology, vol. 142, No. 4 (Dec. 2006), pp. 1343-1345.
Lloyd Jr et al., "Leaf starch degradation comes out of the shadows," Trends in Plant Science, Oxford GB, vol. 10, No. 3 (Mar. 1, 2005), pp. 130-137.
Scheidig Andreas et al., "Downregulation of a chloroplast targeted beta-amylase leads to a starch-excess phenotype in leaves," Plant Journalm vol. 30, No. 5 (Jun. 2002), pp. 581-591.
Niityla Totte et al., "A previously unknown maltose transporter essential for starch degradation in leaves," Science, vol. 303, No. 5654 (Jan. 2, 2004), pp. 87-89.
Smith Alison M et al., "Starch mobilization in leaves," Journal of Experimental Botany, vol. 54, No. 382 (Jan. 1, 2003), pp. 577-583.
Asatsuma Satoru et al., "Involvement of alpha-amylase O-1 in starch degradation in rice chloroplasts," Plant and Cell Physiology, vol. 46, No. 6 (Jun. 2005), pp. 858-869.
ISR and Written Opinion for PCT/US2008/082336, Feb. 17, 2009.

(56) References Cited

OTHER PUBLICATIONS

Majeran, et al., "Functional Differentiation of Bundle Sheath and Mesophyll Maize Chloroplasts Determined by Comparative Proteomics," The Plant Cell, vol. 17, 3111-3140, Nov. 2005.
Wu et al., "Modes of intercellular transcription factor movement in the *Arabidopsis* apex," The Company of Biologists Ltd. (2003) (130) 3735-3745.
Waigmann et al., "Direct functional assay for tobacco mosaic virus cell-to-cell movement protein and identification of a domain involved in increasing plasmodesmal permeability," Proc. Nat'l Acad. Sci. USA, vol. 91, 1433-1437, Feb. 1994.
Wolf et al., "Movement protein of Tobacco Mosaic Virus Modifies Plasmodesmatal Size Exclusion Limit," Science, New Series, vol. 246 (4928), 377-379, Oct. 1989.
Edwards et al., "Compartmentation of photosynthesis in cells and tissues of C4 plants," Journal of Experimental Botany, vol. 52 (356) 577-590, Apr. 2001.
Oparka et al., "Simple, but Not Branched, Plasmodesmata Allow the Nonspecific Trafficking of Proteins in Developing Tobacco Leaves," Cell, vol. 97, 743-754, Jun. 1999.
Crawford and Zambryski, "Subcellular localization determines the availability of non-targeted proteins to plasmodesmatal transport," Current Biology 2000, (10), 1032-1040, Aug. 2000.
Goodwin, "Molecular size limit for movement in the symplast of the Elodea leaf," Planta, (1983) (157), 124-130.
Sowinski et al., "On the mechanism of C4 photosynthesis intermediate exchange between Kranz mesophyll and bundle sheath cells in grasses," Journal of Experimental Botany, vol. 59 (6), 1137-1147, Mar. 2008.
Ziegler, M.T., et al., "Accumulation of Thermostable Endo-1,4-β-D-Glucanase in the Apoplast of *Arabidposis thaliana* Leaves," Molecular Breeding, vol. 6, 2000, pp. 37-46.
Gudesblat et al., "Guard cell-specific inhibition of *Arabidopsis* MPK3 expression causes abnormal stomatal responses to abscisic acid and hydrogen peroxide," New Phytologist, (2007) 173: 713-721.
Altintas, M. M., "Improvement of Ethanol Production from Starch by Recombinant Yeast Through Manipulation of Environmental Factors," Enzyme and Microbial Technology, vol. 31, No. 5, 640-647, 2002.
Aspegren, K., et al., Secretion of Heat-Stable Fungal β-Glucanase from Transgenic, Suspension-Cultured Barley Cells, Molecular Breeding, 1995, pp. 91-99.
Birch, R.G., Plant Transformation: Problems and Strategies for Practical Application, Annual Review of Plant Physiology and Plant Molecular Biology, vol. 48, Jun. 1997, pp. 297-326.
Bird, C.R., et al., The Tomato Polygalacturonase Gene and Ripening-Specific Expressions in Transgenic Plants, Plant Molecular Biology, 1988, pp. 651-662.
Brederode, F.T., et al., Complete Nucleotide Sequence of Alfalfa Mosaic Virus RNA 4, Nucleic Acids Research, vol. 8, No. 10, 1980, pp. 2213-2223.
Broothaerts, W., et al., Gene Transfer to Plants by Diverse Species of Bacteria, Nature, vol. 433, Feb. 2005, pp. 629-633.
Cameron, D.C., et al., Metabolic Engineering of Propanediol Pathways, Biotechnology Progress, 1998, pp. 116-125.
Cheon, B.Y., et al., Overexpression of Human Erythropoietin (EPO) Affects Plant Morphologies; Retarded Vegetative Growth in Tobacco and Male Sterility in Tobacco and Arabidopsis, Transgenic Research, 2004, pp. 541-549.
Chih-Ching, C., et al., Establishment of an Efficient Medium for Anther Culture of Rice Through Comparative Experiments on the Nitrogen Sources, Scientia Sinica, vol. 18, No. 3, 1975, pp. 659-668.
Chin, Hang Gyeong, et al., Protein trans-splicing in transgenic plant chloroplast: Reconstruction of herbicide resistance from split genes, PNAS, vol. 100, No. 8, pp. 4510-4515 (2003).
Chong, et al., "Modulation of Protein Splicing of the *Saccharomyces cerevisiae* Vacuolar Membrane ATPase Intein", Apr. 24, 1998, Journal of Biological Chemistry, vol. 273, No. 17, pp. 10567-10577.
Chong Shaorong, et al.., "Single-column purification of free recombinant proteins using a self-cleavable affinity tag derived from a protein splicing element", Gene: An International Journal of Genes and Genomes, vol. 192, pp. 271-281 (1997).
Clarke, Neil D., "A Proposed Mechanism for the Self-Splicing of Proteins," Proceedings of the National Academy of Science, USA, vol. 91, pp. 11084-11088, Nov. 1994.
Coruzzi, G., et al., Tissue-Specific and Light-Regulated Expression of Pea Nuclear Gene Coding the Small Subunit of Ribulose-1, 5-Bisphosphate Carboxylase, The EMBO Journal, 1984, 1671-1679.
Dai, Z., et al., Expression of Acidothermus Cellulolyticus Endoglucanase E1 in Transgenic Tobacco: Biochemical Characteristics and Physiological Effects, Transgenic Research, 2000, pp. 43-54.
Dai, Z., et al., Improved Plant-Based Production of E1 Endoglucanase Using Potato: Expression Optimization and Tissue Targeting, Molecular Breeding, 2000, pp. 277-285.
Dale, Bruce E., Biobased Industrial Products: Bioprocess Engineering When Costs Really Count, Biotechnology Progress, 1999, pp. 775-776.
Davis et al., "Protein Splicing: The Lengths Some Proteins Will Go to", 1995, Antonie van Leeuwenhoek, vol. 67, pp. 131-137.
Davis, E., et al., "Novel Structure of the recA Locus of *Mycobacterium tuberculosis* Implies Processing of the Gene Product," Journal of Bacteriology, vol. 173, No. 18, 5653-5662 Sep. 1991.
Davis, E., et al., "Protein Splicing in the Maturation of *M. tuberculosis* RecA Protein: A Mechanism for Tolerating a Novel Class of Intervening Sequence," Cell Press, vol. 71, 201-210, Oct. 16, 1992.
Derbyshire, et al., "Lightning Strikes Twice: Intron-Intein Coincidence," Proceedings of the National Academy of Science, USA, vol. 95, pp. 1356-1357, Feb. 17, 1998.
Evans, et al., "Semisynthesis of Cytotoxic Proteins Using a Modified Protein Splicing Element," Protein Science, vol. 7: pp. 2256-2264 (1998).
Gangopadhyay, J.P., et. al., "In Vitro Splicing of Erythropoietin by the *Mycobacterium tuberculosis* RecA Intein Without Substituting Amino Acids at the Splice Junctions," Biochimica et Biophysica Acta, vol. 1619, (2003), pp. 193-200.
Gimble, Frederick S., "Invasion of a Multitude of Genetic Niches by Mobile Endonuclease Genes", Feb. 8, 2000, FEMS Microbiology Letters, vol. 185, pp. 99-107.
Gordon-Kamm, et al., "Transformation of Maize Cells and Regeneration of Fertile Transgenic Plants," The Plant Cell, vol. 2, pp. 603-618, Jul. 1990.
Guilley, H., et al., "Transcription of Cauliflower Mosaic Virus DNA: Detection of Promoter Sequences, and Characterization of Transcripts," Cell, vol. 30, Oct. 1982, pp. 763-773.
Gupta, P.K., et al., "Shoot Multiplication from Mature Trees of Douglas Fir and Sugar Pine," Plant Cell Reports, vol. 4, 1985, pp. 177-179.
Higgins, T.J.V., "Synthesis and Regulation of Major Proteins in Seeds," Annual Review of Plant Physiology, 1984, pp. 191-221.
Hirata, R., et al., "Molecular Structure of a Gene, VMA1, Encoding the Catalytic Subunit of H+-Translocating Adenosine Triphosphatase fro Vacuolar Membranes of *Saccharomyces cerevisiae*," The Journal of Biological Chemistry, vol. 265, No. 12, Apr. 25, 1990, pp. 6726-6733.
Sasaki et al., "GenBank Accession AP003620," Feb. 16, 2008 [online]; downloaded from http://www.ncbi.nlm.nih.gov/nuccore/AP003620 on Mar. 14, 2012.
Sasaki et al., "GenBank Accession AK103463," Dec. 4, 2008 [online]; downloaded from http://www.ncbi.nlm.nih.gov/nuccore/AK103463 on Mar. 14, 2012.
Wilson et al., GenBank Accession AC203259 [online]; downloaded from http://www.ncbi.nlm.nih.gov/nuccore/AC203259 on Mar. 14, 2012, Oct. 28, 2008.

(56) References Cited

OTHER PUBLICATIONS

Gerhard Ritte et al., "The starch—related R1 protein is an alpha-glucan, water dikinase," Proc. Natl Acad Sci USA, 2002, 99(10):7166-7171.
Sean E. Weise et al., "Engineering starch accumulation by manipulation of phosphate metabolism of starch," Plant Biotechnology Journal, 2012, 10(5): 545-554.
Peter A. Stoutjesdijk et al.,"hpRNA-mediated targeting of the *Arabidopsis* FAD2 gene gives highly efficient and stable silencing," Plant Physiology, 2002, 129(4): 1723-1731.
Arjun Krishnan et al.,"Mutant resources in rice for functional genomics of the grasses," Plant Physiology, 2009, 149:165-170.
Bradley J. Till et al., "Discovery of chemically induced mutations in rice by TILLING," BMC Plant Biol., 2007, 7:19.
Neil A. Smith et al., "Total silencing by intron-spliced hairpin RNAs," Nature, 2000, 407:319-320.
Alison M. Smith and Samuel C. Zeeman, "Quantification of starch in plant tissues," Nature Protocols, 2006, 1:1342-1345.
Zheng Zhang et al., "A greedy algorithm for aligning DNA sequences," Journal of Computational Biology, 2000, 7 (1-2):203-214.
Gorou Horiguchi, "RNA silencing in plants: a shortcut to functional analysis," Differentiation, 2004, 72(2-3): 65-73.
Smeekens, et al., "Protein Transport into and Within Chloroplasts," Trends in Biochemical Sciences, vol. 15, Feb. 1990, pp. 73-76.
Sreenath, H.K., et al., "Production of Ethanol from Wood Hydrolyzate by Yeasts," Bioresource Technology, vol. 72, No. 3, 2000, pp. 253-260.
Staub, J.M., et al., "High-Yield Production of a Human Therapeutic Protein in Tobacco Chloroplasts," Nature Biotechnology, vol. 18, Mar. 2000, pp. 333-338.
Sun, et al., "Protein Trans-Splicing to Produce Herbicide-Resistant Acetolactate Synthase," Applied and Environmental Microbiology, Mar. 2001, pp. 1025-1029.
Tague, B.W., et al., "A Short Domain of the Plant Vacuolar Protein Phytohemagglutinin Targets Invertase to the Yeast Vacuole," The Plant Cell, vol. 2, Jun. 1990, pp. 533-546.
Taylor, F., et al., "Dry-Grind Process for Fuel Ethanol by Continuous Fermentation and Stripping," Biotechnology Progress, vol. 16, 2000. pp. 541-547.
Tingey, S.V., et al., "Glutamine Synthetase Genes of Pea Encode Distinct Polypeptides Which are Differentially Expressed in Leaves, Roots and Nodules," The EMBO Journal, vol. 6, No. 1, 1987, pp. 1-9.
Ulgen, K.O., et. al., "Bioconversion of Starch Into Ethanol by a Recombinant *Saccharomyces cerevisiae* Strain YP-GAB," Process Biochemistry, vol. 37, 2002, pp. 1157-1168.
Van Den Broeck, G., et al., Targeting of a Foreign Protein to Chloroplasts by Fusions to the Transmit Peptide from the Small Subunit of Ribulose 1,5-Bisphosphate Carboxylase, Nature, vol. 313, Ksmistu 1985, pp. 358-363.
Von Heijne, G., "Towards a Comparative Anatomy of N-Terminal Topogenic Protein Sequences," Journal of Molecular Biology, vol. 189, 1986, pp. 239-242.
Wallace, Carmichael J.A., "The Curious Case of Protein Splicing: Mechanistic Insights Suggested by Protein Semisynthesis," Protein Science, vol. 2, pp. 697-705 (1993).
Wang, et al., "Identification of an Unusual Intein in Chloroplast CipP Protease of Chlamydomonas Eugametos", May 2, 1997, Journal of Biological Chemistry, vol. 272, No. 18, pp. 11869-11873.
Wenzler, H.C., et al., "Analysis of a Chimeric Class-I Patatin-GUS Gene in Transgenic Potato Plants: High-Level Expression in Tubers and Sucrose-Inducible Expressions in Cultured Leaf and Stem Explants," Plant Molecular Biology, vol. 12, 1989, pp. 41-50.
Xu, M., et al., "In Vitro Protein Splicing of Purified Precursor and the Identification of Branched Intermediate," Cell, vol. 75, Dec. 31, 1993, pp. 1371-1377.
Xu, M., et al., "The Mechanism of Protein Splicing in its Modulation by Mutation," The EMBO Journal, vol. 15, No. 19, 1996, pp. 5146-5153.
Chen et al., "Herbicide resistance from a divided EPSPE protein: the split Synechocystis DnaE intein as an in vivo affinity domain," Gene 263 (2001) 39-48.
Liu et al., "Enhanced enzymatic hydrolysis and structural features of corn stover by FeCl3 pretreatment," Bioresource Technology, 100 (2009) 5853-5858.

* cited by examiner

```
gb|EU908574.1| Solanum lycopersicum glucan water dikinase
(GWD) mRNA, complete cds
Length=4398

 Score =  292 bits (158),  Expect = 2e-82
 Identities = 403/519 (77%), Gaps = 26/519 (5%)
 Strand=Plus/Plus

Query  49    TGGAATTTTTGTTTGGATTAGGTTCATGGCTACAAGGCAACTAATATGGAACAAGAACTA  108
             ||||| | |||| ||||| ||||||||||||||||||| || ||||||||||| |||||
Sbjct  1803  TGGAATTCTTGTATGGATGAGGTTCATGGCTACAAGGCAGCTGATATGGAACAAAAACTA  1862

Query  109   CAATGTGAAGCCACGTGAGATAAGCAAAGCACAAGATAGGTTTACAGATGAT-CTTG-AG  166
              || | ||| |||||||| |||||||| || || || ||  |||||||    | | || ||
Sbjct  1863  TAACGTGAAACCACGTGAAATAAGCAAGGCTCAGGACAGACTTACAGA-CTTGC-TGCAG  1920

Query  167   AAT-ATGTACAGAACTTACCCACAATATCAG-GAGATC-TTAAGAATGATAATGTCTGCT  223
             |||    | ||  | | | || || || | | || | | ||  | ||||| |||||  ||
Sbjct  1921  AATGCT-TTCACCAGTCATCCTCAGTA-CCGTGA-AACTTTGCGGATGATTATGTCAACT  1977

Query  224   GTTGGTCGGGGAGGTGAAGGTGATGTTGGTCAACGCATTCGTGATGAGATATTAGTAATC  283
             ||||| || ||||||||||| ||||| || || || ||| | || || || || || |||
Sbjct  1978  GTTGGACGTGGAGGTGAAGGGGATGTAGGACAGCGAATTAGGGACGAAATTTTGGTCATC  2037

Query  284   CAGA-GAAATAATGACTGCAAAGGTGGAATGATGGAGGAGTGGCACCAGAAACTGCACAA  342
             ||||  ||| ||||||||||| ||||| |||||||| || ||||| |||||| |||| ||
Sbjct  2038  CAGAGGAAA-AATGACTGCAAGGGTGGTATGATGGAAGAATGGCATCAGAAATTGCATAA  2096

Query  343   CAATACAAGCCCAGATGATGTAGTGATCTGCCAGGCCCT-ACTTGATTATATCAAGAGTG  401
              || |  || || |||||||| |||||||| ||||| || | |||| || ||||||||||
Sbjct  2097  TAACACTAGTCCTGATGATGTTGTGATCTGTCAGGCACTGA-TTGACTACATCAAGAGTG  2155

Query  402   ATTTTGATATTGGTGTTTACTGGGACACCTTGAAAAAAGAT-GGTATAACAAAAGAGCGT  460
             ||||| ||||||||||||| ||| | ||| ||||   | ||   || || |||||||||||
Sbjct  2156  ATTTTGATATTGGTGTTTATTGGAAAACCCTGAATGA-GAACGGAATTACAAAAGAGCGT  2214

Query  461   CTATTGAGCTATGATCGACCGATTCATTCAGAGCCAAATTTCAGGAGTGA-A-CAGAAAG  518
             || || || ||||| ||   | || ||||| || |||||||| || || || | || ||||
Sbjct  2215  CTTTTGAGTTATGACCGTGCTATCCATTCTGAACCAAATTTTAG-AG-GAGATCA-AAAG  2271

Query  519   -ATGG-CTTACTCCGTGACTTGGG-CAATTATATGAGAA  554
              |||| |||  | ||||| || || || | |||||||||
Sbjct  2272  GATGGTCTTT-TGCGTGATTTAGGTCACT-ATATGAGAA  2308
```

FIG. 4

Multiple Species Alignments

FIG. 7

```
OsGWD        TGGAATTTTTGTTTGGATTAGGTTCATGGCTACAAGGCA
SbGWD        TGGACTTTTTGTTTGGATTAGGTTCATGGCTACCAGGCA
ZmGWD        NNNNNNNNNNNNNNNNNNNNGATTCATGGCTACCAGGCA
SlGWD        TGGAATTCTTGTATGGATGAGGTTCATGGCTACAAGGCA

dgGWDup2     TGGAATTYTTGTWTGGATKAGRTTCATGGCTACMAGGCA


OsGWD        AGAGCGTCTATTGAGCTATGATCGACCGATTCATTCAGAGCC
SbgWD        AGAGCGTCTCTTGAGCTATGATCGTGCTATTCATTCAGAACC
ZmGWD        AGAGCGTCTCTTGAGCTATGATCGTGCTATTCATTCAGAACC
SlGWD        AGAGCGTCTTTTGAGTTATGACCGTGCTATCCATTCTGAACC

dgGWDdown2   AGAGCGTCTHTTGAGYTATGAYCGWSCKATYCATTCWGARCC
```

PLANTS WITH ALTERED LEVELS OF VEGETATIVE STARCH

CROSS REFERENCE TO RELATED APPLCIATIONS

This application is a 35 U.S.C. §371 national phase application of PCT/US2011/041991, which was filed Jun. 27, 2011, and claims the benefit of United States provisional patent application No. 61/358,720 filed Jun. 25, 2010, both of which are incorporated herein by reference as if fully set forth.

The sequence listing filed with this application, titled "Sequence Listing," having a file size of 219,080 bytes, and created Dec. 21, 2012 is incorporated herein by reference as if fully set forth.

GOVERNMENT SUPPORT STATEMENT

This invention was made at least in part with government support under award number 2009-10001-05118 awarded by the U.S. National Institute of Food and Agriculture, USDA. The government has certain rights in the invention.

FIELD

The disclosure herein relates to plants with altered levels of vegetative starch.

BACKGROUND

Glucose is a preferred molecular feedstock, however, its availability and cost have recently become a limiting factor in the demand for an inexpensive biofuel feedstock and sustainable animal feed. Demand for corn and sugarcane has increased the price of this commodity significantly. Starch is a superior source of glucose because of it's simple molecular structure (α-1-4, and α-1-6 glucose linkages) and the relative ease with which these bonds are accessed and hydrolyzed by inexpensive and highly effective enzymes (e.g.; α-amylase and glucoamylase). Hydrolysis of high-starch plant tissues like grain provides relatively pure glucose that is effectively transformed into meat or chemical end-products.

Sucrose, a soluble storage carbohydrate, is also a plant derived feedstock molecule that is readily utilized by fermentative organisms. Cropping and processing systems that use sucrose feedstocks, such as sugarbeets and sweet sorghum, are constrained by narrow harvest windows and storage and stability limitations. Sweet sorghum must be processed similarly to sugarcane, within days of its harvest to limit microbial fermentation of the sucrose due to the high moisture content in the harvested materials (spoilage). Campaign periods reduce the overall capital effectiveness of dedicated processing facilities.

Lignocellulosic substrates are less attractive feedstocks because of processing difficulties. Lignocellulosic biomass contains a mixture of hexoses and pentoses and their recalcitrance to hydrolysis (crystallinity, and cross-linking to lignin) makes digestion and cost effective degradation into useable sugars difficult. In biofuels production, expensive pretreatments are being developed to aid in complete hydrolysis of lignocellulosic materials. Full utilization of the resultant mixtures of sugars for fuel and chemical production also requires that specialized fermentation organisms transform the resulting sugars into final products, such as ethanol, butanol, succinic acid, and other chemicals.

SUMMARY

In an aspect, the invention relates to a transgenic plant comprising an RNAi construct. The RNAi construct comprises a first driver sequence including a first isolated nucleic acid having at least 90% identity to a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45, and a second driver sequence including a second isolated nucleic acid capable of hybridizing with the first nucleic acid sequence. The RNAi construct also comprises a spacer operably linked to and between the first driver sequence and the second driver sequence, and a promoter operably linked to the first driver sequence, the second driver sequence and the spacer.

In an aspect, the invention relates to a transgenic plant derived from an energy crop, a food crop or a forage crop plant comprising an RNAi construct. The RNAi construct comprises a first driver sequence including a first isolated nucleic acid having at least 90% identity along the length of the isolated nucleic acid to a portion of a gene in the transgenic plant encoding a target protein involved in mobilization of vegetative starch, and a second driver sequence including a second isolated nucleic acid capable of hybridizing to the first isolated nucleic acid. The RNAi construct also comprises a spacer operably linked to the first driver sequence and the second driver sequence, and a promoter operably linked to the first driver sequence, the second driver sequence and the spacer. Upon expression of the first driver sequence, the spacer and the second driver sequence, an RNA sequence transcribed from the first isolated nucleic acid and an RNA sequence transcribed from the second isolated nucleic acid are capable of hybridizing with each other and causing inhibition of expression of the gene.

In an aspect, the invention relates to a method of agricultural processing or preparing animal feed. The method includes providing a transgenic plant. The transgenic plant includes an RNAi construct. The RNAi construct comprises a first driver sequence including a first isolated nucleic acid having at least 90% identity to a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45, and a second driver sequence including a second isolated nucleic acid capable of hybridizing with the first nucleic acid sequence. The RNAi construct also includes a spacer operably linked to and between the first driver sequence and the second driver sequence, and a promoter operably linked to the first driver sequence, the second driver sequence and the spacer. The method also includes processing the transgenic plant, where the first and second driver sequences were expressed in the transgenic plant. The expression of the first and second driver sequences may be before the step of processing. In an aspect, the invention also relates to a product produced by the method of agricultural processing or preparing animal feed.

In an aspect, the invention relates to a method of agricultural processing or preparing animal feed. The method includes providing a transgenic plant derived from an energy crop plant, a food crop plant or a forage crop plant. The transgenic plant comprises an RNAi construct. The RNAi construct comprises a first driver sequence including a first isolated nucleic acid having at least 90% identity along the length of the isolated nucleic acid to a portion of a gene in the transgenic plant encoding a target protein involved in mobilization of vegetative starch, and a second driver sequence including a second isolated nucleic acid capable of hybridizing to the first isolated nucleic acid. The RNAi construct also comprises a spacer operably linked to the first driver sequence and the second driver sequence, and a promoter operably linked to the first driver sequence, the second driver sequence and the spacer. Upon expression of the first driver sequence, the spacer and the second driver sequence, an RNA sequence transcribed from the first isolated nucleic acid and an RNA sequence transcribed from the second isolated nucleic acid are capable of hybridizing with each other and causing inhibition of expression of the gene. The method also includes processing the transgenic plant, where the first and second driver sequences were expressed in the transgenic plant. The expression of the first and second driver sequences may be before the step of processing. In an aspect, the invention also relates to a product produced by the method of agricultural processing or preparing animal feed.

In an aspect, the invention relates to a method of altering vegetative starch levels in a plant. The method includes expressing an isolated nucleic acid in the plant. Expression of the isolated nucleic acid in the plant alters the activity of at least one enzyme related to starch metabolism in the plant.

In an aspect, the invention relates to a method of altering vegetative starch levels in a plant. The method includes expressing an isolated nucleic acid in the plant. Expression of the isolated nucleic acid in the plant alters the activity of at least one enzyme related to starch metabolism in the plant. The plant is a transgenic plant. The transgenic plant includes an RNAi construct. The RNAi construct comprises a first driver sequence including a first isolated nucleic acid having at least 90% identity to a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45, and a second driver sequence including a second isolated nucleic acid capable of hybridizing with the first nucleic acid sequence. The RNAi construct also comprises a spacer operably linked to and between the first driver sequence and the second driver sequence, and a promoter operably linked to the first driver sequence, the second driver sequence and the spacer.

In an aspect, the invention relates to a method of altering vegetative starch levels in a plant. The method includes expressing an isolated nucleic acid in the plant. Expression of the isolated nucleic acid in the plant alters the activity of at least one enzyme related to starch metabolism in the plant. The plant is a transgenic plant derived from an energy crop, a food crop or a forage crop plant. The transgenic plant includes an RNAi construct. The RNAi construct comprises a first driver sequence including a first isolated nucleic acid having at least 90% identity along the length of the isolated nucleic acid to a portion of a gene in the transgenic plant encoding a target protein involved in mobilization of vegetative starch, and a second driver sequence including a second isolated nucleic acid capable of hybridizing to the first isolated nucleic acid. The RNAi construct also comprises a spacer operably linked to the first driver sequence and the second driver sequence, and a promoter operably linked to the first driver sequence, the second driver sequence and the spacer. Upon expression of the first driver sequence, the spacer and the second driver sequence, an RNA sequence transcribed from the first isolated nucleic acid and an RNA sequence transcribed from the second isolated nucleic acid are capable of hybridizing with each other and causing inhibition of expression of the gene.

In an aspect, the invention relates to an isolated nucleic acid comprising a sequence having at least 90% identity to any one of SEQ ID NOS: 7-8, 11-18, 21-23, 32-33, 37, 38 and 39-47.

In an aspect, the invention relates to a vector including an RNAi construct. The RNAi construct includes a first driver sequence including a first isolated nucleic acid having at least 90% identity along the length of the isolated nucleic acid to a portion of a gene in the transgenic plant encoding a target protein involved in mobilization of vegetative starch, and a second driver sequence including a second isolated nucleic acid capable of hybridizing to the first isolated nucleic acid. The RNAi construct also comprises a spacer operably linked to and between the first driver sequence and the second driver sequence, and a promoter operably linked to the first driver sequence, the second driver sequence and the spacer.

In an aspect, the invention relates to a method of making a transgenic plant. The method includes transforming a plant with a vector. The vector including an RNAi construct. The RNAi construct includes a first driver sequence including a first isolated nucleic acid having at least 90% identity along the length of the isolated nucleic acid to a portion of a gene in the transgenic plant encoding a target protein involved in mobilization of vegetative starch, and a second driver sequence including a second isolated nucleic acid capable of hybridizing to the first isolated nucleic acid. The RNAi construct also comprises a spacer operably linked to and between the first driver sequence and the second driver sequence, and a promoter operably linked to the first driver sequence, the second driver sequence and the spacer.

In an aspect, the invention relates to a vector having an isolated nucleic acid with at least 90% identity to a sequence selected from the group consisting of SEQ ID NO: 13 and SEQ ID NO: 14.

BRIEF DESCRIPTION OF THE DRAWINGS

The following detailed description of the preferred embodiment of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 4 illustrates sequence comparison between a portion of GWD2 [SEQ ID NO: 9], derived from the rice glucan water dikinase gene, and a portion of the GWD gene from tomato (*Solanum lycopersicon*) [SEQ ID NO: 10].

FIG. 7 illustrates alignment of excerpts from the GWD genes of rice (OsGWD)[SEQ ID NOS: 24 and 28], sorghum (SbGWD)[SEQ ID NOS: 25 and 29], maize (ZmGWD) [SEQ ID NOS: 26 and 30], and tomato (SlGWD)[SEQ ID NOS: 27 an 31]. Primers dgGWup2 [SEQ ID NO: 32] and dgGWdown2 [SEQ ID NO: 33] are also illustrated.

DETAILED DESCRIPTION OF THE PREFERRED EMBODIMENTS

Figures 1A, 1B, 1C:
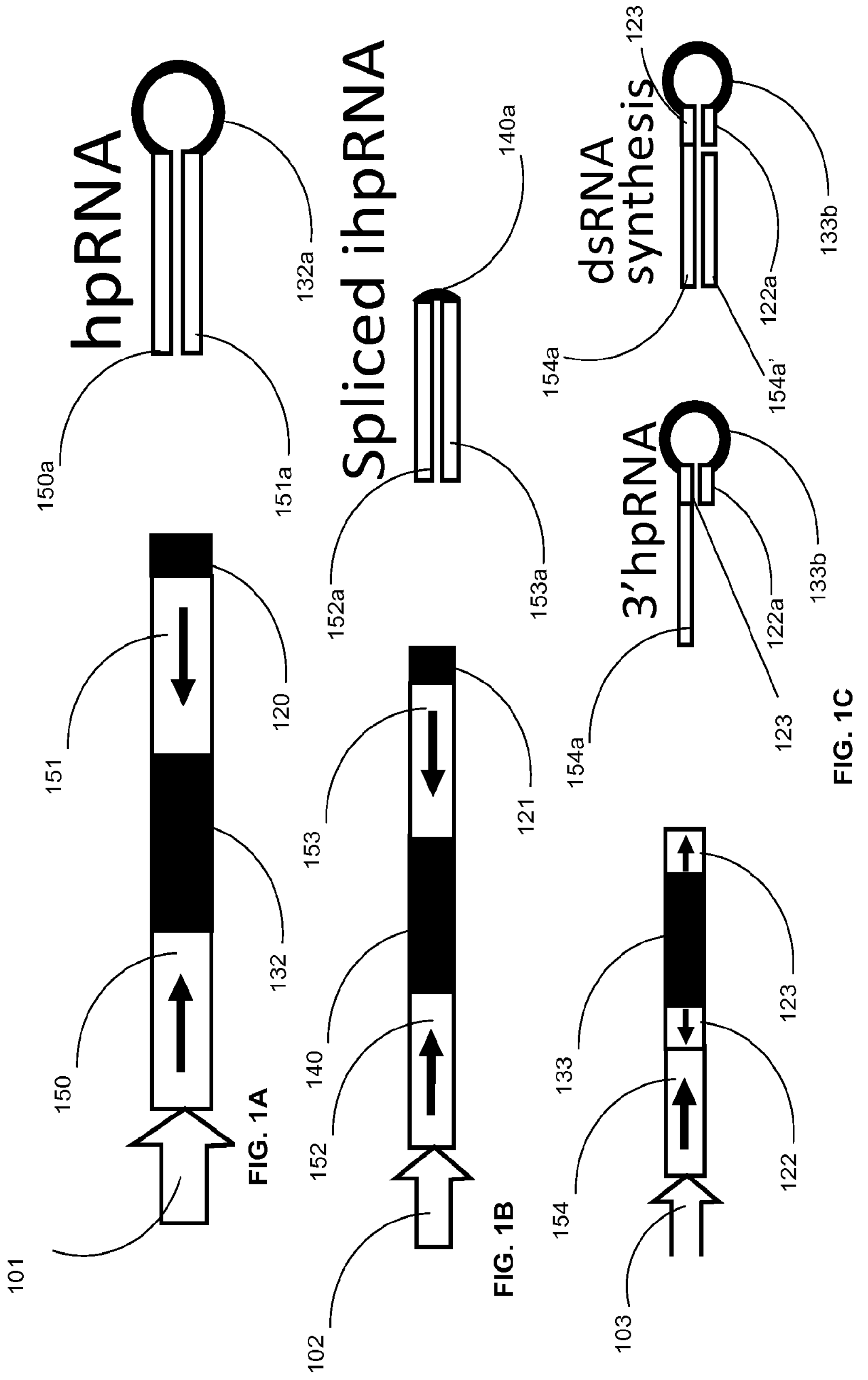
FIGS. 1A-G illustrate strategies for expressing interfering RNAs in transgenic plants.

Certain terminology is used in the following description for convenience only and is not limiting.

"Isolated nucleic acid," "isolated polynucleotide," "isolated oligonucleotide," "isolated DNA," or "isolated RNA" as used herein refers to a nucleic acid, polynucleotide, oligonucleotide, DNA, or RNA separated from the organism from which it originates or from the naturally occurring genome, location, or molecules with which it is normally associated, or is a nucleic acid that was made through a synthetic process.

"Isolated protein," "isolated polypeptide," "isolated oligopeptide," or "isolated peptide" as used herein refers to a protein, polypeptide, oligopeptide or peptide separated from the organism from which it originates or from the naturally occurring location, or molecules with which it is normally associated.

As used herein, "variant" refers to a molecule that retains a biological activity that is the same or substantially similar to that of the original sequence. The variant may be from the same or different species or be a synthetic sequence based on a natural or prior molecule.

Nucleic acids, nucleotide sequences, proteins or amino acid sequences referred to herein can be isolated, purified, synthesized chemically, or produced through recombinant DNA technology. All of these methods are well known in the art.

As used herein, "operably linked" refers to the association of two or more biomolecules in a configuration relative to one another such that the normal function of the biomolecules can be performed. In relation to nucleotide sequences, "operably linked" refers to the association of two or more nucleic acid sequences in a configuration relative to one another such that the normal function of the sequences can be performed. For example, the nucleotide sequence encoding a presequence or secretory leader is operably linked to a nucleotide sequence for a polypeptide if it is expressed as a preprotein that participates in the secretion of the polypeptide; a promoter or enhancer is operably linked to a coding sequence if it affects the transcription of the coding sequence; and a nucleic acid ribosome binding site is operably linked to a coding sequence if it is positioned so as to facilitate binding of the ribosome to the nucleic acid.

The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

The Sequence Listing titled "Sequence Listing," having a file size of about 219,033 bytes and filed herewith is incorporated herein by reference as if fully set forth.

An embodiment provides a method for alteration in the amount of starch that accumulates in vegetative tissues of plants by inhibiting the activity of enzymes that are normally responsible for mobilizing vegetative starch (hereinafter referred to as "Green Starch" or "vegetative starch") during day/night cycles. Isolated nucleic are provided acids for alteration in the amount of starch that accumulates in vegetative tissues of plants by inhibiting the activity of enzymes that are normally responsible for mobilizing Green Starch. Transgenic plants are provided, which include nucleic acids for alteration in the amount of starch that accumulates in vegetative tissues of plants by inhibiting the activity of enzymes that are normally responsible for mobilizing Green Starch. Any plant can be provided as the transgenic plant. In an embodiment, rice, switchgrass, sorghum, or other energy and forage crops are provided as the transgenic plant.

In an embodiment, animal feed applications including increased levels of starch in vegetative tissues are provided. Easily-fermentable sugars available in a fermentation process may be provided by embodiments herein. Production of biofuels may be enhanced by providing easily-fermentable sugars. Methods of providing easily fermentable sugars and methods of enhancing production of biofuels are provided as embodiments herein.

Crops with elevated levels of vegetative starch have a variety of uses and utilities. In an embodiment, biomass from plants that accumulate elevated levels of vegetative starch relative to wild type plants are provided. These plants may have added value as feedstocks for fermentation processes or animal feed applications. For example, in a typical cellulosic process, polysaccharides such as cellulose and hemicelluloses that are present in the biomass are hydrolyzed to simple sugars, which may then be fermented to ethanol, butanol, isobutanol, fatty acids, or other hydrocarbons by microorganisms. Because of the recalcitrance of the biomass, the release of the simple sugars from polymers such as cellulose and hemicelluloses often requires the use of harsh pretreatment conditions and hydrolysis with relatively expensive mixtures of enzymes. In contrast, any starch that is present in the biomass represents an additional source of simple sugars (namely, glucose), which can be released very easily and much less expensively with either dilute acid treatments or hydrolysis by amylases, which are currently available and much less expensive than the enzymes required for the digestion of cellulose and hemicelluloses. As a result, any increase in the amount of starch present in the biomass will simultaneously increase the amount of fermentable sugar that can be recovered (and therefore the amount of ethanol, butanol, etc. that can be made) with only a disproportionately small increase in process costs (i.e. addition of an inexpensive amylase or acid pretreatment). Similarly, biomass that contains elevated levels of starch may have greater value in forage applications, where the plant material is fed to livestock. Again, the excess starch present in this material is more easily digested by most animals than is the cellulosic material, providing more energy per unit biomass than biomass with ordinary levels of starch. Embodiments include utilizing a transgenic plant as set forth herein for any of these methods.

Methods herein, including those in the previous paragraph, may include modifying plants to create transgenic plants, growing the transgenic plants, harvesting the plants and either processing them for animal feed applications as one would other forage crops, or dry them and treat them for use in fermentation processes similar to the manner of treatment that is used in cellulosic processes but with the addition of a treatment such as acid hydrolysis or amylase digestion to hydrolyze the starch to its component sugars. Any one step, set of steps, or all the steps set forth in this paragraphs may be provided in a method herein.

Genes to target for Green Starch alteration were identified. Any enzyme, protein or nucleic acid involved in starch metabolism may be targeted for alteration of Green Starch levels. In an embodiment, alteration is accomplished by suppression of gene expression of genes related to Green Starch. In an embodiment, alteration is an increase in the amount of Green Starch. Particular enzymes that may be targets include but are not limited to Glucan Water Dikinase (also known as GWD, R1, sexl); Phosphoglucan Water Dikinase (also known as PWD); Dual Specificity Protein Phosphatase (also known as DSP, sex4); β-amylase (BAM), isoamylase (also known as ISA3), limit dextrinases (also known as LDA); disproportionating enzyme; and other debranching enzymes. GWD phosphorylates starch, which is then susceptible to starch degrading enzymes. PWD phosphorylates starch, and may be dependent upon prior action by GWD by episatsis. DSP is regulatory, and may activate starch degrading enzymes. DSP may also phosphorylate starch. Also, DSP is suspected of having endo-amylase activity, which may be synergistic with β-amylase and isoamylase starch mobilization. BAM (but not α-amylase) and ISA3 are involved in mobilizing vegetative starch. BAM activity depends on GWD, and ISA3 activity depends on BAM.

In an embodiment, targets are suppressed, and suppression may be achieved through RNAi suppression of gene expression. RNAi constructs are provided to suppress gene expression of target proteins. The target proteins may be enzymes. The target enzyme may be selected from an enzyme involved in Green Starch mobilization. RNAi constructs suppressing at least one of GWD, PWD, DSP, BAM, isoamylase, LDA, disproportionating enzyme and other debranching enzymes are provided.

Figures 1D, 1E, 1F, 1G:
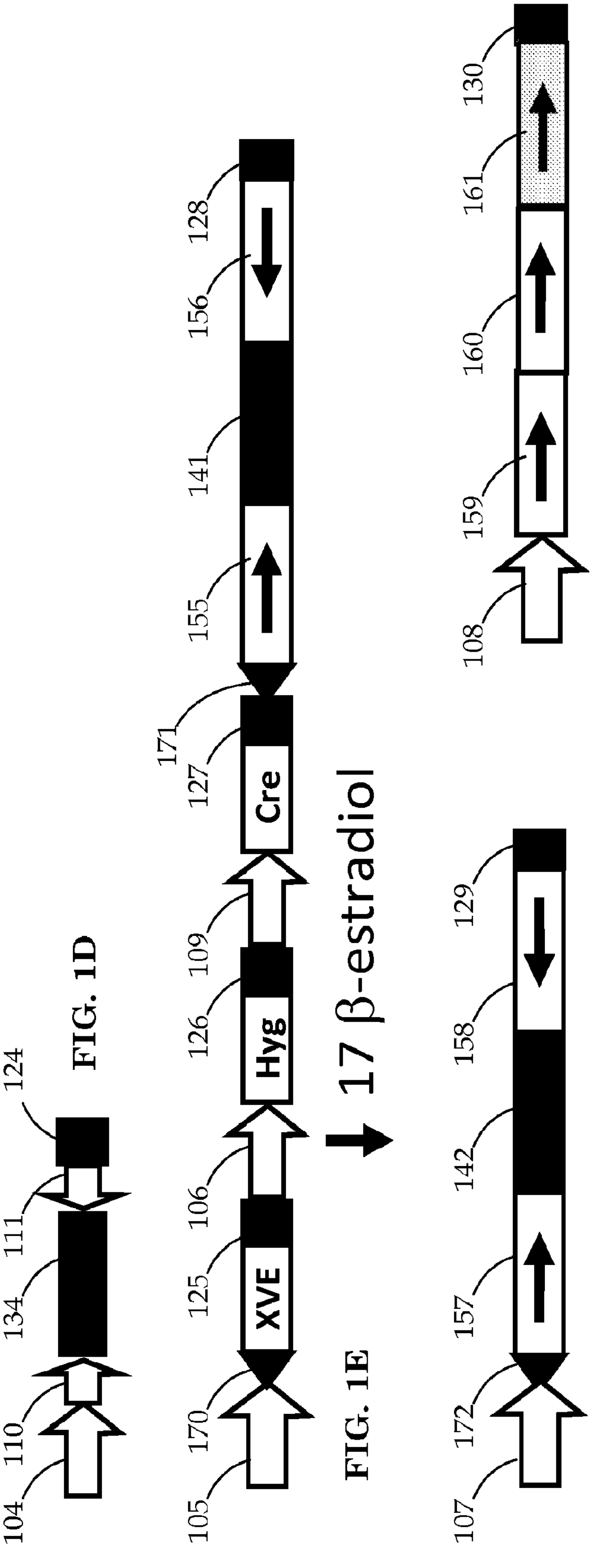

A number of strategies have been developed for expressing RNAi in transgenic plants. See, for example, Horiguchi G., RNA silencing in plants: a shortcut to functional analysis (2004) Differentiation 72(2-3): 65-73, which is incorporated by reference herein as if fully set forth. See also Smith N A, Singh S P, Wang M B, Stoutjesdijk P A, Green A G, Waterhouse P M, Total silencing by intron-spliced hairpin RNAs (2000) Nature 407:319-20; Stoutjesdijk P A, Singh S P, Liu Q, Hurlstone C J, Waterhouse P A, Green A G hpRNA-mediated targeting of the *Arabidopsis* FAD2 gene gives highly efficient and stable silencing (2002) Plant Physiol. 129(4): 1723-31, which are incorporated by reference herein as if fully set forth. Referring to FIGS. 1A-G, exemplary strategies for RNAi are illustrated. Embodiments herein include RNAi constructs, methods and transgenic plants implementing an RNAi strategy. Promoters 101, 102, 103, 104, 105, 106, 107 and 108 may allow transcription of nucleic acid in the constructs. The strategy shown in FIG. 1E includes an XVE responsive promoter 109, and the strategy in FIG. 1D includes promoter fragments 110 and 111. Terminators 120, 121, 122, 123, 124, 125, 126, 127, 128, 129, 130 and 131 are also illustrated, as are transcribed terminator sequences 122a and 123a. Spacers 132, 133 and 134 are illustrated for strategies in FIGS. 1A, 1C and 1D, and the transcribed spacers 132a and 132b are illustrated for FIGS. 1A and 1C. Introns 140, 141 and 142 and transcribed intron 140a are illustrated in FIGS. 1B, 1E and 1F. cDNA fragments 150, 151, 152, 153, 154, 155, 156, 157, 158, 159, 160 and 161 are shown, as well as transcribed cDNA 150a, 151a, 152a, 153a, 154a, and ds RNA strand 154a'. In FIGS. 1E and 1F, loxP sites 170, 171 and 172 are illustrated. Embodiments include methods utilizing driver RNAs separated by an intron spacer as illustrated in FIG. 1B, and RNAi constructs, vectors, intermediate vectors, transformation vectors, primers, and transgenic plants for implementing the strategy of FIG. 1B. But embodiments herein are not limited to the strategy illustrated in FIG. 1B.

In an embodiment, isolated nucleic acids are provided having a sequence as set forth in any one of the nucleic acids listed herein or the complement thereof. In an embodiment, isolated nucleic acids having a sequence that hybridizes to a nucleic acid having the sequence of any nucleic acid listed herein or the complement thereof are provided. In an embodiment, the hybridization conditions are low stringency conditions. In an embodiment, the hybridization conditions are moderate stringency conditions. In an embodiment, the hybridization conditions are high stringency conditions. Examples of hybridization protocols and methods for optimization of hybridization protocols are described in the following books: Molecular Cloning, T. Maniatis, E. F. Fritsch, and J. Sambrook, Cold Spring Harbor Laboratory, 1982; and, Current Protocols in Molecular Biology, F. M. Ausubel, R. Brent, R. E. Kingston, D. D. Moore, J. G. Seidman, J. A. Smith, K. Struhl, Volume 1, John Wiley & Sons, 2000, which are incorporated by reference in their entirety as if fully set forth. By way of example, but not limitation, procedures for hybridization conditions of moderate stringency are as follows: filters containing DNA are pretreated for 2-4 h at 68° C. in a solution containing 6×SSC (Amresco, Inc., Solon, Ohio), 0.5% SDS (Amersco, Inc., Solon, Ohio), 5×Denhardt's solution (Amersco, Inc., Solon, Ohio), and 100 ug/mL denatured, salmon sperm DNA (Invitrogen Life Technologies, Inc., Carlsbad, Calif.). Approximately 0.2 mL of pretreatment solution are used per square centimeter of membrane used. Hybridizations are carried out in the same solution with the following modifications: 0.01 M EDTA (Amersco, Inc., Solon, Ohio), 100 μg/ml salmon sperm DNA, and 5-20×$10^6$ cpm $^{32}$P-labeled or fluorescently labeled probes can be used. Filters are incubated in hybridization mixture for 16-20 h at 68° C. and then washed for 15 minutes at room temperature (within five degrees of 25° C.) in a solution containing 2×SSC and 0.1% SDS, with gentle agitation. The wash solution is replaced with a solution containing 0.1×SSC and 0.5% SDS, and incubated an additional 2 h at 68° C., with gentle agitation. Filters are blotted dry and exposed for development in an imager or by autoradiography. If necessary, filters are washed for a third time and re-exposed for development. By way of example, but not limitation, low stringency refers to hybridizing conditions that employ low temperature for hybridization, for example, temperatures between 37° C. and 60° C. By way of example, but not limitation, high stringency refers to hybridizing conditions as set forth above but with modification to employ high temperatures, for example, hybridization temperatures over 68° C.

In an embodiment, isolated nucleic acids having a sequence that has at least 75, 80, 85, 90, 91, 92, 93, 94, 95, 96, 97, 98, 99 or 100% identity along its length to a contiguous portion of a nucleic acid having any one of the sequences set forth herein or the complements thereof are provided. The contiguous portion may be the entire length of a sequence set forth herein or the complement thereof. Identity can be measured by the Smith-Waterman algorithm (Smith T F, Waterman M S (1981), "Identification of Common Molecular Subsequences," *Journal of Molecular Biology* 147: 195-197, which is incorporated herein by reference as if fully set forth.)

In an embodiment, isolated nucleic acids, polynucleotides, or oligonucleotides are provided having a portion of the sequence as set forth in any one of the nucleic acids listed herein or the complement thereof. These isolated nucleic acids, polynucleotides, or oligonucleotides are not limited to but may have a length in the range from 10 to full length, 10 to 600, 10 to 500, 10 to 400, 10 to 300, 10 to 200, 10 to 100, 10 to 90, 10 to 80, 10 to 70, 10 to 60, 10 to 50, 10 to 40, to 35, 10 to 30, 10 to 25, 10 to 20, 10 to 15, or 20 to 30 nucleotides or 10, 15, 20 or 25 nucleotides. An isolated nucleic acid, polynucleotide, or oligonucleotide having a length within one of the above ranges may have any specific length within the range recited, endpoints inclusive. The recited length of nucleotides may start at any single position within a reference sequence (i.e., any one of the nucleic acids herein) where enough nucleotides follow the single position to accommodate the recited length. In an embodiment, a hybridization probe or primer is 85 to 100%, 90 to 100%, 91 to 100%, 92 to 100%, 93 to 100%, 94 to 100%, 95 to 100%, 96 to 100%, 97 to 100%, 98 to 100%, 99 to 100%, or 100% complementary to a nucleic acid with the same length as the probe or primer and having a sequence chosen from a length of nucleotides corresponding to the probe or primer length within a portion of a sequence as set forth in any one of the nucleic acids listed herein. In an embodiment, a hybridization probe or primer hybridizes along its length to a corresponding length of a nucleic acid having the sequence as set forth in any one of the nucleic acids listed herein. In an embodiment, the hybridization conditions are low stringency. In an embodiment, the hybridization conditions are moderate stringency. In an embodiment, the hybridization conditions are high stringency.

Any of the isolated nucleic acids herein may be provided in a kit. The kit may be used to make an RNAi construct, produce transgenic plants, test a plant for the presence of a gene of interest, test a plant for the presence of an RNAi construct as described herein, or any other method or purpose described herein. A kit may include one or more vector herein or one or more probe or primer herein.

In an embodiment, a transgenic plant is provided. The transgenic plant may be derived from any plant. The transgenic plant may be derived from an energy crop plant, a forage crop plant or a food crop plant. The energy crop plant may be but is not limited to a corn plant, a switchgrass plant, a poplar plant or a miscanthus plant. The forage crop plant may be but is not limited to a sorghum plant. The food crop plant may be but is not limited to a corn plant or a tomato plant. The transgenic plant may include an RNAi construct. The plant may be a rice plant, a switchgrass plant, a sorghum plant, a corn plant or a tomato plant.

The RNAi construct may be designed to implement any RNAi strategy, including but not limited to those illustrated in FIG. 1A-G. An RNAi construct may include a first driver sequence including a first isolated nucleic acid having a sequence corresponding to a portion of a gene in the transgenic plant encoding a target protein involved in mobilization of vegetative starch. The first driver sequence may include a first isolated nucleic acid having at least 75, 80, 85, 90, 91, 92, 93, 94, 95, 96, 97, 98, 99 or 100% identity along the length of the isolated nucleic acid to a portion of a gene in the transgenic plant encoding a target protein involved in mobilization of vegetative starch. The length of the first nucleic acid may be any suitable length to provide an RNAi affect. The RNAi construct may include a second driver sequence including a second isolated nucleic acid. The second isolated nucleic acid may be capable of hybridizing to the first nucleic acid sequence. The second isolated nucleic acid may be capable of hybridizing to the first nucleic acid sequence under in situ conditions in a transgenic plant. The second isolated nucleic acid may be capable of hybridizing to the first nucleic acid sequence under conditions of low stringency. The second isolated nucleic acid may be capable of hybridizing to the first nucleic acid sequence under conditions of moderate stringency. The second isolated nucleic acid may be capable of hybridizing to the first nucleic acid sequence under conditions of high stringency. The second nucleic acid sequence may be an inverted complement of the first nucleic acid sequence. The RNAi construct may also include a spacer operably linked to and between the first driver sequence and the second driver sequence. An operably linked spacer may provide a connection between the first and second isolated nucleic acids such that the RNA sequences transcribed from the first and second isolated nucleic acid can hybridize with one another. An operably linked spacer may be an intron. The intron may splice the first and second driver sequences. The first driver sequence may be upstream from and contiguous with the spacer. The spacer may be upstream from and contiguous with the second driver sequence. The first driver sequence may be upstream from and contiguous with the spacer, and the spacer may be upstream from and contiguous with the second driver sequence. The RNAi construct may also include a promoter operably linked to the first driver sequence, the second driver sequence and the spacer. The operably linked promoter may allow transcription of the first driver sequence, the spacer and the second driver sequence. The operably linked promoter may be any kind of promoter. The operably linked promoter may be an inducible promoter. The operably linked promoter may be a constitutive promoter. Transcription of the first driver sequence, the spacer and the second driver sequence may be referred to as expression of the driver sequences and spacer. Upon expression of the first driver sequence, the spacer and the second driver sequence, the RNA sequence transcribed from the first isolated nucleic acid and the RNA sequence transcribed from the second isolated nucleic acid may be capable of hybridizing with each other. The hybridized RNA transcripts of the first and second driver sequences may be capable of inhibiting expression of the gene. A transgenic plant may include more than one kind of RNAi construct. Each different kind of RNAi construct may be directed to inhibiting a different gene expressing a different target protein.

The RNAi construct may include a first driver sequence. The first driver sequence may include a first nucleic acid sequence that has any suitable sequence to affect RNAi of a gene coding for a target protein. The first driver sequence may include a first isolated nucleic acid having at least 75, 80, 85, 90, 91, 92, 93, 94, 95, 96, 97, 98, 99 or 100% identity to a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO:

45. Identity may be measured along the length of the first isolated nucleic acid. The length of the first isolated nucleic acid may be equal to the length of the reference sequence. The RNAi construct may include a first driver sequence including a first isolated nucleic acid capable of hybridizing to a nucleic acid comprising, consisting essentially of or consisting of a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45 or the complement thereof under conditions of low stringency. The RNAi construct may include a first driver sequence including a first isolated nucleic acid capable of hybridizing to nucleic acid comprising, consisting essentially of or consisting of a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45 or the complement thereof under conditions moderate stringency. The RNAi construct may include a first driver sequence including a first isolated nucleic acid capable of hybridizing to a nucleic comprising, consisting essentially of or consisting of a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45 or the complement thereof under conditions of high stringency. The RNAi construct may include a second driver sequence having a second isolated nucleic acid capable of hybridizing with the first nucleic acid sequence under in situ conditions in the transgenic plant. The RNAi construct may include a second driver sequence having a second isolated nucleic acid capable of hybridizing with the first nucleic acid sequence under conditions of low stringency. The RNAi construct may include a second driver sequence having a second isolated nucleic acid capable of hybridizing with the first nucleic acid sequence under conditions of moderate stringency. The RNAi construct may include a second driver sequence having a second isolated nucleic acid capable of hybridizing with the first nucleic acid sequence under conditions of high stringency. The RNAi construct may include a second driver sequence having at least 75, 80, 85, 90, 91, 92, 93, 94, 95, 96, 97, 98, 99 or 100% identity to the complement of a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45. Identity may be measured along the length of the reference sequence complement. The length of the second nucleic acid may be equal to the length of the reference sequence complement.

The spacer may be any sequence. The spacer may be an intron. The intron may be any intron. The intron may be the OsUbiintron. The sequence of the OsUbiintron may be found with reference to FIG. 2, which illustrates pAL409 with the OsUbiintron between positions 4519-566. The sequence of pAL409 is given below and in SEQ ID NO: 13. Nucleotide numbering in SEQ ID NO: 13 may vary from that labeled in FIG. 2 but comparison of landmark sequences (e.g., restriction sites) between FIG. 2 and SEQ ID NO: 13 allows identification of any specific sequence of a pAL409 feature. The intron may have a sequence that has at least 75, 80, 85, 90, 91, 92, 93, 94, 95, 96, 97, 98, 99 or 100% identity to the OsUbiintron. The intron may have a sequence that hybridizes to the OsUbiintron or a complement thereof under conditions of low stringency. The intron may have a sequence that hybridizes to the OsUbiintron or a complement thereof under conditions of moderate stringency. The intron may have a sequence that hybridizes to the OsUbiintron or a complement thereof under conditions of high stringency.

The promoter may be any promoter. The promoter may be an inducible promoter. Examples of inducible promoters include but are not limited to those that are an alcohol inducible promoter, a tetracycline inducible promoter, a steroid inducible promoter, or a hormone inducible promoter. The promoter may be a constitutive promoter. The promoter may be operably linked to the first driver sequence, the second driver sequence and the spacer. The promoter may be the P-OsUbi promoter. The sequence of the P-OsUbi promoter may be found with reference to FIG. 2, which illustrates pAL409 with the P-OsUbi promoter between positions 3574-4507. The sequence of pAL409 is given below and in SEQ ID NO: 13. Nucleotide numbering in SEQ ID NO: 13 may vary from that labeled in FIG. 2 but comparison of landmark sequences (e.g., restriction sites) between FIG. 2 and SEQ ID NO: 13 allows identification of any specific sequence of a pAL409 feature. The promoter may include a sequence with at least 75, 80, 85, 90, 91, 92, 93, 94, 95, 96, 97, 98, 99 or 100% identity to the P-OsUbi promoter. The promoter may include a sequence that hybridizes to the P-OsUbi promoter or the complement thereof under conditions of low stringency. The promoter may include a sequence that hybridizes to the P-OsUbi promoter or the complement thereof under conditions of moderate stringency. The promoter may include a sequence that hybridizes to the P-OsUbi promoter or the complement thereof under conditions of high stringency.

The first driver sequence may be an isolated nucleic acid having any suitable sequence to affect RNAi of a gene coding for a target protein. The first driver sequence may be an isolated nucleic acid having a sequence with at least 75, 80, 85, 90, 91, 92, 93, 94, 95, 96, 97, 98, 99 or 100% identity to a sequence selected from the group consisting of SEQ ID NO: 7, SEQ ID NO: 8, SEQ ID NO: 11, SEQ ID NO: 12, SEQ ID NO: 21, SEQ ID NO: 22, and SEQ ID NO: 37. The first driver sequence may be an isolated nucleic acid having a sequence that is capable of hybridizing with a nucleic acid comprising, consisting essentially of or consisting of a sequence selected from the group consisting of SEQ ID NO: 7, SEQ ID NO: 8, SEQ ID NO: 11, SEQ ID NO: 12, SEQ ID NO: 21, SEQ ID NO: 22, and SEQ ID NO: 37 or the complement thereof under conditions of low stringency. The first driver sequence may be an isolated nucleic acid having a sequence that is capable of hybridizing with a nucleic acid comprising, consisting essentially of or consisting of a sequence selected from the group consisting of SEQ ID NO: 7, SEQ ID NO: 8, SEQ ID NO: 11, SEQ ID NO: 12, SEQ ID NO: 21, SEQ ID NO: 22, and SEQ ID NO: 37 or the complement thereof under conditions of moderate stringency. The first driver sequence may be an isolated nucleic acid having a sequence that is capable of hybridizing with a nucleic acid comprising, consisting essentially of or consisting of a sequence selected from the group consisting of SEQ ID NO: 7, SEQ ID NO: 8, SEQ ID NO: 11, SEQ ID NO: 12, SEQ ID NO: 21, SEQ ID NO: 22, and SEQ ID NO: 37 or the complement thereof under conditions of high stringency. The second driver sequence may be an isolated nucleic acid having any suitable sequence to affect RNAi of a gene coding for a target protein. The second driver sequence may be an isolated nucleic acid capable of hybridizing to the first driver sequence. The second driver sequence may be an isolated nucleic acid capable of hybridizing to the first driver sequence under in situ conditions in a transgenic plant. The second driver sequence may be an isolated nucleic acid capable of hybridizing to the first driver sequence or the complement thereof under conditions of low stringency. The second driver sequence may be an isolated nucleic acid capable of hybridizing to the first driver sequence or the complement thereof under conditions of moderate stringency. The second driver sequence may be an isolated nucleic acid capable of hybridizing to the first driver sequence or the complement thereof under conditions of high stringency.

The target protein may be any protein involved with regulation of Green Starch. For example, the target protein may be one of Glucan Water Dikinase, Phosphoglucan Water Dikinase, Dual Specificity Protein Phosphatase, β-amylase, isoamylase, limit dextrinase, disproportionating enzyme, or a debranching enzyme. The gene encoding the target protein may have a sequence with at least 75, 80, 85, 90, 91, 92, 93, 94, 95, 96, 97, 98, 99 or 100% identity to a reference sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 10, SEQ ID NO: 19, SEQ ID NO: 20, SEQ ID NO: 34, SEQ ID NO: 35, SEQ ID NO: 36, and SEQ ID NO: 43. The gene encoding the target protein may have a sequence that hybridizes to a reference sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 10, SEQ ID NO: 19, SEQ ID NO: 20, SEQ ID NO: 34, SEQ ID NO: 35, SEQ ID NO: 36, and SEQ ID NO: 43 or the complement thereof under conditions of low stringency. The gene encoding the target protein may have a sequence that hybridizes to a reference sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 10, SEQ ID NO: 19, SEQ ID NO: 20, SEQ ID NO: 34, SEQ ID NO: 35, SEQ ID NO: 36, and SEQ ID NO: 43 or the complement thereof under conditions of moderate stringency. The gene encoding the target protein may have a sequence that hybridizes to a reference sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 10, SEQ ID NO: 19, SEQ ID NO: 20, SEQ ID NO: 34, SEQ ID NO: 35, SEQ ID NO: 36, and SEQ ID NO: 43 or the complement thereof under conditions of high stringency.

A transgenic plant may be constructed by any method of transformation. For example biolistic transformation may be utilized. The transformation may be done with any suitable vector including or consisting of any one or more RNAi construct herein. *Agrobacterium* mediated transformation may be utilized. *Agrobacterium* mediated transformation may utilize any suitable transformation vector harboring any one or more RNAi construct herein. *Agrobacterium* mediated transformation may be done with a vector having a sequence with at least 75, 80, 85, 90, 91, 92, 93, 94, 95, 96, 97, 98, 99 or 100% identity to a sequence selected from the group consisting of SEQ ID NO: 15, SEQ ID NO: 16, SEQ ID NO: 17, SEQ ID NO: 18, SEQ ID NO: 23 and SEQ ID NO: 47.

Any transgenic plant herein may be provided in a method of agricultural processing or animal feed applications. The transgenic plant may include any one or more RNAi construct described herein. A step of providing the transgenic plant may include obtaining it from another party that produced it. A step of providing may include making the transgenic plant. A method of agricultural processing or animal feed applications may include processing the transgenic plant. Driver sequences in an RNAi construct in the transgenic plant may be expressed at any point in the method. Driver sequences in an RNAi construct in the transgenic plant may be expressed prior to the step of processing the plant. Driver sequences in an RNAi construct in the transgenic plant may be expressed during the step of processing the plant. The expression may be induced. Agricultural processing may include utilizing feedstock engineered with elevated levels of starch. The feedstock may include any transgenic plant herein alone or in combination with other components. The other component may include other plant material. Agricultural processing is the manipulation or conversion of any agricultural feedstock for a particular product or use. Agricultural processing would include but is not limited to at least one of the operations of harvesting, baling, grinding, milling, chopping, size reduction, crushing, pellitizing, extracting a component from the feedstock, purifying a component or portion of the feedstock, extracting or purifying starch, hydrolyzing polysaccharides into oligosaccharides or monosaccharides, ensiling, fermentation, chemical conversion, or chemical catalysis of the feedstock.

An embodiment includes a method of altering vegetative starch levels in a plant. The method may include expressing an isolated nucleic acid in the plant. Expression of the isolated nucleic acid in the plant may alter the activity of at least one enzyme related to starch metabolism in the plant. The plant may be any transgenic plant herein. The transgenic plant may include any one or more RNAi construct described herein.

An embodiment provides an isolated nucleic acid comprising, consisting essentially of or consisting of a sequence having at least 75, 80, 85, 90, 91, 92, 93, 94, 95, 96, 97, 98, 99 or 100% identity to any one of SEQ ID NOS: 7-8, 11-18, 21-23, 32-33, 37, 38 and 39-47. An embodiment provides an isolated nucleic acid comprising, consisting essentially of or consisting of a sequence that hybridizes to a nucleic acid comprising, consisting essentially of or consisting of reference sequence selected from the group consisting of SEQ ID NOS: 7-8, 11-18, 21-23, 32-33, 37, 38 and 39-47 or the complement thereof under conditions of low stringency. An embodiment provides an isolated nucleic acid comprising, consisting essentially of or consisting of a sequence that hybridizes to a nucleic acid comprising, consisting essentially of or consisting of a reference sequence selected from the group consisting of SEQ ID NOS: 7-8, 11-18, 21-23, 32-33, 37, 38 and 39-47 or the complement thereof under conditions of moderate stringency. An embodiment provides an isolated nucleic acid comprising, consisting essentially of or consisting of a sequence that hybridizes to a nucleic acid comprising, consisting essentially of or consisting of a reference sequence selected from the group consisting of SEQ ID NOS: 7-8, 11-18, 21-23, 32-33, 37, 38 and 39-47 or the complement thereof under conditions of high stringency.

An embodiment includes a vector having any RNAi construct herein. The vector may be an intermediate vector. The vector may be a transformation vector. The RNAi construct in the vector may have a first driver sequence including a first isolated nucleic acid having at least 75, 80, 85, 90, 91, 92, 93, 94, 95, 96, 97, 98, 99 or 100% identity along the length of the first isolated nucleic acid to a portion of a gene in a plant encoding a target protein involved in mobilization of vegetative starch. The RNAi construct in the vector may also include a second driver sequence including a second isolated nucleic acid capable of hybridizing to the first isolated nucleic acid. The second isolated nucleic acid may be capable of hybridizing to the first isolated nucleic acid under in situ conditions in a plant in which the vector may be transformed. The second isolated nucleic acid may be capable of hybridizing to the first isolated nucleic acid under conditions of low stringency. The second isolated nucleic acid may be capable of hybridizing to the first isolated nucleic acid under conditions of moderate stringency. The second isolated nucleic acid may be capable of hybridizing to the first isolated nucleic acid under conditions of high stringency. The RNAi construct in the vector may also include a spacer operably linked to the first driver sequence and the second driver sequence. The spacer may be between the first driver sequence and the second driver sequence. The RNAi construct in the vector may also include a promoter operably linked to the first driver sequence, the second driver sequence and the spacer.

A vector herein may be configured for expression in a host having the gene targeted by the RNAi construct. Upon expression, an RNA sequence transcribed from the first isolated nucleic acid and an RNA sequence transcribed from the second isolated nucleic acid may be capable of hybridizing with each other and causing inhibition of expression of the gene in the host.

A vector herein may include a first driver sequence with a first isolated nucleic acid having at least 75, 80, 85, 90, 91, 92, 93, 94, 95, 96, 97, 98, 99 or 100% identity to a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45. A vector herein may include a first driver sequence with a first isolated nucleic acid capable of hybridizing to a nucleic acid comprising, consisting essentially of or consisting of a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45 or a complement thereof under conditions of low stringency. A vector herein may include a first driver sequence with a first isolated nucleic acid capable of hybridizing to a nucleic acid comprising, consisting essentially of or consisting of a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45 or a complement thereof under conditions of moderate stringency. A vector herein may include a first driver sequence with a first isolated nucleic acid capable of hybridizing to a nucleic acid comprising, consisting essentially of or consisting of a reference sequence selected from the group consisting of SEQ ID NO: 7, SEQ ID NO: 8, SEQ ID NO: 11, SEQ ID NO: 12, SEQ ID NO: 37, SEQ ID NO: 44, and SEQ ID NO: 45 or a complement thereof under conditions of high stringency. As set forth above, the second isolated nucleic acid in any vector described in this paragraph may be configured to be capable of hybridizing to the first isolated nucleic acid. Hybridization of the first and second isolated nucleic acids may be under in situ conditions found in a plant where the vector may be transformed. Hybridization of the first and second isolated nucleic acids may be under conditions of low stringency. Hybridization of the first and second nucleic acids may be under conditions of moderate stringency. The hybridization of the first and second nucleic acids may be under conditions of high stringency. The second isolated nucleic acid may be an inverted complement of the first isolated nucleic acid.

The spacer in a vector herein may be any sequence. The spacer may be an intron. The intron may be any intron. The intron may be the OsUbiintron. The sequence of the OsUbiintron may be found with reference to FIG. 2, which illustrates pAL409 with the OsUbiintron between positions 4519-566. The sequence of pAL409 is given below and in SEQ ID NO: 13. Nucleotide numbering in SEQ ID NO: 13 may vary from that labeled in FIG. 2 but comparison of landmark sequences (e.g., restriction sites) between FIG. 2 and SEQ ID NO: 13 allows identification of any specific sequence of a pAL409 feature. The intron may have a sequence that has at least 75, 80, 85, 90, 91, 92, 93, 94, 95, 96, 97, 98, 99 or 100% identity to the OsUbiintron. The intron may have a sequence that hybridizes to the OsUbiintron or a complement thereof under conditions of low stringency. The intron may have a sequence that hybridizes to the OsUbiintron or a complement thereof under conditions of moderate stringency. The intron may have a sequence that hybridizes to the OsUbiintron or a complement thereof under conditions of high stringency.

The promoter in a vector may be any promoter. The promoter may be an inducible promoter. The promoter may be a constitutive promoter. The promoter may be operably linked to the first driver sequence, the second driver sequence and the spacer. The promoter may be the P-OsUbi promoter. The sequence of the P-OsUbi promoter may be found with reference to FIG. 2, which illustrates pAL409 with the P-OsUbi promoter between positions 3574-4507. The sequence of pAL409 is given below and in SEQ ID NO: 13. Nucleotide numbering in SEQ ID NO: 13 may vary from that labeled in FIG. 2 but comparison of landmark sequences (e.g., restriction sites) between FIG. 2 and SEQ ID NO: 13 allows identification of any specific sequence of a pAL409 feature. The promoter may include a sequence with at least 75, 80, 85, 90, 91, 92, 93, 94, 95, 96, 97, 98, 99 or 100% identity to the P-OsUbi promoter. The promoter may include a sequence that hybridizes to the P-OsUbi promoter or the complement thereof under conditions of low stringency. The promoter may include a sequence that hybridizes to the P-OsUbi promoter or the complement thereof under conditions of moderate stringency. The promoter may include a sequence that hybridizes to the P-OsUbi promoter or the complement thereof under conditions of high stringency.

The first driver sequence in a vector herein may be an isolated nucleic acid having any suitable sequence to affect RNAi of a gene coding for a target protein. The first driver sequence may be an isolated nucleic acid having a sequence with at least 75, 80, 85, 90, 91, 92, 93, 94, 95, 96, 97, 98, 99 or 100% identity to a sequence selected from the group consisting of SEQ ID NO: 7, SEQ ID NO: 8, SEQ ID NO: 11, SEQ ID NO: 12, SEQ ID NO: 21, SEQ ID NO: 22, and SEQ ID NO: 37. The first driver sequence may be an isolated nucleic acid having a sequence that is capable of hybridizing with a nucleic acid comprising, consisting essentially of or consisting of a sequence selected from the group consisting of SEQ ID NO: 7, SEQ ID NO: 8, SEQ ID NO: 11, SEQ ID NO: 12, SEQ ID NO: 21, SEQ ID NO: 22, and SEQ ID NO: 37 or the complement thereof under conditions of low stringency. The first driver sequence may be an isolated nucleic acid having a sequence that is capable of hybridizing with a nucleic acid comprising, consisting essentially of or consisting of a sequence selected from the group consisting of SEQ ID NO: 7, SEQ ID NO: 8, SEQ ID NO: 11, SEQ ID NO: 12, SEQ ID NO: 21, SEQ ID NO: 22, and SEQ ID NO: 37 or the complement thereof under conditions of moderate stringency. The first driver sequence may be an isolated nucleic acid having a sequence that is capable of hybridizing with a nucleic acid comprising, consisting essentially of or consisting of a sequence selected from the group consisting of SEQ ID NO: 7, SEQ ID NO: 8, SEQ ID NO: 11, SEQ ID NO: 12, SEQ ID NO: 21, SEQ ID NO: 22, and SEQ ID NO: 37 or the complement thereof under conditions of high stringency. The second driver sequence may be an isolated nucleic acid having any suitable sequence to affect RNAi of a gene coding for a target protein. The second driver sequence may be an isolated nucleic acid capable of hybridizing to the first driver sequence. The second driver sequence may be an isolated nucleic acid capable of hybridizing to the first driver sequence under in situ conditions in a transgenic plant. The second driver sequence may be an isolated nucleic acid capable of hybridizing to the first driver sequence or the complement thereof under conditions of low stringency. The second driver sequence may be an isolated nucleic acid capable of hybridizing to the first driver sequence or the complement thereof under conditions of moderate stringency. The second driver sequence may be an isolated nucleic acid capable of hybridizing to the first driver sequence or the complement thereof under conditions of high stringency.

The target protein targeted by an RNAi construct in a vector herein may be any protein involved with regulation of Green Starch. For example, the target protein may be one of Glucan Water Dikinase, Phosphoglucan Water Dikinase, Dual Specificity Protein Phosphatase, O-amylase, isoamylase, limit dextrinase, disproportionating enzyme, or a debranching enzyme. The gene encoding the target protein may have a sequence with at least 75, 80, 85, 90, 91, 92, 93, 94, 95, 96, 97, 98, 99 or 100% identity to a nucleic acid comprising, consisting essentially of or consisting of reference sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 10, SEQ ID NO: 19, SEQ ID NO: 20, SEQ ID NO: 34, SEQ ID NO: 35, SEQ ID NO: 36, and SEQ ID NO: 43. The gene encoding the target protein may have a sequence that hybridizes to a nucleic acid comprising, consisting essentially of or consisting of a reference sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 10, SEQ ID NO: 19, SEQ ID NO: 20, SEQ ID NO: 34, SEQ ID NO: 35, SEQ ID NO: 36, and SEQ ID NO: 43 or the complement thereof under conditions of low stringency. The gene encoding the target protein may have a sequence that hybridizes to a nucleic acid comprising, consisting essentially of or consisting of a reference sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 10, SEQ ID NO: 19, SEQ ID NO: 20, SEQ ID NO: 34, SEQ ID NO: 35, SEQ ID NO: 36, and SEQ ID NO: 43 or the complement thereof under conditions of moderate stringency. The gene encoding the target protein may have a sequence that hybridizes to a nucleic acid comprising, consisting essentially of or consisting of a reference sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 10, SEQ ID NO: 19, SEQ ID NO: 20, SEQ ID NO: 34, SEQ ID NO: 35, SEQ ID NO: 36, and SEQ ID NO: 43 or the complement thereof under conditions of high stringency.

A vector herein may include a first driver sequence upstream of and contiguous with the spacer. A vector herein may include a spacer upstream of and contiguous with the second driver sequence. A vector herein may include a first driver sequence upstream of and contiguous with the spacer, and the spacer upstream of and contiguous with the second driver sequence.

A vector herein may have a sequence comprising, consisting essentially of or consisting of a sequence having at least 75, 80, 85, 90, 91, 92, 93, 94, 95, 96, 97, 98, 99 or 100% identity to a reference sequence selected from the group consisting of SEQ ID NO: 15, SEQ ID NO: 16, SEQ ID NO: 17, SEQ ID NO: 18, SEQ ID NO: 23 and SEQ ID NO: 47.

A vector herein may have a sequence comprising, consisting essentially of or consisting of a sequence having at least 75, 80, 85, 90, 91, 92, 93, 94, 95, 96, 97, 98, 99 or 100% identity to a reference sequence selected from the group consisting of SEQ ID NO: 13 and SEQ ID NO: 14.

An embodiment provides a method of making a transgenic plant. The method includes transforming a plant with any one or more vector herein. The plant may be any kind of plant. The plant may be an energy crop plant, a food crop plant or a forage crop plant. The plant may be a rice plant, a switchgrass plant, a sorghum plant, a corn plant or a tomato plant.

Additional embodiments include those formed by reading any dependent claim in the claim listing below as being dependent on any one or more preceding claim up to and including its base independent claim.

Additional embodiments herein include those that may be formed by supplementing any one embodiment with one or more element from any one or more other embodiment herein.

EXAMPLES

The following non-limiting examples are provided to illustrate particular embodiments. The embodiments throughout may be supplemented with one or more detail from any one or more example below.

Example 1

T-DNA insertion libraries from different organisms may be researched to locate genes in those organisms related to starch regulation. Based on the discovery of such genes, a search may be conducted to find similar genes in a plant of interest. The genes of interest may be used in constructs herein to affect alteration in starch regulation.

A number of other methods have been developed to generate or identify null alleles among genes. Among these are TILLING (Till B J, Cooper J, Tai T H, Colowit P, Greene E A, Henikoff S, Comai L Discovery of chemically induced mutations in rice by TILLING (2007) BMC Plant Biol. 7:19), and gene tagging with Tos17 retrotranspsons or engineered maize (*Zea mays*) Ac and Ds/dSpm transposons (Krishnan A, Guiderdoni E, An G, Hsing Y I, Han C D, Lee M C, Yu S M, Upadhyaya N, Ramachandran S, Zhang Q, Sundaresan V, Hirochika H, Leung H, Pereira A. 2009. Mutant resources in rice for functional genomics of the grasses. Plant Physiol. 149:165-70 and references therein), which are incorporated herein by reference as if fully set forth. These methods may be used to generate or identify null alleles among genes related to starch regulation.

Example 2

Figure 2:
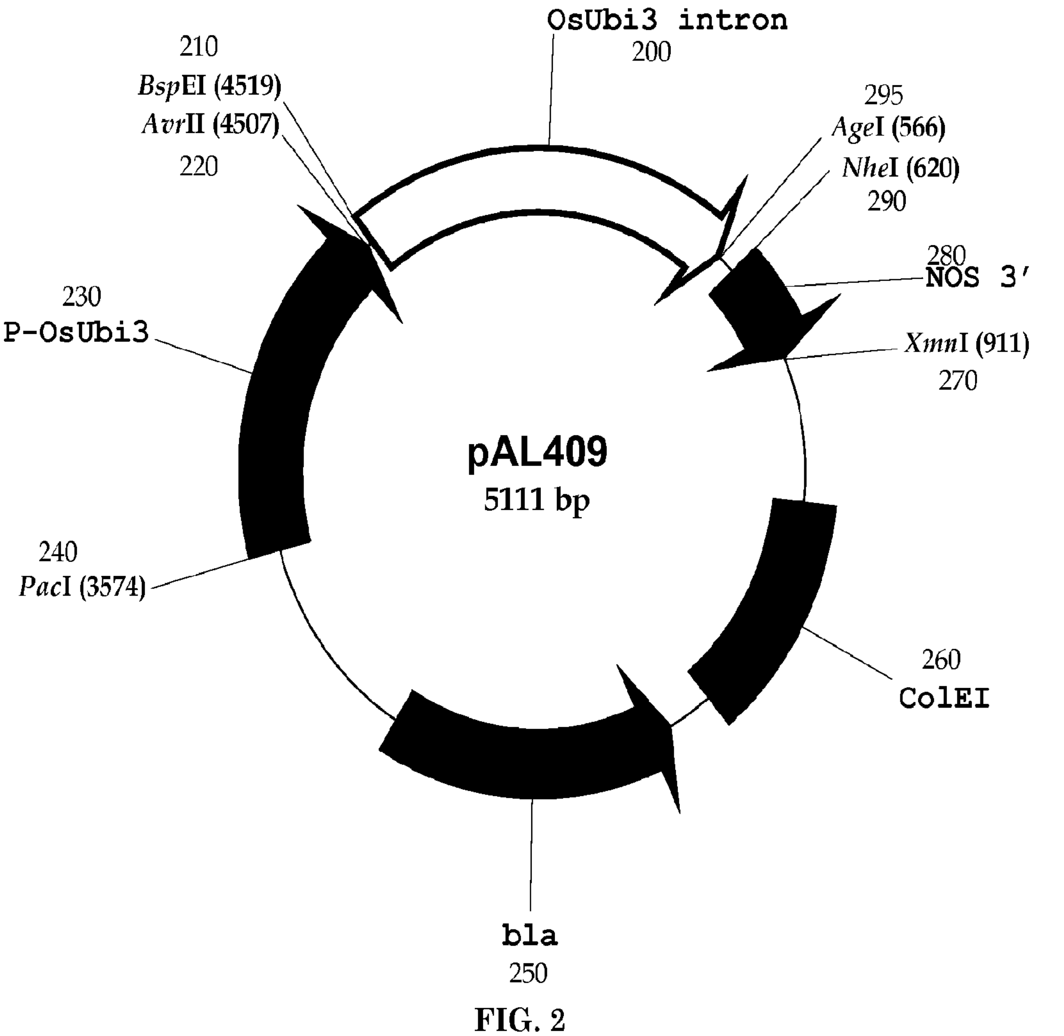
FIG. 2 illustrates an intermediate RNAi vector, pAL409.

An example of an intermediate RNAi vector is pAL409, which is illustrated in FIG. 2. As shown in FIG. 2, inverted copies of segments from a transcribed region from a gene to be targeted can be introduced into pAL409 at the AvrII site 220 (position 4507) and the BspEI site 210 (position 4519), and again at the AgeI site 295 (position 566) and the NheI site 290 (position 620). When transcribed from the rice ubiquitin promoter 230 (P-OsUbi3), the inverted copies of the segments (the driver sequences) allow the resulting RNA to form a hairpin in which the OsUbi3 intron 200 serves as a spacer between the repeated elements. A polyadenylation signal 280 (NOS 3') serves as the transcriptional terminator. The entire expression cassette (from the promoter through the terminator) can be excised from this plasmid as a PacI-XmaI fragment by digesting at the PacI site 240 (position 3574) and the XmaI site 270 (position 911). pAL409 also includes a ColEI, *E. coli* origin of replication 260; and a bla 250 ampicillin resistance marker. The sequence of pAL409 is provided below, but nucleotide numbering and orientation differ from that depicted in FIG. 2. The skilled artisan will be able to align the sequence below with the vector map of FIG. 2 given the landmarks of the vector. An intermediate RNAi vector such as pAL409 can be used to introduce tandem, inverted copies of virtually any driver sequences.

>pAL409 sequence

[SEQ ID NO: 13]

TCGCGCGTTTCGGTGATGACGGTGAAAACCTCTGACACATGCAGCTCCC

GGAGACGGTCACAGCTTGTCTGTAAGCGGATGCCGGGAGCAGACAAGCC

CGTCAGGGCGCGTCAGCGGGTGTTGGCGGGTGTCGGGGCTGGCTTAACT

ATGCGGCATCAGAGCAGATTGTACTGAGAGTGCACCATATGCGGTGTGA

AATACCGCACAGATGCGTAAGGAGAAAATACCGCATCAGGCGCCATTCG

CCATTCAGGCTGCGCAACTGTTGGGAAGGGCGATCGGTGCGGGCCTCTT

CGCTATTACGCCAGCTGGCGAAAGGGGGATGTGCTGCAAGGCGATTAAG

TTGGGTAACGCCAGGGTTTTCCCAGTCACGACGTTGTAAAACGACGGCC

AGTGAATTCGGGCGGTTAATTAACTAATCGACTCTAGTAACGGCCGCCA

GTGTGCTGGAATTAATTCGGCTTGTCGACCACCCAACCCCATATCGACA

GAGGATGTGAAGAACAGGTAAATCACGCAGAAGAACCCATCTCTGATAG

CAGCTATCGATTAGAACAACGAATCCATATTGGGTCCGTGGGAAATACT

TACTGCACAGGAAGGGGGCGATCTGACGAGGCCCCGCCACCGGCCTCGA

CCCGAGGCCGAGGCCGACGAAGCGCCGGCGAGTACGGCGCCGCGGCGGC

CTCTGCCCGTGCCCTCTGCGCGTGGGAGGGAGAGGCCGCGGTGGTGGGG

GCGCGCGCGCGCGCGCGCAGCTGGTGCGGCGGCGCGGGGGTCAGCCG

CCGAGCCGGCGGCGACGGAGGAGCAGGGCGGCGTGGACGCGAACTTCCG

ATCGGTTGGTCAGAGTGCGCGAGTTGGGCTTAGCCAATTAGGTCTCAAC

AATCTATTGGGCCGTAAAATTCATGGGCCCTGGTTTGTCTAGGCCCAAT

ATCCCGTTCATTTCAGCCCACAAATATTTCCCCAGAGGATTATTAAGGC

CCACACGCAGCTTATAGCAGATCAAGTACGATGTTTCCTGATCGTTGGA

TCGGAAACGTACGGTCTTGATCAGGCATGCCGACTTCGTCAAAGAGAGG

CGGCATGACCTGACGCGGAGTTGGTTCCGGGCACCGTCTGGATGGTCGT

ACCGGGACCGGACACGTGTCGCGCCTCCAACTACATGGACACGTGTGGT

GCTGCCATTGGGCCGTACGCGTGGCGGTGACCGCACCGGATGCTGCCTC

GCACCGCCTTGCCCACGCTTTATATAGAGAGGTTTTCTCTCCATTAATC

GCATAGCGAGTCGAATCGACCGAAGGGGAGGGGGAGCGAGAGCTTTGCG

TTCTCTAATCGCCTCGTCAAGCCTAGGTGTGTGTCCGGAGTCAAGGTAA

CTAATCAATCACCTCGTCCTAATCCTCGAATCTCTCGTGGTGCCCGTCT

AATCTCGCGATTTTGATGCTCGTGGTGGAAAGCGTAGGAGGATCCCGTG

-continued

CGAGTTAGTCTCAATCTCTCAGGGTTTCGTGCGATTTTAGGGTGATCCA

CCTCTTAATCGAGTTACGGTTTCGTGCGATTTTAGGGTAATCCTCTTAA

TCTCTCATTGATTTAGGGTTTCGTGAGAATCGAGGTAGGGATCTGTGTT

ATTTATATCGATCTAATAGATGGATTGGTTTTGAGATTGTTCTGTCAGA

TGGGGATTGTTTCGATATATTACCCTAATGATGTGTCAGATGGGGATTG

TTTCGATATATTACCCTAATGATGTGTCAGATGGGGATTGTTTCGATAT

ATTACCCTAATGATGGATAATAAGAGTAGTTCACAGTTATGTTTTGATC

CTGCCACATAGTTTGAGTTTTGTGATCAGATTTAGTTTTACTTATTTGT

GCTTAGTTCGGATGGGATTGTTCTGATATTGTTCCAATAGATGAATAGC

TCGTTAGGTTAAAATCTTTAGGTTGAGTTAGGCGACACATAGTTTATTT

CCTCTGGATTTGGATTGGAATTGTGTTCTTAGTTTTTTTCCCCTGGATT

TGGATTGGAATTGTGTGGAGCTGGGTTAGAGAATTACATCTGTATCGTG

TACACCTACTTGAACTGTAGAGCTTGGGTTCTAAGGTCAATTTAATCTG

TATTGTATCTGGCTCTTTGCCTAGTTGAACTGTAGTGCTGATGTTGTAC

TGTGTTTTTTTACCCGTTTTATTTGCTTTACTCGTGCAAATCAAATCTG

TCAGATGCTAGAACTAGGTGGCTTTATTCTGTGTTCTTACATAGATCTG

TTGTCCTGTAGTTACTTATGTCAGTTTTGTTATTATCTGAAGATATTTT

TGGTTGTTGCTTGTTGATGTGGTGTGAGCTGTGAGCAGCGCTCTTATGA

TTAATGATGCTGTCCAATTGTAGTGTAGTATGATGTGATTGATATGTTC

ATCTATTTTGAGCTGACAGTACCGATATCGTAGGATCTGGTGCCAACTT

ATTCTCCAGCTGCTTTTTTTTACCTATGTTAATTCCAATCCTTTCTTGC

CTCTTCCAGGGATCCACCGGTCCGATCGAGCTTACTGAAAAAATTAACA

TCTCTTGCTAAGCTGGGAGCGCTAGCTCCCCGAATTTCCCCGATCGTTC

AAACATTTGGCAATAAAGTTTCTTAAGATTGAATCCTGTTGCCGGTCTT

GCGATGATTATCATATAATTTCTGTTGAATTACGTTAAGCATGTAATAA

TTAACATGTAATGCATGACGTTATTTATGAGATGGGTTTTTATGATTAG

AGTCCCGCAATTATACATTTAATACGCGATAGAAAACAAAATATAGCGC

GCAAACTAGGATAAATTATCGCGCGCGGTGTCATCTATGTTACTAGATC

GGGAATTGGCGAGCTCGCCCGGGCGGGCGAAGCTTGGCGTAATCATGGT

CATAGCTGTTTCCTGTGTGAAATTGTTATCCGCTCACAATTCCACACAA

CATACGAGCCGGAAGCATAAAGTGTAAAGCCTGGGGTGCCTAATGAGTG

AGCTAACTCACATTAATTGCGTTGCGCTCACTGCCCGCTTTCCAGTCGG

GAAACCTGTCGTGCCAGCTGCATTAATGAATCGGCCAACGCGCGGGGAG

AGGCGGTTTGCGTATTGGGCGCTCTTCCGCTTCCTCGCTCACTGACTCG

CTGCGCTCGGTCGTTCGGCTGCGGCGAGCGGTATCAGCTCACTCAAAGG

CGGTAATACGGTTATCCACAGAATCAGGGGATAACGCAGGAAAGAACAT

GTGAGCAAAAGGCCAGCAAAAGGCCAGGAACCGTAAAAAGGCCGCGTTG

CTGGCGTTTTTCCATAGGCTCCGCCCCCCTGACGAGCATCACAAAAATC

GACGCTCAAGTCAGAGGTGGCGAAACCCGACAGGACTATAAAGATACCA

GGCGTTTCCCCCTGGAAGCTCCCTCGTGCGCTCTCCTGTTCCGACCCTG

CCGCTTACCGGATACCTGTCCGCCTTTCTCCCTTCGGGAAGCGTGGCGC

-continued

```
TTTCTCATAGCTCACGCTGTAGGTATCTCAGTTCGGTGTAGGTCGTTCG

CTCCAAGCTGGGCTGTGTGCACGAACCCCCCGTTCAGCCCGACCGCTGC

GCCTTATCCGGTAACTATCGTCTTGAGTCCAACCCGGTAAGACACGACT

TATCGCCACTGGCAGCAGCCACTGGTAACAGGATTAGCAGAGCGAGGTA

TGTAGGCGGTGCTACAGAGTTCTTGAAGTGGTGGCCTAACTACGGCTAC

ACTAGAAGGACAGTATTTGGTATCTGCGCTCTGCTGAAGCCAGTTACCT

TCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAA

GGATCTCAAGAAGATCCTTTGATCTTTTCTACGGGGTCTGACGCTCAGT

GGAACGAAAACTCACGTTAAGGGATTTTGGTCATGAGATTATCAAAAAG

GATCTTCACCTAGATCCTTTTAAATTAAAAATGAAGTTTTAAATCAATC

TAAAGTATATATGAGTAAACTTGGTCTGACAGTTACCAATGCTTAATCA

GTGAGGCACCTATCTCAGCGATCTGTCTATTTCGTTCATCCATAGTTGC

CTGACTCCCCGTCGTGTAGATAACTACGATACGGGAGGGCTTACCATCT

GGCCCCAGTGCTGCAATGATACCGCGAGACCCACGCTCACCGGCTCCAG

ATTTATCAGCAATAAACCAGCCAGCCGGAAGGGCCGAGCGCAGAAGTGG

TCCTGCAACTTTATCCGCCTCCATCCAGTCTATTAATTGTTGCCGGGAA

GCTAGAGTAAGTAGTTCGCCAGTTAATAGTTTGCGCAACGTTGTTGCCA

TTGCTACAGGCATCGTGGTGTCACGCTCGTCGTTTGGTATGGCTTCATT

CAGCTCCGGTTCCCAACGATCAAGGCGAGTTACATGATCCCCCATGTTG

TGCAAAAAAGCGGTTAGCTCCTTCGGTCCTCCGATCGTTGTCAGAAGTA

AGTTGGCCGCAGTGTTATCACTCATGGTTATGGCAGCACTGCATAATTC

TCTTACTGTCATGCCATCCGTAAGATGCTTTTCTGTGACTGGTGAGTAC

TCAACCAAGTCATTCTGAGAATAGTGTATGCGGCGACCGAGTTGCTCTT

GCCCGGCGTCAATACGGGATAATACCGCGCCACATAGCAGAACTTTAAA

AGTGCTCATCATTGGAAAACGTTCTTCGGGGCGAAAACTCTCAAGGATC

TTACCGCTGTTGAGATCCAGTTCGATGTAACCCACTCGTGCACCCAACT

GATCTTCAGCATCTTTTACTTTCACCAGCGTTTCTGGGTGAGCAAAAAC

AGGAAGGCAAAATGCCGCAAAAAAGGGAATAAGGGCGACACGGAAATGT

TGAATACTCATACTCTTCCTTTTTCAATATTATTGAAGCATTTATCAGG

GTTATTGTCTCATGAGCGGATACATATTTGAATGTATTTAGAAAAATAA

ACAAATAGGGGTTCCGCGCACATTTCCCCGAAAAGTGCCACCTGACGTC

TAAGAAACCATTATTATCATGACATTAACCTATAAAAATAGGCGTATCA

CGAGGCCCTTTCGTC
```

Embodiments herein provide intermediate RNAi vectors that replicate to high copy in *E. coli*, have low complexity, and several convenient restriction sites. pAL409 has these characteristics. Vectors with such characteristics would be useful for assembling RNAi expression cassettes that can then be transferred to an *Agrobacterium* transformation vector.

Example 3

Figure 3:
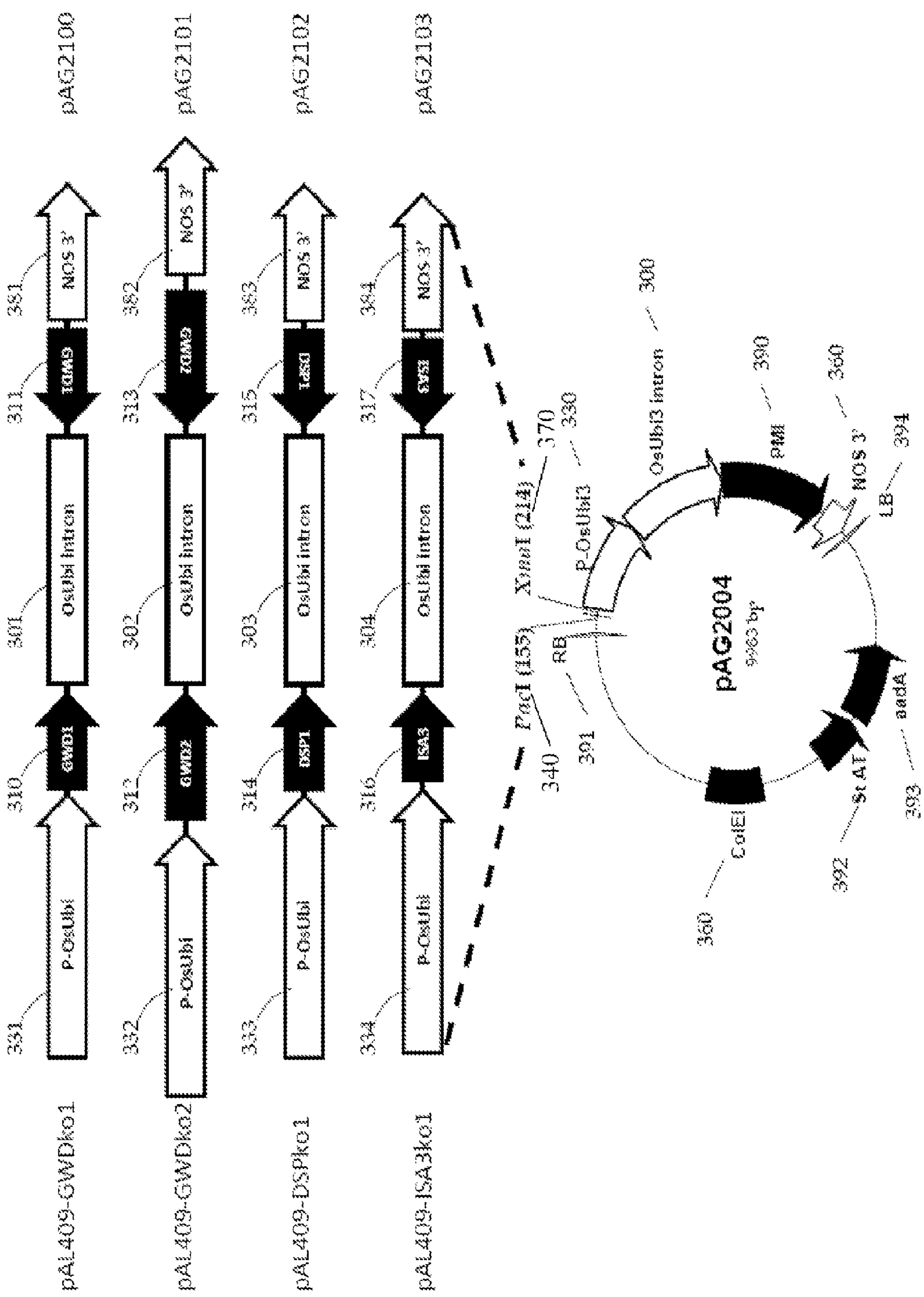
FIG. 3 illustrates RNAi cassettes targeting rice GWD, DSP, and ISA3 genes.

An exemplary transformation vector, pAG2004 is illustrated in FIG. 3. pAG2004 [SEQ ID NO: 14]. pAG2004 includes a rice ubiquitin intron 300 (OsUbi3 intron), a rice ubiquitin promoter 330 (P-OsUbi3), a PacI site 340 (position 155), an XmaI site 370 (position 214), a NOS 3' polyadenylation signal 380, and a ColE1 *E. coli* origin of replication 360. pAG2004 also includes a phosphomannose isomerase (PMI) gene 390, an RB 391, an st AT 392 and an aadA 393. pAG2004 or similar vectors can be transferred from *E. coli* to *Agrobacterium tumefaciens* LBA4404 via conjugal transfer, during which the plasmid will integrate into pSB1 (a resident Ti plasmid) via homologous recombination. Co-culture of the resulting recombinant *Agrobacterium* strain with plant cells can result in the transfer of the pAG2004-derived DNA to the plant genome. Embodiments herein include a transformation vector having any driver sequences related to targets for alteration of Green Starch. Embodiments herein include a transformation vector having a fragment from pAL409 including driver sequences related to targets for alteration of Green Starch. Embodiments herein include a transformation vector having a PacI-XmaI fragment from pAL409 including driver sequences related to targets for alteration of Green Starch in place of the pAG2004 PacI-XmaI fragment.

Example 4

Sequences from any gene related to starch regulation may be provided in an intermediate RNAi vector, a transformation vector, or in a transgenic plant herein. Three exemplary genes to target for RNA interference in rice are GWD, DSP, and ISA3. SEQ ID NOS: 1-3 list the sequences for the rice GWD, DSP and ISA3 genes, respectively. SEQ ID NOS: 4-6 list the predicted coding sequences for the GWD, DSP and ISA3 genes, respectively. The GWD, DSP, and ISA3 gene sequences are from the RiceGE database: accession Nos. Os06g30310 (GWD); Os03g01750 (DSP); and Os09g29404 (ISA3).

Example 5

Based on the coding sequences in SEQ ID NOS: 3-4, artificial cDNAs were synthesized and provided a resource for expressing the corresponding proteins in heterologous systems (e.g., *E. coli* or yeasts), which in turn would make it possible to raise antibodies for use in analyzing the planned transgenic plants.

Plasmid DNAs carrying the entire coding sequences of SEQ ID NOS: 3-4 were used as templates in PCR reactions to prepare driver sequences to be used in the RNAi constructs. For the GWD gene, two separate driver sequences were prepared.

```
>GWD1 driver sequence (one copy)
                                        [SEQ ID NO: 7]
TAGCGCTAAGGAAGGGAGAGATATCCATCCGGATCCCGGAAGCCGAA

TCCATCCATCCATCCATCCCATACTGCCCTTACGATCGAGCTGTTTGA

TATTCGTGCAGATGAGCGGATTCTCCGCGGCAGCTGCTGCGGCCGAG

CGCTTGTCGGAAGGTTCACCCTGGATGCCAACTCCGAGCTTAAGGTG

ACATTGAACCCAGCACCGCAGGGTTCGGTGGTGGAGATCAATCTAGA

GGCAACTAACACCAGCGGCTCCCTGATACTGCATTGGGGCGCCCTTC

GCCCGGATAGAGGAGAATGGCTCCTACCAT
```

-continued

>GWD2 driver sequence (one copy)

[SEQ ID NO: 8]

AGCAGATCTAGTTGACCAAGCAAGAGATAATGGATTATTGGGTATTAT

TGGAATTTTTGTTTGGATTAGGTTCATGGCTACAAGGCAACTAATATG

GAACAAGAACTACAATGTGAAGCCACGTGAGATAAGCAAAGCACAAG

ATAGGTTTACAGATGATCTTGAGAATATGTACAGAACTTACCCACAAT

ATCAGGAGATCTTAAGAATGATAATGTCTGCTGTTGGTCGGGGAGGT

GAAGGTGATGTTGGTCAACGCATTCGTGATGAGATATTAGTAATCCAG

AGAAATAATGACTGCAAAGGTGGAATGATGGAGGAGTGGCACCAGAA

ACTGCACAACAATACAAGCCCAGATGATGTAGTGATCTGCCAGGCCCT

ACTTGATTATATCAAGAGTGATTTTGATATTGGTGTTTACTGGGACAC

CTTGAAAAAAGATGGTATAACAAAAGAGCGTCTATTGAGCTATGATCG

ACCGATTCATTCAGAGCCAAATTTCAGGAGTGAACAGAAAGATGGCTT

ACTCCGTGACTTGGGCAATTATATGAGAAGCCTCAAGATGGAGGGTA

CCC

GWD1 is derived from a region near the 5' end of the GWD coding sequence. The second GWD driver sequence, GWD2 is derived from a region closer to the middle of the GWD coding sequence, which corresponds to a region of relatively higher sequence conservation among GWD genes from divergent species. See FIG. 4, which illustrates a comparison between GWD2, derived from the rice glucan water dikinase gene, and the GWD gene from tomato (*Solanum lycopersicon*). Unexpectedly, BLAST analysis [Zhang Z, Schwartz S, Wagner L, and Miller W, A greedy algorithm for aligning DNA sequences (2000) J Comput Biol 2000; 7(1-2):203-14, which is incorporated herein by reference as if fully set forth] of these two sequences reveals extensive homology, despite the phylogenetic distance that separates these two species (rice is a monocot, while tomato is a dicot). This suggests that this portion of the GWD gene would serve as a broadly applicable target for RNA interference. In FIG. 4, the Query (top sequence) is a portion of rice GWD2 driver sequence [SEQ ID NO: 9]; and the Sbjct (bottom sequence) is tomato GWD cDNA sequence [SEQ ID NO: 10]. Because of the sequence homology across this region, it is possible that an RNAi construct targeted against this region in the rice gene might also be useful for suppressing expression of homologous GWD genes in other plant species. Embodiments include methods, vectors and transgenic plants including sequences for RNAi targeting GWD.

Portions of the DSP and ISA3 genes from rice were also selected to serve as driver sequences.

>DSP1 driver sequence

[SEQ ID NO: 11]

CTCCAATCGTGGGATCCAGGTCCATGAGGCGGCCCTCGCCGCTCAAT

CTGACGATGGTTCGTGGCGGGAGTCGCCGATCAAACACTGTCAAAAC

CGCATCCGGGGCGTCTACTTCTAGCGCCGAGAGTGGCGCAGTGGAGG

CGGGCACGGAGAAATCCGATACGTACAGCACCAACATGACGCAAGCT

ATGGGAGCAGTGTTGACGTATAGACATGAGCTTGGAATGAACTACAA

TTTCATACGCCCAGACTTGATCGTGGGCTCCTGCTTACAGAGCCCACT

-continued

TGATGTTGATAAACTTAGGGACATTGGTGTAAAAACAGTATTCTGCCT

GCAGCAAGATCCAGACCTTGAATATTTTGGAGTTGACATCTGTGCCAT

T

>ISA3 driver sequence

[SEQ ID NO: 12]

CTAGCGAATACACTGAACTGCAACCATCCTGTTGTCAAGGAGCTCATT

CTTGACAGCTTGAGACACTGGGTTGAGGAGTATCACATAGATGGATTT

CGATTTGACCTTGCAAGTGTTCTTTGTCGTGGACCAGATGGTTGTCCT

CTTGATGCACCTCCACTCATCAAGGAAATTGCCAAAGATGCTGTATTA

TCTAGATGTAAGATCATTGCTGAACCTTGGGATTGCGGCGGCCTTTAT

CTCGTAGGGCGTTTCCCTAACTGGGACAGGTGGGCTGAATGGAACGG

CAAATACAGAGATGATCTTCGAAGATTTATTAAGGGTGACCCTGGTAT

GAAGGGGGTGTTTGCGACTCGTGTGTCTGGATCTGCTGATCTCTATCA

GGTGAACGAGCGGAAGCCTTACCATGGTGTAAATTTTGTGATTGCACA

TGATGGATTTACTTTATGTGACCTTGTTTCTTACAACTTAAAGCACAAT

GATGCTAATGGAGAAGGTGGCTGTGATGGATC

GWD1, GWD2, DSP1 and ISA3 driver sequences were each amplified by PCR such that each was flanked with restriction enzyme recognition sites (e.g., NheI and XmaI). The fragments were first ligated into pCRBlunt II TOPO (Invitrogen), confirmed via multiple restriction enzyme digests and sequencing, then excised (using restriction enzymes that cleave the introduced flanking sites) and ligated first into the BspEI and AvrII sites and then the NheI and AgeI sites of pAL409 (FIG. 2), which positioned the two copies in opposite orientations. The resulting RNAi cassettes were excised from the pAL409 derivatives as PacI-XmaI fragments and ligated into pAG2004 (FIG. 3), resulting in the plasmids pAG2100, pAG2102, and pAG2103. FIG. shows RNAi cassettes targeting rice GWD, DSP, and ISA3 genes, where the top two segments are derived from the GWD gene, the middle from DSP and the bottom from ISA3 genes. Each of the driver elements is represented as duplicate inverted copies separated by and proximal to the OsUbi3 intron. On the left are listed the names of the constructs that were assembled in the plasmid pAL409. To the right are listed the names of the plasmids that resulted when the RNAi cassettes were excised from pAL409 as PacI-XmaI fragments and inserted into pAG2004.

Still referring to FIG. 3, the pAL409-6WDko1 construct includes P-OsUbi promoter 331, GWD1 driver sequence 310, OsUBi intron 301, inverted GWD1 driver sequence 311 and the NOS 3' polyadenylation sequence 381. The pAL409-6WDko2 construct includes P-OsUbi promoter 332, GWD2 driver sequence 312, OsUBi intron 302, inverted GWD2 driver sequence 313 and the NOS 3' polyadenylation sequence 382. The pAL409-DSPko1 construct includes P-OsUbi promoter 333, DSP1 driver sequence 314, OsUBi intron 303, inverted DSP1 driver sequence 315 and the NOS 3' polyadenylation sequence 383. The pAL409-ISA3ko1 construct includes P-OsUbi promoter 334, ISA3 driver sequence 316, OsUBi intron 304, inverted ISA3 driver sequence 317 and the NOS 3'polyadenylation sequence 384. Replacement of the PacI-XmaI fragment of pAG2004 with the PacI-XmaI fragments of constructs pAL409-6WDko1, pAL409-6WDko2, pAL409-DSPko1 and pAL409-ISA3ko1 produced the plasmids pAG2100 [SEQ ID NO: 15], pAG2101 [SEQ ID NO: 16], pAG2102 [SEQ ID NO: 17] and pAG2103 [SEQ ID NO: 18], respectively.

Example 6

Generation of Transgenic Plants

*E. coli* strains carrying pAG2100, pAG2101, pAG2102, or pAG2103 were used for conjugation with *Agrobacterium* and subsequent transformation of rice, maize, and switchgrass.

*Sorghum* RNAi construct

A draft of the genomic sequence corresponding to the putative GWD gene from *Sorghum bicolor* [SEQ ID NO: 19] was obtained through the Joint Genome Institute (JGI) *Sorghum bicolor* Home Page (http://genome.jgi-psf.org/Sorbil/Sorbil.home.html). From this sequence, a region corresponding roughly to the GWD2 region of the rice gene [SEQ ID NO: 20] was identified. In sorghum, the coding sequences in this region are interrupted by one or more introns, as identified by JGI, and the introns are at approximately nucleotides 140-342, nucleotides 507-628 and nucleotides 723-795 in SEQ ID NO: 20. A native intron derived from the sorghum genome was utilized in assembling an RNAi cassette for knocking down the GWD gene from sorghum. A portion of the sorghum GWD gene was amplified. The portion amplified included one full exon (based on the JGI prediction) in the highly conserved middle region (described earlier, see FIG. 4), the adjacent intron, and 10 bases of the subsequent exon (to preserve the 3' intron/exon boundary). An XmaI site was incorporated upstream of the first exon, and AgeI and NheI sites were incorporated downstream of the truncated second exon during PCR amplification of this product. This product (SbGWDko2a) was first ligated into pCRBluntII TOPO (Invitrogen), and its composition was confirmed via multiple restriction enzyme digests and sequencing.

```
>SbGWDko2a (with flanking restriction sites)
                                        [SEQ ID NO: 21]
GGTTCAATAACCCGGGAGTGAGATAAGCAAAGCACAAGATAGGTTTA

CAGATGATCTTGAGAATATGTACAGAACTTATCCTCAGTACAGAGAGA

TACTAAGAATGATAATGGCTGCTGTTGGTCGTGGAGGTGAAGGTGAC

GTTGGTCAACGCATTCGTGATGAGATATTAGTAATACAGGTAAAACTG

ATGGTCCTTGGTGAATATACAGTTATTTTCGTTCATTGCTCTGCTGAAT

TGAGCAGTTGGTAGTGCTCATCCAAAACGTAGACATTGTCAACAATAA

AATGTTTGGTGTGTTACAGAGAAATACCGGTGCAAAGCTAGCATGATG

GAAGAATGG
```

A second PCR product (SbGWDko2b), corresponding to only the first exon mentioned above, was also amplified by PCR with flanking NheI and XmaI sites introduced at the 5' and 3' ends (relative to the direction of transcription), and ligated into pCRBluntII TOPO. The composition of this fragment was also confirmed via multiple restriction enzyme digests and sequencing.

```
>SbGWDko2b (with flanking restriction sites)
                                        [SEQ ID NO: 22]
GGTTCAATAAGCTAGCAGTGAGATAAGCAAAGCACAAGATAGGTTTA

CAGATGATCTTGAGAATATGTACAGAACTTATCCTCAGTACAGAGAGA
```

-continued

```
TACTAAGAATGATAATGGCTGCTGTTGGTCGTGGAGGTGAAGGTGAC

GTTGGTCAACGCATTCGTGATGAGATATTAGTAATACAGCCCGGGCTG

ATGGTCC
```

Figure 5:
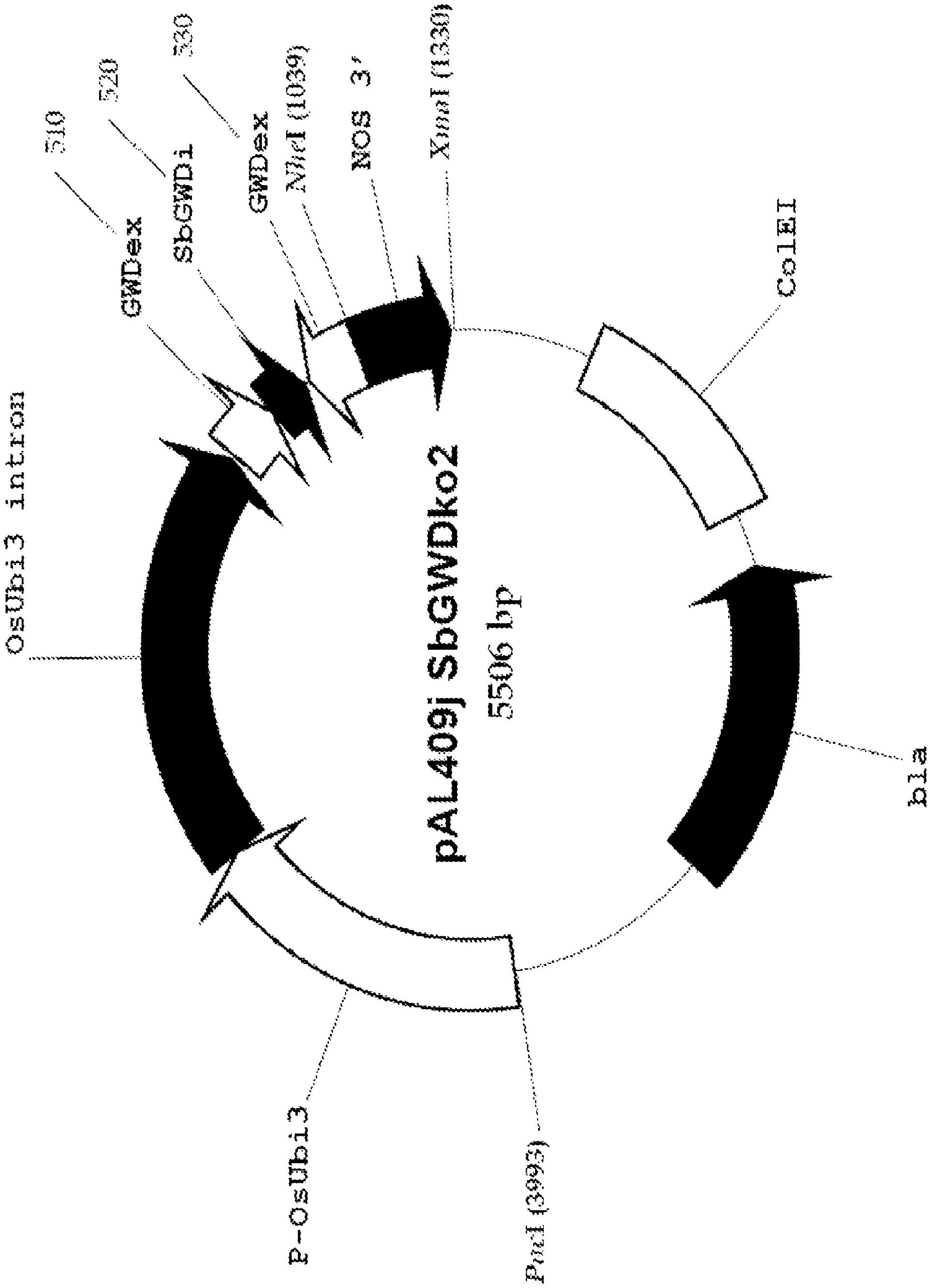
FIG. 5 illustrates pAL409j SbGWDko2.

Next SbGWDko2b was excised from pCRBlunt II as an NheI-XmaI fragment, and ligated into the NheI and AgeI sites of the plasmid carrying SbGWDko2a, positioning SbGWDko2b downstream of the intron and in the opposite orientation of SbGWDko2a. In this orientation, sequences in the sbGWDko2b portion of the plasmid are presented as an inverted complement of sequences within the sbGWDko2a portion. Referring to FIG. 5, this entire cassette was excised as an XmaI-NheI fragment and ligated into pAL409j, resulting in the plasmid pAL409j SbGWDko2 [SEQ ID NO: 47]. pAL409j carries an RNAi cassette targeting the GWD gene of *Sorghum bicolor*. The driver sequence 510 (sbGWDko2a) is illustrated in FIG. 5 upstream of the intron 520 (sbGWDi), which is illustrated upstream of the driver sequence 530 (sbGWDko2b). pAL409j differs from pAL409 only in that the junction between the OsUbi3 promoter and the OsUbi3i intron have been modified to reflect their native context in the rice genome. As such, this orientation may preserve the enhancer functions of OsUbi3i with respect to the OsUbi3 promoter. As shown in FIG. 5, two inverted, homologous driver sequences derived from an exon within the sorghum GWD gene (GWDex) are separated by a native sorghum GWD exon (SbGWDi). Other elements are named as in FIG. 2.

The entire RNAi cassette from pAL409j SbGWDko2 was then excised as a PacI-XmaI fragment and ligated into the Pad and XmaI sites of pAG2004, producing the *Agrobacterium* transformation vector pAG2106 [SEQ ID NO: 23] in a manner similar to that described in reference to FIG. 3. An *E. coli* strain carrying pAG2106 was used for conjugation to *Agrobacterium* and subsequent transformation of sorghum.

Example 7

Sequencing of the Switchgrass GWD Gene(s)

Figure 6:
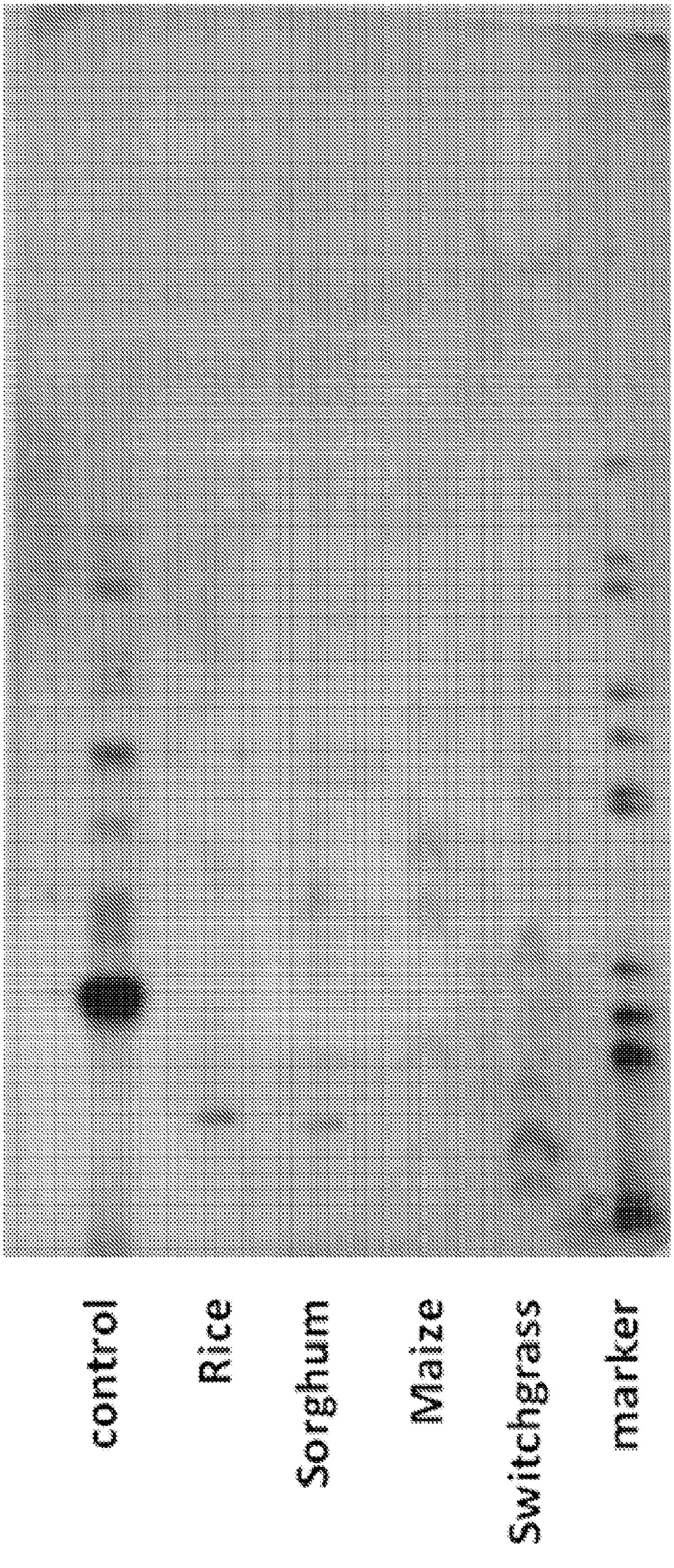
FIG. 6 illustrates detection of ISA3 homologues via Southern blot.

Homologues for GWD and ISA3 were detected in the switchgrass genome and the number of homologues that are present for each were estimated using a Southern blotting strategy. Results with the Southern blot using the rice ISA3 probe are shown in FIG. 6. FIG. 6 shows detection of ISA3 homologues via Southern blot. Genomic DNA was extracted from rice, sorghum, maize, and switchgrass, digested with HindIII, and separated via agarose gel electrophoresis. DNAs were subsequently transferred to nylon membranes via capillary blotting, and the blots probed with DIG-labeled DNA derived from the cloned rice ISA3 gene. Whereas the probe hybridized to only single fragments in rice and sorghum, the same probe hybridized to 3-5 fragments in the maize and switchgrass genomes. The control was plasmid DNA carrying the rice ISA3 coding sequence; and the marker was DNA molecular weight standards. Similar results were obtained when the rice GWD2 fragment was used as a probe (not shown). It was determined that, unlike rice and sorghum, which contain only single copies of GWD and ISA3, switchgrass contains multiple homologues of each of these genes.

A portion of the switchgrass GWD gene was identified and clones using a degenerate PCR approach. Degenerate PCR employs oligonucleotide primers with one or more ambiguous bases that allow the primers to anneal to template sequences for which only approximate sequence information is available. That is, in regions of strong sequence conservation between genes of widely divergent species, one can infer the range of possible sequences that might be present in the correspond gene from an under-characterized species such as switchgrass. One can then design degenerate primers that will anneal to the predicted sequences, permitting PCR amplification and cloning of a portion of the gene in question.

Pursuing the degenerate PCR strategy, portions of the GWD genes derived from rice, sorghum, maize, and tomato were aligned. The strongest alignments occurred in the region of the GWD genes that was described in FIG. 4. Short (~40 nt) regions near the extremities of these regions of homology were selected for a more detailed sequence comparison (FIG. 7). FIG. 7 illustrates alignment of excerpts from the GWD genes of rice (OsGWD)[SEQ ID NOS: 24 (top) and 28 (bottom)], sorghum (SbGWD) [SEQ ID NOS: 25 (top) and 29 (bottom)], maize (ZmGWD) [SEQ ID NOS: 26 (top) and 30 (bottom)], and tomato (SlGWD) [SEQ ID NOS: 27 (top) and 31 (bottom)]. Nucleotide positions that are conserved in at least two of the four sequences are highlighted in light gray. Beneath each set is presented the consensus sequence to which degenerate primers (dgGWDup2 and dgGWDdown2 [SEQ ID NOS: 32 and 33, respectively]) were designed for PCR amplification. Note that only partial sequence is available for the maize homologue, with a region of unknown sequence represented by Ns. The four sequences aligned in the top segment correspond to the portion of the GWD coding sequences that can be found from nucleotides 1803-1840 of the tomato coding sequence (as defined in FIG. 4), while the alignments in the bottom segment correspond to nucleotides 2208-2249 of the tomato sequence. Nucleotide abbreviations for degenerate nucleotides are as follows: Y, C or T; W, A or T; K, G or T; R, A or G, M, A or C; H, A or C or T; S, G or C; D, A or G or T. From this information, degenerate primers were designed (dgGWDup2: 5'-TGGAATTYTTGTWTGGATKAGRTTCATGGCTACMAGGCA-3'[SEQ ID NO: 32]and dgGWDdpwn2: 5'-GGYTCWGAATGRATMGSWCGRTCATARCTCAADAGACGCTCT-3'[SEQ ID NO: 33]). Genomic DNA that had been isolated from sorghum was then used as a template in PCR reactions with these primers. Degenerate PCR with sorghum genomic DNA as a template gave rise to an approximately 800 by PCR product. Sequencing of this PCR product revealed that it closely matched the sequence that was predicted for the sorghum GWD gene by the JGI database (see above), which indicated that the degenerate primers would reliably amplify a segment of the GWD gene.

The same primers were then used in PCR reactions that used switchgrass (ecotype Alamo) genomic DNA as a template. These reactions produced discrete PCR products of approximately 1100 bp. These products were ligated into pCRBluntII TOPO and five of the resulting plasmids were sequenced. From these five sequences, it was determined that:

- Each cloned PCR product was derived from a gene with very strong homology to the rice GWD gene
- Among the five sequenced products, there were clearly three classes of (highly homologous) sequences, suggesting that the clones were derived from three different GWD homologues within the switchgrass genome. This observation agrees with the data from Southern blots that suggested multiple GWD genes reside within the switchgrass genome.
- The main differences in the sizes of the products that arose from degenerate PCR of sorghum and switchgrass can be attributed to differences in the lengths of the putative introns in each of the respective genes.

Figure 8:
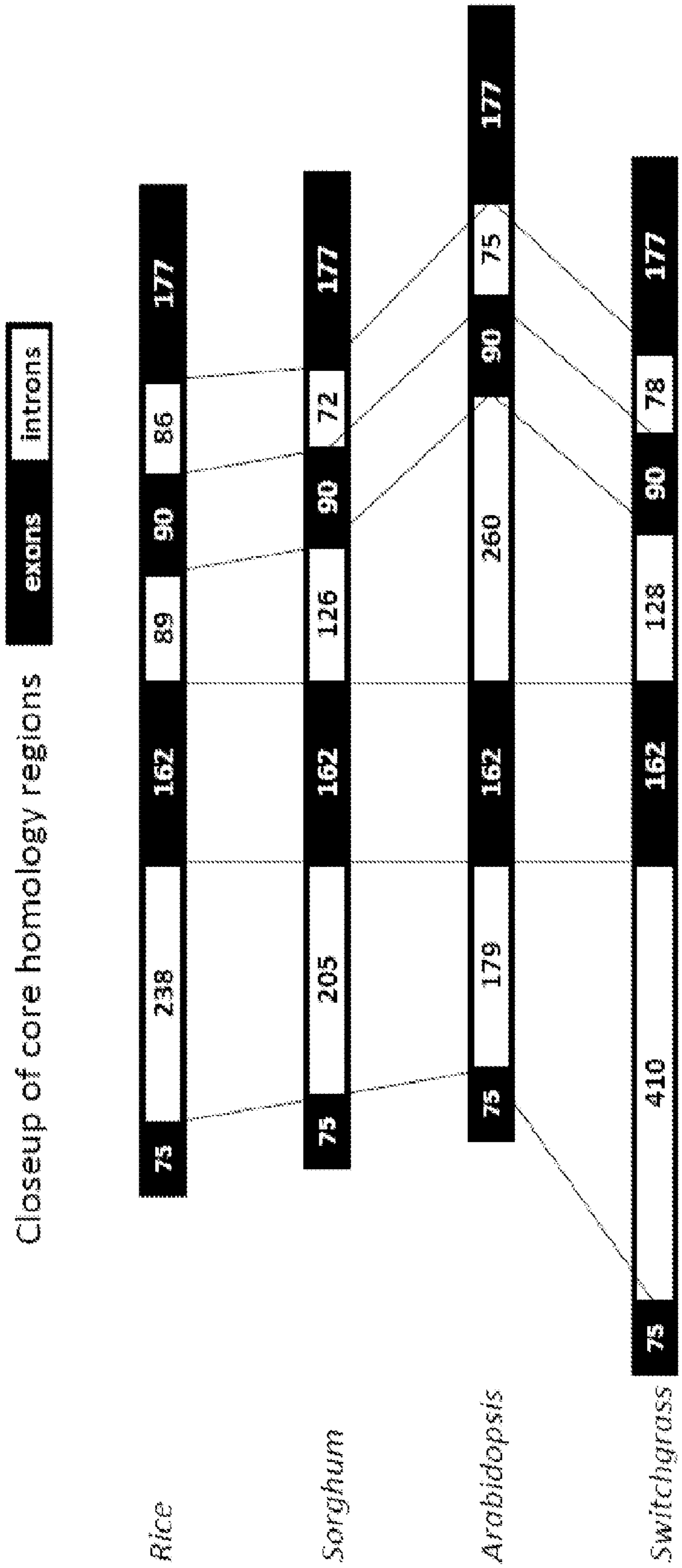
FIG. 8 illustrates comparison of relative length and positioning of introns within the core homology segment of GWD genes from rice, sorghum, *Arabidopsis*, and switchgrass.

Referring to FIG. 8, a comparison of relative length and positioning of introns within the core homology segment of GWD genes from rice, sorghum, *Arabidopsis*, and switchgrass is illustrated. Dark boxes represent exons, and light boxes represent introns. Exon sequences are very well conserved and easily recognized. While the relative positions of each of the introns is also well conserved across species, the length and sequence of the introns is not well conserved. Lengths of the introns and exons are indicated in by within each element.

As shown below, an alignment of the sequences from three of the switchgrass-derived degenerate PCR products, demonstrates that relatively few single nucleotide changes and two somewhat lengthier insertions/deletions distinguish these three GWD homologues in this region. These three products are PvGWD-2 [SEQ ID NO: 34], PvGWD-5 [SEQ ID NO: 35] and PvGWD-1 [SEQ ID NO: 36].

```
CLUSTAL 2.0.10 multiple sequence alignment

PvGWD-2  TGGAATTCTTGTTTGGATGAGATTCATGGCTACCAGGCAACTAACATGGAATAAGAACTA  60
PvGWD-5  TGGAATTCTTGTTTGGATTAGGTTCATGGCTACCAGGCAACTAACATGGAATAAGAACTA  60
PvGWD-1  TGGAATTTTTGTTTGGATGAGATTCATGGCTACAAGACAACTGACATGGAATAAGAACTA  60
         ******* ********** ** *********** ** ***** *****************

PvGWD-2  TAATGTGAAGCCCCGGTATATACCTGTCTTTATCATTTACTTCAGTGATGTTTACTCTCT 120
PvGWD-5  TAATGTGAAGCCCCGGTATATACCTGTCTTTATCATTTACTTCAGTGATGTTTACTCTCT 120
PvGWD-1  TAATGTGAAGCCACGGTATATACCTGTCTTTATTATTTACTTCAGTAATGTTTACTCTCT 120
         ************ ******************** ************ *************

PvGWD-2  GCTTAAAAATTTAAAGAATCTGAAGCTGTCCTTTTCTTTTGTGCGGGAACATAATTGAGA 180
PvGWD-5  GCTTAAAAATTTAAAGAATCTGAAGCTGTCCTTTTCTTTTGTGCGGGAACATATTTGAGA 180
PvGWD-1  GCTTTAAAAGTTAAAGAATCAGAAGTTGTCCCTTTCTTTTGTGCGGGAACATAATTGAAA 180
         **** **** ********** **** ***** ********************* **** *

PvGWD-2  AATTGGTGTTTTTGCCACTACTTCATGATGCAATTGTAATTTTTCCCTCATTTTTTTCAA 240
PvGWD-5  AATTGGTGTTTTTGCCACTACTTCATGATGCAATTGTAATTTTTCCCTCATTTTTTTCAA 240
PvGWD-1  AGTTGGTGTTCTTGCCACTAC--------------------------------------- 201
         * ******** **********

PvGWD-2  CTTTGTGATTTTGCCCTTTACTATTCACAAGTCAACGCAATTTTGCTCCTGTTTTGACCG 300
PvGWD-5  CTTTGTGATTTTGCCCTTTACTATTCACAAGTCAACGCAATTTTGCTCCTGTTTTGACCG 300
PvGWD-1  ----------------------------AAGTCAACGCGATTTTACCCCT-CGTCAACGG 232
                                     ********** ***** * ***   *  ** *
```

-continued

CLUSTAL 2.0.10 multiple sequence alignment

```
PvGWD-2 TTGACTGAG-GGAAAAATCGCGTTAACTTGTGAATAGTAAGTGCAAAATTGCAAAGTTGA  359
PvGWD-5 TTGACTGAG-GGAAAAATCGCGTTAACTTGTGAATAGTAAGTGCAAAATTGCAAAGTTGA  359
PvGWD-1 TCAAAACAGTAGCAAAATCGCGTTGACTTGTGAATAGTAAGGGCAAA-TCACAAAGTTGG  291
        *  *   **  * *********** **************** ***** *  ********

PvGWD-2 AAAAAACAAGGACAAAATCACAATTGCACTGCAAAGTAGGGGTGGAAACACAAATGCCCC  419
PvGWD-5 AAAAAACAAGGACAAAATCACAATTGCACTGCAAAGTAGGGGTGGAAACACAAATGCCCC  419
PvGWD-1 AAAAAACAAGGACAAAATCACAATTGCACTGCAAAGTAGTCGCGGAAACACAAATGCCCC  351
        ***************************************  * *****************

PvGWD-2 AAAATAATTTGGCTGTTTGTCCTGATAGAAAACAATACAATTCAGTACTCAGAGAATATT  479
PvGWD-5 AAAATAATTTGGCTGTTTGTCCTGATAGAAAACAATACAATTCAGTACTAAGAGAATATT  479
PvGWD-1 AAAATAATTTGGCTGTTTGTCCTGATAAAAAACAATACAATTCAGTACTCAGAGAATATT  411
        *************************** ********************* **********

PvGWD-2 ATATTTCTATAAATGAAAAACATAACTCATGTCACATTCTTT--------GGCATCTCAT  531
PvGWD-5 ATATTTCTATAAATGAAAAACATAACTCATGTCACATTCTTT--------GGCATCTCAT  531
PvGWD-1 ATATTTCTATAAATGAAAAACATAACTCATGTCGCATTCTTTCATTCTTTGGCATCTCAT  471
        ********************************* ********        **********

PvGWD-2 ATCGATCAATAACTATGCAGTGAGATAAGCAAAGCACAAGATAGGTTTACAGATGATCTT  591
PvGWD-5 ATCGATCAATAACTATGCAGTGAGATAAGCAAAGCACAAGATAGGTTTACAGATGATCTT  591
PvGWD-1 ATTGATTAATAACTACGCAGTGAGATAAGCAAAGCACAAGATAGGTTTACAGATGATCTT  531
        ** *** ******** ********************************************

PvGWD-2 GAGAACATGTACAAAGCTTATCCTCAGTGCAGAGAGATATTAAGAATGATAATGGCTGCT  651
PvGWD-5 GAGAACATGTACAAAGCTTATCCTCAGTGCAGAGAGATATTAAGAATGATAATGGCTGCT  651
PvGWD-1 GAGAACATGTACAAAGCTTATCCTCAGTACAGAGAGATATTAAGAATGATAATGGCTGCT  591
        **************************** *******************************

PvGWD-2 GTTGGTCGTGGAGGTGAAGGTGATGTTGGTCAACGTATTCGTGATGAGATATTAGTAATA  711
PvGWD-5 GTTGGTCGTGGAGGTGAAGGTGATGTTGGTCAACGTATTCGAGATGAGATATTAGTAATA  711
PvGWD-1 GTTGGTCGTGGAGGTGAAGGTGATGTTGGTCAACGTATTCGTGATGAGATATTAGTAATA  651
        ***************************************** ******************

PvGWD-2 CAGGTAAAATTAATGGTCCTAGGTGAATATACACTTACTTTTATTCATTGCTTCACCGAA  771
PvGWD-5 CAGGTAAAATTAATGGTCCTAGGTGAATATACACTTACTTTTATTCATTGCTTCACTGAA  771
PvGWD-1 CAGGTAAAATTAATGGTCCTAGGTGAATATACACCTACTTTTATTCATTGCTTCACTGAA  711
        ********************************** ********************* ***

PvGWD-2 TTATACGGTTGGTAGTTCTCATCCAAAAGATAGACATTGTGAATAATAATAAAATGCTTG  831
PvGWD-5 TTATACGGTTGGTAGTTCTCATCCAAAAGATAGACATTGTGAATAATAATAAAATGCTTG  831
PvGWD-1 TTATACGGTTGGTAGTTCTGATCCAAAAGATAGACATTGTGAATAATAATAAAATGCTTG  771
        ******************* ****************************************

PvGWD-2 CTGCTTTAATAGAGAAATAATGACTGCAAAGGTGGAATGATGGAAGAATGGCACCAGAAA  891
PvGWD-5 CTGCTTTAATAGAGAAATAATGACTGCAAAGGTGGAATGATGGAAGAATGGCACCAGAAA  891
PvGWD-1 CTGCTTTTATAGAGAAATAATGACTGCAAAGGTGGAATGATGGAAGAATGGCACCAGAAA  831
        ******* ****************************************************

PvGWD-2 TTGCACAACAATACAAGCCCAGATGATGTAGTGATATGCCAGGTAATGGATATTTTGAAT  951
PvGWD-5 TTGCACAACAATACAAGCCCAGATGATGTAGTGATATGCCAGGTAATGGATATTTTGAAT  951
PvGWD-1 TTGCACAACAATACAAGCCCAGATGATGTAGTGATATGCCAGGTATTGGATATTTTGAAT  891
        ********************************************* **************

PvGWD-2 TCTTAATACAGTAAGTATTTAAGCATTGAGGTTTTCATGGTTATGTCTCTCCTTGGGCAG 1011
PvGWD-5 TCTTAATACAGTAAGTATTTAAGCATTGAGGTTTTCATGGTTATGTCTCTCCTTGGGCAG 1011
PvGWD-1 TCTTAATACTGTAAGTATTTAAGCATTGAGGTTTTTATGGTTATGTCTCTCCTTGGGCAG  951
        ********* ************************* ************************

PvGWD-2 GCACTAATTGATTATATCAAGAGTGATTTTGATATAAGTGTTTACTGGGACACCTTGAAC 1071
PvGWD-5 GCACTAATTGATTATATCAAGAGTGATTTTGATATAAGTGTTTACTGGGACACCTTGAAC 1071
PvGWD-1 GCATTAATTGATTATATCAAGAGTGATTTTGATATAAGTGTTTACTGGGACACCTTGAAC 1011
        *** ********************************************************

PvGWD-2 AAAAATGGCATAACCAAAGAGCGTCTCTTGAGCTATGATCGAG-CTATCCATTCAGAACC 1130
PvGWD-5 AAAAATGGCATAACCAAAGAGCGTCTATTGAGTTATGACCGTC-CGATCCATTCCAGACC 1130
PvGWD-1 AAAAATGGCATAACCAAAGAGCGTCTTTTGAGCTATGATCGTTGCTATCCATTCAGAACC 1071
        ************************** ***** ***** **   * ********   ***
```

Sequences of the exons from the switchgrass GWD gene(s) were inferred from the above information. The inferred sequences were used to (1) develop an RNAi construct that would target this central region of one or all of the switchgrass GWD genes, and (2) determine more of the genomic sequence for each of these (at least three) GWD homologues in switchgrass.

To develop an RNAi construct, PCR was used to amplify portions from two of the exons encompassed in the degenerate PCR products described above. These two products were then fused by SOE PCR (Horton R. M., Hunt H. D., Ho S, N., Pullen J. K., Pease L. R., Engineering hybrid genes without the use of restriction enzymes: gene splicing by overlap extension (1989) Gene 77(1):61-8), which is incorporated herein by reference as if fully set forth). The fused products included a contiguous sequence that was expected to more closely match one or more of the switchgrass GWD mRNAs. NheI and XmaI sites were incorporated into the termini of the fused product to enable subsequent cloning into pAL409. The sequence of this product (called "PvG-WDko2" along with the flanking restriction sites) is depicted below.

```
>PvGWDko2 RNAi driver sequence
                                         [SEQ ID NO: 37]
GGCTAGCGAGATAAGCAAAGCACAAGATAGGTTTACAGATGATCTTG

AGAACATGTACAAAGCTTATCCTCAGTACAGAGAGATATTAAGAATGA

TAATGGCTGCTGTTGGTCGTGGAGGTGAAGGTGATGTTGGTCAACGT

ATTCGTGATGAGATATTAGTAATACAGGAGAAATAATGACTGCAAAGG

TGGAATGATGGAAGAATGGCACCAGAAATTGCACAACAATACAAGCC

CAGATGATGTAGTGATATGCCCGGGAGG
```

One copy of this element was ligated into the AvrII and BspEI sites of pAL409, then a second copy was ligated into the NheI and AgeI sites of the resulting plasmid, producing the RNAi cassette pAL409 PvGWDko2, which had the elements arranged in opposite orientations, separated by the OsUbi3 intron, as described in reference to FIG. 3. The RNAi cassette was excised from this plasmid as a PacI-XmaI fragment and ligated into Pad and XmaI sites of pAG2004 (FIG. 3). The resulting *Agrobacterium* transformation vector was named pAG2104 [SEQ ID NO: 38]. An *E. coli* strain carrying this plasmid was used for conjugation with *Agrobacterium* and subsequent transformation of switchgrass.

By learning the complete genomic sequences of each of the GWD genes in switchgrass identification of the potentially unique sequences (5' and 3' untranslated regions) that flank each of these genes may be possible. With this information, it may be able to design RNAi constructs that specifically target one or the other of these genes.

To identify more of the sequences associated with each of the GWD homologues, a strategy was pursued that employed inverse PCR (iPCR) as well as degenerate PCR. Genomic DNA from switchgrass was digested with either EcoRI, HindIII, or Bgl II. These were then subjected to self-ligation, diluted approximately 100-fold, and used as templates in inverse PCR reactions. The sequences of the first primers used in iPCR reactions are summarized in Table 1.

TABLE 1

| Sequences of primers used for inverse PCR | | |
|---|---|---|
| PvGWDi-1 | CCGTGGCTTCACATTATAGTTCTTATTCCA | SEQ ID NO: 39 |
| PvGWDi-2 | GAGATAAGCAAAGCACAAGATAGGT | SEQ ID NO: 40 |
| PvGWDi-3 | GCCTGCCCAAGGAGAGACATAACCA | SEQ ID NO: 41 |
| PvGWDi-4 | GATATAAGTGTTTACTGGGACACCT | SEQ ID NO: 42 |

Inverse PCR reactions with either primers PvGWDi-1 and PvGWDi-2 or primers PvGWDi-3 and PvGWDi-4 were carried out using the EcoRI- or HindIII-digested (and self-ligated) templates. These reactions gave rise to a small number of clear products, which were purified from agarose gels and ligated into pCRBluntII-TOPO. Sequence analysis of the resulting plasmids allowed extending the known sequence from switchgrass GWD genes at both the 5' and 3' ends to a total of 3.4 kb. Again, the sequences from individual clones differed by about 1-2%, consistent with the idea that the cloned PCR products were derived from separate but very similar GWD homologues in the switchgrass genome. This exercise was repeated with newly designed primers, incorporating both inverse PCR and degenerate PCR to extend the known sequence further. Approximately 7 kb of switchgrass GWD sequence was identified.

Figure 9:
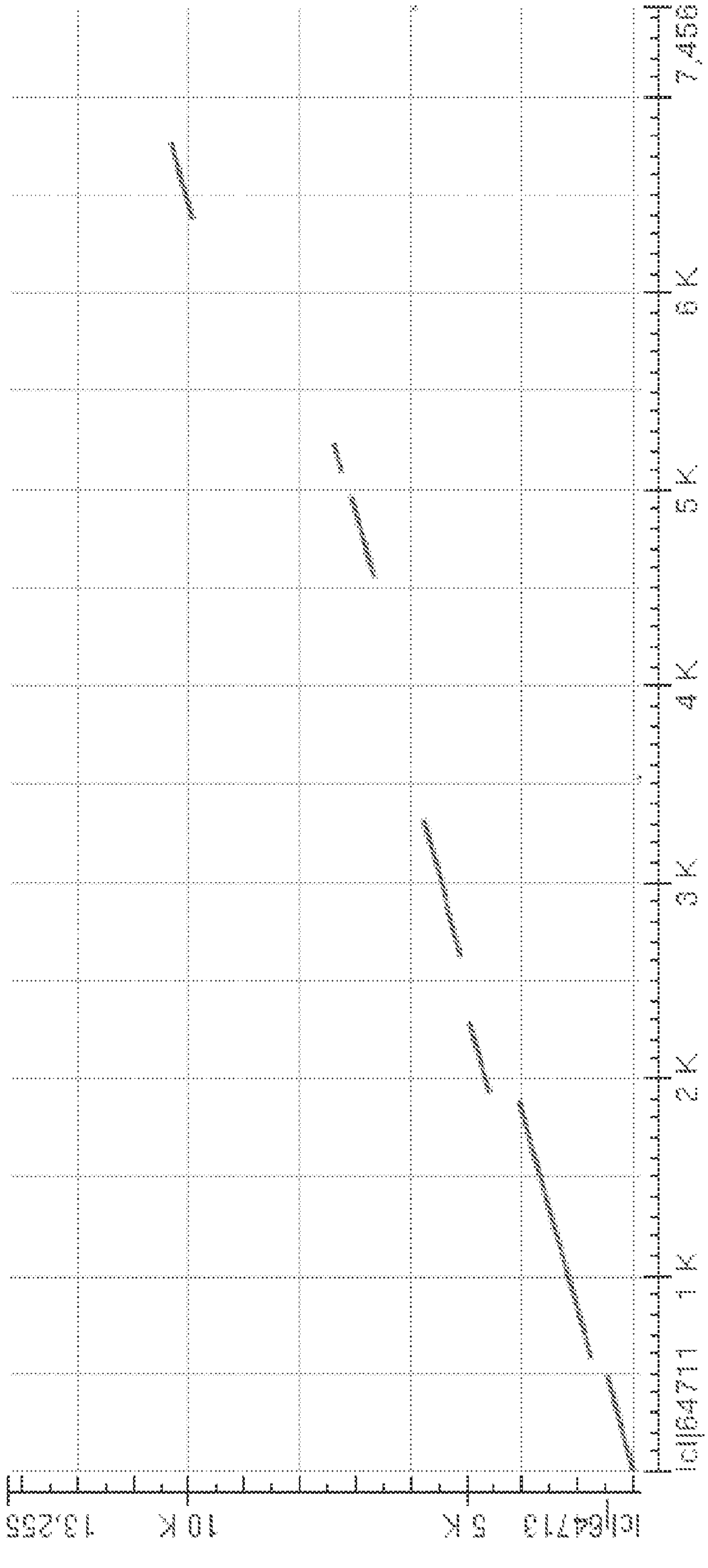
FIG. 9 illustrates a dot matrix depiction of BLASTn alignments between switchgrass and rice genomic sequences for glucan water dikinase genes. Horizontal axis, switchgrass sequence; vertical axis, rice sequence. Diagonal segments represent regions where the two sequences are highly homologous.

An amalgamated sequence is provided representing the switchgrass GWD gene sequences discovered herein. The sequence presented does not include all of the variations identified among the homologues. Thus, the sequence could be viewed as a chimera of these homologues. This sequence straddles a segment of approximately 1-2 kb for which there is no sequence data. This segment is represented as a string of Ns. Referring to FIG. 9, a dot matrix depiction of BLASTn alignments between switchgrass and rice genomic sequences for glucan water dikinase genes is illustrated. The horizontal axis represents the switchgrass sequence; and the vertical axis represents the rice sequence. Diagonal segments represent regions where the two sequences are highly homologous. This diagram shows the similarity of the switchgrass sequence below to the corresponding sequence of the rice GWD gene.

```
>switchgrass GWD homologues
                                                  [SEQ ID NO: 43]
GGAACGACAGTGTACAAGAACAGGGCTCTTCGGACGCCTTTTCTAAAGGTCAGTCTT

GTTACATTATGGATCTCTTTGTTACCACAGAACAGTCTGGTTAGCAGTAATGTCCATA

ACTGTGCAGTCAGGAGGTGATAACTCCACGCTTAGAATTGAGATAGATGATCCTGCG

GTGCAAGCTATTGAATTTCTCATCTTTGATGAGACACAGAACAAATGGTAACCCAGCT

GTTTTCGTTACCATGTAGCACTGTTTGTTTGTTTGAATGCAAAAGGTATATAAACTAT
```

-continued

GCAAAACTCTACATTGCACAGGTTTAAAAATAATGGCCAGAATTTTCAAATTCAGCTC

CAATCGAGCCACCATCATGGTAGTGGCGCATCTGGTGCCTCATCTTCTGCTACTTCTG

CCTTGGTGCCAGAGGATCTTGTGCAGATCCAAGCTTACCTACGGTGGGAAAGAAATG

GAAAGCAGTCATACACACCGGAGCAAGAAAAGGAAAGCTTTTAGTTGTTTTTTTTTAT

CTTCAGTCTGGAAGGAACTCAATGTACTAAGTTGATTAAAAATAAGAGGTGGTGTATT

TTTTCTCCAGGAGGAGTATGAAGCTGCACGAGCTGAGTTAATAGAAGAATTAAATAG

AGGTGTTTCTTTGGAGAAGCTTCGAGCTAAATTGACAAAAGCACCTGAAGTGCCCGA

CTCAGATGAAAATGATTCTCCTGCATCTCAAATTACTGTTGATAAAATTCCAGAGGAC

CTTGTACAAGTCCAGGCTTATATAAGGTGGGAGAAAGCAGGCAAGCCAAACTATCCT

CCTGAGAAGCAACTGGTAATGCATTGATTCAATAGCGTAAAATACCTTGTTGGCTTTA

CACTTTATGGAGGTTCTTATCTCACAATTCGCTAGGTCGAGTTTGAGGAAGCAAGGAA

GGAACTGCAGGCTGAGGTGGACAAGGGAATCTCGATTGATCAGTTGAGGAAGAAGAT

TTTGAAAGGAAACATTGAGAGTAAAGTTTCGAAGCAGCTGAAGAATAAGAAGTACTT

CTCTGTAGAAAGGATTCAGCGCAAAAAGAGAGATATCATGCAGATTCTTAGTAAACAT

AAGCATACTGTCATAGAAGAGCAAGCAGAGGTTGCACCAAAACAACTAACTGTTCTT

GATCTCTTCACCAATTCATTACAGAAGGATGGCTTTGAAGTTCTAAGCAAAAAACTGT

TCAAGTTCGGTGATAAACAGATCCTGGTTAGGATCCTTAAGATATTCTTTGTATCTCC

AGATCTTTTTCTACCATGCTAATTAAGCTTCTCTCTTCTTAAGGCAATCTCCACCAAG

GTTCTAAACAAATCAAAAGTTTACTTGGCAACAAATCATACGGAGCCACTTATCCTTC

ACTGGTCACTAGCGAAAAAGGCTGGAGAGTGGAAGGTTAAATTTCAAAATTGTTTCC

AGTAGTTAAAGCCACAAACTCAGCAGCTTTTTTAAACACTGCTATCAGTACCAATGCG

GTGTTATTTAACTGTGCAGGCACCTCCTTCAAACATATTGCCATCTGGTTCAAAATTG

TTAGACATGGCATGCGAAACTGAATTTACTAAGTCTGAATTGGATGGTTTGCATTATC

AGGTGGAAATAACATCTTCAACCTGTTATTTTATTCTTATTTTTATTAGCCCTCCTGCT

ATCTCAAGGCTCTTAATTTCCAGGTTGTTGAGATAGAGCTTGATGATGGAGGATATAA

AGGGATGCCATTCGTTCTTCGGTCTGGTGAAATGTGGATAAAAAATAATGGCTCTGAT

TTTTACCTTGATCTCAGCACCCGTGATACCAGAAATATTAAGGCAAGTGTTTCTGTCC

ATTTTACCTTTCAAACTTTAAACTATTGTCTTTGTTTTGTCTATGCAACTAGTCGCTAA

ATTGTGAAGTAACCGATCTGTTCTTAATTGAAGGACACTGGTGATGCTGGTAAAGGTA

CTGCTAAGGCATTGCTGGAAAGAATAGCAGAGCTGGAGGAAGATGCCCAGCGATCTC

TTATGCACAGGTCAGGCACTAAAATATCCATAATAATATGACTGAATTTTACATGGAA

AATTCTCCTAAACTACTTCTACTCCTTGACAGATTCAACATTGCAGCAGATCTAGTTG

ACCAAGCCAGAGATGCTGGACTATTGGGTATTGTTGGACTTTTTGTTTGGATTAGATT

CATGGCTACAAGACAACTGACATGGAATAAGAACTATAATGTGAAGCCACGGTATAT

ACCTGTCTTTATTATTTACTTCAGTAATGTTTACTCTCTGCTTTAAAAGTTAAAGAATC

AGAAGTTGTCCCTTTCTTTTGTGCGGGAACATAATTGAAAAGTTGGTGTTCTTGCCAC

TACAAGTCAACGCGATTTTACCCCTCGTCAACGGTCAAAACAGTAGCAAAATCGCGTT

GACTTGTGAATAGTAAGGGCAAATCACAAAGTTGGAAAAAACAAGGACAAAATCACA

ATTGCACTGCAAAGTAGTCGCGGAAACACAAATGCCCCAAAATAATTTGGCTGTTTGT

CCTGATAAAAAACAATACAATTCAGTACTCAGAGAATATTATATTTCTATAAATGAAA

AACATAACTCATGTCGCATTCTTTCATTCTTTGGCATCTCATATTGATTAATAACTACG

-continued

CAGTGAGATAAGCAAAGCACAAGATAGGTTTACAGATGATCTTGAGAACATGTACAA

AGCTTATCCTCAGTACAGAGAGATATTAAGAATGATAATGGCTGCTGTTGGTCGTGG

AGGTGAAGGTGATGTTGGTCAACGTATTCGTGATGAGATATTAGTAATACAGGTAAA

ATTAATGGTCCTAGGTGAATATACACCTACTTTTATTCATTGCTTCACTGAATTATACG

GTTGGTAGTTCTGATCCAAAAGATAGACATTGTGAATAATAATAAAATGCTTGCTGCT

TTTATAGAGAAATAATGACTGCAAAGGTGGAATGATGGAAGAATGGCACCAGAAATT

GCACAACAATACAAGCCCAGATGATGTAGTGATATGCCAGGTATTGGATATTTTGAAT

TCTTAATACTGTAAGTATTTAAGCATTGAGGTTTTTATGGTTATGTCTCTCCTTGGGC

AGGCATTAATTGATTATATCAAGAGTGATTTTGATATAAGTGTTTACTGGGACACCTT

GAACAAAAATGGCATAACCAAAGAGCATCTCTTGAGCTATGATCGTGCGATTCATTCA

GAACCAAATTTCAGAAGTGAACAGAAGGAGGGTTTACTCCATGACCTGGGTAATTAC

ATGAGAAGCCTGAAGGTATGTAAAACACTTAATATGGATATAAAAAAAGGCATGCAA

AAAAATCTGTGCATTATCTTTGAAATTGAGTATGGTATTTTCTAAAGAAAACATAGAA

AAACACATATTGCCCTTTCAGTTCCGGAAAAAAATGATCTGCCATAAAGAGCATACAG

TCAACTCATGTATTAGCACTCGCCTTTTCTGCTAATGGTATGTTGTGTTGTGTTCTGTT

CTATTCAATATATGCTTTCAGTAATAATATTCTAGTGTTGACAACATCATTGCTCACAA

CATACAGAAACTGTAGTATGCCCGGTACAGTATGAACTTGTCCTTGAGTCTCCTCATT

TTTTCCTTATTCACGTCACAGCTTTATATCCTTCCAATGAATAATGATCAACTTGGAAA

TCATTGGCATCTACAGTGAACCGTCCATTGTATTCTGATTTTGAACAACTTTTTTTCCC

CTCAGAACACACAGTAATAGCCAAGTATAACGACCTTACATGGCCAAAACAACAACCT

TACATGGCCAAAATAGCCAGGTAAGGGACAGAAGAAGAGAGAGGGTTGCCCTGCGG

CAGATGTGGACAATGACTGATGATGTGGCTGTCCCAGTTATCAAAACAGGCAAATCC

ACTGTTCATGTGGCCNAAGCCAGTAATGAGCTGGTTTTGGGAAACCCTGGGGGATTG

AGTAAACAATTAGAGGGTTATGTGGATTTGGTCATAGTTGGGGGTAGGAATTTGGAA

ATTTCCCTTTTGCTTGATAATTATGTTAGTCAAGAGATTAGACAAGTATTGTTAGGAG

TTTGTTTCAGCTGGTTGAGATTGGATTTGGTTTCTTAGGTGATTGGTTAGTGCTACCC

TTGCTCTATAATTGGGGATTTGCTTTTAATAAAGAAAGCAGAAATAAACCCAATCCTT

CTCCGGTTCTCCCTCTTTTGTCCGATGTTTGCAGATGCGGCCACTGATAAGGTCCAGG

TCCATGTCCTCCCATCAACCACACACACATACAGCCTAAGATCTAATTCACCCCAGGA

CACCCAAGCTCGTGAAAATATACCATGTCATCCCACTATTCATACTTTTTTTAAAAAA

ATCCCACTAATCCTGCAAATGTCCTAATATAAGAACAACATCATTTTCAGTCATGTTG

TACCTTTTCTTGGTGACAAAAAGAAGACATCCATTTCATCTCTTTTTAAGGGGCATTT

TCTCATCGTTTCTGCAATTGAATATTCTTTCCCTGATGTAATCTTTGAATGAATGCTAT

TGTGATTTGCTCATTCTGTTAGGCTGTGCATTCTGGTGCTGATCTTGAGTCTGCTATA

GCAACTTGCATGGGATACAAATCGGAGGTATCATTCTCATTCCTTTTCATTCCGCTAG

AATTCTTTAGATACCTGTGCTCATATCTAATGAACTAACTTTTGGGTACAGGGTGAAG

GTTTCATGGTCGGTGTTCAGATCAATCCAGTGAAGGGTTTGCCATCTGGATTTCCTGT

AAAAATCCCTCACCTTCTTTTCTCAACACATGTACTTTCTAAGTTTCTTATACTTGTGA

CATTTACCTTTATAGGAATTGCTCAAATTTGTGCTTGACCATGTTGAGGACAAGTCAG

CGGAACCACTTCTTGAGGTCAGTGATATAATCGAAGTTCCTGTTTGTAATAAAACGAA

-continued

```
GAGAAGAAGCTGGGTTTTTCATCACAACTCAAATAATCAGATCTCACATAGCTGATTG

AATTTTTAAACCACCATTTTTTGCGGNTACTATGNGAATCACTTGTTGCTAACAAAAT

GCTACCTTGNAGGGGNNGGTGGAAGCTCNAGTTGAACTCCNCCCTNNNCTTCNTGN

TTCACCNGNACGCATGAAAGAANNTATTTTTTGGNCATTGCNCCTGATTCNACTTT

TANGACAGCTATNGAAAGGNCATATGANGAGCTCCNCCATGGANNCCCCGANGNTG

GGCNCCCNAATATTGNCCCCATGATNNGNNNNANGNNNAGNNCCNNNANNNNNN

NCNNNNNNNNNNNTNNNNNANANNNNGNNTNNNNNANNNNNNNNNNNNGNNNN

NNNNCNNNNNNNNNNNNNNNNNNNNNNNNNNNNNNNNAANNNNNNNNNNNNNN

NANNNCCNNNNNNNNNNNNNNNNNANNNNNNNNANNNNNNNNNNNNNNNNNNC

NNNNNNAANNNNNNNNNATNCNNNNNNNNNNNNNNNNNNNNNNNNNNNNNNA

NNNNNNNNNNNNNNNCNNCNNNNNNNNNNNNNNNTNNNNNNNNANNNNCAACNN

NNNNNNNNNNNNNNNNNCCNNNNNNNNGNNNNNNNNNNNNNANNNNNNNNN

NNNNNNNNNANNNNNNNNANNNNNNNNNNNNNNNNNNANNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNCCNNNNNNNNNNNNNNN

NNNNNNNNNANNNNNNNNNNNNGNNNNNNNNNNNNNNNNNNNNNNNNNN

NNNCNNNNNNNNNNNNNNNNCNNNNNNNNNNNNNNNANNNNNNNNNNNNNN

ANNNNNNNNNNNNNNNNNNNNNNNNNNNNNNNNNNNNNNNNNNNNNNNN

ANNNNNNNNNNNNNNNTNNANNNCNNNNANTANNCNNNNNNNNNTNNNNGNNNN

NNNNNNNNNNNNNNNNNNNNNNNGANNNNNNNNNNNNNNNNAGNNNTNNNANN

NNNCNNNNNNNNNNGNNNTNNNNNNNNNNNNGNNNNNNNNNNNNNNNNNNN

NNNNNTNNNNNNNNNNNNNNNNGNNNNNNTNNNNNNNNGNNNNNNNNCNNN

NNNNNNNNNNNNNNNNNNNNNNNTNACNNNNNNNNNNNNNNTCNCNNNNNNNN

NNNNNNNNNNNNNNNNNNNNNNNNNNNGGCNTNNNNNNNNNNNNNNNNNN

NNNNNNNNNNNNNNNNNANNNNNCNNNNNNNNNNCNNNNNNNNNNNNNNTN

NNNNNCNNNNCNNNNNNNNNNNNNNNNNNNNNNNNNNNNNNNNNNNTGN

NNNNNCNNNNNNNNNNNNNCANNNCNNNNGNAGATCTCGGAGAGTGAACTTCAGC

AATCAAGTTCTCCGGATGCAGAAGCTGGCCATGCAGTACCATCTATTTCATTGGTCAA

TAAGAAGTTTCTTGGAAAATATGCAATATCAGCTGAAGAATTCTCTGAGGAAATGGTT

AGTAATATAAAATTTTGCATTAGGAAATCTGCCATTCGTAAGGAAGTCTTGATGAAAC

CAATTGTTATTATGCTGGTTTCCTTTTCTTTTGGCCTTGTGCTTCTAGTACTCACTTTT

ATGTTTTCAGGTTGGGCTAAGTCTCGGAATATAGCATACCTCAAAGGAAAAGTACCT

TCGTGGGTTGGTGTCCCAACATCAGTTGCGATACCATTTGGCACTTTTGAGAAGGTTT

TATCAGATGGGCTTAATAAGGTTGGTTGGTGGTTTATTTTGATGTATATACTTGAATA

ATAGAACTGCATGGTTCTTGGAGAAGTCAGATTCTTTAACATGTTTGAAATACACTAC

TGGGAAGGTAACAACGTGCAATTTAATGTCCACCAATATCTAAACAGCCATTTTTGGC

ATTCAATTCACTATATATTTTATTTCATGAGCCTGCTCTATAAGTAGCGTCTTCAGTAG

TTGTAGCTCATAGCTTCATAGTCTCATTCTACCATGAACTAATTTTGCTAACTTACATC

TACTCTTGAAATAAGTAATACTTGTATATTATTATCTTTGATTGTAAAAGAACTTCCCT

TGCTCGTTTGTCAAGGTGTCTTTTAGACAGGAGATGGAATTGACTGTTATCAAAGCAA

ATGATAACAAGAAACCTCTTGTTGATTGGTTGAGCAGTTTCAACTAATCCATTTTTTTT
```

-continued

TCTTTTTGGCATGTGATCTTTGTATTATTGGCCCAAATGAAATTCTATTTCTCCCATTA

ACCACCCACAATGGCAGGTTTGGGTACATATAGGCCAACCATGGGTAGGTGGCTTAA

AAGTTGAGTAAAGCATAATTGGGGATAAGGTGCACATAGGCACGGACCACCCACAGA

CAAAGTGCTTGCAGGCACTACTAATACATTATTCTATCACCATCAGGATTCAATTCTA

ACATGTACTGTTTCTTCTTTTTCTTCTTTGTACAGTTCCTGTATAGACCCTTTTGTACA

GTTTCCTAACAAATGAAAAAGATCAGTAGGAGACCCTCTTCTCCTGTTCCACAAAAAA

TGTTAAAATGGTCTTTCTAATATTTGATTGTTCTTTCTTTTATGGCAGGAAGAGCGCA

AAACATAGAAAAGCTT

Example 8

Suppression of mRNAs from Genes Involved in Mobilizing Vegetative Starch

Figure 10:
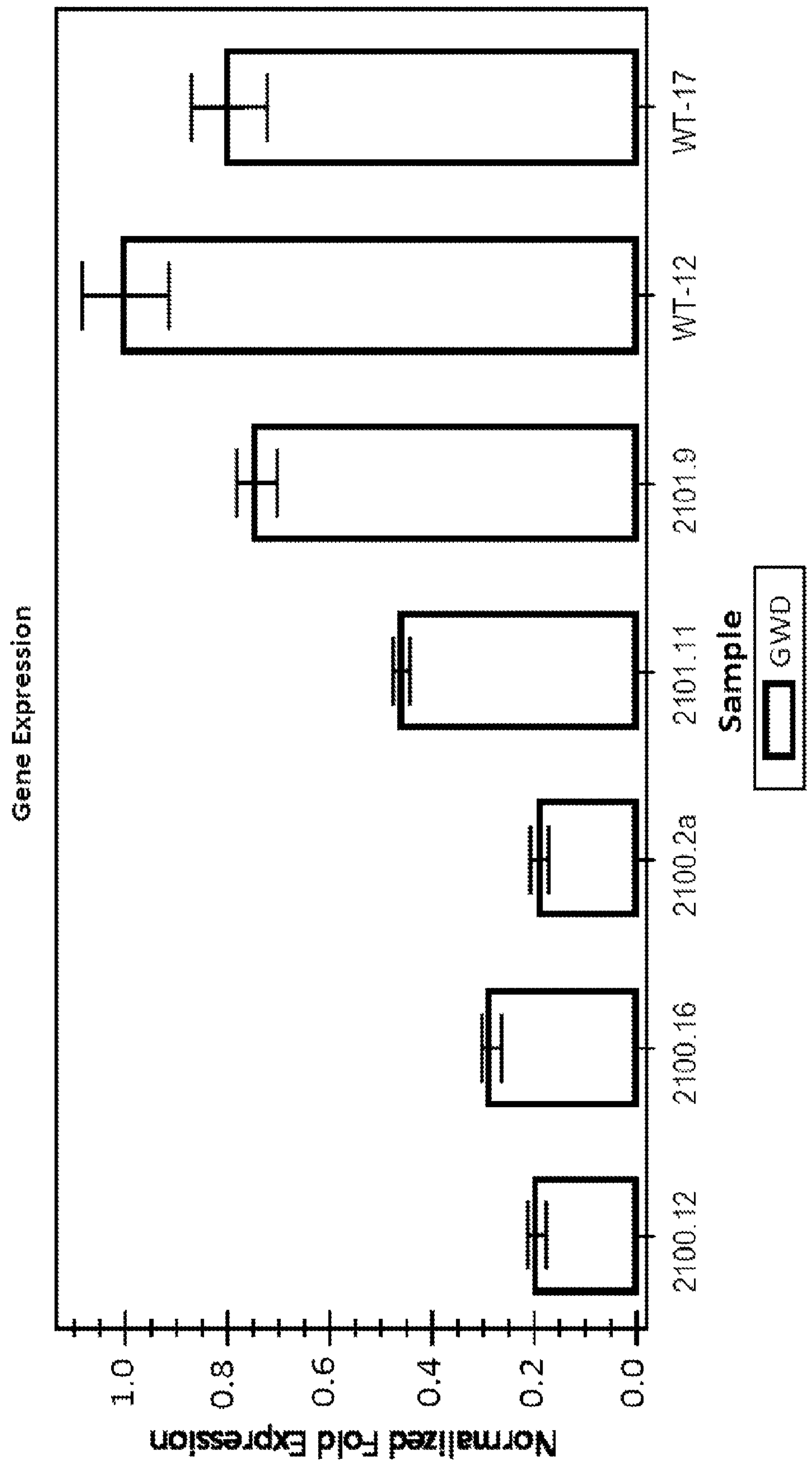
FIG. 10 illustrates GWD mRNA levels among plants carrying either pAG2100 or pAG2101, and wild type (WT) control plants.
Figure 11:
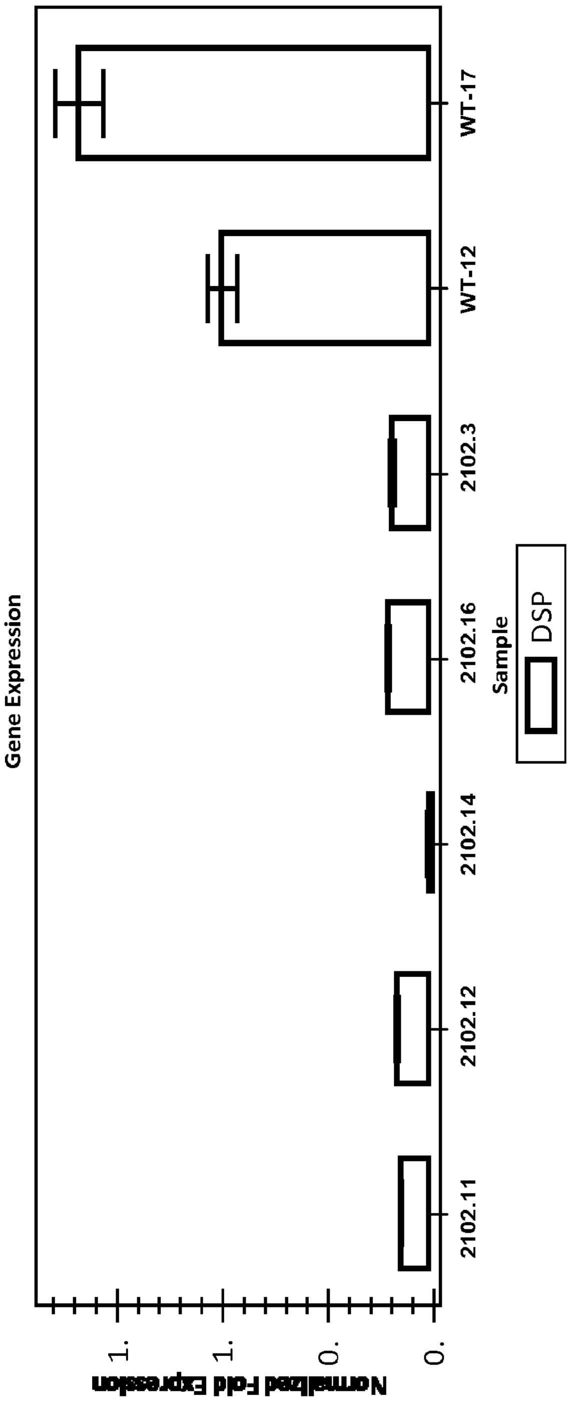
FIG. 11 illustrates DSP mRNA levels among plants carrying pAG2102 and WT controls.
Figure 12:
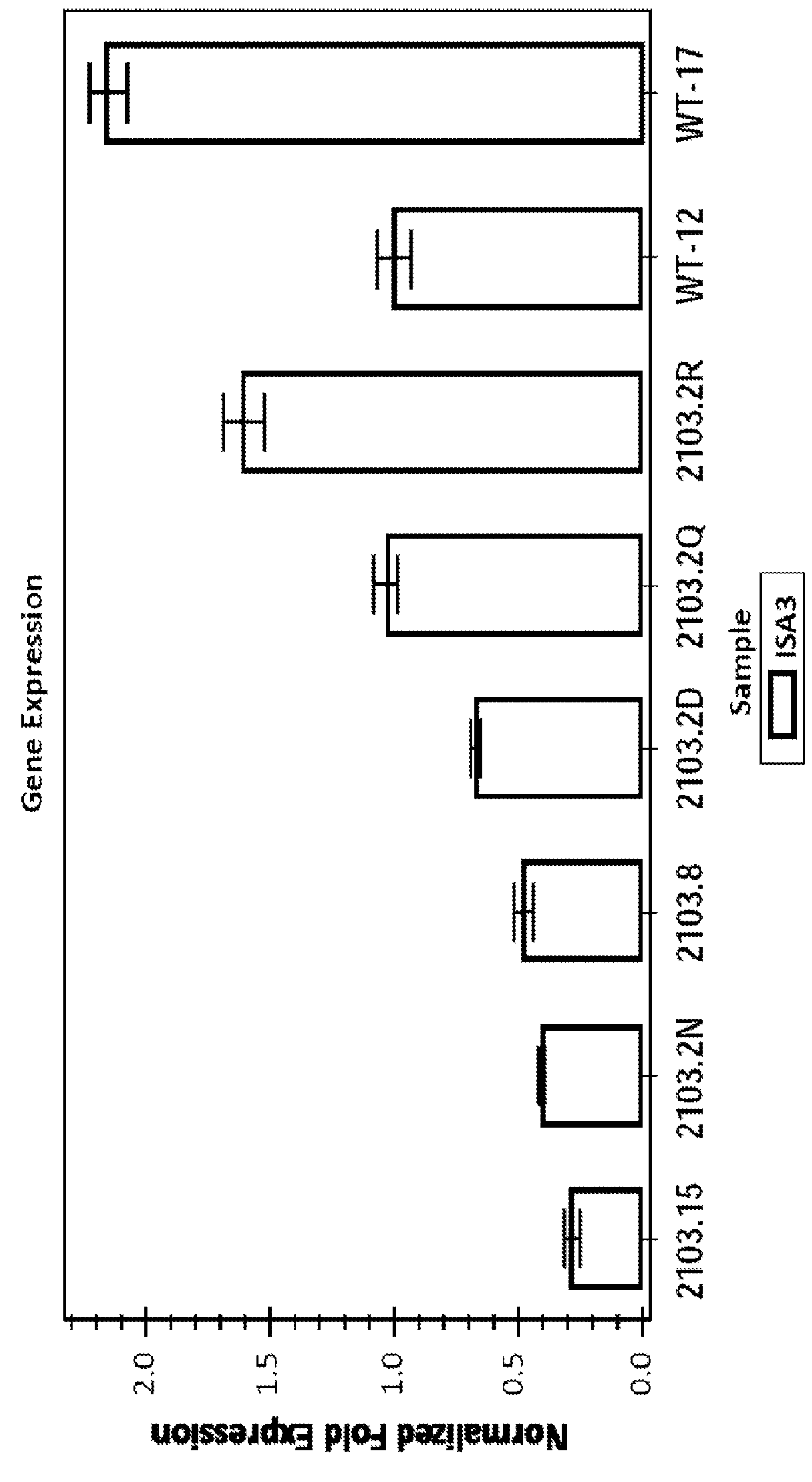
FIG. 12 illustrates ISA3 mRNA levels among plants carrying pAG2103 and WT control plants.

To determine whether the RNAi vectors described above were exerting an effect on targeted mRNAs in transgenic plants, RNA was isolated from several control and transgenic plants, and real time reverse transcriptase PCR (real time RT-PCR) was used to measure the relative abundances of mRNA species (FIGS. 10, 11, and 12). These results confirmed that RNAi can be used to lower the level of native mRNAs in transgenic rice.

Referring to FIGS. 10, 11 and 12, these figures illustrate that RNAi vectors suppress the accumulation of targeted mRNAs in transgenic rice. Real time RT-PCR was employed to measure the abundance of different species of mRNA relative to that of reference genes ("housekeeping genes" that are nominally constitutively expressed in rice). In several of the transgenic lines, levels of the targeted mRNAs were found to be well below those seen among control plants. FIG. 10, GWD mRNA levels among plants carrying wither pAG2100 or pAG2101 and wild type (WT) controls; FIG. 11, DSP mRNA levels among plants carrying pAG2102 and WT controls; FIG. 12, ISA3 mRNA levels among plants carrying pAG2103 and WT controls.

Example 9

Starch Accumulation Among Transgenic Plants

Figure 13:
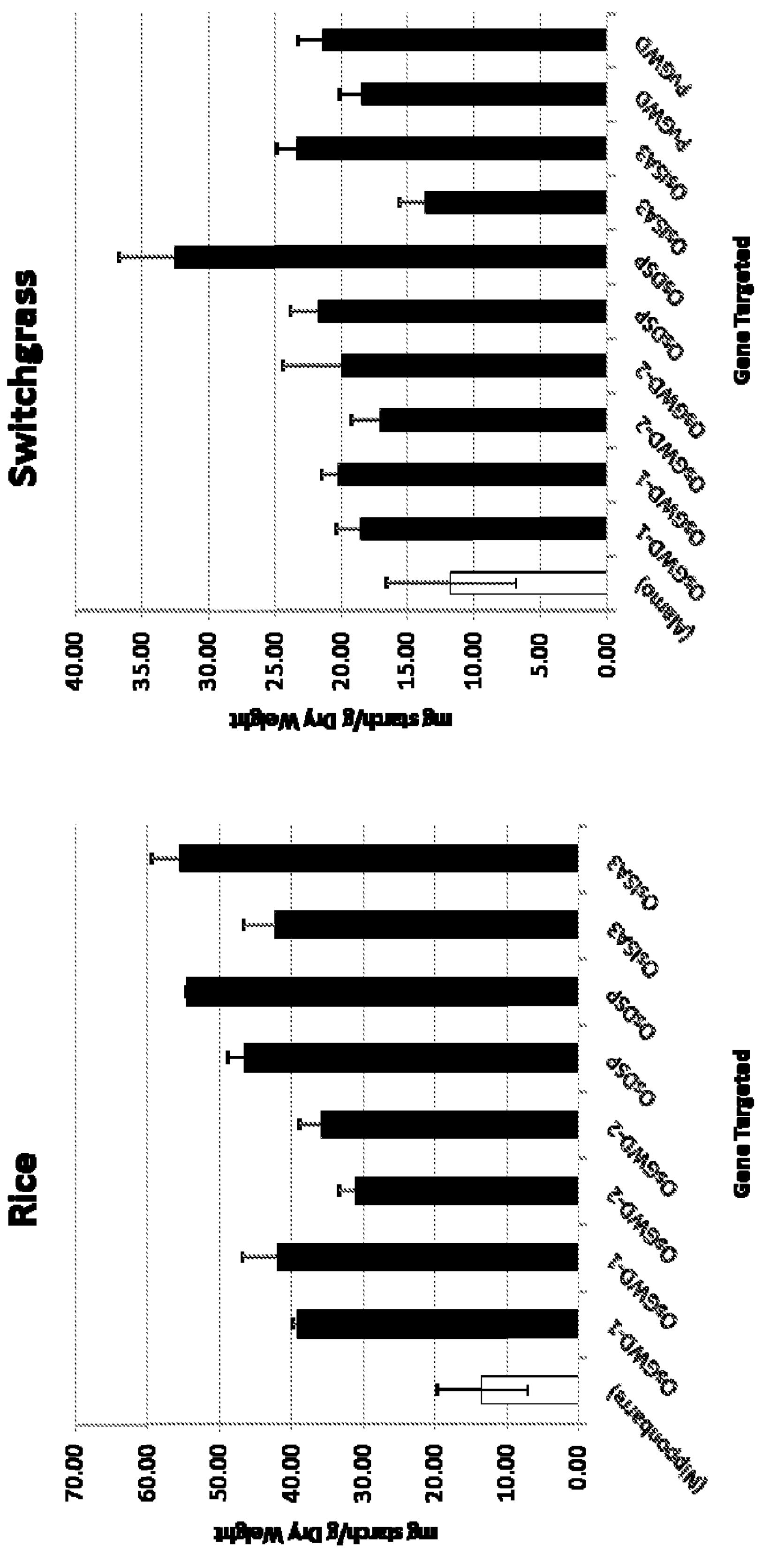
FIG. 13 illustrates elevated starch among select lines of rice and switchgrass that carry RNAi constructs.

Tissues were collected from control plants as well as rice and switchgrass plants that carry integrated copies of the RNAi transgenes described above. These tissues were then dried and milled to a fine powder. The starch content of these tissues was then determined by standard methods (Smith A M and Zeeman S C, Quantification of starch in plant tissues (2006) Nat. Protocols 1:1342-1345, which is incorporated herein by reference as if fully set forth). Referring to FIG. 13, elevated starch among select lines of rice and switchgrass is shown for those lines that carry RNAi constructs. Results from Nipponbarre and Alamo (untransformed control lines for rice and switchgrass, respectively) represent the averages from several different plants. Other results represent 2-3 fold replicate data from single transgenic plants. Transgenic plants are identified according to the starch mobilization gene targeted. OsGWD-1 plants carry the RNAi vector pAG2100; OsGWD-2 plants carry pAG2101; OsDSP plants carry pAG2102; OsISA3 plants carry pAG2103; PvGWD plants carry pAG2104, an RNAi expression vector that specifically targets switchgrass GWD transcripts resembling the sequences described above (see FIG. 9). As shown in FIG. 13, several transgenic lines of rice and switchgrass were identified that accumulate starch above the levels seen among control plants. In these examples, starch accumulated to levels as high as 6% among transgenic rice lines while only accumulating to about 3% in the highest of the control lines. In switchgrass, the highest Alamo line accumulated about 2% starch whereas the highest transgenic line accumulated about 3.5% starch by dry weight.

Figure 14:
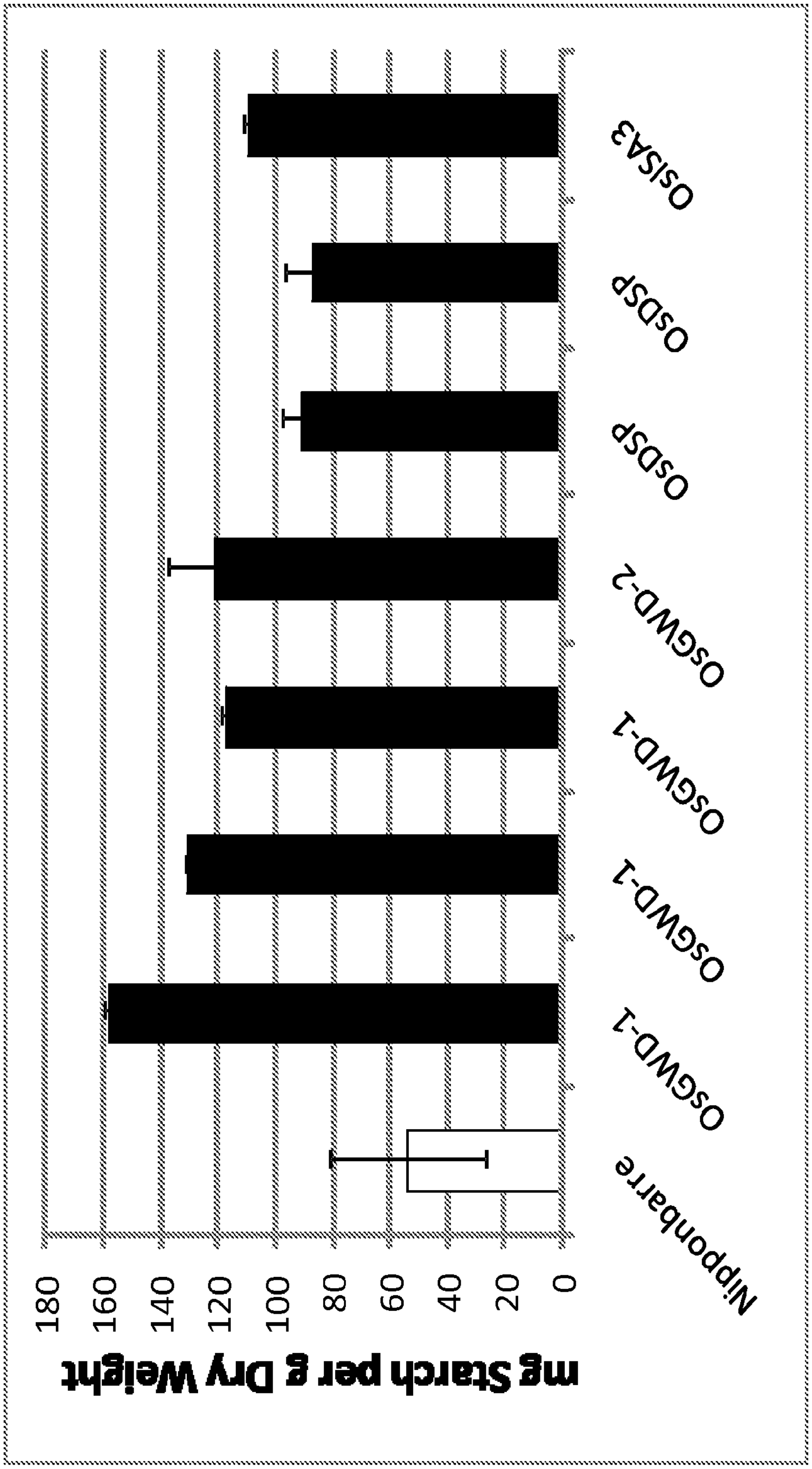
FIG. 14 illustrates starch content in transgenic rice lines, collected approximately 19 weeks after planting.

Referring to FIG. 14, starch content in several rice plants approximately 5 weeks older than those depicted in FIG. 13 was found to be 2 to 3 times than that observed in younger plants. FIG. 14 illustrates starch content in transgenic rice lines, collected approximately 19 weeks after planting. Nomenclature of plants is as in FIG. 13. Among these, one line expressing an RNAi that targets GWD accumulated starch to ~16% dry weight, while control lines accumulated no more than ~8% starch.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A transgenic plant comprising an RNAi construct comprising:

a first driver sequence consisting essentially of a first isolated nucleic acid having the sequence of SEQ ID NO: 8;

a second driver sequence consisting essentially of a second isolated nucleic acid capable of hybridizing with the first nucleic acid sequence;

a spacer operably linked to and between the first driver sequence and the second driver sequence; and a promoter operably linked to the first driver sequence, the second driver sequence and the spacer, wherein upon expression of the RNAi construct, an RNA sequence transcribed from the first isolated nucleic acid and an RNA sequence transcribed from the second isolated nucleic acid are capable of hybridizing with each other and causing inhibition of expression of the gene encoding an enzyme involved in the mobilization of starch, and the transgenic plant has an elevated level of vegetative starch compared to a wild type plant, wherein, the transgenic plant is the product or progeny of *Agrobacterium* mediated transformation utilizing a vector comprising the sequence of SEQ ID NO: 16.

2. The transgenic plant of claim 1, wherein the transgenic plant is one selected from the group consisting of a rice plant, a switchgrass plant, a sorghum plant, a corn plant and a tomato plant.

3. A method of agricultural processing or preparing animal feed comprising:

providing a transgenic plant, the transgenic plant including an RNAi construct comprising a first driver sequence comprising a first isolated nucleic acid having the sequence of SEQ ID NO: 8; a second driver sequence comprising a second isolated nucleic acid capable of hybridizing with the first nucleic acid sequence; a spacer operably linked to and between the first driver sequence and the second driver sequence; and a promoter operably linked to the first driver sequence, the second driver sequence and the spacer, wherein the transgenic plant is the product or progeny of *Agrobacteriurn* mediated transformation utilizing a vector comprising the sequence of SEQ ID NO: 16; and processing the transgenic plant, wherein the first and second driver sequences were expressed in the transgenic plant causing inhibition of expression of the gene encoding an enzyme involved in the mobilization of starch, and an elevated level of vegetative starch compared to a wild type plant.

4. The method of claim 3, wherein the transgenic plant is one selected from the group consisting of a rice plant, a switchgrass plant, a sorghum plant, a corn plant and a tomato plant.

5. The method of claim 3, wherein the step of processing includes at least one selected from the group consisting of processing for animal feed, drying, preparing for fermentation, acid hydrolysis, and amylase digestion.

* * * * *

SEQUENCE LISTING

<160> NUMBER OF SEQ ID NOS: 47

<210> SEQ ID NO 1
<211> LENGTH: 14001
<212> TYPE: DNA
<213> ORGANISM: Oryza sativa

<400> SEQUENCE: 1
ttggcatggt tgaagtcaag cgaaatatga caacggcgag gcgccgacga tgatggagac 60
cgacctaatg catcccgacg gcacggcaga gagcgagatg cacttctcat gcttgccgtc 120

-continued

```
gcgatttgcc tcacaacttg tttggcaact taaggaaaga tgattggaag tttagatcaa    180
gaaattgatg gtgagaataa catgagaatt tggtttttag tcccattttc ttattttata    240
aaggcggtgg gaattaacag ggagtttagt tgaagactag atcttaaatg aaatcagatg    300
gcttagattt gtttaggtaa tgtaaaggag gaatttcctg gccaagccac cccggcccag    360
ccctgctcct ctttttccta ctcccgacta gggttcgttc ggttgatgga tattgaaatt    420
agggggggagt gcaggtgaga gttgccctgg ggggccatat cagcgctagc gtaaattgtg    480
ctgagatgcc taagctcagc gccattatgg ctagcgctga gatcgaggag ccagggaagc    540
aaagcttcga gcggagtgcc gaacctcagt gctagtgtaa atggcgttga gatagctaag    600
ctcaacgtca ttacggctga cgctgagatc gcggatccaa agtagtccag gtgtaagttg    660
ctaagtgctg aacctagtgc cagaaaaaat ggcgctaagg tctgccattc caacgccaag    720
tcatttggag ctgaggtcct tgccacgtag gccaggggaa ggctgggccg cctccctggc    780
aggtgttagc gccaaacact ctagcattga gcacacggct tatttttagt ttaagttttt    840
tacgcgggct aatttataaa taagtttttc aaaagagcca atatttcgta ctaaccaaac    900
aaaatattta atagttttat ccctctaaat tattaatccc tacttaaaag ctgctcacaa    960
ccaaacacac cctagcgcgg ttacagggag agaagagggg aaaatgaatg gctgagagag   1020
cgatgataga ttgaccggtg aagagaaaaa ggtggaccca ctatatgaga tggagcgtcc   1080
gatatttctc ggtgcaccgg acgttttcgt ttttttaagc gttttcgttt ttgtttattt   1140
tcgatatagg aaggagagat atccatccgg atcccggaag ccgaatccat ccatccatcc   1200
atcccatact gcccttacga tcgagctgtt tgatattcgt gcagatgagc ggattctccg   1260
cggcagctgc tgcggccgag cggtgcgcgc tcggcctcgg cgtccacgcg cgccccgcct   1320
cgccctcgcc ggcgctgctc ccgccggcgg ctctccgccg cggccgccgc ctccccgcgg   1380
ccaccaccac cctcgccgtc tcccgtcgga gcctcctcgc ccctcgcgcc atcgccgctt   1440
ccaccggccg cgcctccccg ggcgtacgcg ctttttctcg ctctatcgtg cccgccacgt   1500
gttcgacggt gtgactcact ctctctctat gcttctgttt gtttgcagct tgtcggaagg   1560
ttcaccctgg atgccaactc cgagcttaag gtgctgctga tctaccatgc attttgtggg   1620
gggcgggttc acctggatcg accaatttga tgtgattttt gttcgttcta atggagcata   1680
tgctgcataa atttttgcaa acacaggtga cattgaaccc agcaccgcag ggttcggtgg   1740
tggagatcaa tctagaggca actaacacca gcggctccct gatactgcat tggggcgccc   1800
ttcgcccgga tagagggtga gacttatctt ctgtccctgt tgatgactag tgcgtgcgtg   1860
catgcccaat atcaatatat gcttctgtgt tacatgtttt gtatattttc gatttaaggc   1920
ttggtaatcc ctaacaaagc tttttgactg tacttagaga atggctccta ccatcccgga   1980
aaccagatgg cacgacagtg tacaagaaca gggctcttag gacgcctttt ataaaggtca   2040
gtcttgcatg acggatctgt cttgcaatgt aagtgcacat ggttagtaat ttctattcct   2100
gtctcgaatt tcagtcaggt gataactcca cgctgaaaat tgagatagat gatcctgcag   2160
tgcaagccat tgagttcctc atatttgatg aggcacggaa taattggtca gttctttttg   2220
ggttacccat cctaccctgt ttcttggaat gcagaagata tcaaataaca acactctact   2280
ttggacaggt acaaaaacaa tggccagaat ttccaaattc agctacaagc gagccaatat   2340
caagggcagg gtacatctac tgctacttct tctactgtgg ttccagagga tcttgtgcag   2400
atacaatcat atcttcggtg ggaaagaaag ggaaagcagt catatacacc tgagcaagag   2460
```

-continued

```
aaggcatgtc ctgtttttta atatatgtca cgttgacttt tattataaac tttgaccatt   2520
cgttttattc aaaagttttg tgcaaatctt aaaaatataa atattgctta aggtttctta   2580
gtgataaatc aagccacaac aaaaaaaaag atatttactt caatttttta aataagatga   2640
atggtcaaac atgatgtaaa aattcaatgg cgtcatatat tgaaaaacgg agatagtact   2700
agttttggtt tgccttatac aactcaatgg actaactcat tatttatgtg gttttctcta   2760
ggaggagtat gaagcagcac gaactgagtt gatagaggaa ttaaacaagg gtgtttcttt   2820
ggagaagcta cgagcgaaac tgacaaagac acctgaggca actgatagta atgctcctgc   2880
atctgaaagc actgtgacta ctaaagtccc agaggaactt gtacaagtcc aggcttacat   2940
aaggtgggag aaagcaggca agccaaatta tgccccagag aagcaattgg tactactcta   3000
aattatcagc tcaacaagct tttgctaagg tgactcttta tgaagattta tattttgttt   3060
tcgctaggtc gagtttgagg aagcaaggaa ggaactgcag tctgagttgg ataaggggac   3120
ctcagttgag cagttgagga acaaaatttt gaaagggaac attgagacaa aagtttccaa   3180
gcagctgaag gacaaaaaat acttttctgt ggaaagaatt cagcggaaaa aacgagatat   3240
tgtgcaacta cttaaaaaac acaagcctac tgttatggaa gcgcaagtag agactcctaa   3300
acaacccact gttctggatc tcttcacaaa gtcattacag gagcaggata actgtgaggt   3360
tctaagcaga aagcttttca agttcggtga caaggagata ctggttagga ttcttgactg   3420
acatttcata ttcacaaacc ttgcatccac caatctaatc tggcttaact gtttttaagg   3480
gaattaccac cgttgctcta ggaaaaacca aagttcactt ggcaacaaac tatatggagc   3540
cacttatact tcactgggcg ttgtcaaaag agaatggaga gtggcaggta aaaacaaaca   3600
tgtttgcaac tcctaaagct atgaactcat catctgaaat agacaatgtg ggcctgtact   3660
gatggggtgc tttgtaactg tgaaggcacc tccctcaagc atattgccat ctggttcatc   3720
attgctagac aaggcatgtg aaacttcatt cagtgaatat gaattgaatg gtctgcattg   3780
tcaggtatgg ataattttat cagcctatta ttttccattg tcttttacat ttcctgtcat   3840
ctaagtactt ccccatttcc aggttgttga gatcgagctt gacgatggtg gatacaagcg   3900
gatgcccttt gttctccggt ctggtgaaac atggatgaaa aataatggct ctgactttta   3960
cttggatttc agcaccaaag ttgcaaaaaa tacaaaggca attgcttctg tccacttttt   4020
gcatagcaac catgaaactt ttttcccttt gttttaagga taactttttt tacgacatgt   4080
tttaaggata aattcctcat atgccactga atatttgcta tatcccttat tttccactca   4140
tttcctcact gatatgtgtc aattagcggc atgtaagaga tgacttaggc cttgttcggt   4200
tatgcccgga ttcaatccgg accgggaatg acaagtataa taagaaattt atatagatac   4260
aatgagagac cgggatttat tccaggctgg gaactaattt actcatgata tggacaataa   4320
gagaccggga atcaatccac tagtcaagag gtgtagaact aatctgaatg ttttgttgtc   4380
cctatcatga gtaaattggt tcccgatctg gaataaatcc cggtctctta ttacatctat   4440
cataaatttg ttactatact tctcattccc ggcccggatt gaatccagat gtaaccaaac   4500
aaggccttaa aaattttcaa tgtcaaataa gaatatctaa ataattgtgg taaaaatcac   4560
ttactaataa actgttgaat atattcgtaa ttaaaggata ctggtgatgc tggtaaaggc   4620
actgctaagg ccttgcttga aagaatagca gatctagagg aagatgccca acgatctctt   4680
atgcacaggt caggtgacac aatatctatt acttgtatga cttgttctgt gtgttaaaaa   4740
aatccctgaa ctacctttat tcctctacag attcaatatt gcagcagatc tagttgacca   4800
agcaagagat aatggattat tgggtattat tggaattttt gtttggatta ggttcatggc   4860
```

-continued

```
tacaaggcaa ctaatatgga acaagaacta caatgtgaag ccacggtaga tacttgtttc   4920
atattcttca gtgaattttc tctctgtgca aaaagaaatc aaattaacta cataagtact   4980
tttttcttgt gatgggaata aaaaccttct agtcctaata aagcataaca ggaaaaaaaa   5040
tagaatgctg tttagcagac tgaacctatt ctatttgcat atcacacaaa catgactttg   5100
ttgcatcttc tttaacatcc ataatgatct acaactatgc agtgagataa gcaaagcaca   5160
agataggttt acagatgatc ttgagaatat gtacagaact tacccacaat atcaggagat   5220
cttaagaatg ataatgtctg ctgttggtcg gggaggtgaa ggtgatgttg gtcaacgcat   5280
tcgtgatgag atattagtaa tccaggtaaa ttaatgttcc taggtgaata tcaacttgtt   5340
tgttgatcaa cttgaactat acaacaataa atactagttg gttggtattg tagagaaata   5400
atgactgcaa aggtggaatg atggaggagt ggcaccagaa actgcacaac aatacaagcc   5460
cagatgatgt agtgatctgc caggtaattg acatgcagat atttaatgcc atacagattt   5520
cagcattggg gttttgatat ttatggactt gtgtctcttc atgggtaggc cctacttgat   5580
tatatcaaga gtgattttga tattggtgtt tactgggaca ccttgaaaaa agatggtata   5640
acaaaagagc gtctattgag ctatgatcga ccgattcatt cagagccaaa tttcaggagt   5700
gaacagaaag atggcttact ccgtgacttg ggcaattata tgagaagcct caaggtatgt   5760
caaacatctg gcgtagataa ttgagatatc tatgcagtat ctttacgatt ttacgtaaat   5820
ttttgctttt gcaaaggcct tattttgctt tgtagttaag aaatattaca agatctaccc   5880
taaacaatat actgctaatc acatatgctg aaaggtggca ttctctggta acagtacatg   5940
ttattatgtc ccatatgtgc tgaataaggg tcgaaagatt aggataaagg ctagattgct   6000
ctcgttggta ctgagcttgt cctgatatta agagactctg gtcaagctaa acctaacttt   6060
atgtttcttt tttgcttaat tgataatgtt tcgctttggt ccgttttaga tggagggtac   6120
cctgatacaa tcactgcgaa tggtaacatg ctccttaaga gtaaaatctg cataattgac   6180
atctccagtg aaatcccatt tctattatta ttttagggaa ttgcggcagg aatagaaatt   6240
tatctctttg ccttcatgta tgggaatctt aaggaaatga aacaaaaata tcacactata   6300
gtttctacgt ttcatatagt ttaccaatca ttctcttgaa tcgtctccat tatccagcac   6360
ccctattact agcattgtta ataaaaggca agtgttaaca tcaaactact ccatccaacc   6420
aaatttacca ggcgtacaca ttccaagatt caaactttgt aagtttgacc aataattagg   6480
ctaattatat atacatttag tgatataaaa aggtaccact agatttgtat ttcattctaa   6540
gattgcaaga ttcatttgta tgttttgacc aacaattaaa tggtgccgct agatctgtat   6600
tgcaagtata ttgtcttggt cttctaatta gaaaatttgt cattttcata attatacttt   6660
gattcaatag tattgtacat ttctacttct gttttcttag gcagtgcatt ctggtgctga   6720
tcttgaatct gctatagcaa cttgcatggg atacaaatca gaggtaccat tctcatgtct   6780
gttatactgt gaaagtttca tttggttata tatgatgtaa ttgtttcttt gggatacagg   6840
gtgaaggttt catggttggt gttcagatta atccagtgaa gggtttgcca tctggatttc   6900
ctgtaaaaca tccttgcctt cttttttta aaaaaaacac atttatcata attaaaagct   6960
cataatattc attacttcaa cagaaattgc ttgaatttgt acttgaccat gttgaggata   7020
aatcagcaga accacttctt gaggtgagca atactaaacc caggcatgtt tgcaatattt   7080
ggtgccatgt ccacgggttt acctccgttc cattatctaa aaaaataaag aaaaacaaaa   7140
ttacaagaca atacttagat ttcttataaa tgactgatag ctgacctgcc taatccatct   7200
```

-continued ggtctttgca acttccatat gcatcctttg ttgccaatgt tgaaatgcta ccttgcaggg 7260
gttattggag gctcgagctg aactacaccc tttgctcctt ggctctcctg aacgcatgaa 7320
ggatcttatc tttttagaca ttgctcttga ttctactttc aggacagcag ttgaaagatc 7380
atatgaggag ctcaataatg tagaaccaga ggttggttaa cacaggatgt tgctataggt 7440
tacattatgg catgtgtttg tctcacattg tatcttgtct ttttgacgat tcaaatgtat 7500
taagtcatgt tcctgtttta tctaatccag aaaattatgt acttcatcag tcttgtcctt 7560
gaaaatcttg ctttatccac cgacgacaat gaagatatcc tatattgctt aaaggtacaa 7620
ctgttctgtt tttttccatg ttatgtacac aattgtttag agaaatttac cttagttgtt 7680
ccattttcct aataaaagat acgaatagtg gcagagcaca acataactat ttatgtatat 7740
cagacagctg ctgagaatat ttgtcatatt gctgttcatc tgtgcttgtt atcctttttt 7800
ccatgtagca attagtttgg ctgttgtcct gagttttctt ttttcctgaa ataattaaaa 7860
aaaaagaatg aatcgactgt cttcagtata taactttgac catcagtttt ggtttataat 7920
tagaaacatt ttttaaaata atattatgaa agtcactgtt aatgatacta tggaagtatg 7980
gatatggtac cgacgttctt gttttagatg ttttactgga atgtatgcag tcatcagttt 8040
aattttctaa tctctttttc gcacaaaatt atttggattt gtcatgtgga tgatactact 8100
agatttgcca taaaaaacat taatgtcgtt gtatgtttaa taattttatt aagttataca 8160
atcaaacaaa taattgttaa aggtgcttgt tggtaatggt ggctgtctga aatgacaaag 8220
ttaaaaggag ctgaagttgt agcattttca tgtagccaat cttcgcatta caaagatgcc 8280
tatggttgag tggcatataa tgcaaaagtg tctttcttta tggactggag tgattataac 8340
tagtttttta aaagaaactt ttttatttga actatttgtg atttatgcat tacaaacttt 8400
taaaatgcaa actaacctag tatgtgtcat gaagggatgg aatcaagcct tggaaatggc 8460
taaacagaaa aacaaccaat gggctctcta tgctaaagca tttctggaca gaaccagact 8520
tgcccttgca agcaagggag aacaatacta taatttgatg cagccctcag ctgaatatct 8580
tggctcgtta cttaacattg accaatgggc agtaagtgct taggaacttc agctattttt 8640
ctatccagac acttaggaac tagtcttaag tatcattttt ggcaggttaa tatctttaca 8700
gaagaaatta ttcgtggtgg atcagctgct accctgtctg ctcttctgaa tcggattgat 8760
cctgttctta ggaatgttgc acagcttgga aggtaaactg caaattcttg attatcattg 8820
tattctttac cttgtgcctg acatttattg cctaacagtt ggcaggttat aagcccagtt 8880
gaagtatcag gttacattgt agtggttgat gaattgcttg ctgttcaaaa caaatcctat 8940
gataaaccaa ctatccttgt ggcaaagagt gtcaagggag aggaagaaat accagatgga 9000
gttgttggtg ttattacacc tgatatgcca gatgttctct cccatgtatc agtccgagca 9060
aggaattgca aggttttccc agttcacagt tatgtgcaat ctttaataag attcgtcttt 9120
tttattgatg taacattgac tatcttttct ttttgaaggt tttatttgca acatgctttg 9180
atcctaacac cttgtctgaa ctccaaggac atgatgggaa agtgttttcc ttcaaaccta 9240
cttctgcaga tatcacctat aggtaattct tgttattgtt ctgtgaatta catatatgat 9300
atatctgatg atgtgtgagc tatgctacgg atttcatcat gctagtaact tattttttc 9360
agaggtttct tctatgagac tagatcgttt ttatttaata ccttaagttc cggttagggt 9420
gaggataatt aaatctcttg ggaactactg gtagttgttt tttgaaggac agtttcaata 9480
ccataacaat ggccagtaag atttggttta cagggttaat aaaatcttcg gttatatagg 9540
gcctgtttgg gtgagctttt agcttctgca gcttctccca gaatcagcag ctcccctaaa 9600

```
cagtctagct tttggtccag attctgagaa gctgtagttg tagaatccag aaaatgaact   9660
agaagccaga agctggaaaa cctagctttt ccagattctc agaagctggc taccaaccaa   9720
ctacttctcc gaatcttaag ctcccccaaa caggcccata gataaccagc agcttaagtc   9780
cctttactat caccatgtgg tgatttcagt tagtcaagtc aaccagtttt taatagctta   9840
gtttttagt gttttttct tgataatgca cagctttgct taattgtcca tcaaatgttt   9900
acattctagt atctaccatt tgatagggag attccagaga gtgaactgca atcaggttct   9960
ctaaatgcag aagctggcca ggcagtgcca tctgtgtcat tagtcaagaa gaagtttctt  10020
ggaaaatatg caatatcagc agaagaattc tctgaggaaa tggtaaataa aacaattata  10080
ctccgttata ttaatcgact tctttttgaa ttaagacttt gccgcattag ctgttgttat  10140
tctttttccc attacctttg accttgagct agcttcacta ttcattgtca ggttggggcc  10200
aagtctcgca acgtagcata cctcaaagga aaagtaccct catgggttgg tgtccctaca  10260
tcagttgcga ttccatttgg gacctttgag aaggttttgt ctgatgaaat caataaggtt  10320
ggcaattttt ttgtgaacat taaatactga caggagcttg tgattgtgtg atgagcctgt  10380
ttattcttca agatcaacat atacttacaa aaataaaaaa caaatgtaca gtttgatatt  10440
ctcaaccaaa gttcttttta tgtttctatc aaacgacatt ttctgcattc cacaggtctc  10500
ttttgtatgc aaaacccaga taagtttcta gcaggcaatt atttattgat cctttagtag  10560
catcttcaga agccggtagg tctagctcat tgcattacat caactaaatt agctggttta  10620
caatgacacg ttgaatatgt aatgattttt gagacagttg attgtttttt ctttattggc  10680
aggaagtcgc gcaaaccata caaatgctga agggaaaact tgctcaagat gattttagtg  10740
ctctaggcga aatacggaaa actgttctca atttaactgc tcctactcaa ctggtaagat  10800
attatagcgc aacataaagc tgattaagta ttctccatct ccgcatattt caatagaaaa  10860
aatagaacat aaactcttgt ttgcatttgt tccaatcaaa aacctaaatc tttactttgt  10920
ttaaattttc tgtttggaag aacaaggctt atttcttttg tttaccagat caaggaactg  10980
aaggagaaga tgctaggctc tggaatgccc tggcctggag atgaaggtga ccaacgttgg  11040
gagcaagcat ggatggcaat taaaaaggtc tgctgtccta ccattcatac cggagataga  11100
tccagacata tatctctctt atttctttct tttagctctt tagaatacgt tttaccagtt  11160
taaatactgg aattggactt ctttgcatat aactttagct tctttgcata gagtacattt  11220
tctcataata tattcatggg atcatttgac accacaaatg gcacctggat ttgttatggg  11280
tagggagagt tattaatcgt aaaatacgaa tgttaaagaa gccctttcta aaagtggtca  11340
tcagatatct aactttattg tatttaggtt tgggcgtcaa aatggaatga aagagcatat  11400
tttagcactc gtaaggtgaa gcttgatcat gactaccttt ccatggctgt acttgtacaa  11460
gaaattgtca atgcagacta tgcctttgtc attcatacta ctaacccatc atcgggagat  11520
tcgtctgaga tatatgctga agtggtgaaa gggcttggag aaacacttgt aggagcctat  11580
cctggtcgcg ccatgagctt tgtatgtaag aaaaacgacc ttgactctcc caaggtaaaa  11640
gatttcttat taccacttga aattgtatgt taaggtctac ctgagctaaa tgcattccat  11700
ttgataggta ctgggtttcc caagcaagcc aattggtctc ttcataaaga gatcaatcat  11760
ctttcgttca gattccaacg gtgaggattt agaagggtat gctggagcag gactgtatga  11820
taggttagtg aaagtccatc ataatttttg tagttcgctc aagaatttat ttggcattac  11880
aactaagctg actgcttgtt tcagtgtccc tatggatgag gaagatgaag tcatactcga  11940
```

-continued

```
ctacaccacc gaccccctca ttacagatca gggattccaa aaatctatcc tctcgagcat  12000
tgcacgggct ggtcatgcca ttgaggagct ttatgggtcc ccacaggatg ttgagggtgc  12060
agtgaaggaa gggaagctat acgtagtaca gacaagacca cagatgtaat ctatatgtat  12120
attttatagc caagtcaatc aggcaatgtt gtagagtaag atatacgggc cgtgggacat  12180
gtataacacg ttacgccctt ttttttatta tttgctttca tactcacaat acactaattt  12240
atagggctta ttttatcgcc aataagtgta atctgactat gatcataaat aagcctccta  12300
ggctactgaa aaccattaaa ggttattttg atcaactgga ttttgcttct gcaatgataa  12360
tgtaaatatc agtggtctgc ttgcttttgg tcctatccct ttaaataaag ccaagaagtt  12420
gaaaagtatc agaaagttct tataaatata tgttctctga aatggacagc tacatggaga  12480
tatctgaagc aaatatttga agagagctat ccccagtcga ctgtaaccaa atactgaaag  12540
acacaaatgg tgggattctt cagcctctgt acttccactc aatattatcg catgcagctc  12600
aggaatggat cagttcagta tgaactgatt agaccaatta agtacagacc aaagagcatc  12660
atcaggtgct gcagctctaa aggggaaaag ccagggagga ctactaccaa gtgctgggag  12720
tgacggttaa ttcaacgcct caggagatca aggaggctta caggaagctc cagaaacgac  12780
accatatcct gatattgctg gctacaaggt gtgtcgtcca tccgcatccg catctacttc  12840
gattttggtg ttgctagcta cagggttcag tttttagttt cttggaagcc cggatagaaa  12900
tgttatacct ttatcgatat caagcttatt ttgttctttc ttgtggagtt taaacgtgaa  12960
attcgcactt gaattttcag ggtcatgcat gactacaccc tactgctgaa tgaggcatac  13020
aaggtattga tgaggaatta atagttcaag gaacggtgat gctagtggca gaggctttgg  13080
gagaggtttc actggaaaag ggtacagttg tttgtaatgg gcctgtgaga agccatgcac  13140
tctttgagga cgagaacaaa tacataggta cgtagcatca acatttctga tcatatatga  13200
aggtctcccg gtacatgcca tcttataagg tggaccttta tgatttteta aagaattaat  13260
ttttgaatgg gctaagaccc aaccattaat tccaacacta attagtgcag aagatacagg  13320
taccaatagt tgttcgagtt tctaacgaag catacactgt cattcaaact gtttgaggca  13380
ctatttatca gggtaccaat gtactaaaat tatttaaatt tttgaacaaa atttgaacaa  13440
aatattgcca aatttacaaa aaaaattgaa aaaaataaaa atttcggatg taataatatc  13500
atatcggggt ctgatagaac caaaatgtcg taaatttcat cccggaattt tgaaccctgc  13560
tatttattag ttccatatcc attgctccat tggagatttt ttataccaat atttttttat  13620
ctaaacacat gcattcatct aattcgagat gtatgcatgc aaatccagca tttaaatttg  13680
taggcatatt cttacatgtg tactgattgt tccatcacat caaactgttc gtccaacaaa  13740
ctactaaatc cctggtgaat tgtcctttct tgctcatctc tctactaatg cagcaaacaa  13800
ttttgcttga gttcagatgg tgtttttttt tattttggaa attggaactg tatcggacat  13860
ttagttaaat agacaaccta gttattttgt tgggcatcag gccatcagct caaccagatt  13920
gacatggtca cttgtgcatg ttgcttagaa acagaattta ttaagggagc cgcatgtgtt  13980
tacatgacaa aattttggtt a                                             14001
```

<210> SEQ ID NO 2
<211> LENGTH: 5287
<212> TYPE: DNA
<213> ORGANISM: Oryza sativa

<400> SEQUENCE: 2

```
acccacctca cctcacatcc tcttcctctc gtctcgcccc cggccccctt cttctctcct     60
```

-continued

```
cttcgcggcg actgcgaaag ccatctagta tctccttcct tccttctcga ctcgcctacg    120
ccaacgccaa cgcgagatat ttttgggctc ctcggcctcg gcgtcctcgc tcgccgtcgc    180
gcccgcgcgg gcagggcacg ggagggaagc catgaactgc ctccagaacc tgctcaagta    240
agtgagtgcg gtggccgagg ccccggcgcc tcctcctcct ccccgcttcg attcgattcg    300
acacttgttt cgcctgttcg tcactgctgg atttcctcgt tttcgcccag ggagcctcca    360
atcgtgggat ccaggtccat gaggcggccc tcgccgctca atctggtgac ccctcttcca    420
ttccattcca ttcacgtcct tgtttttttcc cctattattg atggatcggc tcccttattt    480
gttcctcttt ttgatgtcca tgatgactag acgatggttc gtggcgggag tcgccgatca    540
aacactgtca aaaccgtaag cattcccttc acctgcatat gaattgatct acccgagatt    600
agaggcagtt aactcgtcaa atccccgaca ataataatta tcatatgata gaatccgctg    660
cagtgcagcc tgcatgtttc accccattgt gtaaaccttg tcctgtaaac attccaggca    720
tccggggcgt ctacttctag cgccgagagt ggcgcagtgg aggcgggcac ggagaaatcc    780
gatacgtaca gcaccaacat gacgcaagct atgggagcag gtaaagaccc attatgcctt    840
acctgcaatc aatactacat gttagctgta ccacgacttg tcggattgta ctcgacctgc    900
tgctcgctga ctttaatggt tccttaccca gatgataaat ggggaaatgc actaacatca    960
tgtagatgtc accatcaaag tgttgtgcca ccggtgtgtt tttgtgtctg tcggtgcaaa   1020
ctcacatgct tgttttactt actccctccg tttcacaata taagtcattc tagcatttcc   1080
tacattcata ttgatggtaa tgaatctaga catatatacc tatctagatt cattaccatc   1140
aatatgaatg tgagaaatgt tataatgact tacattgtga aatggaggaa gtagcattta   1200
tgtgtcattt ttctccattc ctcatgaaca agtcacgacg cattcacaat tttttttctt   1260
actcttacct tccccttctt ccaacaattg accttgcaga gggtgcatta gtcatgtgta   1320
caaacattgt tctgccactg atttttatct taaaagtatt cttgcttgtc cattgtctta   1380
agattttcat acaactttat agtttacacc gaacagttga aatattattt ctttgaggac   1440
aatggttgtg accatattta tggacaggct tgtactattc actaagcttt tactggatta   1500
ctgtctatca ttgatcactc ctgagatcat ttcctttttt tctaaatcat ttctagtgtt   1560
gacgtataga catgagcttg gaatgaacta caatttcata cgcccagact tgatcgtggg   1620
ctcctgctta caggttctca aatatcatct atctcaacca atttacagaa ggaaaaaaaa   1680
acacttctta actctgtctg attagctgca ttcatgtgca gagcccactt gatgttgata   1740
aacttaggga cattggtgta aaaacagtat tctgcctgca gcaagatcca gaccttgagt   1800
atccctatta ttgatttttt tttctcatca tgcttataaa aagaaaggag catgccaatt   1860
atgttgcctg gtttagagaa tttgagcctc ttgattcttg aaatgtatgc tgtcacttac   1920
tgtgaatcac accaactata tcgaagagaa ttataaaatt ctggtgatgg ctttttatca   1980
aaataactat tggaataggg agtgctttta tgtcagcatg ccttcttcct aattatgtta   2040
ctgtgctatt ggacaataac cataattcta ttgaacaatt acatttgctc ctcacttccc   2100
tgctactgta cttcttctgc agctatgata ttcagcacaa tgcatattgt acatctcata   2160
aaaatagttc tattttatac tgacagcata gttgcttgtt gtttccattg ctgcccaatg   2220
tgttctttca gtgaatagtt gtattccatc cttaaccagt tcagatattt tggagttgac   2280
atctgtgcca ttcaagaata ttgtctacaa tgtaaagata tagagcactg tcgtgccgaa   2340
attaggtacc taaagttcta taacttcgtt ttactttgag aaactaagaa ttttggtgat   2400
```

```
ttggtgtagt ctatgtcaaa tgcaatagaa atccctttat tttcattaat aatgtctaca   2460
agatggcatg atctgaacgt ctatctcttt tccccttct ctttccaatt ataattccta   2520
tgctcttcta tttttggaat agatgattca tctttccttg aatcagcatt tatttgtcaa   2580
atgtaacttt tcctgcattg acttgaatgc cttttccatt gtctgttctg tccatatttt   2640
caaagtctta aagtggcata atgtttaatt acaccaggga ttttgatgct tttgatttgc   2700
gattgaggct tcctgctgtg attagcaaac tgcacaagct tgtcaaccat aatggtgggg   2760
taacatatat acactgtacc gctggacttg ggagagctcc tgctgtgaca gtaggtttcc   2820
atggtctttt ctttttgtt tcccaagaat tcttataata ggtttaggtt tacattataa   2880
tattgtcttc ttctttcctg ttcagttagt tgttggccca cccacaaaaa gggaagaaaa   2940
atggaaaaca catatataca ttcccaaata atgaacatta actagtgtct agtgagtcct   3000
agactataac ataatcatca caggtatagt cggtaaattg ttctatttgc acaatgttat   3060
agtacttaaa taatccaata gtatcacaac tgactttcac tctcatgata ttgctgatgc   3120
ctgtccaagt ttcacgctgg attgatgatt atagtatcag gatcctctat gatttgatgg   3180
tgtccattat cttgagagca gcaatattct gatcctgata ccattatata aattttcagt   3240
tggcgtatat gttctggatt cttggctaca gtcttaatga agggcatcag ctactacagg   3300
tatcttatac tgtttagaac agtacaaaac aatgtgtgtg ggaaaataat tttgtttta   3360
taatttgtgt gcactggtaa taccaatgga taccaacagg ttgcctgtgt gtacatctct   3420
cacaactatc ttacaaagta aagtctgttg gtggtctggt gtcctgttac cacattgcta   3480
ctagttatgt tactatgcta cttgcttccc ctgaacatat gtttcttctg cagagtaaac   3540
gagcttgctt tccaaagttg gaagccatta aattggctac tgctgacatt gtaagtgaac   3600
actcaccaat atttcttttt ttttccctca gtgtgtagtt atgatggtta agataaaagg   3660
cactgcttgt acaattttgt gctaagtgat gactctctta atgtttagct gacaggctta   3720
tcaaagaatt ccatcacttt gaagtgggaa agtgatagtt gttcttctgt tgaaatttct   3780
gggcttgatg tcgggtgggg acaggtatgc ttttgtgcca actatggtag atatattaat   3840
gtcgaaaact catccactcg gtggagtttt ttttaaagaa cttttttaag tttactttcc   3900
agtgtaatag aagctaactg tggtgttagc accttttttt tttttgcaga aggcattctt   3960
aattgatttc ctgtttatga tttgcatttg ttctgcttac tcagataatt cctttgacat   4020
acaacaagga gaaaagagct tggtatcttg agagggagtt gcctgtgagt atcaaaatca   4080
gcattatatt atcaatttct agactttatt ttttatcact catcattcta gtgcttgtat   4140
agtagatgcc ggatgccacc aacgtgtaac ttctagttgg atcatctaaa agtctttacg   4200
tttgaggaat acttgaggat ttgaaccgag ggttctgaaa gactgtaact agagaacctt   4260
agtttgaacc gtatttggga tatcctaatc tcatatgttg acactggagg caatcgtttt   4320
ggtcctttcc ctttacagtt attgatttgc catatctgtt acacagttgg actcgatttt   4380
acagtagcta acttcacact cacttttcct tatacatttg ccttgtgttt cccgaaggaa   4440
ggaaggtatg aatacaaata tatagtggac ggcaaatggg tgtgcaatga caatgagaag   4500
aagaccaaag caaatgctga tggccatgtg aataactacg tccaggtgag ttacttccca   4560
gctccctagt tccctgtatc tgtggacgtg ttggatagga taacgtaact tgacgtcttc   4620
attgcaggtc tccagggatg gtaccagcga tgaagagaga gaattaaggg agcgtttgac   4680
tggtcaaaat cccgatctta cgaaggagga aaggctgatg attagagagt acttggaaca   4740
gtacgttgag cgatagaggt aagttgaaat ttattcagac tactagtatt gtgttgcagg   4800
```

ggttttgctg attatgctta tgcatgaaca tatcattcgg attggactgc actaatctgc 4860
agaattgaca ttggattatc gactcgtttt gggctcgctg tgcaacaggg aagacctgct 4920
gatgatcaac aacagatcat ggagcttccc gatgaacaga gtagacggag cttccaaatg 4980
ttatcatctt gggtcgccat gtcaatacta ttaattaatt agttcaaatc aaccctgtaa 5040
atggtttact catgagtaat cacgagtcgt cgctgtaaac aaacgatgca taagacgagc 5100
aatatgcgtt tgctcatagt aacactgtgg ccgtataaca aggtagaatt aataaggctg 5160
ttagactgta ataagggctg ttaattaaca taacaggtta caaagttgtg taacatatat 5220
gttattaatg ctgactcgtg aatggaagac aaattaattt tgtttgggac agttgctccc 5280
gaagtga 5287

<210> SEQ ID NO 3
<211> LENGTH: 7001
<212> TYPE: DNA
<213> ORGANISM: Oryza sativa

<400> SEQUENCE: 3
cttaaaggat gtaatatatc tcagttttac ctatggacat ccaaatacca aattattaat 60
tatattttct gttaagcctt tatttataca gctttacagc tggttacttt taagaaaaat 120
gctatgattt atttctgaaa ttactgcttg tgtatcttgc tgatctaaca tgtttaatga 180
ctagatactt acatatcaca tgatttgttc aaaatttttga aagtgtaatt gtttcacttt 240
taagtcttaa cggtatgttt tggttcaacc tagggaatac actgaactgc aaccatcctg 300
ttgtcaagga gctcattctt gacagcttga gacactggta tggacaactt gcagctaaga 360
tttttctcat aaatccaatt gtgtgtagat tcatccatat ttctttgttt catcttgact 420
atgtcggcat tattcataat caagtgtcaa aaaatatcta tatcgatttg agctttcatg 480
ttggtatgat cagaccaaga tgatgtatcg acagcctaaa attattcaaa atttcctcta 540
ggctatagca catgcttgta gctatttggc ttgtagcaag acagttgata tatgagagat 600
agttcatggc tatgtcttat tgtgaacctt ggaaaacaag atagccagaa actgcaacaa 660
aaacagttat ttttatacaa ataactgaat tatagcatgc atttttattt tctctttgac 720
aatggttttg tcatatttca aatgtcattt ctaatctcca tgcttgtttt aatgcatcaa 780
gggttgagga gtatcacata gatggatttc gatttgacct tgcaagtgtt ctttgtcgtg 840
gaccagatgg ttgtcctctt gatgcacctc cactcatcaa ggtataatgt agatgcagac 900
tttaggtttg aacactaaat atgtatggct gcttaccaag cctgtgcaga ccgaattttg 960
tttgtctaaa taagtgaatt taatagattt catgtaaaaa caacccgtac gttacattat 1020
atggatgatt ggatgcaaat tatgatgtac tgaagtactg aacttccagc aatcaattct 1080
aatcaacttt gcactattgt tgattgtttt cttgtttgca tggttttgtt cattgaatac 1140
atatctagtg caagctcaca ggaatgcaat catgaaaatt tgcaatgtgg gcagctatat 1200
aagatacagt atggactaga tgtagggctc ttgaggttca tttgaaagtt tttttagtga 1260 ccccccctcaa acgttagaaa attgtattta tgacaaattc caccttttca agaccatcta 1320
aatcctaatc catcaatctc tggtcataca actcacgttg atgtatcgag actagtggct 1380
tttatgtttc ttcatattaa tttatttggt tgtaggaaat tgccaaagat gctgtattat 1440
ctagatgtaa gatcattgct gaaccttggg attgcggcgg cctttatctc gtagggcgtt 1500
tccctaactg ggacaggtga tttgaacact tctatatttc tataaaaaga atttggtggt 1560

-continued atagatgttt tatccttgct tcttttagga ctaaagattt ggtgatacag taacacaaaa 1620
cagtaactat tttctgttat ggataatatc atgctgagat gctcattcct aaagtactta 1680
acaactgaat tcttgaaatg agagaattat tgctagtatc acttttctca ttggacttgg 1740
caaacatgct tcattgtgcg gttcagtgac ctttccctac catgcataca cagatcagtt 1800
attctataat gagtttcatt tatttttaaa ggtatggtga tcatgtttaa cattcctctt 1860
gcaggtgggc tgaatggaac ggcaaataca gagatgatct tcgaagattt attaaggtaa 1920
tatgccggga gagaagattt tttagaaaat acagataaga aaaattgtac tcacctgcaa 1980
tttatggtag agatttcatc atggcagtat atcaggaatt actgctgagg aataggattg 2040
ttatgccctt atgctaatct atcattccct tgcctcatcc ctttctgcca gagtatttta 2100
attaaccatg ccataggata gttattttac tgagcatgtt aatgaagttt agcttctcac 2160
tgtacctata tttagtttta attgtccttg atggtgtatg aacattagcg gcaaacttag 2220
gttattgtgg aacagccaat ggctaggaaa catggagatt ttgttaaatg tttaactaga 2280
tataggatca gtacccttgc aaaatcagta ttttatttaa tttaatgggc aattctgaag 2340
catacgatca cagttccgca tattatttga gaaaatggca acatactttt atgcaatagc 2400
tctgtaccag ttgtgtaaag attaccaggt tactgaaaca taggggtaga attaggtggc 2460
tgcagtttcc caaactctga tcttggctat ccataactcc attcttgagc caaatattta 2520
gatgatctcc ttcagaactt gagcataatt ttttttaacc atttcaaaca tcagtgagtt 2580
ttttcaactg aagatctgaa tttactgaac attctgcatt ttatcagtgc ttgcctagca 2640
tagccatgag aattcttctg tttgtgttct tttattcttg tttctataat aacgaccgaa 2700
tgactgattg gatgctgcta aacatttgga gttgtttctc agggtgaccc tggtatgaag 2760
ggggtgtttg cgactcgtgt gtctggatct gctgatctct atcaggtccc cctcttttag 2820
atgttatttt ccctttactg ttattttttta tccatttgct taggatatcg cttgtttttg 2880
aactttgatc cccccccaca cacacaaaat aaataaaata aaaatccatt tccaaacaag 2940
agcggcttcc aaagttattg ctaataagtt taggtttaat tacatgcttg ttacttttgt 3000
atcactgtta gagcataggt cattatcaac atttagcgtg ccccaaattc tatcatgtca 3060
attgtgttag ttcagtagga tttctccagt atccaattgt ttaatggata taaatgtatt 3120
cagggtctag tgacatacca tttgatagtg caaaacacag tatggtatga tgccacctat 3180
tatttcattt tgtgaggatg tgtaaggaac ctctgtggac aaatttttaa gaactactgt 3240
tacactgaag ggttcagac tcagttattt tttgtcaaga aacaaaaata tgtaaaataa 3300
aattcacctg atgtggcagg tgaacgagcg gaagccttac catggtgtaa attttgtgat 3360
tgcacatgat ggatttactt tatgtgacct tgtttcttac aacttaaagg taactggagt 3420
aagctaagca gtttagttaa gatcatttat ttatactgtg aagtgtatgc taatctgcct 3480
tctttttatc aaaatcatat agcacaatga tgctaatgga gaaggtggct gtgatggatg 3540
caatgacaac tttagctgga actgtggtgt tgaaggtacc tgctttaccg aatatctatt 3600
ttcttttgta cattgaaatc atgattccat gaaactgcaa aaagatgctt attttcatat 3660
cccatcaaat tgatacatct gactgatgta gggtactgta aagatagaaa acttggtcga 3720
gtttattatt aaaacaaccc tttgtatgaa ttaaaggtat agtcataaag agaatgacat 3780
agtttgattt tgttgaaatt tagtgtcttg tattgatttt gttgaaattt aatgtcttgt 3840
aattcaacag aactaaaaga ttgcccctag tagtgaagct tcaatgtcaa gatggatcca 3900
aatagctcta tgagctgtgc agaactttcc aaatgcaacc atagatggct atccctcttt 3960

-continued

```
gaatcagaaa taattatttt tagggttaat tggatccatg ccactgcaaa tgtggcaaat   4020
caaaaaaatg ccacacatat ttgcgttatc ggctggatgc cactgcaaat ttttaaaata   4080
agaaccatgc cactccatca cgatttccgt ccaatccgtc acattttccg ccgtctccgt   4140
cttcgtcctc tcgtcgtcct cgtctcgacg gcagcaccag cacggcagta cgaaggcggg   4200
cgcggatggc agcacggcgc acggcggcac ggcagcacgg tggtggatgg cagcacggca   4260
ccggcgacgg tcgtgcccgc gtccgctccc cgcgcccctc cgcgacctcc tcgccgactt   4320
cctctctctc caccgttgca gccgtcgtcg ttgaccattt ccgcggtgga cccgccgccg   4380
ttgacctcat ctgcgcggga gagctcggga gccgccgccg ccgttgctgt cctcgtcgtg   4440
gtcgtcgacg agccgcaccg cctccgccca gatctggcga ggagggccgc tcgtcgttgc   4500
tgccgatgga ggaggcgtcg agcctcgaac tccgccgctg ttggccccaa gctttgtcac   4560
tagtgctgcc gacgcccatc tcctctctcc acatgaccat cctcggcagc agctgcgccc   4620
cctccgcgac ctccccgcga agcgtcctcg tcggcggcgg cggcctcgct cgcgaccgtc   4680
ctcgccggta gtggctatgc ccgcgtccgc ctccacggcc gtcctcggca gcagctatgc   4740
cccctccccg acctccccgc gagcgtcctc gctggcggcg gctacgcccg cgcccgcctc   4800
cgtgaccttc ctcggcggcg gccatgcccc tccgcgaccg tgctcgtcgg cggcggcaaa   4860
gatcgatggt tgtatgttga ttggtttagt tagctagcta gctagcctcg cgcgctgcat   4920
ctgtagcagc tagctagcta ctccctgagc ttgttgggtg tttctgcctg agctccattc   4980
cgcgccgaac cccgtcaggc ccggccgcga ccgcgccggg ctgtcctccg cccgtgccag   5040
ccgtcgcgcc agctccccat cctcttctcc gttttgccgc gtgaagccga tgcgttttgt   5100
cgcgtgcgcc tcatcggctt cgactccggt ggttgagctg ctcacacgcg tccgggggca   5160
gcagaagtga gagagagaga gaggaggacg gaaatcgtga tggagtggca tggttcttat   5220
tttaaaaatt tgcagtggca tccagccgat aacgcgaata tgtgtggcat ttttttgatt   5280
tgccacattt gcagtggcat ggatccaatt aacccttatt tttaacctaa tgctatgcga   5340
aatgtttgat gttagaattg atgctcttgt tctgtaacag gagaaacaaa tgatctgaat   5400
gtgttaagtc tgcgttcaag acaaatgaaa aacttccatg tagctttaat gatttctcag   5460
gtaaacattg tgaagtaacc tacagtttat tttatgtgtg catcatgtat aaacttatca   5520
cataatcacc attttcatat atcagggcac cccaatgatg ttgatgggcg atgaatatgg   5580
tcatacacgt tatgggaaca acaatagcta tggacatgat acttgcatta ataatttcca   5640
atgggaacag gttgcattac cgtaactatt ttagttttca accaggaata tgtttatgaa   5700
tttggcagat ctatatataa tttgttttct ccgaatccat gtgaatatag ttggaacaaa   5760
gaagagatgg ccatttcagg tttttctcag agatgataaa gtttcgtcac agcaacccaa   5820
tattaagacg agacaggttt cttaataaag taagtaatac ctagaagtgc tatcattgca   5880
attaactggt ttattgaaga caatcatttc atcatcttct caaaaaatag ctgctggtgt   5940
ctgtcgaaat tccaagtata ttttctcagt caagtctgat tagaatagta taatacagca   6000
aatatacact ttgcagcttt tgcagttgca tctcttagtt ttttttcgt ctcaaatgtt    6060
cttcattgta ttgtgatctt ccttgttggt agaacgatgt cacctggcac gaggattgtt   6120
gggagaacca ggaaagcaaa tttttggcat tcacgtaagt ttgttgatca ctttcgttta   6180
tgcaccttat tatggtattt gtttatgatg ctccaaaatc caaattcttg gcttctgact   6240
ttcattgcca ttttactgta gagtacatga tcacaactct ggtggagata tctatttggc   6300
```

```
attcaatgca catgactatt ttgtggacgc tgtaattccc ccaccaccac accataaatg   6360

ttggaaccgt gtggtatgga tacttttcag cattgctaaa tttcttacgt atagtaaagt   6420

aaattcctac ataatcctag catggtgtgg ttgtaatttc taaatatgta gaagtgctgc   6480

cagtactcat tctgaatttt actacattag acgctcggac aaataccaac tcttaaaaga   6540

agatatacaa gtttccacaa aatttctcag gaatagacat aggtagtact gatacagttc   6600

tacaaccaaa agctgtatac ggttgttact tgtgctagca atcctgctaa aactggtttg   6660

gagtttattg ctcattagct acttttaatt tttacaatga ttggtctggc tggatttgat   6720

cactcttttc tcacaccttt ccgctcctat tgtcattcta aatctgctct aataatcttt   6780

ttgtaggtgg ataccaacct ggaatcacca aatgatattg taccagaagg ggtgccattt   6840

acaggaccaa aatacagaat tgctccatac tcttccattc tgctcaaggc aaagccttag   6900

aaaagttagt agttgagagc ataaaaataa tgccaccaat gctggcttgg ttggttaata   6960

acaggttgat cacattagca gtctgcactt caaaaaggca a                       7001
```

<210> SEQ ID NO 4
<211> LENGTH: 4518
<212> TYPE: DNA
<213> ORGANISM: Oryza sativa

<400> SEQUENCE: 4

```
ggaaggccca gccggcccat gagcggattc tccgcggcag ctgctgcggc cgagcggtgc     60

gcgctcggcc tcggcgtcca cgcgcgcccc gcctcgccct cgccggcgct gctcccgccg    120

gcggctctcc gccgcggccg ccgcctcatg gcgctaagga aggagagata tccatccgga    180

tcccggaagc cgaatccatc catccatcca tcccatactg cccttacgat cgagctgttt    240

gatattcgtg cagatgagcg gattctccgc ggcagctgct gcggccgagc gcttgtcgga    300

aggttcaccc tggatgccaa ctccgagctt aaggtgacat tgaacccagc accgcagggt    360

tcggtggtgg agatcaatct agaggcaact aacaccagcg gctccctgat actgcattgg    420

ggcgcccttc gcccggatag aggagaatgg ctcctaccat cccggaaacc agatggcacg    480

acagtgtaca agaacagggc tcttaggacg ccttttataa agtcaggtga taactccacg    540

ctgaaaattg agatagatga tcctgcagtg caagccattg agttcctcat atttgatgag    600

gcacggaata attggtcagt tctttttggg ttacccatcc taccctgttt cttggaatgc    660

agaagatatc aaataacaac actctacttt ggacaggagg agtatgaagc agcacgaact    720

gagttgatag aggaattaaa caagggtgtt tctttggaga agctacgagc gaaactgaca    780

aagacacctg aggcaactga tagtaatgct cctgcatctg aaagcactgt gactactaaa    840

gtcccagagg aacttgtaca agtccaggct tacataaggt gggagaaagc aggcaagcca    900

aattatgccc cagagaagca attggtcgag tttgaggaag caaggaagga actgcagtct    960

gagttggata aggggacctc agttgagcag ttgaggaaca aaattttgaa agggaacatt   1020

gagacaaaag tttccaagca gctgaaggac aaaaaatact tttctgtgga aagaattcag   1080

cggaaaaaac gagatattgt gcaactactt aaaaaacaca agcctactgt tatggaagcg   1140

caagtagaga ctcctaaaca acccactgtt ctggatctct tcacaaagtc attacaggag   1200

caggataact gtgaggttct aagcagaaag cttttcaagt tcggtgacaa ggagatactg   1260

gaaaaaccaa agttcacttg gcaacaaact atatggagcc acttatactt cactgggcgt   1320

tgtcaaaaga gaatggagag tggcagacaa tgtgggcctg tactgatggg gtgctttgta   1380

actgtgaagg cacctccctc aagcatattg ccatctggtt catcattgct agacaaggca   1440
```

-continued

```
tgtgaaactt cattcagtga atatgaattg aatggtctgc attgtcagga tactggtgat   1500
gctggtaaag gcactgctaa ggccttgctt gaaagaatag cagatctaga ggaagatgcc   1560
caacgatctc ttatgcacag attcaatatt gcagcagatc tagttgacca agcaagagat   1620
aatggattat tgggtattat tggaattttt gtttggatta ggttcatggc tacaaggcaa   1680
ctaatatgga acaagaacta caatgtgaag ccacgtgaga taagcaaagc acaagatagg   1740
tttacagatg atcttgagaa tatgtacaga acttacccac aatatcagga gatcttaaga   1800
atgataatgt ctgctgttgg tcggggaggt gaaggtgatg ttggtcaacg cattcgtgat   1860
gagatattag taatccagag aaataatgac tgcaaaggtg gaatgatgga ggagtggcac   1920
cagaaactgc acaacaatac aagcccagat gatgtagtga tctgccaggc cctacttgat   1980
tatatcaaga gtgattttga tattggtgtt tactgggaca ccttgaaaaa agatggtata   2040
acaaaagagc gtctattgag ctatgatcga ccgattcatt cagagccaaa tttcaggagt   2100
gaacagaaag atggcttact ccgtgacttg ggcaattata tgagaagcct caagatggag   2160
ggtaccctga tacaatcact gcgaatggca gtgcattctg gtgctgatct tgaatctgct   2220
atagcaactt gcatgggata caaatcagag ggtgaaggtt tcatggttgg tgttcagatt   2280
aatccagtga agggtttgcc atctggattt cctaaattgc ttgaatttgt acttgaccat   2340
gttgaggata aatcagcaga accacttctt gaggggttat tggaggctcg agctgaacta   2400
cacccctttgc tccttggctc tcctgaacgc atgaaggatc ttatcttttt agacattgct   2460
cttgattcta ctttcaggac agcagttgaa agatcatatg aggagctcaa taatgtagaa   2520
ccagagaaaa ttatgtactt catcagtctt gtccttgaaa atcttgcttt atccaccgac   2580
gacaatgaag atatcctata ttgcttaaag ggatggaatc aagccttgga aatggctaaa   2640
cagaaaaaca accaatgggc tctctatgct aaagcatttc tggacagaac cagacttgcc   2700
cttgcaagca agggagaaca atactataat ttgatgcagc cctcagctga atatcttggc   2760
tcgttactta acattgacca atgggcagtt aatatcttta cagaagaaat tattcgtggt   2820
ggatcagctg ctaccctgtc tgctcttctg aatcggattg atcctgttct taggaatgtt   2880
gcacagcttg gaagttggca ggttataagc ccagttgaag tatcaggtta cattgtagtg   2940
gttgatgaat tgcttgctgt tcaaaacaaa tcctatgata aaccaactat ccttgtggca   3000
aagagtgtca agggagagga agaaatacca gatggagttg ttggtgttat tacacctgat   3060
atgccagatg ttctctccca tgtatcagtc cgagcaagga attgcaaggt tttatttgca   3120
acatgctttg atcctaacac cttgtctgaa ctccaaggac atgatgggaa agtgttttcc   3180
ttcaaaccta cttctgcaga tatcacctat agggagattc cagagagtga actgcaatca   3240
ggttctctaa atgcagaagc tggccaggca gtgccatctg tgtcattagt caagaagaag   3300
tttcttggaa aatatgcaat atcagcagaa gaattctctg aggaaatggt tggggccaag   3360
tctcgcaacg tagcatacct caaaggaaaa gtaccctcat gggttggtgt ccctacatca   3420
gttgcgattc catttgggac ctttgagaag gttttgtctg atgaaatcaa taaggaagtc   3480
gcgcaaacca tacaaatgct gaagggaaaa cttgctcaag atgattttag tgctctaggc   3540
gaaatacgga aaactgttct caatttaact gctcctactc aactgatcaa ggaactgaag   3600
gagaagatgc taggctctgg aatgccctgg cctggagatg aaggtgacca acgttgggag   3660
caagcatgga tggcaattaa aaaggtttgg gcgtcaaaat ggaatgaaag agcatatttt   3720
agcactcgta aggtgaagct tgatcatgac tacctttcca tggctgtact tgtacaagaa   3780
```

-continued

```
attgtcaatg cagactatgc ctttgtcatt catactacta acccatcatc gggagattcg   3840

tctgagatat atgctgaagt ggtgaaaggg cttggagaaa cacttgtagg agcctatcct   3900

ggtcgcgcca tgagctttgt atgtaagaaa aacgaccttg actctcccaa ggtactgggt   3960

ttcccaagca agccaattgg tctcttcata aagagatcaa tcatctttcg ttcagattcc   4020

aacggtgagg atttagaagg gtatgctgga gcaggactgt atgatagttc gctcaagaat   4080

ttatttggca ttacaactaa gctgactgct tgtttcagtg tccctatgga tgaggaagat   4140

gaagtcatac tcgactacac caccgacccc ctcattacag atcagggatt ccaaaaatct   4200

atcctctcga gcattgcacg ggctggtcat gccattgagg agctttatgg gtccccacag   4260

gatgttgagg gtgcagtgaa ggaagggaag ctatacgtag tacagacaag accacagatg   4320

ggaaaagcca gggaggacta ctaccaagtg ctgggagtga cggttaattc aacgcctcag   4380

gagatcaagg aggcttacag gaagctccag aaacgacacc atatcctgat attgctggct   4440

acaagggtca tgcatgacta caccctactg ctgaatgagg catacaaggt attgatgagg   4500

aattaagcgg ccgcaacc                                                 4518
```

<210> SEQ ID NO 5
<211> LENGTH: 1137
<212> TYPE: DNA
<213> ORGANISM: Oryza sativa

<400> SEQUENCE: 5

```
ggaaggccca gccggcccat gaactgcctc cagaacctgc tcaaggagcc tccaatcgtg     60

ggatccaggt ccatgaggcg gccctcgccg ctcaatctga cgatggttcg tggcgggagt    120

cgccgatcaa acactgtcaa aaccgcatcc ggggcgtcta cttctagcgc cgagagtggc    180

gcagtggagg cgggcacgga gaaatccgat acgtacagca ccaacatgac gcaagctatg    240

ggagcagtgt tgacgtatag acatgagctt ggaatgaact acaatttcat acgcccagac    300

ttgatcgtgg gctcctgctt acagagccca cttgatgttg ataaacttag ggacattggt    360

gtaaaaacag tattctgcct gcagcaagat ccagaccttg aatattttgg agttgacatc    420

tgtgccattc aagaatattg tctacaatgt aaagatatag agcactgtcg tgccgaaatt    480

agggattttg atgcttttga tttgcgattg aggcttcctg ctgtgattag caaactgcac    540

aagcttgtca accataatgg tggggtaaca tatatacact gtaccgctgg acttgggaga    600

gctcctgctg tgacattggc gtatatgttc tggattcttg gctacagtct taatgaaggg    660

catcagctac tacagagtaa acgagcttgc tttccaaagt tggaagccat taaattggct    720

actgctgaca ttctgacagg cttatcaaag aattccatca ctttgaagtg ggaaagtgat    780

agttgttctt ctgttgaaat ttctgggctt gatgtcgggt ggggacagat aattcctttg    840

acatacaaca aggagaaaag agcttggtat cttgagaggg agttgcctga aggaaggtat    900

gaatacaaat atatagtgga cggcaaatgg gtgtgcaatg acaatgagaa gaagaccaaa    960

gcaaatgctg atggccatgt gaataactac gtccaggtct ccagggatgg taccagcgat   1020

gaagagagag aattaaggga gcgtttgact ggtcaaaatc ccgatcttac gaaggaggaa   1080

aggctgatga ttagagagta cttggaacag tacgttgagc gataggcggc cgcaacc      1137
```

<210> SEQ ID NO 6
<211> LENGTH: 1131
<212> TYPE: DNA
<213> ORGANISM: Oryza sativa

<400> SEQUENCE: 6
atgttttggt tcaacctagg gaatacactg aactgcaacc atcctgttgt caaggagctc 60
attcttgaca gcttgagaca ctgggttgag gagtatcaca tagatggatt tcgatttgac 120
cttgcaagtg ttctttgtcg tggaccagat ggttgtcctc ttgatgcacc tccactcatc 180
aaggaaattg ccaaagatgc tgtattatct agatgtaaga tcattgctga accttgggat 240
tgcggcggcc tttatctcgt agggcgtttc cctaactggg acaggtgggc tgaatggaac 300
ggcaaataca gagatgatct tcgaagattt attaagggtg accctggtat gaagggggtg 360
tttgcgactc gtgtgtctgg atctgctgat ctctatcagg tgaacgagcg gaagccttac 420
catggtgtaa attttgtgat tgcacatgat ggatttactt tatgtgacct tgtttcttac 480
aacttaaagc acaatgatgc taatggagaa ggtggctgtg atggatgcaa tgacaacttt 540
agctggaact gtggtgttga aggagaaaca aatgatctga atgtgttaag tctgcgttca 600
agacaaatga aaaacttcca tgtagcttta atgatttctc agggcacccc aatgatgttg 660
atgggcgatg aatatggtca tacacgttat gggaacaaca atagctatgg acatgatact 720
tgcattaata atttccaatg ggaacagttg gaacaaagaa gagatggcca tttcaggttt 780
ttctcagaga tgataaagtt tcgtcacagc aacccaatat taagacgaga caggtttctt 840
aataaaaacg atgtcacctg gcacgaggat tgttgggaga accaggaaag caaatttttg 900
gcattcacag tacatgatca caactctggt ggagatatct atttggcatt caatgcacat 960
gactattttg tggacgctgt aattccccca ccaccacacc ataaatgttg gaaccgtgtg 1020
gtggatacca acctggaatc accaaatgat attgtaccag aaggggtgcc atttacagga 1080
ccaaaataca gaattgctcc atactcttcc attctgctca aggcaaagcc t 1131

<210> SEQ ID NO 7
<211> LENGTH: 313
<212> TYPE: DNA
<213> ORGANISM: Artificial Sequence
<220> FEATURE:
<223> OTHER INFORMATION: Synthetic construct, GWD1 driver sequence

<400> SEQUENCE: 7
tagcgctaag gaagggagag atatccatcc ggatcccgga agccgaatcc atccatccat 60
ccatcccata ctgcccttac gatcgagctg tttgatattc gtgcagatga gcggattctc 120
cgcggcagct gctgcggccg agcgcttgtc ggaaggttca ccctggatgc caactccgag 180
cttaaggtga cattgaaccc agcaccgcag ggttcggtgg tggagatcaa tctagaggca 240
actaacacca gcggctccct gatactgcat tggggcgccc ttcgcccgga tagaggagaa 300
tggctcctac cat 313

<210> SEQ ID NO 8
<211> LENGTH: 575
<212> TYPE: DNA
<213> ORGANISM: Artificial Sequence
<220> FEATURE:
<223> OTHER INFORMATION: Synthetic seqence, GWD2 driver sequence

<400> SEQUENCE: 8
agcagatcta gttgaccaag caagagataa tggattattg ggtattattg gaatttttgt 60
ttggattagg ttcatggcta caaggcaact aatatggaac aagaactaca atgtgaagcc 120
acgtgagata agcaaagcac aagataggtt tacagatgat cttgagaata tgtacagaac 180
ttacccacaa tatcaggaga tcttaagaat gataatgtct gctgttggtc ggggaggtga 240

-continued

```
aggtgatgtt ggtcaacgca ttcgtgatga gatattagta atccagagaa ataatgactg    300

caaaggtgga atgatggagg agtggcacca gaaactgcac aacaatacaa gcccagatga    360

tgtagtgatc tgccaggccc tacttgatta tatcaagagt gattttgata ttggtgttta    420

ctgggacacc ttgaaaaaag atggtataac aaaagagcgt ctattgagct atgatcgacc    480

gattcattca gagccaaatt tcaggagtga acagaaagat ggcttactcc gtgacttggg    540

caattatatg agaagcctca agatggaggg taccc                               575


<210> SEQ ID NO 9
<211> LENGTH: 506
<212> TYPE: DNA
<213> ORGANISM: Oryza sativa

<400> SEQUENCE: 9

tggaattttt gtttggatta ggttcatggc tacaaggcaa ctaatatgga acaagaacta     60

caatgtgaag ccacgtgaga taagcaaagc acaagatagg tttacagatg atcttgagaa    120

tatgtacaga acttacccac aatatcagga gatcttaaga atgataatgt ctgctgttgg    180

tcggggaggt gaaggtgatg ttggtcaacg cattcgtgat gagatattag taatccagag    240

aaataatgac tgcaaaggtg gaatgatgga ggagtggcac cagaaactgc acaacaatac    300

aagcccagat gatgtagtga tctgccaggc cctacttgat tatatcaaga gtgattttga    360

tattggtgtt tactgggaca ccttgaaaaa agatggtata acaaaagagc gtctattgag    420

ctatgatcga ccgattcatt cagagccaaa tttcaggagt gaacagaaag atggcttact    480

ccgtgacttg ggcaattata tgagaa                                         506


<210> SEQ ID NO 10
<211> LENGTH: 506
<212> TYPE: DNA
<213> ORGANISM: Oryza sativa

<400> SEQUENCE: 10

tggaattctt gtatggatga ggttcatggc tacaaggcag ctgatatgga acaaaaacta     60

taacgtgaaa ccacgtgaaa taagcaaggc tcaggacaga cttacagact tgctgcagaa    120

tgctttcacc agtcatcctc agtaccgtga aactttgcgg atgattatgt caactgttgg    180

acgtggaggt gaaggggatg taggacagcg aattagggac gaaattttgg tcatccagag    240

gaaaaatgac tgcaagggtg gtatgatgga agaatggcat cagaaattgc ataataacac    300

tagtcctgat gatgttgtga tctgtcaggc actgattgac tacatcaaga gtgattttga    360

tattggtgtt tattggaaaa ccctgaatga gaacggaatt acaaaagagc gtcttttgag    420

ttatgaccgt gctatccatt ctgaaccaaa ttttagagga gatcaaaagg atggtctttt    480

gcgtgattta ggtcactata tgagaa                                         506


<210> SEQ ID NO 11
<211> LENGTH: 380
<212> TYPE: DNA
<213> ORGANISM: Oryza sativa

<400> SEQUENCE: 11

ctccaatcgt gggatccagg tccatgaggc ggccctcgcc gctcaatctg acgatggttc     60

gtggcgggag tcgccgatca aacactgtca aaaccgcatc cggggcgtct acttctagcg    120

ccgagagtgg cgcagtggag gcgggcacgg agaaatccga tacgtacagc accaacatga    180

cgcaagctat gggagcagtg ttgacgtata gacatgagct tggaatgaac tacaatttca    240
```

```
tacgcccaga cttgatcgtg ggctcctgct tacagagccc acttgatgtt gataaactta    300

gggacattgg tgtaaaaaca gtattctgcc tgcagcaaga tccagacctt gaatattttg    360

gagttgacat ctgtgccatt                                                380
```

<210> SEQ ID NO 12
<211> LENGTH: 512
<212> TYPE: DNA
<213> ORGANISM: Oryza sativa

<400> SEQUENCE: 12

```
ctagcgaata cactgaactg caaccatcct gttgtcaagg agctcattct tgacagcttg     60

agacactggg ttgaggagta tcacatagat ggatttcgat ttgaccttgc aagtgttctt    120

tgtcgtggac cagatggttg tcctcttgat gcacctccac tcatcaagga aattgccaaa    180

gatgctgtat tatctagatg taagatcatt gctgaacctt gggattgcgg cggcctttat    240

ctcgtagggc gtttccctaa ctgggacagg tgggctgaat ggaacggcaa atacagagat    300

gatcttcgaa gatttattaa gggtgaccct ggtatgaagg gggtgtttgc gactcgtgtg    360

tctggatctg ctgatctcta tcaggtgaac gagcggaagc cttaccatgg tgtaaatttt    420

gtgattgcac atgatggatt tactttatgt gaccttgttt cttacaactt aaagcacaat    480

gatgctaatg gagaaggtgg ctgtgatgga tc                                  512
```

<210> SEQ ID NO 13
<211> LENGTH: 5111
<212> TYPE: DNA
<213> ORGANISM: Artificial Sequence
<220> FEATURE:
<223> OTHER INFORMATION: Synthetic sequence, pAL409

<400> SEQUENCE: 13

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgggcggtta attaactaat    420

cgactctagt aacggccgcc agtgtgctgg aattaattcg gcttgtcgac cacccaaccc    480

catatcgaca gaggatgtga agaacaggta aatcacgcag aagaacccat ctctgatagc    540

agctatcgat tagaacaacg aatccatatt gggtccgtgg gaaatactta ctgcacagga    600

agggggcgat ctgacgaggc cccgccaccg gcctcgaccc gaggccgagg ccgacgaagc    660

gccggcgagt acggcgccgc ggcggcctct gcccgtgccc tctgcgcgtg ggagggagag    720

gccgcggtgg tgggggcgcg cgcgcgcgcg cgcgcagctg gtgcggcggc gcgggggtca    780

gccgccgagc cggcggcgac ggaggagcag ggcggcgtgg acgcgaactt ccgatcggtt    840

ggtcagagtg cgcgagttgg gcttagccaa ttaggtctca acaatctatt gggccgtaaa    900

attcatgggc cctggtttgt ctaggcccaa tatcccgttc atttcagccc acaaatattt    960

ccccagagga ttattaaggc ccacacgcag cttatagcag atcaagtacg atgtttcctg   1020

atcgttggat cggaaacgta cggtcttgat caggcatgcc gacttcgtca aagagaggcg   1080
```

gcatgacctg acgcggagtt ggttccgggc accgtctgga tggtcgtacc gggaccggac 1140
acgtgtcgcg cctccaacta catggacacg tgtggtgctg ccattgggcc gtacgcgtgg 1200
cggtgaccgc accggatgct gcctcgcacc gccttgccca cgctttatat agagaggttt 1260
tctctccatt aatcgcatag cgagtcgaat cgaccgaagg ggaggggag cgagagcttt 1320
gcgttctcta atcgcctcgt caagcctagg tgtgtgtccg gagtcaaggt aactaatcaa 1380
tcacctcgtc ctaatcctcg aatctctcgt ggtgcccgtc taatctcgcg attttgatgc 1440
tcgtggtgga aagcgtagga ggatcccgtg cgagttagtc tcaatctctc agggtttcgt 1500
gcgattttag ggtgatccac ctcttaatcg agttacggtt tcgtgcgatt ttagggtaat 1560
cctcttaatc tctcattgat ttagggtttc gtgagaatcg aggtagggat ctgtgttatt 1620
tatatcgatc taatagatgg attggttttg agattgttct gtcagatggg gattgtttcg 1680
atatattacc ctaatgatgt gtcagatggg gattgtttcg atatattacc ctaatgatgt 1740
gtcagatggg gattgtttcg atatattacc ctaatgatgg ataataagag tagttcacag 1800
ttatgttttg atcctgccac atagtttgag ttttgtgatc agatttagtt ttacttattt 1860
gtgcttagtt cggatgggat tgttctgata ttgttccaat agatgaatag ctcgttaggt 1920
taaaatcttt aggttgagtt aggcgacaca tagtttattt cctctggatt tggattggaa 1980
ttgtgttctt agttttttc ccctggattt ggattggaat tgtgtggagc tgggttagag 2040
aattacatct gtatcgtgta cacctacttg aactgtagag cttgggttct aaggtcaatt 2100
taatctgtat tgtatctggc tctttgccta gttgaactgt agtgctgatg ttgtactgtg 2160
ttttttacc cgttttattt gctttactcg tgcaaatcaa atctgtcaga tgctagaact 2220
aggtggcttt attctgtgtt cttacataga tctgttgtcc tgtagttact tatgtcagtt 2280
ttgttattat ctgaagatat ttttggttgt tgcttgttga tgtggtgtga gctgtgagca 2340
gcgctcttat gattaatgat gctgtccaat tgtagtgtag tatgatgtga ttgatatgtt 2400
catctatttt gagctgacag taccgatatc gtaggatctg gtgccaactt attctccagc 2460
tgcttttttt tacctatgtt aattccaatc ctttcttgcc tcttccaggg atccaccggt 2520
ccgatcgagc ttactgaaaa aattaacatc tcttgctaag ctgggagcgc tagctccccg 2580
aatttccccg atcgttcaaa catttggcaa taaagtttct taagattgaa tcctgttgcc 2640
ggtcttgcga tgattatcat ataatttctg ttgaattacg ttaagcatgt aataattaac 2700
atgtaatgca tgacgttatt tatgagatgg gtttttatga ttagagtccc gcaattatac 2760
atttaatacg cgatagaaaa caaaatatag cgcgcaaact aggataaatt atcgcgcgcg 2820
gtgtcatcta tgttactaga tcgggaattg gcgagctcgc ccgggcgggc gaagcttggc 2880
gtaatcatgg tcatagctgt ttcctgtgtg aaattgttat ccgctcacaa ttccacacaa 2940
catacgagcc ggaagcataa agtgtaaagc ctggggtgcc taatgagtga gctaactcac 3000
attaattgcg ttgcgctcac tgcccgcttt ccagtcggga aacctgtcgt gccagctgca 3060
ttaatgaatc ggccaacgcg cggggagagg cggtttgcgt attgggcgct cttccgcttc 3120
ctcgctcact gactcgctgc gctcggtcgt tcggctgcgg cgagcggtat cagctcactc 3180
aaaggcggta atacggttat ccacagaatc aggggataac gcaggaaaga acatgtgagc 3240
aaaaggccag caaaaggcca ggaaccgtaa aaaggccgcg ttgctggcgt ttttccatag 3300
gctccgcccc cctgacgagc atcacaaaaa tcgacgctca agtcagaggt ggcgaaaccc 3360
gacaggacta taaagatacc aggcgtttcc ccctggaagc tccctcgtgc gctctcctgt 3420
tccgaccctg ccgcttaccg gatacctgtc cgcctttctc ccttcgggaa gcgtggcgct 3480
ttctcatagc tcacgctgta ggtatctcag ttcggtgtag gtcgttcgct ccaagctggg 3540
ctgtgtgcac gaaccccccg ttcagcccga ccgctgcgcc ttatccggta actatcgtct 3600
tgagtccaac ccggtaagac acgacttatc gccactggca gcagccactg gtaacaggat 3660
tagcagagcg aggtatgtag gcggtgctac agagttcttg aagtggtggc ctaactacgg 3720
ctacactaga aggacagtat ttggtatctg cgctctgctg aagccagtta ccttcggaaa 3780
aagagttggt agctcttgat ccggcaaaca aaccaccgct ggtagcggtg gtttttttgt 3840
ttgcaagcag cagattacgc gcagaaaaaa aggatctcaa gaagatcctt tgatcttttc 3900
tacggggtct gacgctcagt ggaacgaaaa ctcacgttaa gggattttgg tcatgagatt 3960
atcaaaaagg atcttcacct agatcctttt aaattaaaaa tgaagtttta aatcaatcta 4020
aagtatatat gagtaaactt ggtctgacag ttaccaatgc ttaatcagtg aggcacctat 4080
ctcagcgatc tgtctatttc gttcatccat agttgcctga ctccccgtcg tgtagataac 4140
tacgatacgg gagggcttac catctggccc cagtgctgca atgataccgc gagacccacg 4200
ctcaccggct ccagatttat cagcaataaa ccagccagcc ggaagggccg agcgcagaag 4260
tggtcctgca actttatccg cctccatcca gtctattaat tgttgccggg aagctagagt 4320
aagtagttcg ccagttaata gtttgcgcaa cgttgttgcc attgctacag gcatcgtggt 4380
gtcacgctcg tcgtttggta tggcttcatt cagctccggt tcccaacgat caaggcgagt 4440
tacatgatcc cccatgttgt gcaaaaaagc ggttagctcc ttcggtcctc cgatcgttgt 4500
cagaagtaag ttggccgcag tgttatcact catggttatg gcagcactgc ataattctct 4560
tactgtcatg ccatccgtaa gatgcttttc tgtgactggt gagtactcaa ccaagtcatt 4620
ctgagaatag tgtatgcggc gaccgagttg ctcttgcccg gcgtcaatac gggataatac 4680
cgcgccacat agcagaactt taaaagtgct catcattgga aaacgttctt cggggcgaaa 4740
actctcaagg atcttaccgc tgttgagatc cagttcgatg taacccactc gtgcacccaa 4800
ctgatcttca gcatctttta ctttcaccag cgtttctggg tgagcaaaaa caggaaggca 4860
aaatgccgca aaaaagggaa taagggcgac acggaaatgt tgaatactca tactcttcct 4920
ttttcaatat tattgaagca tttatcaggg ttattgtctc atgagcggat acatatttga 4980
atgtatttag aaaaataaac aaataggggt tccgcgcaca tttccccgaa aagtgccacc 5040
tgacgtctaa gaaaccatta ttatcatgac attaacctat aaaaataggc gtatcacgag 5100
gccctttcgt c 5111

<210> SEQ ID NO 14
<211> LENGTH: 9983
<212> TYPE: DNA
<213> ORGANISM: Artificial Sequence
<220> FEATURE:
<223> OTHER INFORMATION: Synthetic Sequence, pAG2004

<400> SEQUENCE: 14
ccgatggccg agctgtggat gggcgcacat ccgaaaagca gttcacgagt gcagaatgcc 60
gccggagata tcgtttcact gcgtgatgtg attgagagtg ataaatcgac tctgctcgga 120
gaggccgttg ccaaacgctt tggcgaactg cctttcctgt tcaaagtatt atgcgcagca 180
cagccactct ccattcaggt tcatccaaac aaacacaatt ctgaaatcgg ttttgccaaa 240
gaaaatgccg caggtatccc gatggatgcc gccgagcgta actataaaga tcctaaccac 300
aagccggagc tggtttttgc gctgacgcct ttccttgcga tgaacgcgtt tcgtgaattt 360

-continued

```
tccgagattg tctccctact ccagccggtc gcaggtgcac atccggcgat tgctcacttt    420

ttacaacagc ctgatgccga acgtttaagc gaactgttcg ccagcctgtt gaatatgcag    480

ggtgaagaaa aatcccgcgc gctggcgatt ttaaaatcgg ccctcgatag ccagcagggt    540

gaaccgtggc aaacgattcg tttaatttct gaattttacc cggaagacag cggtctgttc    600

tccccgctat tgctgaatgt ggtgaaattg aaccctggcg aagcgatgtt cctgttcgct    660

gaaacaccgc acgcttacct gcaaggcgtg gcgctggaag tgatggcaaa ctccgataac    720

gtgctgcgtg cgggtctgac gcctaaatac attgatattc cggaactggt tgccaatgtg    780

aaattcgaag ccaaaccggc taaccagttg ttgacccagc cggtgaaaca aggtgcagaa    840

ctggacttcc cgattccagt ggatgatttt gccttctcgc tgcatgacct tagtgataaa    900

gaaaccacca ttagccagca gagtgccgcc attttgttct gcgtcgaagg cgatgcaacg    960

ttgtggaaag gttctcagca gttacagctt aaaccgggtg aatcagcgtt tattgccgcc   1020

aacgaatcac cggtgactgt caaaggccac ggccgtttag cgcgtgttta caacaagctg   1080

taagagctta ctgaaaaaat taacatctct tgctaagctg ggagctctag atccccgaat   1140

ttccccgatc gttcaaacat ttggcaataa agtttcttaa gattgaatcc tgttgccggt   1200

cttgcgatga ttatcatata atttctgttg aattacgtta agcatgtaat aattaacatg   1260

taatgcatga cgttatttat gagatgggtt tttatgatta gagtcccgca attatacatt   1320

taatacgcga tagaaaacaa aatatagcgc gcaaactagg ataaattatc gcgcgcggtg   1380

tcatctatgt tactagatcg ggaattggcg agctcgaatt aattcagtac attaaaaacg   1440

tccgcaatgt gttattaagt tgtctaagcg tcaatttgtt tacaccacaa tatatcctgc   1500

caccagccag ccaacagctc cccgaccggc agctcggcac aaaatcacca ctcgatacag   1560

gcagcccatc agtccgggac ggcgtcagcg ggagagccgt tgtaaggcgg cagactttgc   1620

tcatgttacc gatgctattc ggaagaacgg caactaagct gccgggtttg aaacacggat   1680

gatctcgcgg agggtagcat gttgattgta acgatgacag agcgttgctg cctgtgatca   1740

aatatcatct ccctcgcaga gatccgaatt atcagccttc ttattcattt ctcgcttaac   1800

cgtgacaggc tgtcgatctt gagaactatg ccgacataat aggaaatcgc tggataaagc   1860

cgctgaggaa gctgagtggc gctatttctt tagaagtgaa cgttgacgat cgtcgaccgt   1920

accccgatga attaattcgg acgtacgttc tgaacacagc tggatactta cttgggcgat   1980

tgtcatacat gacatcaaca atgtacccgt ttgtgtaacc gtctcttgga ggttcgtatg   2040

acactagtgg ttcccctcag cttgcgacta gatgttgagg cctaacattt tattagagag   2100

caggctagtt gcttagatac atgatcttca ggccgttatc tgtcagggca agcgaaaatt   2160

ggccatttat gacgaccaat gccccgcaga agctcccatc tttgccgcca tagacgccgc   2220

gcccccccttt tggggtgtag aacatccttt tgccagatgt ggaaaagaag ttcgttgtcc   2280

cattgttggc aatgacgtag tagccggcga aagtgcgaga cccatttgcg ctatatataa   2340

gcctacgatt tccgttgcga ctattgtcgt aattggatga actattatcg tagttgctct   2400

cagagttgtc gtaatttgat ggactattgt cgtaattgct tatggagttg tcgtagttgc   2460

ttggagaaat gtcgtagttg gatggggagt agtcataggg aagacgagct tcatccacta   2520

aaacaattgg caggtcagca agtgcctgcc ccgatgccat cgcaagtacg aggcttagaa   2580

ccaccttcaa cagatcgcgc atagtcttcc ccagctctct aacgcttgag ttaagccgcg   2640

ccgcgaagcg gcgtcggctt gaacgaattg ttagacatta tttgccgact accttggtga   2700

tctcgccttt cacgtagtga acaaattctt ccaactgatc tgcgcgcgag gccaagcgat   2760
```

-continued

```
cttcttgtcc aagataagcc tgcctagctt caagtatgac gggctgatac tgggccggca   2820
ggcgctccat tgcccagtcg gcagcgacat ccttcggcgc gattttgccg gttactgcgc   2880
tgtaccaaat gcgggacaac gtaagcacta catttcgctc atcgccagcc cagtcgggcg   2940
gcgagttcca tagcgttaag gtttcattta gcgcctcaaa tagatcctgt tcaggaaccg   3000
gatcaaagag ttcctccgcc gctggaccta ccaaggcaac gctatgttct cttgcttttg   3060
tcagcaagat agccagatca atgtcgatcg tggctggctc gaagatacct gcaagaatgt   3120
cattgcgctg ccattctcca aattgcagtt cgcgcttagc tggataacgc cacggaatga   3180
tgtcgtcgtg cacaacaatg gtgacttcta cagcgcggag aatctcgctc tctccagggg   3240
aagccgaagt ttccaaaagg tcgttgatca aagctcgccg cgttgtttca tcaagcctta   3300
cggtcaccgt aaccagcaaa tcaatatcac tgtgtggctt caggccgcca tccactgcgg   3360
agccgtacaa atgtacggcc agcaacgtcg gttcgagatg gcgctcgatg acgccaacta   3420
cctctgatag ttgagtcgat acttcggcga tcaccgcttc cctcatgatg tttaactcct   3480
gaattaagcc gcgccgcgaa gcggtgtcgg cttgaatgaa ttgttaggcg tcatcctgtg   3540
ctcccgagaa ccagtaccag tacatcgctg tttcgttcga gacttgaggt ctagttttat   3600
acgtgaacag gtcaatgccg ccgagagtaa agccacattt tgcgtacaaa ttgcaggcag   3660
gtacattgtt cgtttgtgtc tctaatcgta tgccaaggag ctgtctgctt agtgcccact   3720
ttttcgcaaa ttcgatgaga ctgtgcgcga ctcctttgcc tcggtgcgtg tgcgacacaa   3780
caatgtgttc gatagaggct agatcgttcc atgttgagtt gagttcaatc ttcccgacaa   3840
gctcttggtc gatgaatgcg ccatagcaag cagagtcttc atcagagtca tcatccgaga   3900
tgtaatcctt ccggtagggg ctcacacttc tggtagatag ttcaaagcct tggtcggata   3960
ggtgcacatc gaacacttca cgaacaatga aatggttctc agcatccaat gtttccgcca   4020
cctgctcagg gatcaccgaa atcttcatat gacgcctaac gcctggcaca gcggatcgca   4080
aacctggcgc ggcttttggc acaaaaggcg tgacaggttt gcgaatccgt tgctgccact   4140
tgttaaccct tttgccagat ttggtaacta taatttatgt tagaggcgaa gtcttgggta   4200
aaaactggcc taaaattgct ggggatttca ggaaagtaaa catcaccttc cggctcgatg   4260
tctattgtag atatatgtag tgtatctact tgatcggggg atctgctgcc tcgcgcgttt   4320
cggtgatgac ggtgaaaacc tctgacacat gcagctcccg gagacggtca cagcttgtct   4380
gtaagcggat gccgggagca gacaagcccg tcagggcgcg tcagcgggtg ttggcgggtg   4440
tcggggcgca gccatgaccc agtcacgtag cgatagcgga gtgtatactg gcttaactat   4500
gcggcatcag agcagattgt actgagagtg caccatatgc ggtgtgaaat accgcacaga   4560
tgcgtaagga gaaaataccg catcaggcgc tcttccgctt cctcgctcac tgactcgctg   4620
cgctcggtcg ttcggctgcg gcgagcggta tcagctcact caaaggcggt aatacggtta   4680
tccacagaat caggggataa cgcaggaaag aacatgtgag caaaaggcca gcaaaaggcc   4740
aggaaccgta aaaaggccgc gttgctggcg tttttccata ggctccgccc ccctgacgag   4800
catcacaaaa atcgacgctc aagtcagagg tggcgaaacc cgacaggact ataaagatac   4860
caggcgtttc cccctggaag ctccctcgtg cgctctcctg ttccgaccct gccgcttacc   4920
ggatacctgt ccgcctttct cccttcggga agcgtggcgc tttctcatag ctcacgctgt   4980
aggtatctca gttcggtgta ggtcgttcgc tccaagctgg gctgtgtgca cgaacccccc   5040
gttcagcccg accgctgcgc cttatccggt aactatcgtc ttgagtccaa cccggtaaga   5100
```

-continued

```
cacgacttat cgccactggc agcagccact ggtaacagga ttagcagagc gaggtatgta   5160
ggcggtgcta cagagttctt gaagtggtgg cctaactacg gctacactag aaggacagta   5220
tttggtatct gcgctctgct gaagccagtt accttcggaa aaagagttgg tagctcttga   5280
tccggcaaac aaaccaccgc tggtagcggt ggtttttttg tttgcaagca gcagattacg   5340
cgcagaaaaa aaggatctca agaagatcct ttgatctttt ctacggggtc tgacgctcag   5400
tggaacgaaa actcacgtta agggattttg gtcatgagat tatcaaaaag gatcttcacc   5460
tagatccttt taaattaaaa atgaagtttt aaatcaatct aaagtatata tgagtaaact   5520
tggtctgaca gttaccaatg cttaatcagt gaggcaccta tctcagcgat ctgtctattt   5580
cgttcatcca tagttgcctg actccccgtc gtgtagataa ctacgatacg ggagggctta   5640
ccatctggcc ccagtgctgc aatgataccg cgagacccac gctcaccggc tccagattta   5700
tcagcaataa accagccagc cggaagggcc gagcgcagaa gtggtcctgc aactttatcc   5760
gcctccatcc agtctattaa ttgttgccgg gaagctagag taagtagttc gccagttaat   5820
agtttgcgca acgttgttgc cattgctgca gggggggggg gggggggggtt ccattgttca   5880
ttccacggac aaaaacagag aaaggaaacg acagaggcca aaaagctcgc tttcagcacc   5940
tgtcgtttcc tttcttttca gagggtattt taaataaaaa cattaagtta tgacgaagaa   6000
gaacggaaac gccttaaacc ggaaaatttt cataaatagc gaaaacccgc gaggtcgccg   6060
ccccgtaacc tgtcggatca ccggaaagga cccgtaaagt gataatgatt atcatctaca   6120
tatcacaacg tgcgtggagg ccatcaaacc acgtcaaata atcaattatg acgcaggtat   6180
cgtattaatt gatctgcatc aacttaacgt aaaaacaact tcagacaata caaatcagcg   6240
acactgaata cggggcaacc tcatgtcccc cccccccccc ccctgcaggc atcgtggtgt   6300
cacgctcgtc gtttggtatg gcttcattca gctccggttc ccaacgatca aggcgagtta   6360
catgatcccc catgttgtgc aaaaaagcgg ttagctcctt cggtcctccg atcgttgtca   6420
gaagtaagtt ggccgcagtg ttatcactca tggttatggc agcactgcat aattctctta   6480
ctgtcatgcc atccgtaaga tgcttttctg tgactggtga gtactcaacc aagtcattct   6540
gagaatagtg tatgcggcga ccgagttgct cttgcccggc gtcaacacgg gataataccg   6600
cgccacatag cagaacttta aaagtgctca tcattggaaa acgttcttcg gggcgaaaac   6660
tctcaaggat cttaccgctg ttgagatcca gttcgatgta acccactcgt gcacccaact   6720
gatcttcagc atcttttact ttcaccagcg tttctgggtg agcaaaaaca ggaaggcaaa   6780
atgccgcaaa aaagggaata agggcgacac ggaaatgttg aatactcata ctcttccttt   6840
ttcaatatta ttgaagcatt tatcagggtt attgtctcat gagcggatac atatttgaat   6900
gtatttagaa aaataaacaa ataggggttc cgcgcacatt tccccgaaaa gtgccacctg   6960
acgtctaaga aaccattatt atcatgacat taacctataa aaataggcgt atcacgaggc   7020
cctttcgtct tcaagaattg gtcgacgatc ttgctgcgtt cggatatttt cgtggagttc   7080
ccgccacaga cccggattga aggcgagatc cagcaactcg cgccagatca tcctgtgacg   7140
gaactttggc gcgtgatgac tggccaggac gtcggccgaa agagcgacaa gcagatcacg   7200
cttttcgaca gcgtcggatt tgcgatcgag gatttttcgg cgctgcgcta cgtccgcgac   7260
cgcgttgagg gatcaagcca cagcagccca ctcgaccttc tagccgaccc agacgagcca   7320
agggatcttt ttggaatgct gctccgtcgt caggctttcc gacgtttggg tggttgaaca   7380
gaagtcatta tcgcacggaa tgccaagcac tcccgagggg aaccctgtgg ttggcatgca   7440
catacaaatg gacgaacgga taaacctttt cacgcccttt taaatatccg attattctaa   7500
```

-continued

```
taaacgctct tttctcttag gtttacccgc caatatatcc tgtcaaacac tgatagttta   7560
aactgaaggc gggaaacgac aacctgatca tgagcggaga attaagggag tcacgttatg   7620
acccccgccg atgacgcggg acaagccgtt ttacgtttgg aactgacaga accgcaacgt   7680
tgaaggagcc actcagctta attaagtcta actcgagtta ctggtacgta ccaaatccat   7740
ggaatcaagg taccatcaat cccgggtatt catcctaggt atccaagaat tcatactaaa   7800
gcttgcatgc ctgcaggtcg actctagtaa cggccgccag tgtgctggaa ttaattcggc   7860
ttgtcgacca cccaacccca tatcgacaga ggatgtgaag aacaggtaaa tcacgcagaa   7920
gaacccatct ctgatagcag ctatcgatta gaacaacgaa tccatattgg gtccgtggga   7980
aatacttact gcacaggaag gggcgatct gacgaggccc cgccaccggc ctcgacccga    8040
ggccgaggcc gacgaagcgc cggcgagtac ggcgccgcgg cggcctctgc ccgtgccctc   8100
tgcgcgtggg agggagaggc cgcggtggtg ggggcgcgcg cgcgcgcgcg cgcagctggt   8160
gcggcggcgc gggggtcagc cgccgagccg gcggcgacgg aggagcaggg cggcgtggac   8220
gcgaacttcc gatcggttgg tcagagtgcg cgagttgggc ttagccaatt aggtctcaac   8280
aatctattgg gccgtaaaat tcatgggccc tggtttgtct aggcccaata tcccgttcat   8340
ttcagcccac aaatatttcc ccagaggatt attaaggccc acacgcagct tatagcagat   8400
caagtacgat gtttcctgat cgttggatcg gaaacgtacg gtcttgatca ggcatgccga   8460
cttcgtcaaa gagaggcggc atgacctgac gcggagttgg ttccgggcac cgtctggatg   8520
gtcgtaccgg gaccggacac gtgtcgcgcc tccaactaca tggacacgtg tggtgctgcc   8580
attgggccgt acgcgtggcg gtgaccgcac cggatgctgc ctcgcaccgc cttgcccacg   8640
ctttatatag agaggttttc tctccattaa tcgcatagcg agtcgaatcg accgaagggg   8700
agggggagcg aagctttgcg ttctctaatc gcctcgtcaa ggtaactaat caatcacctc   8760
gtcctaatcc tcgaatctct cgtggtgccc gtctaatctc gcgattttga tgctcgtggt   8820
ggaaagcgta ggaggatccc gtgcgagtta gtctcaatct ctcagggttt cgtgcgattt   8880
tagggtgatc cacctcttaa tcgagttacg gtttcgtgcg attttagggt aatcctctta   8940
atctctcatt gatttagggt ttcgtgagaa tcgaggtagg gatctgtgtt atttatatcg   9000
atctaataga tggattggtt ttgagattgt tctgtcagat ggggattgtt tcgatatatt   9060
accctaatga tgtgtcagat ggggattgtt tcgatatatt accctaatga tgtgtcagat   9120
ggggattgtt tcgatatatt accctaatga tggataataa gagtagttca cagttatgtt   9180
ttgatcctgc cacatagttt gagttttgtg atcagattta gttttactta tttgtgctta   9240
gttcggatgg gattgttctg atattgttcc aatagatgaa tagctcgtta ggttaaaatc   9300
tttaggttga gttaggcgac acatagttta tttcctctgg atttggattg gaattgtgtt   9360
cttagttttt ttcccctgga tttggattgg aattgtgtgg agctgggtta gagaattaca   9420
tctgtatcgt gtacacctac ttgaactgta gagcttgggt tctaaggtca atttaatctg   9480
tattgtatct ggctctttgc ctagttgaac tgtagtgctg atgttgtact gtgttttttt   9540
acccgtttta tttgctttac tcgtgcaaat caaatctgtc agatgctaga actaggtggc   9600
tttattctgt gttcttacat agatctgttg tcctgtagtt acttatgtca gttttgttat   9660
tatctgaaga tatttttggt tgttgcttgt tgatgtggtg tgagctgtga gcagcgctct   9720
tatgattaat gatgctgtcc aattgtagtg tagtatgatg tgattgatat gttcatctat   9780
tttgagctga cagtaccgat atcgtaggat ctggtgccaa cttattctcc agctgctttt   9840
```

-continued

```
ttttacctat gttaattcca atcctttctt gcctcttcca gatccagata atgcagaaac   9900

tcattaactc agtgcaaaac tatgcctggg gcagcaaaac ggcgttgact gaactttatg   9960

gtatggaaaa tccgtccagc cag                                           9983


<210> SEQ ID NO 15
<211> LENGTH: 12936
<212> TYPE: DNA
<213> ORGANISM: Artificial Sequence
<220> FEATURE:
<223> OTHER INFORMATION: Synthetic sequence, pAG2100

<400> SEQUENCE: 15

atccagataa tgcagaaact cattaactca gtgcaaaact atgcctgggg cagcaaaacg     60

gcgttgactg aactttatgg tatggaaaat ccgtccagcc agccgatggc cgagctgtgg    120

atgggcgcac atccgaaaag cagttcacga gtgcagaatg ccgccggaga tatcgtttca    180

ctgcgtgatg tgattgagag tgataaatcg actctgctcg gagaggccgt tgccaaacgc    240

tttggcgaac tgcctttcct gttcaaagta ttatgcgcag cacagccact ctccattcag    300

gttcatccaa acaaacacaa ttctgaaatc ggttttgcca aagaaaatgc cgcaggtatc    360

ccgatggatg ccgccgagcg taactataaa gatcctaacc acaagccgga gctggttttt    420

gcgctgacgc ctttccttgc gatgaacgcg tttcgtgaat tttccgagat tgtctcccta    480

ctccagccgg tcgcaggtgc acatccggcg attgctcact tttacaaca gcctgatgcc    540

gaacgtttaa gcgaactgtt cgccagcctg ttgaatatgc agggtgaaga aaaatcccgc    600

gcgctggcga ttttaaaatc ggccctcgat agccagcagg gtgaaccgtg gcaaacgatt    660

cgtttaattt ctgaatttta cccggaagac agcggtctgt tctccccgct attgctgaat    720

gtggtgaaat tgaaccctgg cgaagcgatg ttcctgttcg ctgaaacacc gcacgcttac    780

ctgcaaggcg tggcgctgga agtgatggca aactccgata acgtgctgcg tgcgggtctg    840

acgcctaaat acattgatat tccggaactg gttgccaatg tgaaattcga agccaaaccg    900

gctaaccagt tgttgaccca gccggtgaaa caaggtgcag aactggactt cccgattcca    960

gtggatgatt ttgccttctc gctgcatgac cttagtgata aagaaaccac cattagccag   1020

cagagtgccg ccattttgtt ctgcgtcgaa ggcgatgcaa cgttgtggaa aggttctcag   1080

cagttacagc ttaaaccggg tgaatcagcg tttattgccg ccaacgaatc accggtgact   1140

gtcaaaggcc acggccgttt agcgcgtgtt tacaacaagc tgtaagagct tactgaaaaa   1200

attaacatct cttgctaagc tgggagctct agatccccga atttccccga tcgttcaaac   1260

atttggcaat aaagtttctt aagattgaat cctgttgccg gtcttgcgat gattatcata   1320

taatttctgt tgaattacgt taagcatgta ataattaaca tgtaatgcat gacgttattt   1380

atgagatggg tttttatgat tagagtcccg caattataca tttaatacgc gatagaaaac   1440

aaaatatagc gcgcaaacta ggataaatta tcgcgcgcgg tgtcatctat gttactagat   1500

cgggaattgg cgagctcgaa ttaattcagt acattaaaaa cgtccgcaat gtgttattaa   1560

gttgtctaag cgtcaatttg tttacaccac aatatatcct gccaccagcc agccaacagc   1620

tccccgaccg gcagctcggc acaaaatcac cactcgatac aggcagccca tcagtccggg   1680

acggcgtcag cgggagagcc gttgtaaggc ggcagacttt gctcatgtta ccgatgctat   1740

tcggaagaac ggcaactaag ctgccgggtt tgaaacacgg atgatctcgc ggagggtagc   1800

atgttgattg taacgatgac agagcgttgc tgcctgtgat caaatatcat ctccctcgca   1860

gagatccgaa ttatcagcct tcttattcat ttctcgctta accgtgacag gctgtcgatc   1920
```

-continued

```
ttgagaacta tgccgacata ataggaaatc gctggataaa gccgctgagg aagctgagtg   1980
gcgctatttc tttagaagtg aacgttgacg atcgtcgacc gtaccccgat gaattaattc   2040
ggacgtacgt tctgaacaca gctggatact tacttgggcg attgtcatac atgacatcaa   2100
caatgtaccc gtttgtgtaa ccgtctcttg gaggttcgta tgacactagt ggttcccctc   2160
agcttgcgac tagatgttga ggcctaacat tttattagag agcaggctag ttgcttagat   2220
acatgatctt caggccgtta tctgtcaggg caagcgaaaa ttggccattt atgacgacca   2280
atgccccgca gaagctccca tctttgccgc catagacgcc gcgcccccct tttggggtgt   2340
agaacatcct tttgccagat gtggaaaaga agttcgttgt cccattgttg gcaatgacgt   2400
agtagccggc gaaagtgcga gacccatttg cgctatatat aagcctacga tttccgttgc   2460
gactattgtc gtaattggat gaactattat cgtagttgct ctcagagttg tcgtaatttg   2520
atggactatt gtcgtaattg cttatggagt tgtcgtagtt gcttggagaa atgtcgtagt   2580
tggatgggga gtagtcatag ggaagacgag cttcatccac taaaacaatt ggcaggtcag   2640
caagtgcctg ccccgatgcc atcgcaagta cgaggcttag aaccaccttc aacagatcgc   2700
gcatagtctt ccccagctct ctaacgcttg agttaagccg cgccgcgaag cggcgtcggc   2760
ttgaacgaat tgttagacat tatttgccga ctaccttggt gatctcgcct ttcacgtagt   2820
gaacaaattc ttccaactga tctgcgcgcg aggccaagcg atcttcttgt ccaagataag   2880
cctgcctagc ttcaagtatg acgggctgat actgggccgg caggcgctcc attgcccagt   2940
cggcagcgac atccttcggc gcgattttgc cggttactgc gctgtaccaa atgcgggaca   3000
acgtaagcac tacatttcgc tcatcgccag cccagtcggg cggcgagttc catagcgtta   3060
aggtttcatt tagcgcctca aatagatcct gttcaggaac cggatcaaag agttcctccg   3120
ccgctggacc taccaaggca acgctatgtt ctcttgcttt tgtcagcaag atagccagat   3180
caatgtcgat cgtggctggc tcgaagatac ctgcaagaat gtcattgcgc tgccattctc   3240
caaattgcag ttcgcgctta gctggataac gccacggaat gatgtcgtcg tgcacaacaa   3300
tggtgacttc tacagcgcgg agaatctcgc tctctccagg ggaagccgaa gtttccaaaa   3360
ggtcgttgat caaagctcgc cgcgttgttt catcaagcct tacggtcacc gtaaccagca   3420
aatcaatatc actgtgtggc ttcaggccgc catccactgc ggagccgtac aaatgtacgg   3480
ccagcaacgt cggttcgaga tggcgctcga tgacgccaac tacctctgat agttgagtcg   3540
atacttcggc gatcaccgct tccctcatga tgtttaactc ctgaattaag ccgcgccgcg   3600
aagcggtgtc ggcttgaatg aattgttagg cgtcatcctg tgctcccgag aaccagtacc   3660
agtacatcgc tgtttcgttc gagacttgag gtctagtttt atacgtgaac aggtcaatgc   3720
cgccgagagt aaagccacat tttgcgtaca aattgcaggc aggtacattg ttcgtttgtg   3780
tctctaatcg tatgccaagg agctgtctgc ttagtgccca ctttttcgca aattcgatga   3840
gactgtgcgc gactcctttg cctcggtgcg tgtgcgacac aacaatgtgt tcgatagagg   3900
ctagatcgtt ccatgttgag ttgagttcaa tcttcccgac aagctcttgg tcgatgaatg   3960
cgccatagca agcagagtct tcatcagagt catcatccga gatgtaatcc ttccggtagg   4020
ggctcacact tctggtagat agttcaaagc cttggtcgga taggtgcaca tcgaacactt   4080
cacgaacaat gaaatggttc tcagcatcca atgtttccgc cacctgctca gggatcaccg   4140
aaatcttcat atgacgccta acgcctggca cagcggatcg caaacctggc gcggcttttg   4200
gcacaaaagg cgtgacaggt ttgcgaatcc gttgctgcca cttgttaacc cttttgccag   4260
```

-continued

```
atttggtaac tataatttat gttagaggcg aagtcttggg taaaaactgg cctaaaattg   4320
ctggggattt caggaaagta aacatcacct tccggctcga tgtctattgt agatatatgt   4380
agtgtatcta cttgatcggg ggatctgctg cctcgcgcgt ttcggtgatg acggtgaaaa   4440
cctctgacac atgcagctcc cggagacggt cacagcttgt ctgtaagcgg atgccgggag   4500
cagacaagcc cgtcagggcg cgtcagcggg tgttggcggg tgtcggggcg cagccatgac   4560
ccagtcacgt agcgatagcg gagtgtatac tggcttaact atgcggcatc agagcagatt   4620
gtactgagag tgcaccatat gcggtgtgaa ataccgcaca gatgcgtaag gagaaaatac   4680
cgcatcaggc gctcttccgc ttcctcgctc actgactcgc tgcgctcggt cgttcggctg   4740
cggcgagcgg tatcagctca ctcaaaggcg gtaatacggt tatccacaga atcaggggat   4800
aacgcaggaa agaacatgtg agcaaaaggc cagcaaaagg ccaggaaccg taaaaaggcc   4860
gcgttgctgg cgtttttcca taggctccgc ccccctgacg agcatcacaa aaatcgacgc   4920
tcaagtcaga ggtggcgaaa cccgacagga ctataaagat accaggcgtt tccccctgga   4980
agctccctcg tgcgctctcc tgttccgacc ctgccgctta ccggatacct gtccgccttt   5040
ctcccttcgg gaagcgtggc gctttctcat agctcacgct gtaggtatct cagttcggtg   5100
taggtcgttc gctccaagct gggctgtgtg cacgaacccc ccgttcagcc cgaccgctgc   5160
gccttatccg gtaactatcg tcttgagtcc aacccggtaa gacacgactt atcgccactg   5220
gcagcagcca ctggtaacag gattagcaga gcgaggtatg taggcggtgc tacagagttc   5280
ttgaagtggt ggcctaacta cggctacact agaaggacag tatttggtat ctgcgctctg   5340
ctgaagccag ttaccttcgg aaaaagagtt ggtagctctt gatccggcaa acaaaccacc   5400
gctggtagcg gtggtttttt tgtttgcaag cagcagatta cgcgcagaaa aaaaggatct   5460
caagaagatc ctttgatctt ttctacgggg tctgacgctc agtggaacga aaactcacgt   5520
taagggattt tggtcatgag attatcaaaa aggatcttca cctagatcct tttaaattaa   5580
aaatgaagtt ttaaatcaat ctaaagtata tatgagtaaa cttggtctga cagttaccaa   5640
tgcttaatca gtgaggcacc tatctcagcg atctgtctat ttcgttcatc catagttgcc   5700
tgactccccg tcgtgtagat aactacgata cgggagggct taccatctgg ccccagtgct   5760
gcaatgatac cgcgagaccc acgctcaccg gctccagatt tatcagcaat aaaccagcca   5820
gccggaaggg ccgagcgcag aagtggtcct gcaactttat ccgcctccat ccagtctatt   5880
aattgttgcc gggaagctag agtaagtagt tcgccagtta atagtttgcg caacgttgtt   5940
gccattgctg caggggggggg gggggggggg ttccattgtt cattccacgg acaaaaacag   6000
agaaaggaaa cgacagaggc caaaaagctc gctttcagca cctgtcgttt cctttctttt   6060
cagagggtat tttaaataaa aacattaagt tatgacgaag aagaacggaa acgccttaaa   6120
ccggaaaatt ttcataaata gcgaaaaccc gcgaggtcgc cgccccgtaa cctgtcggat   6180
caccggaaag gacccgtaaa gtgataatga ttatcatcta catatcacaa cgtgcgtgga   6240
ggccatcaaa ccacgtcaaa taatcaatta tgacgcaggt atcgtattaa ttgatctgca   6300
tcaacttaac gtaaaaacaa cttcagacaa tacaaatcag cgacactgaa tacggggcaa   6360
cctcatgtcc cccccccccc ccccctgcag gcatcgtggt gtcacgctcg tcgtttggta   6420
tggcttcatt cagctccggt tcccaacgat caaggcgagt tacatgatcc cccatgttgt   6480
gcaaaaaagc ggttagctcc ttcggtcctc cgatcgttgt cagaagtaag ttggccgcag   6540
tgttatcact catggttatg gcagcactgc ataattctct tactgtcatg ccatccgtaa   6600
gatgcttttc tgtgactggt gagtactcaa ccaagtcatt ctgagaatag tgtatgcggc   6660
```

-continued gaccgagttg ctcttgcccg gcgtcaacac gggataatac cgcgccacat agcagaactt 6720
taaaagtgct catcattgga aaacgttctt cggggcgaaa actctcaagg atcttaccgc 6780
tgttgagatc cagttcgatg taacccactc gtgcacccaa ctgatcttca gcatctttta 6840
ctttcaccag cgtttctggg tgagcaaaaa caggaaggca aaatgccgca aaaaagggaa 6900
taagggcgac acggaaatgt tgaatactca tactcttcct ttttcaatat tattgaagca 6960
tttatcaggg ttattgtctc atgagcggat acatatttga atgtatttag aaaaataaac 7020
aaataggggt tccgcgcaca tttccccgaa aagtgccacc tgacgtctaa gaaaccatta 7080
ttatcatgac attaacctat aaaaataggc gtatcacgag gccctttcgt cttcaagaat 7140
tggtcgacga tcttgctgcg ttcggatatt ttcgtggagt tcccgccaca gacccggatt 7200
gaaggcgaga tccagcaact cgcgccagat catcctgtga cggaactttg gcgcgtgatg 7260
actggccagg acgtcggccg aaagagcgac aagcagatca cgcttttcga cagcgtcgga 7320
tttgcgatcg aggatttttc ggcgctgcgc tacgtccgcg accgcgttga gggatcaagc 7380
cacagcagcc cactcgacct tctagccgac ccagacgagc caagggatct tttggaatg 7440
ctgctccgtc gtcaggcttt ccgacgtttg ggtggttgaa cagaagtcat tatcgcacgg 7500
aatgccaagc actcccgagg ggaaccctgt ggttggcatg cacatacaaa tggacgaacg 7560
gataaacctt ttcacgccct tttaaatatc cgattattct aataaacgct cttttctctt 7620
aggtttaccc gccaatatat cctgtcaaac actgatagtt taaactgaag gcgggaaacg 7680
acaacctgat catgagcgga gaattaaggg agtcacgtta tgacccccgc cgatgacgcg 7740
ggacaagccg ttttacgttt ggaactgaca gaaccgcaac gttgaaggag ccactcagct 7800
taattaacta atcgactcta gtaacggccg ccagtgtgct ggaattaatt cggcttgtcg 7860
accacccaac cccatatcga cagaggatgt gaagaacagg taaatcacgc agaagaaccc 7920
atctctgata gcagctatcg attagaacaa cgaatccata ttgggtccgt gggaaatact 7980
tactgcacag gaagggggcg atctgacgag gccccgccac cggcctcgac ccgaggccga 8040
ggccgacgaa gcgccggcga gtacggcgcc gcggcggcct ctgcccgtgc cctctgcgcg 8100
tgggagggag aggccgcggt ggtgggggcg cgcgcgcgcg cgcgcgcagc tggtgcggcg 8160
gcgcgggggt cagccgccga gccggcggcg acggaggagc agggcggcgt ggacgcgaac 8220
ttccgatcgg ttggtcagag tgcgcgagtt gggcttagcc aattaggtct caacaatcta 8280
ttgggccgta aaattcatgg gccctggttt gtctaggccc aatatcccgt tcatttcagc 8340
ccacaaatat ttccccagag gattattaag gcccacacgc agcttatagc agatcaagta 8400
cgatgtttcc tgatcgttgg atcggaaacg tacggtcttg atcaggcatg ccgacttcgt 8460
caaagagagg cggcatgacc tgacgcggag ttggttccgg gcaccgtctg gatggtcgta 8520
ccgggaccgg acacgtgtcg cgcctccaac tacatggaca cgtgtggtgc tgccattggg 8580
ccgtacgcgt ggcggtgacc gcaccggatg ctgcctcgca ccgccttgcc cacgctttat 8640
atagagaggt tttctctcca ttaatcgcat agcgagtcga atcgaccgaa ggggaggggg 8700
agcgagagct ttgcgttctc taatcgcctc gtcaagccta gcgctaagga agggagagat 8760
atccatccgg atcccggaag ccgaatccat ccatccatcc atcccatact gcccttacga 8820
tcgagctgtt tgatattcgt gcagatgagc ggattctccg cggcagctgc tgcggccgag 8880
cgcttgtcgg aaggttcacc ctggatgcca actccgagct taaggtgaca ttgaacccag 8940
caccgcaggg ttcggtggtg gagatcaatc tagaggcaac taacaccagc ggctccctga 9000
tactgcattg gggcgccctt cgcccggata gaggagaatg gctcctacca tcccggagtc 9060
aaggtaacta atcaatcacc tcgtcctaat cctcgaatct ctcgtggtgc ccgtctaatc 9120
tcgcgatttt gatgctcgtg gtggaaagcg taggaggatc ccgtgcgagt tagtctcaat 9180
ctctcagggt ttcgtgcgat tttagggtga tccacctctt aatcgagtta cggtttcgtg 9240
cgattttagg gtaatcctct taatctctca ttgatttagg gtttcgtgag aatcgaggta 9300
gggatctgtg ttatttatat cgatctaata gatggattgg ttttgagatt gttctgtcag 9360
atggggattg tttcgatata ttaccctaat gatgtgtcag atggggattg tttcgatata 9420
ttaccctaat gatgtgtcag atggggattg tttcgatata ttaccctaat gatggataat 9480
aagagtagtt cacagttatg ttttgatcct gccacatagt ttgagttttg tgatcagatt 9540
tagttttact tatttgtgct tagttcggat gggattgttc tgatattgtt ccaatagatg 9600
aatagctcgt taggttaaaa tctttaggtt gagttaggcg acacatagtt tatttcctct 9660
ggatttggat tggaattgtg ttcttagttt ttttcccctg gatttggatt ggaattgtgt 9720
ggagctgggt tagagaatta catctgtatc gtgtacacct acttgaactg tagagcttgg 9780
gttctaaggt caatttaatc tgtattgtat ctggctcttt gcctagttga actgtagtgc 9840
tgatgttgta ctgtgttttt ttacccgttt tatttgcttt actcgtgcaa atcaaatctg 9900
tcagatgcta gaactaggtg gctttattct gtgttcttac atagatctgt tgtcctgtag 9960
ttacttatgt cagttttgtt attatctgaa gatatttttg gttgttgctt gttgatgtgg 10020
tgtgagctgt gagcagcgct cttatgatta atgatgctgt ccaattgtag tgtagtatga 10080
tgtgattgat atgttcatct attttgagct gacagtaccg atatcgtagg atctggtgcc 10140
aacttattct ccagctgctt ttttttacct atgttaattc caatcctttc ttgcctcttc 10200
cagggatcca ccgggatggt aggagccatt ctcctctatc cgggcgaagg gcgccccaat 10260
gcagtatcag ggagccgctg gtgttagttg cctctagatt gatctccacc accgaaccct 10320
gcggtgctgg gttcaatgtc accttaagct cggagttggc atccagggtg aaccttccga 10380
caagcgctcg gccgcagcag ctgccgcgga gaatccgctc atctgcacga atatcaaaca 10440
gctcgatcgt aagggcagta tgggatggat ggatggatgg attcggcttc cgggatccgg 10500
atggatatct ctcccttcct tagcgctagc tccccgaatt tccccgatcg ttcaaacatt 10560
tggcaataaa gtttcttaag attgaatcct gttgccggtc ttgcgatgat tatcatataa 10620
tttctgttga attacgttaa gcatgtaata attaacatgt aatgcatgac gttatttatg 10680
agatgggttt ttatgattag agtcccgcaa ttatacattt aatacgcgat agaaaacaaa 10740
atatagcgcg caaactagga taaattatcg cgcgcggtgt catctatgtt actagatcgg 10800
gaattggcga gctcgcccgg gtattcatcc taggtatcca agaattcata ctaaagcttg 10860
catgcctgca ggtcgactct agtaacggcc gccagtgtgc tggaattaat tcggcttgtc 10920
gaccacccaa ccccatatcg acagaggatg tgaagaacag gtaaatcacg cagaagaacc 10980
catctctgat agcagctatc gattagaaca acgaatccat attgggtccg tgggaaatac 11040
ttactgcaca ggaagggggc gatctgacga ggccccgcca ccggcctcga cccgaggccg 11100
aggccgacga agcgccggcg agtacggcgc cgcggcggcc tctgcccgtg ccctctgcgc 11160
gtgggaggga gaggccgcgg tggtgggggc gcgcgcgcgc gcgcgcgcag ctggtgcggc 11220
ggcgcggggg tcagccgccg agccggcggc gacggaggag cagggcggcg tggacgcgaa 11280
cttccgatcg gttggtcaga gtgcgcgagt tgggcttagc caattaggtc tcaacaatct 11340
attgggccgt aaaattcatg ggccctggtt tgtctaggcc caatatcccg ttcatttcag 11400
cccacaaata tttccccaga ggattattaa ggcccacacg cagcttatag cagatcaagt 11460
acgatgtttc ctgatcgttg gatcggaaac gtacggtctt gatcaggcat gccgacttcg 11520
tcaaagagag gcggcatgac ctgacgcgga gttggttccg ggcaccgtct ggatggtcgt 11580
accgggaccg gacacgtgtc gcgcctccaa ctacatggac acgtgtggtg ctgccattgg 11640
gccgtacgcg tggcggtgac cgcaccggat gctgcctcgc accgccttgc ccacgcttta 11700
tatagagagg ttttctctcc attaatcgca tagcgagtcg aatcgaccga aggggagggg 11760
gagcgaagct ttgcgttctc taatcgcctc gtcaaggtaa ctaatcaatc acctcgtcct 11820
aatcctcgaa tctctcgtgg tgcccgtcta atctcgcgat tttgatgctc gtggtggaaa 11880
gcgtaggagg atcccgtgcg agttagtctc aatctctcag ggtttcgtgc gattttaggg 11940
tgatccacct cttaatcgag ttacggtttc gtgcgatttt agggtaatcc tcttaatctc 12000
tcattgattt agggtttcgt gagaatcgag gtagggatct gtgttattta tatcgatcta 12060
atagatggat tggttttgag attgttctgt cagatgggga ttgtttcgat atattaccct 12120
aatgatgtgt cagatgggga ttgtttcgat atattaccct aatgatgtgt cagatgggga 12180
ttgtttcgat atattaccct aatgatggat aataagagta gttcacagtt atgttttgat 12240
cctgccacat agtttgagtt ttgtgatcag atttagtttt acttatttgt gcttagttcg 12300
gatgggattg ttctgatatt gttccaatag atgaatagct cgttaggtta aaatctttag 12360
gttgagttag gcgacacata gtttatttcc tctggatttg gattggaatt gtgttcttag 12420
tttttttccc ctggatttgg attggaattg tgtggagctg ggttagagaa ttacatctgt 12480
atcgtgtaca cctacttgaa ctgtagagct tgggttctaa ggtcaattta atctgtattg 12540
tatctggctc tttgcctagt tgaactgtag tgctgatgtt gtactgtgtt tttttacccg 12600
ttttatttgc tttactcgtg caaatcaaat ctgtcagatg ctagaactag gtggctttat 12660
tctgtgttct tacatagatc tgttgtcctg tagttactta tgtcagtttt gttattatct 12720
gaagatattt ttggttgttg cttgttgatg tggtgtgagc tgtgagcagc gctcttatga 12780
ttaatgatgc tgtccaattg tagtgtagta tgatgtgatt gatatgttca tctatttga 12840 gctgacagta ccgatatcgt aggatctggt gccaacttat tctccagctg cttttttta 12900 cctatgttaa ttccaatcct ttcttgcctc ttccag 12936

<210> SEQ ID NO 16
<211> LENGTH: 13462
<212> TYPE: DNA
<213> ORGANISM: Artificial Sequence
<220> FEATURE:
<223> OTHER INFORMATION: Synthetic sequence, pAG2101

<400> SEQUENCE: 16
atccagataa tgcagaaact cattaactca gtgcaaaact atgcctgggg cagcaaaacg 60
gcgttgactg aactttatgg tatggaaaat ccgtccagcc agccgatggc cgagctgtgg 120
atgggcgcac atccgaaaag cagttcacga gtgcagaatg ccgccggaga tatcgtttca 180
ctgcgtgatg tgattgagag tgataaatcg actctgctcg gagaggccgt tgccaaacgc 240
tttggcgaac tgcctttcct gttcaaagta ttatgcgcag cacagccact ctccattcag 300
gttcatccaa acaaacacaa ttctgaaatc ggttttgcca aagaaaatgc cgcaggtatc 360
ccgatggatg ccgccgagcg taactataaa gatcctaacc acaagccgga gctggttttt 420
gcgctgacgc ctttccttgc gatgaacgcg tttcgtgaat tttccgagat tgtctcccta 480

-continued

```
ctccagccgg tcgcaggtgc acatccggcg attgctcact ttttacaaca gcctgatgcc    540

gaacgtttaa gcgaactgtt cgccagcctg ttgaatatgc agggtgaaga aaaatcccgc    600

gcgctggcga ttttaaaatc ggccctcgat agccagcagg gtgaaccgtg gcaaacgatt    660

cgtttaattt ctgaatttta cccggaagac agcggtctgt tctccccgct attgctgaat    720

gtggtgaaat tgaaccctgg cgaagcgatg ttcctgttcg ctgaaacacc gcacgcttac    780

ctgcaaggcg tggcgctgga agtgatggca aactccgata acgtgctgcg tgcgggtctg    840

acgcctaaat acattgatat tccggaactg gttgccaatg tgaaattcga agccaaaccg    900

gctaaccagt tgttgaccca gccggtgaaa caaggtgcag aactggactt cccgattcca    960

gtggatgatt ttgccttctc gctgcatgac cttagtgata aagaaaccac cattagccag   1020

cagagtgccg ccattttgtt ctgcgtcgaa ggcgatgcaa cgttgtggaa aggttctcag   1080

cagttacagc ttaaaccggg tgaatcagcg tttattgccg ccaacgaatc accggtgact   1140

gtcaaaggcc acggccgttt agcgcgtgtt tacaacaagc tgtaagagct tactgaaaaa   1200

attaacatct cttgctaagc tgggagctct agatccccga atttccccga tcgttcaaac   1260

atttggcaat aaagtttctt aagattgaat cctgttgccg gtcttgcgat gattatcata   1320

taatttctgt tgaattacgt taagcatgta ataattaaca tgtaatgcat gacgttattt   1380

atgagatggg tttttatgat tagagtcccg caattataca tttaatacgc gatagaaaac   1440

aaaatatagc gcgcaaacta ggataaatta tcgcgcgcgg tgtcatctat gttactagat   1500

cgggaattgg cgagctcgaa ttaattcagt acattaaaaa cgtccgcaat gtgttattaa   1560

gttgtctaag cgtcaatttg tttacaccac aatatatcct gccaccagcc agccaacagc   1620

tccccgaccg gcagctcggc acaaaatcac cactcgatac aggcagccca tcagtccggg   1680

acggcgtcag cgggagagcc gttgtaaggc ggcagacttt gctcatgtta ccgatgctat   1740

tcggaagaac ggcaactaag ctgccgggtt tgaaacacgg atgatctcgc ggagggtagc   1800

atgttgattg taacgatgac agagcgttgc tgcctgtgat caaatatcat ctccctcgca   1860

gagatccgaa ttatcagcct tcttattcat ttctcgctta accgtgacag gctgtcgatc   1920

ttgagaacta tgccgacata ataggaaatc gctggataaa gccgctgagg aagctgagtg   1980

gcgctatttc tttagaagtg aacgttgacg atcgtcgacc gtaccccgat gaattaattc   2040

ggacgtacgt tctgaacaca gctggatact tacttgggcg attgtcatac atgacatcaa   2100

caatgtaccc gtttgtgtaa ccgtctcttg gaggttcgta tgacactagt ggttcccctc   2160

agcttgcgac tagatgttga ggcctaacat tttattagag agcaggctag ttgcttagat   2220

acatgatctt caggccgtta tctgtcaggg caagcgaaaa ttggccattt atgacgacca   2280

atgccccgca gaagctccca tctttgccgc catagacgcc gcgcccccct tttggggtgt   2340

agaacatcct tttgccagat gtggaaaaga agttcgttgt cccattgttg gcaatgacgt   2400

agtagccggc gaaagtgcga gacccatttg cgctatatat aagcctacga tttccgttgc   2460

gactattgtc gtaattggat gaactattat cgtagttgct ctcagagttg tcgtaatttg   2520

atggactatt gtcgtaattg cttatggagt tgtcgtagtt gcttggagaa atgtcgtagt   2580

tggatgggga gtagtcatag ggaagacgag cttcatccac taaaacaatt ggcaggtcag   2640

caagtgcctg ccccgatgcc atcgcaagta cgaggcttag aaccaccttc aacagatcgc   2700

gcatagtctt ccccagctct ctaacgcttg agttaagccg cgccgcgaag cggcgtcggc   2760

ttgaacgaat tgttagacat tatttgccga ctaccttggt gatctcgcct ttcacgtagt   2820

gaacaaattc ttccaactga tctgcgcgcg aggccaagcg atcttcttgt ccaagataag   2880
```

```
cctgcctagc ttcaagtatg acgggctgat actgggccgg caggcgctcc attgcccagt   2940
cggcagcgac atccttcggc gcgattttgc cggttactgc gctgtaccaa atgcgggaca   3000
acgtaagcac tacatttcgc tcatcgccag cccagtcggg cggcgagttc catagcgtta   3060
aggtttcatt tagcgcctca aatagatcct gttcaggaac cggatcaaag agttcctccg   3120
ccgctggacc taccaaggca acgctatgtt ctcttgcttt tgtcagcaag atagccagat   3180
caatgtcgat cgtggctggc tcgaagatac ctgcaagaat gtcattgcgc tgccattctc   3240
caaattgcag ttcgcgctta gctggataac gccacggaat gatgtcgtcg tgcacaacaa   3300
tggtgacttc tacagcgcgg agaatctcgc tctctccagg ggaagccgaa gtttccaaaa   3360
ggtcgttgat caaagctcgc cgcgttgttt catcaagcct tacggtcacc gtaaccagca   3420
aatcaatatc actgtgtggc ttcaggccgc catccactgc ggagccgtac aaatgtacgg   3480
ccagcaacgt cggttcgaga tggcgctcga tgacgccaac tacctctgat agttgagtcg   3540
atacttcggc gatcaccgct tccctcatga tgtttaactc ctgaattaag ccgcgccgcg   3600
aagcggtgtc ggcttgaatg aattgttagg cgtcatcctg tgctcccgag aaccagtacc   3660
agtacatcgc tgtttcgttc gagacttgag gtctagtttt atacgtgaac aggtcaatgc   3720
cgccgagagt aaagccacat tttgcgtaca aattgcaggc aggtacattg ttcgtttgtg   3780
tctctaatcg tatgccaagg agctgtctgc ttagtgccca ctttttcgca aattcgatga   3840
gactgtgcgc gactcctttg cctcggtgcg tgtgcgacac aacaatgtgt tcgatagagg   3900
ctagatcgtt ccatgttgag ttgagttcaa tcttcccgac aagctcttgg tcgatgaatg   3960
cgccatagca agcagagtct tcatcagagt catcatccga gatgtaatcc ttccggtagg   4020
ggctcacact tctggtagat agttcaaagc cttggtcgga taggtgcaca tcgaacactt   4080
cacgaacaat gaaatggttc tcagcatcca atgtttccgc cacctgctca gggatcaccg   4140
aaatcttcat atgacgccta acgcctggca cagcggatcg caaacctggc gcggcttttg   4200
gcacaaaagg cgtgacaggt ttgcgaatcc gttgctgcca cttgttaacc cttttgccag   4260
atttggtaac tataatttat gttagaggcg aagtcttggg taaaaactgg cctaaaattg   4320
ctggggattt caggaaagta aacatcacct tccggctcga tgtctattgt agatatatgt   4380
agtgtatcta cttgatcggg ggatctgctg cctcgcgcgt ttcggtgatg acggtgaaaa   4440
cctctgacac atgcagctcc cggagacggt cacagcttgt ctgtaagcgg atgccgggag   4500
cagacaagcc cgtcagggcg cgtcagcggg tgttggcggg tgtcggggcg cagccatgac   4560
ccagtcacgt agcgatagcg gagtgtatac tggcttaact atgcggcatc agagcagatt   4620
gtactgagag tgcaccatat gcggtgtgaa ataccgcaca gatgcgtaag gagaaaatac   4680
cgcatcaggc gctcttccgc ttcctcgctc actgactcgc tgcgctcggt cgttcggctg   4740
cggcgagcgg tatcagctca ctcaaaggcg gtaatacggt tatccacaga atcaggggat   4800
aacgcaggaa agaacatgtg agcaaaaggc cagcaaaagg ccaggaaccg taaaaaggcc   4860
gcgttgctgg cgtttttcca taggctccgc ccccctgacg agcatcacaa aaatcgacgc   4920
tcaagtcaga ggtggcgaaa cccgacagga ctataaagat accaggcgtt tccccctgga   4980
agctccctcg tgcgctctcc tgttccgacc ctgccgctta ccggatacct gtccgccttt   5040
ctcccttcgg gaagcgtggc gctttctcat agctcacgct gtaggtatct cagttcggtg   5100
taggtcgttc gctccaagct gggctgtgtg cacgaacccc ccgttcagcc cgaccgctgc   5160
gccttatccg gtaactatcg tcttgagtcc aacccggtaa gacacgactt atcgccactg   5220
```

-continued

```
gcagcagcca ctggtaacag gattagcaga gcgaggtatg taggcggtgc tacagagttc   5280
ttgaagtggt ggcctaacta cggctacact agaaggacag tatttggtat ctgcgctctg   5340
ctgaagccag ttaccttcgg aaaaagagtt ggtagctctt gatccggcaa acaaaccacc   5400
gctggtagcg gtggtttttt tgtttgcaag cagcagatta cgcgcagaaa aaaaggatct   5460
caagaagatc ctttgatctt ttctacgggg tctgacgctc agtggaacga aaactcacgt   5520
taagggattt tggtcatgag attatcaaaa aggatcttca cctagatcct tttaaattaa   5580
aaatgaagtt ttaaatcaat ctaaagtata tatgagtaaa cttggtctga cagttaccaa   5640
tgcttaatca gtgaggcacc tatctcagcg atctgtctat ttcgttcatc catagttgcc   5700
tgactccccg tcgtgtagat aactacgata cgggagggct taccatctgg ccccagtgct   5760
gcaatgatac cgcgagaccc acgctcaccg gctccagatt tatcagcaat aaaccagcca   5820
gccggaaggg ccgagcgcag aagtggtcct gcaactttat ccgcctccat ccagtctatt   5880
aattgttgcc gggaagctag agtaagtagt tcgccagtta atagtttgcg caacgttgtt   5940
gccattgctg caggggggggg ggggggggg ttccattgtt cattccacgg acaaaaacag   6000
agaaaggaaa cgacagaggc caaaaagctc gctttcagca cctgtcgttt cctttctttt   6060
cagagggtat tttaaataaa aacattaagt tatgacgaag aagaacggaa acgccttaaa   6120
ccggaaaatt ttcataaata gcgaaaaccc gcgaggtcgc cgccccgtaa cctgtcggat   6180
caccggaaag gacccgtaaa gtgataatga ttatcatcta catatcacaa cgtgcgtgga   6240
ggccatcaaa ccacgtcaaa taatcaatta tgacgcaggt atcgtattaa ttgatctgca   6300
tcaacttaac gtaaaaacaa cttcagacaa tacaaatcag cgacactgaa tacggggcaa   6360
cctcatgtcc cccccccccc cccccctgcag gcatcgtggt gtcacgctcg tcgtttggta   6420
tggcttcatt cagctccggt tcccaacgat caaggcgagt tacatgatcc cccatgttgt   6480
gcaaaaaagc ggttagctcc ttcggtcctc cgatcgttgt cagaagtaag ttggccgcag   6540
tgttatcact catggttatg gcagcactgc ataattctct tactgtcatg ccatccgtaa   6600
gatgcttttc tgtgactggt gagtactcaa ccaagtcatt ctgagaatag tgtatgcggc   6660
gaccgagttg ctcttgcccg gcgtcaacac gggataatac cgcgccacat agcagaactt   6720
taaaagtgct catcattgga aaacgttctt cggggcgaaa actctcaagg atcttaccgc   6780
tgttgagatc cagttcgatg taacccactc gtgcacccaa ctgatcttca gcatctttta   6840
ctttcaccag cgtttctggg tgagcaaaaa caggaaggca aaatgccgca aaaaagggaa   6900
taagggcgac acggaaatgt tgaatactca tactcttcct ttttcaatat tattgaagca   6960
tttatcaggg ttattgtctc atgagcggat acatatttga atgtatttag aaaaataaac   7020
aaataggggt tccgcgcaca tttccccgaa aagtgccacc tgacgtctaa gaaaccatta   7080
ttatcatgac attaacctat aaaaataggc gtatcacgag gccctttcgt cttcaagaat   7140
tggtcgacga tcttgctgcg ttcggatatt ttcgtggagt tcccgccaca gacccggatt   7200
gaaggcgaga tccagcaact cgcgccagat catcctgtga cggaactttg gcgcgtgatg   7260
actggccagg acgtcggccg aaagagcgac aagcagatca cgcttttcga cagcgtcgga   7320
tttgcgatcg aggatttttc ggcgctgcgc tacgtccgcg accgcgttga gggatcaagc   7380
cacagcagcc cactcgacct tctagccgac ccagacgagc caagggatct tttggaatg   7440
ctgctccgtc gtcaggcttt ccgacgtttg ggtggttgaa cagaagtcat tatcgcacgg   7500
aatgccaagc actcccgagg ggaaccctgt ggttggcatg cacatacaaa tggacgaacg   7560
gataaacctt ttcacgccct tttaaatatc cgattattct aataaacgct cttttctctt   7620
```

aggtttaccc gccaatatat cctgtcaaac actgatagtt taaactgaag gcgggaaacg 7680
acaacctgat catgagcgga gaattaaggg agtcacgtta tgaccccccgc cgatgacgcg 7740
ggacaagccg ttttacgttt ggaactgaca gaaccgcaac gttgaaggag ccactcagct 7800
taattaacta atcgactcta gtaacggccg ccagtgtgct ggaattaatt cggcttgtcg 7860
accacccaac cccatatcga cagaggatgt gaagaacagg taaatcacgc agaagaaccc 7920
atctctgata gcagctatcg attagaacaa cgaatccata ttgggtccgt gggaaatact 7980
tactgcacag gaagggggcg atctgacgag gccccgccac cggcctcgac ccgaggccga 8040
ggccgacgaa gcgccggcga gtacggcgcc gcggcggcct ctgcccgtgc cctctgcgcg 8100
tgggagggag aggccgcggt ggtgggggcg cgcgcgcgcg cgcgcgcagc tggtgcggcg 8160
gcgcgggggt cagccgccga gccggcggcg acggaggagc agggcggcgt ggacgcgaac 8220
ttccgatcgg ttggtcagag tgcgcgagtt gggcttagcc aattaggtct caacaatcta 8280
ttgggccgta aaattcatgg gccctggttt gtctaggccc aatatcccgt tcatttcagc 8340
ccacaaatat ttccccagag gattattaag gcccacacgc agcttatagc agatcaagta 8400
cgatgtttcc tgatcgttgg atcggaaacg tacggtcttg atcaggcatg ccgacttcgt 8460
caaagagagg cggcatgacc tgacgcggag ttggttccgg gcaccgtctg gatggtcgta 8520
ccgggaccgg acacgtgtcg cgcctccaac tacatggaca cgtgtggtgc tgccattggg 8580
ccgtacgcgt ggcggtgacc gcaccggatg ctgcctcgca ccgccttgcc cacgctttat 8640
atagagaggt tttctctcca ttaatcgcat agcgagtcga atcgaccgaa ggggaggggg 8700
agcgagagct ttgcgttctc taatcgcctc gtcaagccta gcagcagatc tagttgacca 8760
agcaagagat aatggattat tgggtattat tggaattttt gtttggatta ggttcatggc 8820
tacaaggcaa ctaatatgga acaagaacta caatgtgaag ccacgtgaga taagcaaagc 8880
acaagatagg tttacagatg atcttgagaa tatgtacaga acttacccac aatatcagga 8940
gatcttaaga atgataatgt ctgctgttgg tcggggaggt gaaggtgatg ttggtcaacg 9000
cattcgtgat gagatattag taatccagag aaataatgac tgcaaaggtg gaatgatgga 9060
ggagtggcac cagaaactgc acaacaatac aagcccagat gatgtagtga tctgccaggc 9120
cctacttgat tatatcaaga gtgattttga tattggtgtt tactgggaca ccttgaaaaa 9180
agatggtata acaaaagagc gtctattgag ctatgatcga ccgattcatt cagagccaaa 9240
tttcaggagt gaacagaaag atggcttact ccgtgacttg ggcaattata tgagaagcct 9300
caagatggag ggtacccgga gtcaaggtaa ctaatcaatc acctcgtcct aatcctcgaa 9360
tctctcgtgg tgcccgtcta atctcgcgat tttgatgctc gtggtggaaa gcgtaggagg 9420
atcccgtgcg agttagtctc aatctctcag ggtttcgtgc gattttaggg tgatccacct 9480
cttaatcgag ttacggtttc gtgcgatttt agggtaatcc tcttaatctc tcattgattt 9540
agggtttcgt gagaatcgag gtagggatct gtgttattta tatcgatcta atagatggat 9600
tggttttgag attgttctgt cagatgggga ttgtttcgat atattaccct aatgatgtgt 9660
cagatgggga ttgtttcgat atattaccct aatgatgtgt cagatgggga ttgtttcgat 9720
atattaccct aatgatggat aataagagta gttcacagtt atgttttgat cctgccacat 9780
agtttgagtt ttgtgatcag atttagtttt acttatttgt gcttagttcg gatgggattg 9840
ttctgatatt gttccaatag atgaatagct cgttaggtta aaatctttag gttgagttag 9900
gcgacacata gtttatttcc tctggatttg gattggaatt gtgttcttag ttttttttccc 9960

-continued

```
ctggatttgg attggaattg tgtggagctg ggttagagaa ttacatctgt atcgtgtaca  10020
cctacttgaa ctgtagagct tgggttctaa ggtcaattta atctgtattg tatctggctc  10080
tttgcctagt tgaactgtag tgctgatgtt gtactgtgtt tttttacccg ttttatttgc  10140
tttactcgtg caaatcaaat ctgtcagatg ctagaactag gtggctttat tctgtgttct  10200
tacatagatc tgttgtcctg tagttactta tgtcagtttt gttattatct gaagatattt  10260
ttggttgttg cttgttgatg tggtgtgagc tgtgagcagc gctcttatga ttaatgatgc  10320
tgtccaattg tagtgtagta tgatgtgatt gatatgttca tctattttga gctgacagta  10380
ccgatatcgt aggatctggt gccaacttat tctccagctg cttttttttta cctatgttaa  10440
ttccaatcct ttcttgcctc ttccagggat ccaccgggta ccctccatct tgaggcttct  10500
catataattg cccaagtcac ggagtaagcc atctttctgt tcactcctga aatttggctc  10560
tgaatgaatc ggtcgatcat agctcaatag acgctctttt gttataccat ctttttttcaa  10620
ggtgtcccag taaacaccaa tatcaaaatc actcttgata taatcaagta gggcctggca  10680
gatcactaca tcatctgggc ttgtattgtt gtgcagtttc tggtgccact cctccatcat  10740
tccacctttg cagtcattat ttctctggat tactaatatc tcatcacgaa tgcgttgacc  10800
aacatcacct tcacctcccc gaccaacagc agacattatc attcttaaga tctcctgata  10860
ttgtgggtaa gttctgtaca tattctcaag atcatctgta aacctatctt gtgctttgct  10920
tatctcacgt ggcttcacat tgtagttctt gttccatatt agttgccttg tagccatgaa  10980
cctaatccaa acaaaaattc caataatacc caataatcca ttatctcttg cttggtcaac  11040
tagatctgct gctagctccc cgaatttccc cgatcgttca aacatttggc aataaagttt  11100
cttaagattg aatcctgttg ccggtcttgc gatgattatc atataatttc tgttgaatta  11160
cgttaagcat gtaataatta acatgtaatg catgacgtta tttatgagat gggtttttat  11220
gattagagtc ccgcaattat acatttaata cgcgatagaa aacaaaatat agcgcgcaaa  11280
ctaggataaa ttatcgcgcg cggtgtcatc tatgttacta gatcgggaat tggcgagctc  11340
gcccgggtat tcatcctagg tatccaagaa ttcatactaa agcttgcatg cctgcaggtc  11400
gactctagta acggccgcca gtgtgctgga attaattcgg cttgtcgacc acccaacccc  11460
atatcgacag aggatgtgaa gaacaggtaa atcacgcaga agaacccatc tctgatagca  11520
gctatcgatt agaacaacga atccatattg ggtccgtggg aaatacttac tgcacaggaa  11580
gggggcgatc tgacgaggcc ccgccaccgg cctcgacccg aggccgaggc cgacgaagcg  11640
ccggcgagta cggcgccgcg gcggcctctg cccgtgccct ctgcgcgtgg gagggagagg  11700
ccgcggtggt gggggcgcgc gcgcgcgcgc gcgcagctgg tgcggcggcg cgggggtcag  11760
ccgccgagcc ggcggcgacg gaggagcagg gcggcgtgga cgcgaacttc cgatcggttg  11820
gtcagagtgc gcgagttggg cttagccaat taggtctcaa caatctattg ggccgtaaaa  11880
ttcatgggcc ctggtttgtc taggcccaat atcccgttca tttcagccca caaatatttc  11940
cccagaggat tattaaggcc cacacgcagc ttatagcaga tcaagtacga tgtttcctga  12000
tcgttggatc ggaaacgtac ggtcttgatc aggcatgccg acttcgtcaa agagaggcgg  12060
catgacctga cgcggagttg gttccgggca ccgtctggat ggtcgtaccg ggaccggaca  12120
cgtgtcgcgc ctccaactac atggacacgt gtggtgctgc cattgggccg tacgcgtggc  12180
ggtgaccgca ccggatgctg cctcgcaccg ccttgcccac gctttatata gagaggtttt  12240
ctctccatta atcgcatagc gagtcgaatc gaccgaaggg gagggggagc gaagctttgc  12300
gttctctaat cgcctcgtca aggtaactaa tcaatcacct cgtcctaatc ctcgaatctc  12360
```

tcgtggtgcc cgtctaatct cgcgattttg atgctcgtgg tggaaagcgt aggaggatcc 12420
cgtgcgagtt agtctcaatc tctcagggtt tcgtgcgatt ttagggtgat ccacctctta 12480
atcgagttac ggtttcgtgc gattttaggg taatcctctt aatctctcat tgatttaggg 12540
tttcgtgaga atcgaggtag ggatctgtgt tatttatatc gatctaatag atggattggt 12600
tttgagattg ttctgtcaga tggggattgt ttcgatatat taccctaatg atgtgtcaga 12660
tggggattgt ttcgatatat taccctaatg atgtgtcaga tggggattgt ttcgatatat 12720
taccctaatg atggataata agagtagttc acagttatgt tttgatcctg ccacatagtt 12780
tgagttttgt gatcagattt agttttactt atttgtgctt agttcggatg ggattgttct 12840
gatattgttc caatagatga atagctcgtt aggttaaaat ctttaggttg agttaggcga 12900
cacatagttt atttcctctg gatttggatt ggaattgtgt tcttagtttt tttcccctgg 12960
atttggattg gaattgtgtg gagctgggtt agagaattac atctgtatcg tgtacaccta 13020
cttgaactgt agagcttggg ttctaaggtc aatttaatct gtattgtatc tggctctttg 13080
cctagttgaa ctgtagtgct gatgttgtac tgtgtttttt tacccgtttt atttgcttta 13140
ctcgtgcaaa tcaaatctgt cagatgctag aactaggtgg ctttattctg tgttcttaca 13200
tagatctgtt gtcctgtagt tacttatgtc agttttgtta ttatctgaag atatttttgg 13260
ttgttgcttg ttgatgtggt gtgagctgtg agcagcgctc ttatgattaa tgatgctgtc 13320
caattgtagt gtagtatgat gtgattgata tgttcatcta ttttgagctg acagtaccga 13380
tatcgtagga tctggtgcca acttattctc cagctgcttt tttttaccta tgttaattcc 13440
aatcctttct tgcctcttcc ag 13462

<210> SEQ ID NO 17
<211> LENGTH: 13078
<212> TYPE: DNA
<213> ORGANISM: Artificial Sequence
<220> FEATURE:
<223> OTHER INFORMATION: Synthetic sequence, pAG2102

<400> SEQUENCE: 17
atccagataa tgcagaaact cattaactca gtgcaaaact atgcctgggg cagcaaaacg 60
gcgttgactg aactttatgg tatggaaaat ccgtccagcc agccgatggc cgagctgtgg 120
atgggcgcac atccgaaaag cagttcacga gtgcagaatg ccgccggaga tatcgtttca 180
ctgcgtgatg tgattgagag tgataaatcg actctgctcg gagaggccgt tgccaaacgc 240
tttggcgaac tgcctttcct gttcaaagta ttatgcgcag cacagccact ctccattcag 300
gttcatccaa acaaacacaa ttctgaaatc ggttttgcca aagaaaatgc cgcaggtatc 360
ccgatggatg ccgccgagcg taactataaa gatcctaacc acaagccgga gctggttttt 420
gcgctgacgc ctttccttgc gatgaacgcg tttcgtgaat tttccgagat tgtctcccta 480
ctccagccgg tcgcaggtgc acatccggcg attgctcact ttttacaaca gcctgatgcc 540
gaacgtttaa gcgaactgtt cgccagcctg ttgaatatgc agggtgaaga aaaatcccgc 600
gcgctggcga ttttaaaatc ggccctcgat agccagcagg gtgaaccgtg gcaaacgatt 660
cgtttaattt ctgaatttta cccggaagac agcggtctgt tctccccgct attgctgaat 720
gtggtgaaat tgaaccctgg cgaagcgatg ttcctgttcg ctgaaacacc gcacgcttac 780
ctgcaaggcg tggcgctgga agtgatggca aactccgata acgtgctgcg tgcgggtctg 840
acgcctaaat acattgatat tccggaactg gttgccaatg tgaaattcga agccaaaccg 900

-continued

```
gctaaccagt tgttgaccca gccggtgaaa caaggtgcag aactggactt cccgattcca    960
gtggatgatt ttgccttctc gctgcatgac cttagtgata aagaaaccac cattagccag   1020
cagagtgccg ccattttgtt ctgcgtcgaa ggcgatgcaa cgttgtggaa aggttctcag   1080
cagttacagc ttaaaccggg tgaatcagcg tttattgccg ccaacgaatc accggtgact   1140
gtcaaaggcc acggccgttt agcgcgtgtt tacaacaagc tgtaagagct tactgaaaaa   1200
attaacatct cttgctaagc tgggagctct agatccccga atttccccga tcgttcaaac   1260
atttggcaat aaagtttctt aagattgaat cctgttgccg gtcttgcgat gattatcata   1320
taatttctgt tgaattacgt taagcatgta ataattaaca tgtaatgcat gacgttattt   1380
atgagatggg tttttatgat tagagtcccg caattataca tttaatacgc gatagaaaac   1440
aaaatatagc gcgcaaacta ggataaatta tcgcgcgcgg tgtcatctat gttactagat   1500
cgggaattgg cgagctcgaa ttaattcagt acattaaaaa cgtccgcaat gtgttattaa   1560
gttgtctaag cgtcaatttg tttacaccac aatatatcct gccaccagcc agccaacagc   1620
tccccgaccg gcagctcggc acaaaatcac cactcgatac aggcagccca tcagtccggg   1680
acggcgtcag cgggagagcc gttgtaaggc ggcagacttt gctcatgtta ccgatgctat   1740
tcggaagaac ggcaactaag ctgccgggtt tgaaacacgg atgatctcgc ggagggtagc   1800
atgttgattg taacgatgac agagcgttgc tgcctgtgat caaatatcat ctccctcgca   1860
gagatccgaa ttatcagcct tcttattcat ttctcgctta accgtgacag gctgtcgatc   1920
ttgagaacta tgccgacata ataggaaatc gctggataaa gccgctgagg aagctgagtg   1980
gcgctatttc tttagaagtg aacgttgacg atcgtcgacc gtaccccgat gaattaattc   2040
ggacgtacgt tctgaacaca gctggatact tacttgggcg attgtcatac atgacatcaa   2100
caatgtaccc gtttgtgtaa ccgtctcttg gaggttcgta tgacactagt ggttcccctc   2160
agcttgcgac tagatgttga ggcctaacat tttattagag agcaggctag ttgcttagat   2220
acatgatctt caggccgtta tctgtcaggg caagcgaaaa ttggccattt atgacgacca   2280
atgccccgca gaagctccca tctttgccgc catagacgcc gcgccccccct tttggggtgt   2340
agaacatcct tttgccagat gtggaaaaga agttcgttgt cccattgttg gcaatgacgt   2400
agtagccggc gaaagtgcga gacccatttg cgctatatat aagcctacga tttccgttgc   2460
gactattgtc gtaattggat gaactattat cgtagttgct ctcagagttg tcgtaatttg   2520
atggactatt gtcgtaattg cttatggagt tgtcgtagtt gcttggagaa atgtcgtagt   2580
tggatgggga gtagtcatag ggaagacgag cttcatccac taaaacaatt ggcaggtcag   2640
caagtgcctg ccccgatgcc atcgcaagta cgaggcttag aaccaccttc aacagatcgc   2700
gcatagtctt ccccagctct ctaacgcttg agttaagccg cgccgcgaag cggcgtcggc   2760
ttgaacgaat tgttagacat tatttgccga ctaccttggt gatctcgcct ttcacgtagt   2820
gaacaaattc ttccaactga tctgcgcgcg aggccaagcg atcttcttgt ccaagataag   2880
cctgcctagc ttcaagtatg acgggctgat actgggccgg caggcgctcc attgcccagt   2940
cggcagcgac atccttcggc gcgattttgc cggttactgc gctgtaccaa atgcgggaca   3000
acgtaagcac tacatttcgc tcatcgccag cccagtcggg cggcgagttc catagcgtta   3060
aggtttcatt tagcgcctca aatagatcct gttcaggaac cggatcaaag agttcctccg   3120
ccgctggacc taccaaggca acgctatgtt ctcttgcttt tgtcagcaag atagccagat   3180
caatgtcgat cgtggctggc tcgaagatac ctgcaagaat gtcattgcgc tgccattctc   3240
caaattgcag ttcgcgctta gctggataac gccacggaat gatgtcgtcg tgcacaacaa   3300
```

```
tggtgacttc tacagcgcgg agaatctcgc tctctccagg ggaagccgaa gtttccaaaa   3360
ggtcgttgat caaagctcgc cgcgttgttt catcaagcct tacggtcacc gtaaccagca   3420
aatcaatatc actgtgtggc ttcaggccgc catccactgc ggagccgtac aaatgtacgg   3480
ccagcaacgt cggttcgaga tggcgctcga tgacgccaac tacctctgat agttgagtcg   3540
atacttcggc gatcaccgct tccctcatga tgtttaactc ctgaattaag ccgcgccgcg   3600
aagcggtgtc ggcttgaatg aattgttagg cgtcatcctg tgctcccgag aaccagtacc   3660
agtacatcgc tgtttcgttc gagacttgag gtctagtttt atacgtgaac aggtcaatgc   3720
cgccgagagt aaagccacat tttgcgtaca aattgcaggc aggtacattg ttcgtttgtg   3780
tctctaatcg tatgccaagg agctgtctgc ttagtgccca ctttttcgca aattcgatga   3840
gactgtgcgc gactcctttg cctcggtgcg tgtgcgacac aacaatgtgt tcgatagagg   3900
ctagatcgtt ccatgttgag ttgagttcaa tcttcccgac aagctcttgg tcgatgaatg   3960
cgccatagca agcagagtct tcatcagagt catcatccga gatgtaatcc ttccggtagg   4020
ggctcacact tctggtagat agttcaaagc cttggtcgga taggtgcaca tcgaacactt   4080
cacgaacaat gaaatggttc tcagcatcca atgtttccgc cacctgctca gggatcaccg   4140
aaatcttcat atgacgccta acgcctggca cagcggatcg caaacctggc gcggcttttg   4200
gcacaaaagg cgtgacaggt ttgcgaatcc gttgctgcca cttgttaacc cttttgccag   4260
atttggtaac tataatttat gttagaggcg aagtcttggg taaaaactgg cctaaaattg   4320
ctggggattt caggaaagta aacatcacct tccggctcga tgtctattgt agatatatgt   4380
agtgtatcta cttgatcggg ggatctgctg cctcgcgcgt ttcggtgatg acggtgaaaa   4440
cctctgacac atgcagctcc cggagacggt cacagcttgt ctgtaagcgg atgccgggag   4500
cagacaagcc cgtcagggcg cgtcagcggg tgttggcggg tgtcggggcg cagccatgac   4560
ccagtcacgt agcgatagcg gagtgtatac tggcttaact atgcggcatc agagcagatt   4620
gtactgagag tgcaccatat gcggtgtgaa ataccgcaca gatgcgtaag gagaaaatac   4680
cgcatcaggc gctcttccgc ttcctcgctc actgactcgc tgcgctcggt cgttcggctg   4740
cggcgagcgg tatcagctca ctcaaaggcg gtaatacggt tatccacaga atcaggggat   4800
aacgcaggaa agaacatgtg agcaaaaggc cagcaaaagg ccaggaaccg taaaaaggcc   4860
gcgttgctgg cgtttttcca taggctccgc ccccctgacg agcatcacaa aaatcgacgc   4920
tcaagtcaga ggtggcgaaa cccgacagga ctataaagat accaggcgtt tccccctgga   4980
agctccctcg tgcgctctcc tgttccgacc ctgccgctta ccggatacct gtccgccttt   5040
ctcccttcgg gaagcgtggc gctttctcat agctcacgct gtaggtatct cagttcggtg   5100
taggtcgttc gctccaagct gggctgtgtg cacgaacccc ccgttcagcc cgaccgctgc   5160
gccttatccg gtaactatcg tcttgagtcc aacccggtaa gacacgactt atcgccactg   5220
gcagcagcca ctggtaacag gattagcaga gcgaggtatg taggcggtgc tacagagttc   5280
ttgaagtggt ggcctaacta cggctacact agaaggacag tatttggtat ctgcgctctg   5340
ctgaagccag ttaccttcgg aaaaagagtt ggtagctctt gatccggcaa acaaaccacc   5400
gctggtagcg gtggtttttt tgtttgcaag cagcagatta cgcgcagaaa aaaaggatct   5460
caagaagatc ctttgatctt ttctacgggg tctgacgctc agtggaacga aaactcacgt   5520
taagggattt tggtcatgag attatcaaaa aggatcttca cctagatcct tttaaattaa   5580
aaatgaagtt ttaaatcaat ctaaagtata tatgagtaaa cttggtctga cagttaccaa   5640
```

-continued

```
tgcttaatca gtgaggcacc tatctcagcg atctgtctat ttcgttcatc catagttgcc   5700
tgactccccg tcgtgtagat aactacgata cgggagggct taccatctgg ccccagtgct   5760
gcaatgatac cgcgagaccc acgctcaccg gctccagatt tatcagcaat aaaccagcca   5820
gccggaaggg ccgagcgcag aagtggtcct gcaactttat ccgcctccat ccagtctatt   5880
aattgttgcc gggaagctag agtaagtagt tcgccagtta atagtttgcg caacgttgtt   5940
gccattgctg caggggggggg gggggggggg ttccattgtt cattccacgg acaaaaacag   6000
agaaaggaaa cgacagaggc caaaaagctc gctttcagca cctgtcgttt cctttctttt   6060
cagagggtat tttaaataaa aacattaagt tatgacgaag aagaacggaa acgccttaaa   6120
ccggaaaatt ttcataaata gcgaaaaccc gcgaggtcgc cgccccgtaa cctgtcggat   6180
caccggaaag gacccgtaaa gtgataatga ttatcatcta catatcacaa cgtgcgtgga   6240
ggccatcaaa ccacgtcaaa taatcaatta tgacgcaggt atcgtattaa ttgatctgca   6300
tcaacttaac gtaaaaacaa cttcagacaa tacaaatcag cgacactgaa tacggggcaa   6360
cctcatgtcc cccccccccc cccctgcag gcatcgtggt gtcacgctcg tcgtttggta   6420
tggcttcatt cagctccggt tcccaacgat caaggcgagt tacatgatcc cccatgttgt   6480
gcaaaaaagc ggttagctcc ttcggtcctc cgatcgttgt cagaagtaag ttggccgcag   6540
tgttatcact catggttatg gcagcactgc ataattctct tactgtcatg ccatccgtaa   6600
gatgcttttc tgtgactggt gagtactcaa ccaagtcatt ctgagaatag tgtatgcggc   6660
gaccgagttg ctcttgcccg gcgtcaacac gggataatac cgcgccacat agcagaactt   6720
taaaagtgct catcattgga aaacgttctt cggggcgaaa actctcaagg atcttaccgc   6780
tgttgagatc cagttcgatg taacccactc gtgcacccaa ctgatcttca gcatctttta   6840
ctttcaccag cgtttctggg tgagcaaaaa caggaaggca aaatgccgca aaaaagggaa   6900
taagggcgac acggaaatgt tgaatactca tactcttcct ttttcaatat tattgaagca   6960
tttatcaggg ttattgtctc atgagcggat acatatttga atgtatttag aaaaataaac   7020
aaataggggt tccgcgcaca tttccccgaa aagtgccacc tgacgtctaa gaaaccatta   7080
ttatcatgac attaacctat aaaaataggc gtatcacgag gccctttcgt cttcaagaat   7140
tggtcgacga tcttgctgcg ttcggatatt ttcgtggagt tcccgccaca gacccggatt   7200
gaaggcgaga tccagcaact cgcgccagat catcctgtga cggaactttg gcgcgtgatg   7260
actggccagg acgtcggccg aaagagcgac aagcagatca cgcttttcga cagcgtcgga   7320
tttgcgatcg aggatttttc ggcgctgcgc tacgtccgcg accgcgttga gggatcaagc   7380
cacagcagcc cactcgacct tctagccgac ccagacgagc caagggatct tttggaatg   7440
ctgctccgtc gtcaggcttt ccgacgtttg ggtggttgaa cagaagtcat tatcgcacgg   7500
aatgccaagc actcccgagg ggaaccctgt ggttggcatg cacatacaaa tggacgaacg   7560
gataaacctt ttcacgccct tttaaatatc cgattattct aataaacgct cttttctctt   7620
aggtttaccc gccaatatat cctgtcaaac actgatagtt taaactgaag gcgggaaacg   7680
acaacctgat catgagcgga gaattaaggg agtcacgtta tgacccccgc cgatgacgcg   7740
ggacaagccg ttttacgttt ggaactgaca gaaccgcaac gttgaaggag ccactcagct   7800
taattaacta atcgactcta gtaacggccg ccagtgtgct ggaattaatt cggcttgtcg   7860
accacccaac cccatatcga cagaggatgt gaagaacagg taaatcacgc agaagaaccc   7920
atctctgata gcagctatcg attagaacaa cgaatccata ttgggtccgt gggaaatact   7980
tactgcacag gaagggggcg atctgacgag gccccgccac cggcctcgac ccgaggccga   8040
```

```
ggccgacgaa gcgccggcga gtacggcgcc gcggcggcct ctgcccgtgc cctctgcgcg   8100
tgggagggag aggccgcggt ggtgggggcg cgcgcgcgcg cgcgcgcagc tggtgcggcg   8160
gcgcgggggt cagccgccga gccggcggcg acggaggagc agggcggcgt ggacgcgaac   8220
ttccgatcgg ttggtcagag tgcgcgagtt gggcttagcc aattaggtct caacaatcta   8280
ttgggccgta aaattcatgg gccctggttt gtctaggccc aatatcccgt tcatttcagc   8340
ccacaaatat ttccccagag gattattaag gcccacacgc agcttatagc agatcaagta   8400
cgatgtttcc tgatcgttgg atcggaaacg tacggtcttg atcaggcatg ccgacttcgt   8460
caaagagagg cggcatgacc tgacgcggag ttggttccgg gcaccgtctg gatggtcgta   8520
ccgggaccgg acacgtgtcg cgcctccaac tacatggaca cgtgtggtgc tgccattggg   8580
ccgtacgcgt ggcggtgacc gcaccggatg ctgcctcgca ccgccttgcc cacgctttat   8640
atagagaggt tttctctcca ttaatcgcat agcgagtcga atcgaccgaa ggggaggggg   8700
agcgagagct ttgcgttctc taatcgcctc gtcaagccta gcctccaatc gtgggatcca   8760
ggtccatgag gcggccctcg ccgctcaatc tgacgatggt tcgtggcggg agtcgccgat   8820
caaacactgt caaaaccgca tccggggcgt ctacttctag cgccgagagt ggcgcagtgg   8880
aggcgggcac ggagaaatcc gatacgtaca gcaccaacat gacgcaagct atgggagcag   8940
tgttgacgta tagacatgag cttggaatga actacaattt catacgccca gacttgatcg   9000
tgggctcctg cttacagagc ccacttgatg ttgataaact tagggacatt ggtgtaaaaa   9060
cagtattctg cctgcagcaa gatccagacc ttgaatattt tggagttgac atctgtgcca   9120
ttcccggagt caaggtaact aatcaatcac ctcgtcctaa tcctcgaatc tctcgtggtg   9180
cccgtctaat ctcgcgattt tgatgctcgt ggtggaaagc gtaggaggat cccgtgcgag   9240
ttagtctcaa tctctcaggg tttcgtgcga ttttagggtg atccacctct taatcgagtt   9300
acggtttcgt gcgattttag ggtaatcctc ttaatctctc attgatttag ggtttcgtga   9360
gaatcgaggt agggatctgt gttatttata tcgatctaat agatggattg gttttgagat   9420
tgttctgtca gatggggatt gtttcgatat attaccctaa tgatgtgtca gatggggatt   9480
gtttcgatat attaccctaa tgatgtgtca gatggggatt gtttcgatat attaccctaa   9540
tgatggataa taagagtagt tcacagttat gttttgatcc tgccacatag tttgagtttt   9600
gtgatcagat ttagttttac ttatttgtgc ttagttcgga tgggattgtt ctgatattgt   9660
tccaatagat gaatagctcg ttaggttaaa atctttaggt tgagttaggc gacacatagt   9720
ttatttcctc tggatttgga ttggaattgt gttcttagtt tttttcccct ggatttggat   9780
tggaattgtg tggagctggg ttagagaatt acatctgtat cgtgtacacc tacttgaact   9840
gtagagcttg ggttctaagg tcaatttaat ctgtattgta tctggctctt tgcctagttg   9900
aactgtagtg ctgatgttgt actgtgtttt tttacccgtt ttatttgctt tactcgtgca   9960
aatcaaatct gtcagatgct agaactaggt ggctttattc tgtgttctta catagatctg  10020
ttgtcctgta gttacttatg tcagttttgt tattatctga agatattttt ggttgttgct  10080
tgttgatgtg gtgtgagctg tgagcagcgc tcttatgatt aatgatgctg tccaattgta  10140
gtgtagtatg atgtgattga tatgttcatc tattttgagc tgacagtacc gatatcgtag  10200
gatctggtgc caacttattc tccagctgct tttttttacc tatgttaatt ccaatccttt  10260
cttgcctctt ccagggatcc accgggaatg gcacagatgt caactccaaa atattcaagg  10320
tctggatctt gctgcaggca gaatactgtt tttacaccaa tgtccctaag tttatcaaca  10380
```

-continued

```
tcaagtgggc tctgtaagca ggagcccacg atcaagtctg ggcgtatgaa attgtagttc  10440
attccaagct catgtctata cgtcaacact gctcccatag cttgcgtcat gttggtgctg  10500
tacgtatcgg atttctccgt gcccgcctcc actgcgccac tctcggcgct agaagtagac  10560
gccccggatg cggttttgac agtgtttgat cggcgactcc cgccacgaac catcgtcaga  10620
ttgagcggcg agggccgcct catggacctg gatcccacga ttggaggcta gctccccgaa  10680
tttccccgat cgttcaaaca tttggcaata aagtttctta agattgaatc ctgttgccgg  10740
tcttgcgatg attatcatat aatttctgtt gaattacgtt aagcatgtaa taattaacat  10800
gtaatgcatg acgttattta tgagatgggt ttttatgatt agagtcccgc aattatacat  10860
ttaatacgcg atagaaaaca aaatatagcg cgcaaactag gataaattat cgcgcgcggt  10920
gtcatctatg ttactagatc gggaattggc gagctcgccc gggtattcat cctaggtatc  10980
caagaattca tactaaagct tgcatgcctg caggtcgact ctagtaacgg ccgccagtgt  11040
gctggaatta attcggcttg tcgaccaccc aaccccatat cgacagagga tgtgaagaac  11100
aggtaaatca cgcagaagaa cccatctctg atagcagcta tcgattagaa caacgaatcc  11160
atattgggtc cgtgggaaat acttactgca caggaagggg gcgatctgac gaggccccgc  11220
caccggcctc gacccgaggc cgaggccgac gaagcgccgg cgagtacggc gccgcggcgg  11280
cctctgcccg tgccctctgc gcgtgggagg gagaggccgc ggtggtgggg gcgcgcgcgc  11340
gcgcgcgcgc agctggtgcg gcggcgcggg ggtcagccgc cgagccggcg gcgacggagg  11400
agcagggcgg cgtggacgcg aacttccgat cggttggtca gagtgcgcga gttgggctta  11460
gccaattagg tctcaacaat ctattgggcc gtaaaattca tgggccctgg tttgtctagg  11520
cccaatatcc cgttcatttc agcccacaaa tatttcccca gaggattatt aaggcccaca  11580
cgcagcttat agcagatcaa gtacgatgtt tcctgatcgt tggatcggaa acgtacggtc  11640
ttgatcaggc atgccgactt cgtcaaagag aggcggcatg acctgacgcg gagttggttc  11700
cgggcaccgt ctggatggtc gtaccgggac cggacacgtg tcgcgcctcc aactacatgg  11760
acacgtgtgg tgctgccatt gggccgtacg cgtggcggtg accgcaccgg atgctgcctc  11820
gcaccgcctt gcccacgctt tatatagaga ggttttctct ccattaatcg catagcgagt  11880
cgaatcgacc gaaggggagg gggagcgaag ctttgcgttc tctaatcgcc tcgtcaaggt  11940
aactaatcaa tcacctcgtc ctaatcctcg aatctctcgt ggtgcccgtc taatctcgcg  12000
attttgatgc tcgtggtgga aagcgtagga ggatcccgtg cgagttagtc tcaatctctc  12060
agggtttcgt gcgattttag ggtgatccac ctcttaatcg agttacggtt tcgtgcgatt  12120
ttagggtaat cctcttaatc tctcattgat ttagggtttc gtgagaatcg aggtagggat  12180
ctgtgttatt tatatcgatc taatagatgg attggttttg agattgttct gtcagatggg  12240
gattgtttcg atatattacc ctaatgatgt gtcagatggg gattgtttcg atatattacc  12300
ctaatgatgt gtcagatggg gattgtttcg atatattacc ctaatgatgg ataataagag  12360
tagttcacag ttatgttttg atcctgccac atagtttgag ttttgtgatc agatttagtt  12420
ttacttattt gtgcttagtt cggatgggat tgttctgata ttgttccaat agatgaatag  12480
ctcgttaggt taaaatcttt aggttgagtt aggcgacaca tagtttattt cctctggatt  12540
tggattggaa ttgtgttctt agttttttttc ccctggattt ggattggaat tgtgtggagc  12600
tgggttagag aattacatct gtatcgtgta cacctacttg aactgtagag cttgggttct  12660
aaggtcaatt taatctgtat tgtatctggc tctttgccta gttgaactgt agtgctgatg  12720
ttgtactgtg tttttttacc cgttttattt gctttactcg tgcaaatcaa atctgtcaga  12780
```

-continued tgctagaact aggtggcttt attctgtgtt cttacataga tctgttgtcc tgtagttact 12840
tatgtcagtt ttgttattat ctgaagatat ttttggttgt tgcttgttga tgtggtgtga 12900
gctgtgagca gcgctcttat gattaatgat gctgtccaat tgtagtgtag tatgatgtga 12960
ttgatatgtt catctatttt gagctgacag taccgatatc gtaggatctg gtgccaactt 13020
attctccagc tgcttttttt tacctatgtt aattccaatc ctttcttgcc tcttccag 13078

<210> SEQ ID NO 18
<211> LENGTH: 13330
<212> TYPE: DNA
<213> ORGANISM: Artificial Sequence
<220> FEATURE:
<223> OTHER INFORMATION: Synthetic sequence, pAG2103

<400> SEQUENCE: 18
atccagataa tgcagaaact cattaactca gtgcaaaact atgcctgggg cagcaaaacg 60
gcgttgactg aactttatgg tatggaaaat ccgtccagcc agccgatggc cgagctgtgg 120
atgggcgcac atccgaaaag cagttcacga gtgcagaatg ccgccggaga tatcgtttca 180
ctgcgtgatg tgattgagag tgataaatcg actctgctcg gagaggccgt tgccaaacgc 240
tttggcgaac tgcctttcct gttcaaagta ttatgcgcag cacagccact ctccattcag 300
gttcatccaa acaaacacaa ttctgaaatc ggttttgcca aagaaaatgc cgcaggtatc 360
ccgatggatg ccgccgagcg taactataaa gatcctaacc acaagccgga gctggttttt 420
gcgctgacgc ctttccttgc gatgaacgcg tttcgtgaat tttccgagat tgtctcccta 480
ctccagccgg tcgcaggtgc acatccggcg attgctcact ttttacaaca gcctgatgcc 540
gaacgtttaa gcgaactgtt cgccagcctg ttgaatatgc agggtgaaga aaaatcccgc 600
gcgctggcga ttttaaaatc ggccctcgat agccagcagg gtgaaccgtg gcaaacgatt 660
cgtttaattt ctgaatttta cccggaagac agcggtctgt tctccccgct attgctgaat 720
gtggtgaaat tgaaccctgg cgaagcgatg ttcctgttcg ctgaaacacc gcacgcttac 780
ctgcaaggcg tggcgctgga agtgatggca aactccgata acgtgctgcg tgcgggtctg 840
acgcctaaat acattgatat tccggaactg gttgccaatg tgaaattcga agccaaaccg 900
gctaaccagt tgttgaccca gccggtgaaa caaggtgcag aactggactt cccgattcca 960
gtggatgatt ttgccttctc gctgcatgac cttagtgata aagaaaccac cattagccag 1020
cagagtgccg ccattttgtt ctgcgtcgaa ggcgatgcaa cgttgtggaa aggttctcag 1080
cagttacagc ttaaaccggg tgaatcagcg tttattgccg ccaacgaatc accggtgact 1140
gtcaaaggcc acggccgttt agcgcgtgtt tacaacaagc tgtaagagct tactgaaaaa 1200
attaacatct cttgctaagc tgggagctct agatccccga atttccccga tcgttcaaac 1260
atttggcaat aaagtttctt aagattgaat cctgttgccg gtcttgcgat gattatcata 1320
taatttctgt tgaattacgt taagcatgta ataattaaca tgtaatgcat gacgttattt 1380
atgagatggg tttttatgat tagagtcccg caattataca tttaatacgc gatagaaaac 1440
aaaatatagc gcgcaaacta ggataaatta tcgcgcgcgg tgtcatctat gttactagat 1500
cgggaattgg cgagctcgaa ttaattcagt acattaaaaa cgtccgcaat gtgttattaa 1560
gttgtctaag cgtcaatttg tttacaccac aatatatcct gccaccagcc agccaacagc 1620
tccccgaccg gcagctcggc acaaaatcac cactcgatac aggcagccca tcagtccggg 1680
acggcgtcag cgggagagcc gttgtaaggc ggcagacttt gctcatgtta ccgatgctat 1740

-continued

```
tcggaagaac ggcaactaag ctgccgggtt tgaaacacgg atgatctcgc ggagggtagc   1800
atgttgattg taacgatgac agagcgttgc tgcctgtgat caaatatcat ctccctcgca   1860
gagatccgaa ttatcagcct tcttattcat ttctcgctta accgtgacag gctgtcgatc   1920
ttgagaacta tgccgacata ataggaaatc gctggataaa gccgctgagg aagctgagtg   1980
gcgctatttc tttagaagtg aacgttgacg atcgtcgacc gtaccccgat gaattaattc   2040
ggacgtacgt tctgaacaca gctggatact tacttgggcg attgtcatac atgacatcaa   2100
caatgtaccc gtttgtgtaa ccgtctcttg gaggttcgta tgacactagt ggttcccctc   2160
agcttgcgac tagatgttga ggcctaacat tttattagag agcaggctag ttgcttagat   2220
acatgatctt caggccgtta tctgtcaggg caagcgaaaa ttggccattt atgacgacca   2280
atgccccgca gaagctccca tctttgccgc catagacgcc gcgccccct tttggggtgt   2340
agaacatcct tttgccagat gtggaaaaga agttcgttgt cccattgttg gcaatgacgt   2400
agtagccggc gaaagtgcga gacccatttg cgctatatat aagcctacga tttccgttgc   2460
gactattgtc gtaattggat gaactattat cgtagttgct ctcagagttg tcgtaatttg   2520
atggactatt gtcgtaattg cttatggagt tgtcgtagtt gcttggagaa atgtcgtagt   2580
tggatgggga gtagtcatag ggaagacgag cttcatccac taaaacaatt ggcaggtcag   2640
caagtgcctg ccccgatgcc atcgcaagta cgaggcttag aaccaccttc aacagatcgc   2700
gcatagtctt ccccagctct ctaacgcttg agttaagccg cgccgcgaag cggcgtcggc   2760
ttgaacgaat tgttagacat tatttgccga ctaccttggt gatctcgcct ttcacgtagt   2820
gaacaaattc ttccaactga tctgcgcgcg aggccaagcg atcttcttgt ccaagataag   2880
cctgcctagc ttcaagtatg acgggctgat actgggccgg caggcgctcc attgcccagt   2940
cggcagcgac atccttcggc gcgattttgc cggttactgc gctgtaccaa atgcgggaca   3000
acgtaagcac tacatttcgc tcatcgccag cccagtcggg cggcgagttc catagcgtta   3060
aggtttcatt tagcgcctca aatagatcct gttcaggaac cggatcaaag agttcctccg   3120
ccgctggacc taccaaggca acgctatgtt ctcttgcttt tgtcagcaag atagccagat   3180
caatgtcgat cgtggctggc tcgaagatac ctgcaagaat gtcattgcgc tgccattctc   3240
caaattgcag ttcgcgctta gctggataac gccacggaat gatgtcgtcg tgcacaacaa   3300
tggtgacttc tacagcgcgg agaatctcgc tctctccagg ggaagccgaa gtttccaaaa   3360
ggtcgttgat caaagctcgc cgcgttgttt catcaagcct tacggtcacc gtaaccagca   3420
aatcaatatc actgtgtggc ttcaggccgc catccactgc ggagccgtac aaatgtacgg   3480
ccagcaacgt cggttcgaga tggcgctcga tgacgccaac tacctctgat agttgagtcg   3540
atacttcggc gatcaccgct tccctcatga tgtttaactc ctgaattaag ccgcgccgcg   3600
aagcggtgtc ggcttgaatg aattgttagg cgtcatcctg tgctcccgag aaccagtacc   3660
agtacatcgc tgtttcgttc gagacttgag gtctagtttt atacgtgaac aggtcaatgc   3720
cgccgagagt aaagccacat tttgcgtaca aattgcaggc aggtacattg ttcgtttgtg   3780
tctctaatcg tatgccaagg agctgtctgc ttagtgccca ctttttcgca aattcgatga   3840
gactgtgcgc gactcctttg cctcggtgcg tgtgcgacac aacaatgtgt tcgatagagg   3900
ctagatcgtt ccatgttgag ttgagttcaa tcttcccgac aagctcttgg tcgatgaatg   3960
cgccatagca agcagagtct tcatcagagt catcatccga gatgtaatcc ttccggtagg   4020
ggctcacact tctggtagat agttcaaagc cttggtcgga taggtgcaca tcgaacactt   4080
cacgaacaat gaaatggttc tcagcatcca atgtttccgc cacctgctca gggatcaccg   4140
```

aaatcttcat atgacgccta acgcctggca cagcggatcg caaacctggc gcggcttttg 4200
gcacaaaagg cgtgacaggt ttgcgaatcc gttgctgcca cttgttaacc cttttgccag 4260
atttggtaac tataatttat gttagaggcg aagtcttggg taaaaactgg cctaaaattg 4320
ctggggattt caggaaagta aacatcacct tccggctcga tgtctattgt agatatatgt 4380
agtgtatcta cttgatcggg ggatctgctg cctcgcgcgt ttcggtgatg acggtgaaaa 4440
cctctgacac atgcagctcc cggagacggt cacagcttgt ctgtaagcgg atgccgggag 4500
cagacaagcc cgtcagggcg cgtcagcggg tgttggcggg tgtcggggcg cagccatgac 4560
ccagtcacgt agcgatagcg gagtgtatac tggcttaact atgcggcatc agagcagatt 4620
gtactgagag tgcaccatat gcggtgtgaa ataccgcaca gatgcgtaag gagaaaatac 4680
cgcatcaggc gctcttccgc ttcctcgctc actgactcgc tgcgctcggt cgttcggctg 4740
cggcgagcgg tatcagctca ctcaaaggcg gtaatacggt tatccacaga atcaggggat 4800
aacgcaggaa agaacatgtg agcaaaaggc cagcaaaagg ccaggaaccg taaaaaggcc 4860
gcgttgctgg cgtttttcca taggctccgc ccccctgacg agcatcacaa aaatcgacgc 4920
tcaagtcaga ggtggcgaaa cccgacagga ctataaagat accaggcgtt tccccctgga 4980
agctccctcg tgcgctctcc tgttccgacc ctgccgctta ccggatacct gtccgccttt 5040
ctcccttcgg gaagcgtggc gctttctcat agctcacgct gtaggtatct cagttcggtg 5100
taggtcgttc gctccaagct gggctgtgtg cacgaacccc ccgttcagcc cgaccgctgc 5160
gccttatccg gtaactatcg tcttgagtcc aacccggtaa gacacgactt atcgccactg 5220
gcagcagcca ctggtaacag gattagcaga gcgaggtatg taggcggtgc tacagagttc 5280
ttgaagtggt ggcctaacta cggctacact agaaggacag tatttggtat ctgcgctctg 5340
ctgaagccag ttaccttcgg aaaaagagtt ggtagctctt gatccggcaa acaaaccacc 5400
gctggtagcg gtggtttttt tgtttgcaag cagcagatta cgcgcagaaa aaaaggatct 5460
caagaagatc ctttgatctt ttctacgggg tctgacgctc agtggaacga aaactcacgt 5520
taagggattt tggtcatgag attatcaaaa aggatcttca cctagatcct tttaaattaa 5580
aaatgaagtt ttaaatcaat ctaaagtata tatgagtaaa cttggtctga cagttaccaa 5640
tgcttaatca gtgaggcacc tatctcagcg atctgtctat ttcgttcatc catagttgcc 5700
tgactccccg tcgtgtagat aactacgata cgggagggct taccatctgg ccccagtgct 5760
gcaatgatac cgcgagaccc acgctcaccg gctccagatt tatcagcaat aaaccagcca 5820
gccggaaggg ccgagcgcag aagtggtcct gcaactttat ccgcctccat ccagtctatt 5880
aattgttgcc gggaagctag agtaagtagt tcgccagtta atagtttgcg caacgttgtt 5940
gccattgctg caggggggggg gggggggggg ttccattgtt cattccacgg acaaaaacag 6000
agaaaggaaa cgacagaggc caaaaagctc gctttcagca cctgtcgttt cctttctttt 6060
cagagggtat tttaaataaa aacattaagt tatgacgaag aagaacggaa acgccttaaa 6120
ccggaaaatt ttcataaata gcgaaaaccc gcgaggtcgc cgccccgtaa cctgtcggat 6180
caccggaaag gacccgtaaa gtgataatga ttatcatcta catatcacaa cgtgcgtgga 6240
ggccatcaaa ccacgtcaaa taatcaatta tgacgcaggt atcgtattaa ttgatctgca 6300
tcaacttaac gtaaaaacaa cttcagacaa tacaaatcag cgacactgaa tacggggcaa 6360
cctcatgtcc cccccccccc ccccctgcag gcatcgtggt gtcacgctcg tcgtttggta 6420
tggcttcatt cagctccggt tcccaacgat caaggcgagt tacatgatcc cccatgttgt 6480

```
gcaaaaaagc ggttagctcc ttcggtcctc cgatcgttgt cagaagtaag ttggccgcag   6540
tgttatcact catggttatg gcagcactgc ataattctct tactgtcatg ccatccgtaa   6600
gatgcttttc tgtgactggt gagtactcaa ccaagtcatt ctgagaatag tgtatgcggc   6660
gaccgagttg ctcttgcccg gcgtcaacac gggataatac cgcgccacat agcagaactt   6720
taaaagtgct catcattgga aaacgttctt cggggcgaaa actctcaagg atcttaccgc   6780
tgttgagatc cagttcgatg taacccactc gtgcacccaa ctgatcttca gcatctttta   6840
ctttcaccag cgtttctggg tgagcaaaaa caggaaggca aaatgccgca aaaaagggaa   6900
taagggcgac acggaaatgt tgaatactca tactcttcct ttttcaatat tattgaagca   6960
tttatcaggg ttattgtctc atgagcggat acatatttga atgtatttag aaaaataaac   7020
aaataggggt tccgcgcaca tttccccgaa aagtgccacc tgacgtctaa gaaaccatta   7080
ttatcatgac attaacctat aaaaataggc gtatcacgag gccctttcgt cttcaagaat   7140
tggtcgacga tcttgctgcg ttcggatatt ttcgtggagt tcccgccaca gacccggatt   7200
gaaggcgaga tccagcaact cgcgccagat catcctgtga cggaactttg gcgcgtgatg   7260
actggccagg acgtcggccg aaagagcgac aagcagatca cgcttttcga cagcgtcgga   7320
tttgcgatcg aggatttttc ggcgctgcgc tacgtccgcg accgcgttga gggatcaagc   7380
cacagcagcc cactcgacct tctagccgac ccagacgagc caagggatct tttggaatg    7440
ctgctccgtc gtcaggcttt ccgacgtttg ggtggttgaa cagaagtcat tatcgcacgg   7500
aatgccaagc actcccgagg ggaaccctgt ggttggcatg cacatacaaa tggacgaacg   7560
gataaacctt ttcacgccct tttaaatatc cgattattct aataaacgct cttttctctt   7620
aggtttaccc gccaatatat cctgtcaaac actgatagtt taaactgaag gcgggaaacg   7680
acaacctgat catgagcgga gaattaaggg agtcacgtta tgacccccgc cgatgacgcg   7740
ggacaagccg ttttacgttt ggaactgaca gaaccgcaac gttgaaggag ccactcagct   7800
taattaacta atcgactcta gtaacggccg ccagtgtgct ggaattaatt cggcttgtcg   7860
accacccaac cccatatcga cagaggatgt gaagaacagg taaatcacgc agaagaaccc   7920
atctctgata gcagctatcg attagaacaa cgaatccata ttgggtccgt gggaaatact   7980
tactgcacag gaagggggcg atctgacgag gccccgccac cggcctcgac ccgaggccga   8040
ggccgacgaa gcgccggcga gtacggcgcc gcggcggcct ctgcccgtgc cctctgcgcg   8100
tgggagggag aggccgcggt ggtgggggcg cgcgcgcgcg cgcgcgcagc tggtgcggcg   8160
gcgcgggggt cagccgccga gccggcggcg acggaggagc agggcggcgt ggacgcgaac   8220
ttccgatcgg ttggtcagag tgcgcgagtt gggcttagcc aattaggtct caacaatcta   8280
ttgggccgta aaattcatgg gccctggttt gtctaggccc aatatcccgt tcatttcagc   8340
ccacaaatat ttccccagag gattattaag gcccacacgc agcttatagc agatcaagta   8400
cgatgtttcc tgatcgttgg atcggaaacg tacggtcttg atcaggcatg ccgacttcgt   8460
caaagagagg cggcatgacc tgacgcggag ttggttccgg gcaccgtctg gatggtcgta   8520
ccgggaccgg acacgtgtcg cgcctccaac tacatggaca cgtgtggtgc tgccattggg   8580
ccgtacgcgt ggcggtgacc gcaccggatg ctgcctcgca ccgccttgcc cacgctttat   8640
atagagaggt tttctctcca ttaatcgcat agcgagtcga atcgaccgaa ggggaggggg   8700
agcgagagct ttgcgttctc taatcgcctc gtcaagccta gcgaatacac tgaactgcaa   8760
ccatcctgtt gtcaaggagc tcattcttga cagcttgaga cactgggttg aggagtatca   8820
catagatgga tttcgatttg accttgcaag tgttctttgt cgtggaccag atggttgtcc   8880
```

```
tcttgatgca cctccactca tcaaggaaat tgccaaagat gctgtattat ctagatgtaa   8940
gatcattgct gaaccttggg attgcggcgg cctttatctc gtagggcgtt tccctaactg   9000
ggacaggtgg gctgaatgga acggcaaata cagagatgat cttcgaagat ttattaaggg   9060
tgaccctggt atgaaggggg tgtttgcgac tcgtgtgtct ggatctgctg atctctatca   9120
ggtgaacgag cggaagcctt accatggtgt aaattttgtg attgcacatg atggatttac   9180
tttatgtgac cttgtttctt acaacttaaa gcacaatgat gctaatggag aaggtggctg   9240
tgatggatcc cggagtcaag gtaactaatc aatcacctcg tcctaatcct cgaatctctc   9300
gtggtgcccg tctaatctcg cgattttgat gctcgtggtg gaaagcgtag gaggatcccg   9360
tgcgagttag tctcaatctc tcagggtttc gtgcgatttt agggtgatcc acctcttaat   9420
cgagttacgg tttcgtgcga ttttagggta atcctcttaa tctctcattg atttagggtt   9480
tcgtgagaat cgaggtaggg atctgtgtta tttatatcga tctaatagat ggattggttt   9540
tgagattgtt ctgtcagatg ggattgttt cgatatatta ccctaatgat gtgtcagatg   9600
gggattgttt cgatatatta ccctaatgat gtgtcagatg gggattgttt cgatatatta   9660
ccctaatgat ggataataag agtagttcac agttatgttt tgatcctgcc acatagtttg   9720
agttttgtga tcagatttag ttttacttat ttgtgcttag ttcggatggg attgttctga   9780
tattgttcca atagatgaat agctcgttag gttaaaatct ttaggttgag ttaggcgaca   9840
catagtttat ttcctctgga tttggattgg aattgtgttc ttagtttttt tcccctggat   9900
ttggattgga attgtgtgga gctgggttag agaattacat ctgtatcgtg tacacctact   9960
tgaactgtag agcttgggtt ctaaggtcaa tttaatctgt attgtatctg gctctttgcc  10020
tagttgaact gtagtgctga tgttgtactg tgttttttta cccgttttat ttgctttact  10080
cgtgcaaatc aaatctgtca gatgctagaa ctaggtggct ttattctgtg ttcttacata  10140
gatctgttgt cctgtagtta cttatgtcag ttttgttatt atctgaagat atttttggtt  10200
gttgcttgtt gatgtggtgt gagctgtgag cagcgctctt atgattaatg atgctgtcca  10260
attgtagtgt agtatgatgt gattgatatg ttcatctatt ttgagctgac agtaccgata  10320
tcgtaggatc tggtgccaac ttattctcca gctgcttttt tttacctatg ttaattccaa  10380
tcctttcttg cctcttccag ggatccaccg ggatccatca cagccacctt ctccattagc  10440
atcattgtgc tttaagttgt aagaaacaag gtcacataaa gtaaatccat catgtgcaat  10500
cacaaaattt acaccatggt aaggcttccg ctcgttcacc tgatagagat cagcagatcc  10560
agacacacga gtcgcaaaca ccccccttcat accagggtca cccttaataa atcttcgaag  10620
atcatctctg tatttgccgt tccattcagc ccacctgtcc cagttaggga aacgccctac  10680
gagataaagg ccgccgcaat cccaaggttc agcaatgatc ttacatctag ataatacagc  10740
atctttggca atttccttga tgagtggagg tgcatcaaga ggacaaccat ctggtccacg  10800
acaaagaaca cttgcaaggt caaatcgaaa tccatctatg tgatactcct caacccagtg  10860
tctcaagctg tcaagaatga gctccttgac aacaggatgg ttgcagttca gtgtattcgc  10920
tagctccccg aatttccccg atcgttcaaa catttggcaa taaagtttct taagattgaa  10980
tcctgttgcc ggtcttgcga tgattatcat ataatttctg ttgaattacg ttaagcatgt  11040
aataattaac atgtaatgca tgacgttatt tatgagatgg gtttttatga ttagagtccc  11100
gcaattatac atttaatacg cgatagaaaa caaaatatag cgcgcaaact aggataaatt  11160
atcgcgcgcg gtgtcatcta tgttactaga tcgggaattg gcgagctcgc ccgggtattc  11220
```

-continued

```
atcctaggta tccaagaatt catactaaag cttgcatgcc tgcaggtcga ctctagtaac  11280
ggccgccagt gtgctggaat taattcggct tgtcgaccac ccaaccccat atcgacagag  11340
gatgtgaaga acaggtaaat cacgcagaag aacccatctc tgatagcagc tatcgattag  11400
aacaacgaat ccatattggg tccgtgggaa atacttactg cacaggaagg gggcgatctg  11460
acgaggcccc gccaccggcc tcgacccgag gccgaggccg acgaagcgcc ggcgagtacg  11520
gcgccgcggc ggcctctgcc cgtgccctct gcgcgtggga gggagaggcc gcggtggtgg  11580
gggcgcgcgc gcgcgcgcgc gcagctggtg cggcggcgcg ggggtcagcc gccgagccgg  11640
cggcgacgga ggagcagggc ggcgtggacg cgaacttccg atcggttggt cagagtgcgc  11700
gagttgggct tagccaatta ggtctcaaca atctattggg ccgtaaaatt catgggccct  11760
ggtttgtcta ggcccaatat cccgttcatt tcagcccaca aatatttccc cagaggatta  11820
ttaaggccca cacgcagctt atagcagatc aagtacgatg tttcctgatc gttggatcgg  11880
aaacgtacgg tcttgatcag gcatgccgac ttcgtcaaag agaggcggca tgacctgacg  11940
cggagttggt tccgggcacc gtctggatgg tcgtaccggg accggacacg tgtcgcgcct  12000
ccaactacat ggacacgtgt ggtgctgcca ttgggccgta cgcgtggcgg tgaccgcacc  12060
ggatgctgcc tcgcaccgcc ttgcccacgc tttatataga gaggttttct ctccattaat  12120
cgcatagcga gtcgaatcga ccgaagggga gggggagcga agctttgcgt tctctaatcg  12180
cctcgtcaag gtaactaatc aatcacctcg tcctaatcct cgaatctctc gtggtgcccg  12240
tctaatctcg cgattttgat gctcgtggtg gaaagcgtag gaggatcccg tgcgagttag  12300
tctcaatctc tcagggtttc gtgcgatttt agggtgatcc acctcttaat cgagttacgg  12360
tttcgtgcga ttttagggta atcctcttaa tctctcattg atttagggtt tcgtgagaat  12420
cgaggtaggg atctgtgtta tttatatcga tctaatagat ggattggttt tgagattgtt  12480
ctgtcagatg gggattgttt cgatatatta ccctaatgat gtgtcagatg gggattgttt  12540
cgatatatta ccctaatgat gtgtcagatg gggattgttt cgatatatta ccctaatgat  12600
ggataataag agtagttcac agttatgttt tgatcctgcc acatagtttg agttttgtga  12660
tcagatttag ttttacttat ttgtgcttag ttcggatggg attgttctga tattgttcca  12720
atagatgaat agctcgttag gttaaaatct ttaggttgag ttaggcgaca catagtttat  12780
ttcctctgga tttggattgg aattgtgttc ttagtttttt tcccctggat ttggattgga  12840
attgtgtgga gctgggttag agaattacat ctgtatcgtg tacacctact tgaactgtag  12900
agcttgggtt ctaaggtcaa tttaatctgt attgtatctg gctctttgcc tagttgaact  12960
gtagtgctga tgttgtactg tgttttttta cccgttttat ttgctttact cgtgcaaatc  13020
aaatctgtca gatgctagaa ctaggtggct ttattctgtg ttcttacata gatctgttgt  13080
cctgtagtta cttatgtcag ttttgttatt atctgaagat atttttggtt gttgcttgtt  13140
gatgtggtgt gagctgtgag cagcgctctt atgattaatg atgctgtcca attgtagtgt  13200
agtatgatgt gattgatatg ttcatctatt ttgagctgac agtaccgata tcgtaggatc  13260
tggtgccaac ttattctcca gctgcttttt tttacctatg ttaattccaa tcctttcttg  13320
cctcttccag                                                         13330
```

<210> SEQ ID NO 19
<211> LENGTH: 13731
<212> TYPE: DNA
<213> ORGANISM: Sorghum bicolor

<400> SEQUENCE: 19

-continued

```
aacctgatgg aacgacggtg tacaagaaca gggctcttag gacgcctttt gtaaaggtca     60
gtcgtcctgc atcaatgatc tttgtgctac cacggaacag tagttactaa tgtctataac    120
tgtgcagtct ggtgataact ctactcttag aattgagata gatgatcctg cggtgcaagc    180
tattgagttc ctcatctttg gcgagacaca gaacaaatgg taatgctgct gtttggatta    240
ctgtgtacca ctgcgtgagt gcttgtttat ttgaatgcac aagatatcaa ccatctgaac    300
tctactttgg acaggtttaa aaacaatggc cagaattttc agattcagct ccagtcgagc    360
cgccatcagg gtaatggtgc atctggtgcc tcctcttctg ctacttctac cttggtgcca    420
gaggatcttg tgcagatcca agcttacctt cggtgggaaa gaaagggaaa gcagtcatac    480
acaccagagc aagaaaaggc aagcttttag tactaaactt ttcatcgtcc atccggaagg    540
aacttgatgc actaagttat tagttagcta aagataggta gctgttgcat tttctccag    600
gaggagtatg aagctgcacg agctgagtta atagaggaat taaatagagg tgtttcttta    660
gagaagcttc gagctaaatt gacaaaaaca cctgaagcac ctgagtcaga tgaacgtaaa    720
tctcctgcat ctcgaatgcc cgttgataaa cttccagagg accttgtaca ggtgcaggct    780
tatataaggt gggagaaagc gggcaagcca aattatcctc ctgagaagca actggtaata    840
cattgattca acagcgtaaa atagcttgtt ggcttaacgc ttcatggagg ttcttatttc    900
ataatttgct aggtagaact tgaggaagca aggaaggaac tgcaggctga ggtggacaag    960
ggaatctcta ttgatcaatt gaggcagaaa attttgaaag gaaacattga gagtaaagtt   1020
tccaagcagc tgaagaacaa gaagtacttc tctgtagaaa ggattcagcg caaaaagaga   1080
gatatcatgc aacttctcag taaacataag catacagtta tggaagagaa agtagaggtt   1140
gcaccaaaac aaccaactgt tcttgatctc ttcaccaagt ctttacatga gaaggatggc   1200
tgtgaagttc taagcagaaa gctcttcaag ttcggtgata aagagatact ggttaggatc   1260
cttgacagat tctttgcatt tcccgccctt gcttccacca ggctaattaa gcttctccct   1320
tcttaaggca atttccacca aggttcaaaa taaaacagaa gttcacttgg caacaaacca   1380
tacggagcca cttattcttc actggtcttt ggcaaaaaag gctggagaat ggaaggtaaa   1440
accccaaaat cttttccatt ttttaaagct gcaagaagct gtattaaaca ctgttatcag   1500
tgccaatgcg gtgttattta actgtgcagg cacctccttc aaatatattg ccatctggtt   1560
ccaaattgct agacatggcg tgtgaaactg aatttactag atctgaattg gatggtttgt   1620
gttaccaggt ggaactaaca ccgtcaactt gttttaattc cctctttata ttagccgtct   1680
tgccatctca aggttcttat tgtccaggtt gttgagatag agcttgatga tggaggatac   1740
aaaggaatgc catttgttct taggtctggt gaaacatgga taaaaaataa tggttccgat   1800
tttttcctag atttcagcac ccgtgatacc agaaatatta aggcaattgc ttctgtccac   1860
tttaccttgc aaacttcata ctgcttcttc tgctttgact gttttacagt ctcttacttg   1920
taaaactctc caatttgttc ttagttaaag gacaatggcg atgctggtaa aggcactgct   1980
aaggcgttgc tggagagaat agcagatctg gaggaagatg cccagcgatc tcttatgcat   2040
aggtcaggca ctaaattatc cataatgata tgactgcctt tttcatggaa agttctccta   2100
aactacttct ttcttcaaca ggttcaatat tgcagcagat ctagctgacg aagccagaga   2160
tgctggactg ttgggtattg ttggactttt tgtttggatt aggttcatgg ctaccaggca   2220
actaacatgg aataagaact ataatgtgaa gccacggtat atacctgttt ttattattta   2280
cttaagtaac cttttactct ctgtttaaaa taatcagaaa ttgtcctttt cttttggcat   2340
```

-continued

```
gcgaacctaa tttgactgtt ggtcatcata aatgacaaaa cagtatacaa ttaatagttg   2400
tagaatattg tatagataca aacaaaaaca taactctcat aatgttcaat aaccatgcag   2460
tgagataagc aaagcacaag ataggtttac agatgatctt gagaatatgt acagaactta   2520
tcctcagtac agagagatac taagaatgat aatggctgct gttggtcgtg gaggtgaagg   2580
tgacgttggt caacgcattc gtgatgagat attagtaata caggtaaaac tgatggtcct   2640
tggtgaatat acagttattt tcgttcattg ctctgctgaa ttgagcagtt ggtagtgctc   2700
atccaaaacg tagacattgt caacaataaa atgtttggtg tgttacagag aaataatgac   2760
tgcaaaggtg gaatgatgga agaatggcac cagaaattgc acaacaatac aagcccagat   2820
gatgtagtga tatgccaggt attggatgct tcgaattctt aatactgcaa aatttaggct   2880
ttgaggtttt gacggtttca tctctccttg ggcaggcatt aattgattat ataaaaaatg   2940
attttgatat aagcgtttac tgggacacct tgaacaaaaa tggcataacc aaagagcgtc   3000
tcttgagcta tgatcgtgct attcattcag aaccaaattt cagaagtgaa cagaaggagg   3060
gtttactccg tgacctggga aattacatga gaagcctaaa ggtatgtgac acagctaata   3120
tggataataa aaggtagggg aaaattgtgc cttatgtttg aaatgagtat agttttgcaa   3180
agacaacata tgaaaacaca tattgtgcta tcaattcaga aaaaaaggat aaaaaaaatat   3240
acagacaaat tgtatactag tttacctttt tctgctaatg gtatatgctg ttctgtccag   3300
tatatgcttt caatagtaat atttctagct ttgacaatgt gcaaaaaccc tggtatgccc   3360
attactgtat gaacttgtcc ttgagtctcc tcatttttc cttatccata taacagctta   3420
tccttgaatc tccagtgaaa cctcctgatt ttaaccaatt tcaatgtaaa aaaaaaatcc   3480
atatctttgc ctttatacat tttctttatg agaaaagagt gaaacaaaca cagttctaaa   3540
atcaggtaag aacttccaaa taatttttca cttctaatct attgatgtgc agctctccta   3600
tgtttttcga gaaaaaaaac cctcaaaata atttaacagt ttgatgtatg gtgctagaat   3660
catatagtta gttgctaatc atcgcattgt gttcaatcta gcaccgactc ccagttgcag   3720
tagatcaaat tattttacct ttttttggtc aaacataagt gataaataca gttattcgtt   3780
tttttaaaaa aactatataa ttccctcatt tttagatttc tctgcttgat gctattattg   3840
gaaaaaacac cccatctcat atatatctaa ggaaatttcc aggggctaac ttttgtgttc   3900
tttgctgagg catacttatt cgattgcata gctggccaag ttaacataga catgtgatgt   3960
ttatttatta atttcattta tgtcattgtg atccttcttc tacagccagc acaacaagaa   4020
ggctacctca gctagccacg ccgagtaggt caaccagtta gctgctggct attttgcttg   4080
atggttaagt tagtgaaggg atcagataat aaggattgtt agggccttat gggtttgttt   4140
caggttggtt tattaggata ttagttagtg ctacccttgc tctataaaag gggatttgct   4200
tttcttgaat aaagcatgca gaattaaatt gaatccttct ccctcttcga tttctacctt   4260
gctgttgcag ccatgctgat gtggtctagg gccacatcct ctggtcgacc atacctatgg   4320
cctaagttct aattcactct aagacagcta agctagtgag aataaaatatg atgctgtccc   4380
aattatgcta gtgcatgatt ttcttatggc ttgccattcg aaataaatgc tggacagcag   4440
atagatcagc acaaagaggc ctcccttatc caggacaagt gtgtgctgtg tgaccaagat   4500
gaagaatcag tccagcacat cctctccact tgtgtatttg cttgacagtt ctgaactgtt   4560
agaacgcctt ggtcttgaaa gagttgcacc ccgatacaat gaactgagat ttgcagattg   4620
gtggaggaag acaagtcaga agatagaaaa gacaaggaaa aaggggttta actgtgttgt   4680
gattttgggt gcttggacac tttggattca gagtaacaaa tgtgtctttg atggcgcctc   4740
```

-continued

```
tcctctcaga gatgctcaat aatactttta ggaagagatg agaatgtgga gtatggctgg   4800
agcatgaaag ctccaagagt tggtcgttct tccctagtaa taggcgattt gtctcacgtt   4860
cttttgttgc aacctgccct tgacatcctg ttggttcaag ggtgattgg tatatacccc   4920
tgacttcttt ttgggttaag ggtggtgtgt gtttcttttg ttgggcagtt ttttcctctc   4980
tatatataaa gatgtgcagt tctcctgtgc actcgagaaa agtcactgtt tgcctagtgg   5040
agtgtctgga tcgtctatat gacacttaga tcctaattga gacccaagtc tggcttctag   5100
gaagtatgga tgtgcaatta gaacttagat tctgattagt taagattaat cactagccgt   5160
gaagtggtcg tttgtctagt gtgttgtgta gataatactg gtcacgttgt aacttttttt   5220
tgtgacaaaa aaagaagata tacatttact catcttttct gtgattgaat gttctttccc   5280
tgacataatg tttgattaat gctattatgt ttttctcatt ctgttaggct gtgcattctg   5340
gtgctgatct tgaatctgct atagcaactt gtatgggata caaatcagag gtatcatcct   5400
catccctgtt tgttctgcta caatgcttta catacctgtg ctcatttcta atgaactaac   5460
tttttggata cagggtgaag gtttcatggt tggcgttcag atcaatccag tgaagggttt   5520
gccatctgga tttcctgtaa aaatctctca actccttttc gcaaaacatg taccttcata   5580
gtttcttaca tttgtgacat ttactgcctg gtacaggagt tgcttgaatt tgtgcttgac   5640
catgttgagg ataaatcagc agaaccactt cttgaggtca gtgataatag atccaagttc   5700
atggtttcta ataaaacaaa gagcagatgc taggattcat tgtctcaatt caaacagcta   5760
gatctccata actgactgaa ttctttagtg catccatttt tgtggttttg ctttgtggat   5820
cagttattga caacaaattg ttaacttata ggggctattg gaagctcgag ttgatctgcg   5880
ccctttgctt cttgattcgc ctgaacgcat gaaagatctt atatttttgg acattgctct   5940
tgattctacc ttcaggacag caattgaaag gtcatatgag gagctcaatg atgcagcccc   6000
agaggttggt caccagaagt attgctatag aagacattat taaatgcacc ttttcccgta   6060
tcgcatgttg cttttagctt tttccaaatg cattatctca tgatgccctt tttctcaatc   6120
cagaaaataa tgtacttcat cagtcttgtc cttgaaaatc ttgcgttttc aattgacgac   6180
aatgaagaca tcctgtattg cttaaaggta cacttcgagt ctttattatc cagaaataca   6240
aagattttta tagtggagtt tacattattt tgtgaattaa taatcaaatt gatatgcatg   6300
tcctaatcta gttgtttatg tagattagat agactctgca aatttcattt ttcttgtttt   6360
ctatttcttg tttcttgacc atgtgccttt cttaaaaatg ttttctccaa aatctctaga   6420
aaattattca tattttgata tacttcaaat aagtaccatg ccaaaatttg ctaacgaaaa   6480
gacgcagata gagcactatt aagtaatacc atactgctgt tgaaatcctt actttgatca   6540
ctgcaagtaa gaggggaatg ttatttgcct cagcatggtc attaacaagt agtgtatgaa   6600
ctctgtccta tatattttga tactacattt tagtgacagc tattaatttt gttgtattat   6660
ggatttacat ttcatttttt gtgtgccttt agcactttgt tattattcag cacattaaac   6720
acatggatgg tcaaagtttc aactgtttga atcacatgga tacagaagtg acacttgttt   6780
tacgagggca tttgtgctat ctagaaacaa ttgtttgttt gaacttattt gtgattctat   6840
tttgtgatgc ttaacaatgg tgatgttgtc taaatgtttt tttcctgaag ggatggaacc   6900
aagccttgga aatggctaag caaaaagacg accaatgggc tctttacgct aaagcatttc   6960
ttgacagaat cagacttgcc cttgcgagca agggagaaca gtaccataat atgatgcagc   7020
cctcagctga atatcttggc tcgttactca gcatagacaa atgggcagtg agtacttcat   7080
```

-continued

```
agaaatcaaa tctaatgttc catttgttca tcaagaaatt aataataaat atcacttttt   7140
ttcaggtcaa tatcttcaca gaagaaatta tacgcggtgg atcagctgct actctgtccg   7200
ctcttctgaa ccgatttgat cctgttctaa ggaacgttgc taaccttgga aggtaaaaat   7260
gtaaaatcta tgactactgt tgaacttctt acattgtctc cccggtaaat gaacacataa   7320
ttctaaaagt ggtactagtg acctctccac agttttatgt gaaccacaga aattaaatat   7380
gataatatat tctattactc tgcacctgac atctggctcc tgataacagt tggcaggtta   7440
taagcccagt tgaagtatca ggttatgtgg ttgtggttga tgagttactt gctgtccaga   7500
acaaatctta tgataaacca accatccttg tggcaaagag tgtcaaggga gaggaagaaa   7560
taccagatgg agtagttggt gtaattacac ctgatatgcc agatgttctg tcccatgtgt   7620
cagtccgagc aaggaatagc aaggtttatt ttcacagtta tgttgcaagc tttctcagat   7680
ttttttcttgtatcgatgt tgacatacca gtttttttcct aatgatgaag gtactgtttg   7740
caacctgttt tgaccatacc actctgtctg aacttgaagg atatgatcag aaactgcttt   7800
ccttcaagcc tacttctgca gatataacct ataggtactt gaggttattt gaacttcatt   7860
catgtctaat gaagctaggt tataaaggct aataactaat tattttttaa tatttccttc   7920
catcagcttg ttcattcatt tggtaactta gatccataca tccatacata ttgatatttt   7980
gaaagacaat tttgggttgt ttttcctaaa atatgcagtg tatcattgca ttaacaaagg   8040
aaattgaaaa ggtaccacgc aaacacacta ccacgaaaac aacacacttg caacacctac   8100
attaaccagg tccagggatt ccaacgtgca acactgaata aaaataaaga aagcaactaa   8160
agtaattttt gtgttgttat taatgacata caggatatgt ctataggggt aatatagggg   8220
tgtttggttc tccgccgacg taagccacgc catagactgt ggtggcggtt ctgtggctgc   8280
tgcttggttc ctgtcaaaac tgtggctgcc actactactc ccagcacaaa ataacaccac   8340
acctgtgcgc tgaaattcgg cgcctaacct tcggtgccgc cgttgttgcg gcatggcaac   8400
ccatggccag gaaccaagca gacccacaat cttcttctgt gtaaacgaca agtgtctata   8460
tacctgccta attatcaccg tgtttgagaa aaaaaaactt catactttac acaatttata   8520
tggtcaagct acacttgatg gcacaccatc aactttggcc aatatctgac tgagtggtcc   8580
catgttacca acatttcaca gctgatctgg tattatctgt tacatgctca catctcatat   8640
cttgcattca atagggagat cacagagagt gagcttcagc aatcaagttc tccaaatgca   8700
gaagttggcc atgcagtacc atctatttca ttggccaaga agaaatttct tggaaaatat   8760
gcaatatcag ctgaagaatt caccgaggaa atggtacata atataaactt ttgcataagg   8820
agttcttttc attgaaaaga aaagctttga tgaaaccagc tgttagtatg ctggttttct   8880
tttcttttgg ccttgtgctt atgctcacat ttctattttc aggttggggc caagtctcgg   8940
aatatagcat acctcaaagg aaaagtacct tcatgggttg gtgttccaac gtcagttgcg   9000
ataccatttg gcacttttga gaaggttttg tcagatggtc ttaataaggt cagtttctgg   9060
ttcttttttta acattatact tgaacaatag cgctatatat ttgttggaga agtctgtttc   9120
tttaaaatac actattggga agctatcaat gtgcacttaa atgtccacca atttctaagg   9180
ggccattttg gtattcaaaa caccaatgca ttttttcaga gcctgctctg taagtagcat   9240
cttcagtagt atgtatttca tagctttata ttctcattct accatgaact ctaatttttct   9300
aaagctaaac tacatatacg cttgaaataa gctatgatgt tattatcttt gatggtaaat   9360
gaccctacca tgctcatcgg aaggtgtctt tagacaggaa caaagcaaat gataacaaga   9420
agcctcttct tagggatttg ttgtgcagtt tgaactagtg ttctcccccc cccccccccc   9480
```

-continued

```
ccctcttttt cctcgaatat gcaggagagc tgcgtatcat tgtattaaga gaggaaaaaa   9540
cggtcctgta taattgtact ccctactctg cgctgagctg taggagggtc ctaaaacata   9600
gtttttctaa ccgataaaag cacacactct aggtgagacc tgaccaatgc tgtaaccccc   9660
ttgttctgtc ttttttttt gtttctttct ttttcttttc tacggtttcc ttataaaaaa   9720
aatatcagtt ggggaccctc tgctgtttca tcaaaaacga tctgccttat attccattgt   9780
tcttttatgg caggaagtag cacaaaccat agagaagctt aagatcaggc ttgctcaaga   9840
agattttagt gctctaggtg aaataagaaa agccgttctt aatcttactg ctcctatgca   9900
attggtaaga tatctctata ttcttatatt tgttgcaatt aagacttaat tatgacattg   9960
atctttttat tattccatgt atgccttatt ttgtgtctca ggttaatgag ctgaaggaga  10020
ggatgctagg ctctggaatg ccctggcctg gtgatgaagg caacaggcgc tgggagcaag  10080
catggatggc tattaaaaag gtaccctcat ctacaattaa tactagtaat tgatccataa  10140
gtttcggcat atccttgtag gtcattagct taggaacacc aggggcttta acttttaagt  10200
tgtacctctt tgcctttatt cgtggggtca cttgatccca cagattgtag atagatcgat  10260
tacaagtaag caatatgcat ggaaaattga atctaagaaa atatttttcc tagtatgatc  10320
attgtatatc tcaatttcct ttttaggttt gggcatcaaa atggaatgaa agagcatatt  10380
ttagcacacg caaggtgaaa ctcaatcatg agtacctttc gatggctgtt cttgtgcaag  10440
aagttgtgaa tgcagattat gcttttgtca ttcatactac aaacccatcg tctggagatt  10500
cttctgagat atatgctgaa gtcgtgaaag ggctcggaga gactctcgtg ggagcctatc  10560
ctggtcgtgc tatgagcttt gtttgcaaaa aagatgacct tgactctccc aaggttagtt  10620
cttggaaatt gtcttatggt aggctaatat catgcaatcc gcttcagttg ggaagttgat  10680
gaatttatta tattgtgtgc tggtctttct ctgccccgcc tgcgggtaat ttatcactta  10740
tcaaaaattt tcttacttat aaagtagact gcatatgaac atactttata catagtaaa  10800
ctggtaaaaa catgtaaatt aatcggggaa attttcatgg tcagtaggtc ccccaaccag  10860
attgcaaatt tgctactaag gatatggttt acctggtttg ccagatctaa tctgttgccc  10920
atttgtagtt acttggttac ccgagcaagc caattggtct cttcataagg cgatcgatca  10980
tctttcgttc tgactccaac ggcgaggatc tggaaggtta tgccggagca ggattatatg  11040
ataggttagg gaaatcccat tcttgaatgt atgttaaggt gcttattggt ttggaatgac  11100
agataaattg tctgtttctt cagtgtaccg atggatgagg aggatgaagt cgtacttgat  11160
tacacaactg accctcttat agtagatcgt ggattccgaa attcaatact ctcaagcatc  11220
gcacgggctg gccatgccat tgaagagcta tatggttctc ctcaggacgt cgagggtgta  11280
gtgaaggatg gaaaaatcta tgtagtccag acaagaccac agatgtagca tgtatgtatt  11340
agctagctca ataagcactg ttgtacgctt gtatggttgg gacatatggg tgttatggca  11400
tgtatagttt atgcctagat gtacaacacg tgtaaactct tatatatgta tatatgctga  11460
aacaagcatt ggtcctgcaa tttcattgtg accagtcttt gaaaatgaac atgccgactt  11520
attgggcaaa aaaaagttta cattcatact tgtgcaaata ttttctaaag atgttgaaaa  11580
gtgtaaccag cttctcatga gtataccaga gttataccag ttagagcagt gtgctcgggg  11640
atctcttgct agtccgtgtt ttttttttat tttgaaaagg aagtatggag gggagagatt  11700
ccccgcctag atttcattaa aatcgggaga aaagttcagg atacaaagca taaattagga  11760
gctaatcgaa gccctgatta gaagtacaag aatgtaaacc aaaacagcac cccagcata  11820
```

-continued

```
agggccagat tgtggcatat gtttcaccag tacaacaaat agagaaaaag aaaactacaa  11880
caccaagtca cgggaggtgg atgatgatgc gacataatca tcatcagcca agcaacaaga  11940
ggtgacgcca taggagcttg gcagggcttt caacagtggg gttgaaatgg gccgactata  12000
gagaaacggt agcaagagat tttgtagcga tgccttgaag gagatgattg tcgctagcga  12060
ctcacctgag gcgagctttc acctagaacc tttatcagta ctcctactga cccatccgtg  12120
acaaatggag gtgcacgcac cgacgagcaa ccgtaccttg ccacacctcg tggagttgtt  12180
tccggactcg cccacgatga tgggaggcat gcaccgcatg gacagaggag ggggtgttgg  12240
tcaccacccc accgtgtgga gccgttgtga gactcaccct cgcctgcaat gatgggaggt  12300
gcgcaccgac aattgtccat gcttggatag gtgttggtgc tagccacctc cacacctcgc  12360
gaagttgttc tcagacttgc ccgtgttggt gggcggcaca cacccacaat tatccgcgct  12420
tggacgatgg tggtgccgac cacctccata cctcacggag ccattcttgg tctcacccgc  12480
gtcggtggga ggtgtgcacc ggcaatcgtt tgaacggggg tggcggtgtt ggccgcctcc  12540
acaccttgtg gaaccgttct cggactcgcc catgatggta ggaggcgggc actggcagtc  12600
gtccgtgcct agacgaggtg gtgctagccg cctccacacc tcgtggagct gttcgctgac  12660
ttgcccgtgt caatgggagg tgcgcatcga cagttatcta cgtctggact ggaggtgccg  12720
cccgcctcta ggagtcggtc gccgccacac aaggagccgc tgtcagactc gcttgcgatg  12780
gtgggagggg cgtactgcag acgtccacgc ctagacggag ggggtgccag acgcccacgc  12840
ctgtgccgtc gctggcccga ggcggtggca gcagccaacc gagcacgtag aggaggtgag  12900
agtatttagg ccttatttag ttcacatcaa aaaccaaaaa aatttcaaga ttccccatca  12960
catcgaatac tgcggcacat gcatgaagta ctaaatatag atgaaaaaaa actaattgca  13020
cattttacct gtaaatcgcg agataaatct tttgagtttt gttagttcat gattggacaa  13080
tgtttgtcaa atacaaacga aaatgctacg gtaccaaaac cccaaactta gttgtcactt  13140
aaatggttct gccggtcctt gttcgaatcc tggtacaatt tcttcagtgc ccaagggcat  13200
cttccccggt tgtggccttg tttactttgc gaaaagaaaa ctgttgggtg tctaatcgaa  13260
tataccggca catatttgaa atactaaatg cacacattta aagtatttaa tgctctatac  13320
atgtgtcgaa agatttaatg gaatggataa aaagtgcaga aattgagaaa gttcctgcga  13380
atatctactc tatgaaaagg acagctattt ggaaatatct acagaaaata tctgaacaga  13440
actatcccca ttagctggga aaaaccaaag acagaaggaa atcaccacag tccatacaga  13500
aatggtaggg ttctttggca cctctgctgc atctgatcac tgtcatttgc taccaaaaaa  13560
tggatcagtt caccatgaac tgataagacc acaccataac agatcaagaa gtgtgatcag  13620
gtgctgcagc gcagcaaggg gaaggaccag ggattattac taccaggtgc tcggtatcac  13680
agttcattcc acacctcagg aaatcaagga ggcttacagg aaactccaga a           13731
```

<210> SEQ ID NO 20
<211> LENGTH: 984
<212> TYPE: DNA
<213> ORGANISM: Sorghum bicolor

<400> SEQUENCE: 20

```
acaggttcaa tattgcagca gatctagctg acgaagccag agatgctgga ctgttgggta     60
ttgttggact ttttgtttgg attaggttca tggctaccag gcaactaaca tggaataaga    120
actataatgt gaagccacgg tatatacctg tttttattat ttacttaagt aaccttttac    180
tctctgttta aaataatcag aaattgtcct tttcttttgg catgcgaacc taatttgact    240
```

gttggtcatc ataaatgaca aaacagtata caattaatag ttgtagaata ttgtatagat 300
acaaacaaaa acataactct cataatgttc aataaccatg cagtgagata agcaaagcac 360
aagataggtt tacagatgat cttgagaata tgtacagaac ttatcctcag tacagagaga 420
tactaagaat gataatggct gctgttggtc gtggaggtga aggtgacgtt ggtcaacgca 480
ttcgtgatga gatattagta atacaggtaa aactgatggt ccttggtgaa tatacagtta 540
ttttcgttca ttgctctgct gaattgagca gttggtagtg ctcatccaaa acgtagacat 600
tgtcaacaat aaaatgtttg gtgtgttaca gagaaataat gactgcaaag gtggaatgat 660
ggaagaatgg caccagaaat tgcacaacaa tacaagccca gatgatgtag tgatatgcca 720
ggtattggat gcttcgaatt cttaatactg caaaatttag gctttgaggt tttgacggtt 780
tcatctctcc ttgggcaggc attaattgat tatataaaaa atgattttga tataagcgtt 840
tactgggaca ccttgaacaa aaatggcata accaaagagc gtctcttgag ctatgatcgt 900
gctattcatt cagaaccaaa tttcagaagt gaacagaagg agggtttact ccgtgacctg 960
ggaaattaca tgagaagcct aaag 984

<210> SEQ ID NO 21
<211> LENGTH: 344
<212> TYPE: DNA
<213> ORGANISM: Artificial Sequence
<220> FEATURE:
<223> OTHER INFORMATION: Synthetic sequence, SbGWDko2a

<400> SEQUENCE: 21
ggttcaataa cccgggagtg agataagcaa agcacaagat aggtttacag atgatcttga 60
gaatatgtac agaacttatc ctcagtacag agagatacta agaatgataa tggctgctgt 120
tggtcgtgga ggtgaaggtg acgttggtca acgcattcgt gatgagatat tagtaataca 180
ggtaaaactg atggtccttg gtgaatatac agttattttc gttcattgct ctgctgaatt 240
gagcagttgg tagtgctcat ccaaaacgta gacattgtca acaataaaat gtttggtgtg 300
ttacagagaa ataccggtgc aaagctagca tgatggaaga atgg 344

<210> SEQ ID NO 22
<211> LENGTH: 197
<212> TYPE: DNA
<213> ORGANISM: Artificial Sequence
<220> FEATURE:
<223> OTHER INFORMATION: Synthetic sequence, SbGWDko2b

<400> SEQUENCE: 22
ggttcaataa gctagcagtg agataagcaa agcacaagat aggtttacag atgatcttga 60
gaatatgtac agaacttatc ctcagtacag agagatacta agaatgataa tggctgctgt 120
tggtcgtgga ggtgaaggtg acgttggtca acgcattcgt gatgagatat tagtaataca 180
gcccgggctg atggtcc 197

<210> SEQ ID NO 23
<211> LENGTH: 12767
<212> TYPE: DNA
<213> ORGANISM: Artificial Sequence
<220> FEATURE:
<223> OTHER INFORMATION: Synthetic sequence, pAG2106

<400> SEQUENCE: 23
atccagataa tgcagaaact cattaactca gtgcaaaact atgcctgggg cagcaaaacg 60

-continued

```
gcgttgactg aactttatgg tatggaaaat ccgtccagcc agccgatggc cgagctgtgg    120
atgggcgcac atccgaaaag cagttcacga gtgcagaatg ccgccggaga tatcgtttca    180
ctgcgtgatg tgattgagag tgataaatcg actctgctcg gagaggccgt tgccaaacgc    240
tttggcgaac tgcctttcct gttcaaagta ttatgcgcag cacagccact ctccattcag    300
gttcatccaa acaaacacaa ttctgaaatc ggttttgcca aagaaaatgc cgcaggtatc    360
ccgatggatg ccgccgagcg taactataaa gatcctaacc acaagccgga gctggttttt    420
gcgctgacgc ctttccttgc gatgaacgcg tttcgtgaat tttccgagat tgtctcccta    480
ctccagccgg tcgcaggtgc acatccggcg attgctcact ttttacaaca gcctgatgcc    540
gaacgtttaa gcgaactgtt cgccagcctg ttgaatatgc agggtgaaga aaaatcccgc    600
gcgctggcga ttttaaaatc ggccctcgat agccagcagg gtgaaccgtg gcaaacgatt    660
cgtttaattt ctgaatttta cccggaagac agcggtctgt tctccccgct attgctgaat    720
gtggtgaaat tgaaccctgg cgaagcgatg ttcctgttcg ctgaaacacc gcacgcttac    780
ctgcaaggcg tggcgctgga agtgatggca aactccgata acgtgctgcg tgcgggtctg    840
acgcctaaat acattgatat tccggaactg gttgccaatg tgaaattcga agccaaaccg    900
gctaaccagt tgttgaccca gccggtgaaa caaggtgcag aactggactt cccgattcca    960
gtggatgatt ttgccttctc gctgcatgac cttagtgata aagaaaccac cattagccag   1020
cagagtgccg ccattttgtt ctgcgtcgaa ggcgatgcaa cgttgtggaa aggttctcag   1080
cagttacagc ttaaaccggg tgaatcagcg tttattgccg ccaacgaatc accggtgact   1140
gtcaaaggcc acggccgttt agcgcgtgtt tacaacaagc tgtaagagct tactgaaaaa   1200
attaacatct cttgctaagc tgggagctct agatccccga atttccccga tcgttcaaac   1260
atttggcaat aaagtttctt aagattgaat cctgttgccg gtcttgcgat gattatcata   1320
taatttctgt tgaattacgt taagcatgta ataattaaca tgtaatgcat gacgttattt   1380
atgagatggg tttttatgat tagagtcccg caattataca tttaatacgc gatagaaaac   1440
aaaatatagc gcgcaaacta ggataaatta tcgcgcgcgg tgtcatctat gttactagat   1500
cgggaattgg cgagctcgaa ttaattcagt acattaaaaa cgtccgcaat gtgttattaa   1560
gttgtctaag cgtcaatttg tttacaccac aatatatcct gccaccagcc agccaacagc   1620
tccccgaccg gcagctcggc acaaaatcac cactcgatac aggcagccca tcagtccggg   1680
acggcgtcag cgggagagcc gttgtaaggc ggcagacttt gctcatgtta ccgatgctat   1740
tcggaagaac ggcaactaag ctgccgggtt tgaaacacgg atgatctcgc ggagggtagc   1800
atgttgattg taacgatgac agagcgttgc tgcctgtgat caaatatcat ctccctcgca   1860
gagatccgaa ttatcagcct tcttattcat ttctcgctta accgtgacag gctgtcgatc   1920
ttgagaacta tgccgacata ataggaaatc gctggataaa gccgctgagg aagctgagtg   1980
gcgctatttc tttagaagtg aacgttgacg atcgtcgacc gtaccccgat gaattaattc   2040
ggacgtacgt tctgaacaca gctggatact tacttgggcg attgtcatac atgacatcaa   2100
caatgtaccc gtttgtgtaa ccgtctcttg gaggttcgta tgacactagt ggttcccctc   2160
agcttgcgac tagatgttga ggcctaacat tttattagag agcaggctag ttgcttagat   2220
acatgatctt caggccgtta tctgtcaggg caagcgaaaa ttggccattt atgacgacca   2280
atgccccgca gaagctccca tctttgccgc catagacgcc gcgcccccct tttggggtgt   2340
agaacatcct tttgccagat gtggaaaaga agttcgttgt cccattgttg gcaatgacgt   2400
agtagccggc gaaagtgcga gacccatttg cgctatatat aagcctacga tttccgttgc   2460
```

```
gactattgtc gtaattggat gaactattat cgtagttgct ctcagagttg tcgtaatttg   2520
atggactatt gtcgtaattg cttatggagt tgtcgtagtt gcttggagaa atgtcgtagt   2580
tggatgggga gtagtcatag ggaagacgag cttcatccac taaaacaatt ggcaggtcag   2640
caagtgcctg ccccgatgcc atcgcaagta cgaggcttag aaccaccttc aacagatcgc   2700
gcatagtctt ccccagctct ctaacgcttg agttaagccg cgccgcgaag cggcgtcggc   2760
ttgaacgaat tgttagacat tatttgccga ctaccttggt gatctcgcct ttcacgtagt   2820
gaacaaattc ttccaactga tctgcgcgcg aggccaagcg atcttcttgt ccaagataag   2880
cctgcctagc ttcaagtatg acgggctgat actgggccgg caggcgctcc attgcccagt   2940
cggcagcgac atccttcggc gcgattttgc cggttactgc gctgtaccaa atgcgggaca   3000
acgtaagcac tacatttcgc tcatcgccag cccagtcggg cggcgagttc catagcgtta   3060
aggtttcatt tagcgcctca aatagatcct gttcaggaac cggatcaaag agttcctccg   3120
ccgctggacc taccaaggca acgctatgtt ctcttgcttt tgtcagcaag atagccagat   3180
caatgtcgat cgtggctggc tcgaagatac ctgcaagaat gtcattgcgc tgccattctc   3240
caaattgcag ttcgcgctta gctggataac gccacggaat gatgtcgtcg tgcacaacaa   3300
tggtgacttc tacagcgcgg agaatctcgc tctctccagg ggaagccgaa gtttccaaaa   3360
ggtcgttgat caaagctcgc cgcgttgttt catcaagcct tacggtcacc gtaaccagca   3420
aatcaatatc actgtgtggc ttcaggccgc catccactgc ggagccgtac aaatgtacgg   3480
ccagcaacgt cggttcgaga tggcgctcga tgacgccaac tacctctgat agttgagtcg   3540
atacttcggc gatcaccgct tccctcatga tgtttaactc ctgaattaag ccgcgccgcg   3600
aagcggtgtc ggcttgaatg aattgttagg cgtcatcctg tgctcccgag aaccagtacc   3660
agtacatcgc tgtttcgttc gagacttgag gtctagtttt atacgtgaac aggtcaatgc   3720
cgccgagagt aaagccacat tttgcgtaca aattgcaggc aggtacattg ttcgtttgtg   3780
tctctaatcg tatgccaagg agctgtctgc ttagtgccca ctttttcgca aattcgatga   3840
gactgtgcgc gactcctttg cctcggtgcg tgtgcgacac aacaatgtgt tcgatagagg   3900
ctagatcgtt ccatgttgag ttgagttcaa tcttcccgac aagctcttgg tcgatgaatg   3960
cgccatagca agcagagtct tcatcagagt catcatccga gatgtaatcc ttccggtagg   4020
ggctcacact tctggtagat agttcaaagc cttggtcgga taggtgcaca tcgaacactt   4080
cacgaacaat gaaatggttc tcagcatcca atgtttccgc cacctgctca gggatcaccg   4140
aaatcttcat atgacgccta acgcctggca cagcggatcg caaacctggc gcggcttttg   4200
gcacaaaagg cgtgacaggt ttgcgaatcc gttgctgcca cttgttaacc cttttgccag   4260
atttggtaac tataatttat gttagaggcg aagtcttggg taaaaactgg cctaaaattg   4320
ctggggattt caggaaagta aacatcacct tccggctcga tgtctattgt agatatatgt   4380
agtgtatcta cttgatcggg ggatctgctg cctcgcgcgt ttcggtgatg acggtgaaaa   4440
cctctgacac atgcagctcc cggagacggt cacagcttgt ctgtaagcgg atgccgggag   4500
cagacaagcc cgtcagggcg cgtcagcggg tgttggcggg tgtcggggcg cagccatgac   4560
ccagtcacgt agcgatagcg gagtgtatac tggcttaact atgcggcatc agagcagatt   4620
gtactgagag tgcaccatat gcggtgtgaa ataccgcaca gatgcgtaag gagaaaatac   4680
cgcatcaggc gctcttccgc ttcctcgctc actgactcgc tgcgctcggt cgttcggctg   4740
cggcgagcgg tatcagctca ctcaaaggcg gtaatacggt tatccacaga atcaggggat   4800
```

-continued

```
aacgcaggaa agaacatgtg agcaaaaggc cagcaaaagg ccaggaaccg taaaaaggcc   4860
gcgttgctgg cgtttttcca taggctccgc ccccctgacg agcatcacaa aaatcgacgc   4920
tcaagtcaga ggtggcgaaa cccgacagga ctataaagat accaggcgtt tccccctgga   4980
agctccctcg tgcgctctcc tgttccgacc ctgccgctta ccggatacct gtccgccttt   5040
ctcccttcgg gaagcgtggc gctttctcat agctcacgct gtaggtatct cagttcggtg   5100
taggtcgttc gctccaagct gggctgtgtg cacgaacccc ccgttcagcc cgaccgctgc   5160
gccttatccg gtaactatcg tcttgagtcc aacccggtaa gacacgactt atcgccactg   5220
gcagcagcca ctggtaacag gattagcaga gcgaggtatg taggcggtgc tacagagttc   5280
ttgaagtggt ggcctaacta cggctacact agaaggacag tatttggtat ctgcgctctg   5340
ctgaagccag ttaccttcgg aaaaagagtt ggtagctctt gatccggcaa acaaaccacc   5400
gctggtagcg gtggtttttt tgtttgcaag cagcagatta cgcgcagaaa aaaaggatct   5460
caagaagatc ctttgatctt ttctacgggg tctgacgctc agtggaacga aaactcacgt   5520
taagggattt tggtcatgag attatcaaaa aggatcttca cctagatcct tttaaattaa   5580
aaatgaagtt ttaaatcaat ctaaagtata tatgagtaaa cttggtctga cagttaccaa   5640
tgcttaatca gtgaggcacc tatctcagcg atctgtctat ttcgttcatc catagttgcc   5700
tgactccccg tcgtgtagat aactacgata cgggagggct taccatctgg ccccagtgct   5760
gcaatgatac cgcgagaccc acgctcaccg gctccagatt tatcagcaat aaaccagcca   5820
gccggaaggg ccgagcgcag aagtggtcct gcaactttat ccgcctccat ccagtctatt   5880
aattgttgcc gggaagctag agtaagtagt tcgccagtta atagtttgcg caacgttgtt   5940
gccattgctg caggggggggg gggggggggg ttccattgtt cattccacgg acaaaaacag   6000
agaaaggaaa cgacagaggc caaaaagctc gctttcagca cctgtcgttt cctttctttt   6060
cagagggtat tttaaataaa aacattaagt tatgacgaag aagaacggaa acgccttaaa   6120
ccggaaaatt ttcataaata gcgaaaaccc gcgaggtcgc cgccccgtaa cctgtcggat   6180
caccggaaag gacccgtaaa gtgataatga ttatcatcta catatcacaa cgtgcgtgga   6240
ggccatcaaa ccacgtcaaa taatcaatta tgacgcaggt atcgtattaa ttgatctgca   6300
tcaacttaac gtaaaaacaa cttcagacaa tacaaatcag cgacactgaa tacggggcaa   6360
cctcatgtcc cccccccccc ccccctgcag gcatcgtggt gtcacgctcg tcgtttggta   6420
tggcttcatt cagctccggt tcccaacgat caaggcgagt tacatgatcc cccatgttgt   6480
gcaaaaaagc ggttagctcc ttcggtcctc cgatcgttgt cagaagtaag ttggccgcag   6540
tgttatcact catggttatg gcagcactgc ataattctct tactgtcatg ccatccgtaa   6600
gatgcttttc tgtgactggt gagtactcaa ccaagtcatt ctgagaatag tgtatgcggc   6660
gaccgagttg ctcttgcccg gcgtcaacac gggataatac cgcgccacat agcagaactt   6720
taaaagtgct catcattgga aaacgttctt cggggcgaaa actctcaagg atcttaccgc   6780
tgttgagatc cagttcgatg taacccactc gtgcacccaa ctgatcttca gcatctttta   6840
ctttcaccag cgtttctggg tgagcaaaaa caggaaggca aaatgccgca aaaaagggaa   6900
taagggcgac acggaaatgt tgaatactca tactcttcct ttttcaatat tattgaagca   6960
tttatcaggg ttattgtctc atgagcggat acatatttga atgtatttag aaaaataaac   7020
aaataggggt tccgcgcaca tttccccgaa aagtgccacc tgacgtctaa gaaaccatta   7080
ttatcatgac attaacctat aaaaataggc gtatcacgag gccctttcgt cttcaagaat   7140
tggtcgacga tcttgctgcg ttcggatatt ttcgtggagt tcccgccaca gacccggatt   7200
```

-continued gaaggcgaga tccagcaact cgcgccagat catcctgtga cggaactttg gcgcgtgatg 7260
actggccagg acgtcggccg aaagagcgac aagcagatca cgcttttcga cagcgtcgga 7320
tttgcgatcg aggatttttc ggcgctgcgc tacgtccgcg accgcgttga gggatcaagc 7380
cacagcagcc cactcgacct tctagccgac ccagacgagc caagggatct tttggaatg 7440
ctgctccgtc gtcaggcttt ccgacgtttg ggtggttgaa cagaagtcat tatcgcacgg 7500
aatgccaagc actcccgagg ggaaccctgt ggttggcatg cacatacaaa tggacgaacg 7560
gataaacctt ttcacgccct tttaaatatc cgattattct aataaacgct cttttctctt 7620
aggtttaccc gccaatatat cctgtcaaac actgatagtt taaactgaag gcgggaaacg 7680
acaacctgat catgagcgga gaattaaggg agtcacgtta tgacccccgc cgatgacgcg 7740
ggacaagccg ttttacgttt ggaactgaca gaaccgcaac gttgaaggag ccactcagct 7800
taattaacta atcgactcta gtaacggccg ccagtgtgct ggaattaatt cggcttgtcg 7860
accacccaac cccatatcga cagaggatgt gaagaacagg taaatcacgc agaagaaccc 7920
atctctgata gcagctatcg attagaacaa cgaatccata ttgggtccgt gggaaatact 7980
tactgcacag gaagggggcg atctgacgag gccccgccac cggcctcgac ccgaggccga 8040
ggccgacgaa gcgccggcga gtacggcgcc gcggcggcct ctgcccgtgc cctctgcgcg 8100
tgggagggag aggccgcggt ggtgggggcg cgcgcgcgcg cgcgcgcagc tggtgcggcg 8160
gcgcgggggt cagccgccga gccggcggcg acggaggagc agggcggcgt ggacgcgaac 8220
ttccgatcgg ttggtcagag tgcgcgagtt gggcttagcc aattaggtct caacaatcta 8280
ttgggccgta aaattcatgg gccctggttt gtctaggccc aatatcccgt tcatttcagc 8340
ccacaaatat ttccccagag gattattaag gcccacacgc agcttatagc agatcaagta 8400
cgatgtttcc tgatcgttgg atcggaaacg tacggtcttg atcaggcatg ccgacttcgt 8460
caaagagagg cggcatgacc tgacgcggag ttggttccgg gcaccgtctg gatggtcgta 8520
ccgggaccgg acacgtgtcg cgcctccaac tacatggaca cgtgtggtgc tgccattggg 8580
ccgtacgcgt ggcggtgacc gcaccggatg ctgcctcgca ccgccttgcc cacgctttat 8640
atagagaggt tttctctcca ttaatcgcat agcgagtcga atcgaccgaa ggggaggggg 8700
agcgagagct ttgcgttctc taatcgcctc gtcaaggtaa ctaatcaatc acctcgtcct 8760
aatcctcgaa tctctcgtgg tgcccgtcta atctcgcgat tttgatgctc gtggtggaaa 8820
gcgtaggagg atcccgtgcg agttagtctc aatctctcag ggtttcgtgc gattttaggg 8880
tgatccacct cttaatcgag ttacggtttc gtgcgatttt agggtaatcc tcttaatctc 8940
tcattgattt agggtttcgt gagaatcgag gtagggatct gtgttattta tatcgatcta 9000
atagatggat tggttttgag attgttctgt cagatgggga ttgtttcgat atattaccct 9060
aatgatgtgt cagatgggga ttgtttcgat atattaccct aatgatgtgt cagatgggga 9120
ttgtttcgat atattaccct aatgatggat aataagagta gttcacagtt atgttttgat 9180
cctgccacat agtttgagtt ttgtgatcag atttagtttt acttatttgt gcttagttcg 9240
gatgggattg ttctgatatt gttccaatag atgaatagct cgttaggtta aaatctttag 9300
gttgagttag gcgacacata gtttatttcc tctggatttg gattggaatt gtgttcttag 9360
ttttttttccc ctggatttgg attggaattg tgtggagctg ggttagagaa ttacatctgt 9420
atcgtgtaca cctacttgaa ctgtagagct tgggttctaa ggtcaattta atctgtattg 9480
tatctggctc tttgcctagt tgaactgtag tgctgatgtt gtactgtgtt tttttacccg 9540

```
ttttatttgc tttactcgtg caaatcaaat ctgtcagatg ctagaactag gtggctttat   9600
tctgtgttct tacatagatc tgttgtcctg tagttactta tgtcagtttt gttattatct   9660
gaagatattt ttggttgttg cttgttgatg tggtgtgagc tgtgagcagc gctcttatga   9720
ttaatgatgc tgtccaattg tagtgtagta tgatgtgatt gatatgttca tctattttga   9780
gctgacagta ccgatatcgt aggatctggt gccaacttat tctccagctg ctttttttta   9840
cctatgttaa ttccaatcct ttcttgcctc ttccagggat ccaccgggag tgagataagc   9900
aaagcacaag ataggtttac agatgatctt gagaatatgt acagaactta tcctcagtac   9960
agagagatac taagaatgat aatggctgct gttggtcgtg gaggtgaagg tgacgttggt  10020
caacgcattc gtgatgagat attagtaata caggtaaaac tgatggtcct tggtgaatat  10080
acagttattt tcgttcattg ctctgctgaa ttgagcagtt ggtagtgctc atccaaaacg  10140
tagacattgt caacaataaa atgtttggtg tgttacagag aaataccggg ctgtattact  10200
aatatctcat cacgaatgcg ttgaccaacg tcaccttcac ctccacgacc aacagcagcc  10260
attatcattc ttagtatctc tctgtactga ggataagttc tgtacatatt ctcaagatca  10320
tctgtaaacc tatcttgtgc tttgcttatc tcactgctag ctccccgaat ttccccgatc  10380
gttcaaacat ttggcaataa agtttcttaa gattgaatcc tgttgccggt cttgcgatga  10440
ttatcatata atttctgttg aattacgtta agcatgtaat aattaacatg taatgcatga  10500
cgttatttat gagatgggtt tttatgatta gagtcccgca attatacatt taatacgcga  10560
tagaaaacaa aatatagcgc gcaaactagg ataaattatc gcgcgcggtg tcatctatgt  10620
tactagatcg ggaattggcg agctcgcccg ggtattcatc ctaggtatcc aagaattcat  10680
actaaagctt gcatgcctgc aggtcgactc tagtaacggc cgccagtgtg ctggaattaa  10740
ttcggcttgt cgaccaccca accccatatc gacagaggat gtgaagaaca ggtaaatcac  10800
gcagaagaac ccatctctga tagcagctat cgattagaac aacgaatcca tattgggtcc  10860
gtgggaaata cttactgcac aggaaggggg cgatctgacg aggccccgcc accggcctcg  10920
acccgaggcc gaggccgacg aagcgccggc gagtacggcg ccgcggcggc ctctgcccgt  10980
gccctctgcg cgtgggaggg agaggccgcg gtggtggggg cgcgcgcgcg cgcgcgcgca  11040
gctggtgcgg cggcgcgggg gtcagccgcc gagccggcgg cgacggagga gcagggcggc  11100
gtggacgcga acttccgatc ggttggtcag agtgcgcgag ttgggcttag ccaattaggt  11160
ctcaacaatc tattgggccg taaaattcat gggccctggt ttgtctaggc ccaatatccc  11220
gttcatttca gcccacaaat atttccccag aggattatta aggcccacac gcagcttata  11280
gcagatcaag tacgatgttt cctgatcgtt ggatcggaaa cgtacggtct tgatcaggca  11340
tgccgacttc gtcaaagaga ggcggcatga cctgacgcgg agttggttcc gggcaccgtc  11400
tggatggtcg taccgggacc ggacacgtgt cgcgcctcca actacatgga cacgtgtggt  11460
gctgccattg ggccgtacgc gtggcggtga ccgcaccgga tgctgcctcg caccgccttg  11520
cccacgcttt atatagagag gttttctctc cattaatcgc atagcgagtc gaatcgaccg  11580
aaggggaggg ggagcgaagc tttgcgttct ctaatcgcct cgtcaaggta actaatcaat  11640
cacctcgtcc taatcctcga atctctcgtg gtgcccgtct aatctcgcga ttttgatgct  11700
cgtggtggaa agcgtaggag gatcccgtgc gagttagtct caatctctca gggtttcgtg  11760
cgattttagg gtgatccacc tcttaatcga gttacggttt cgtgcgattt tagggtaatc  11820
ctcttaatct ctcattgatt tagggtttcg tgagaatcga ggtagggatc tgtgttattt  11880
atatcgatct aatagatgga ttggttttga gattgttctg tcagatgggg attgtttcga  11940
```

-continued

```
tatattaccc taatgatgtg tcagatgggg attgtttcga tatattaccc taatgatgtg  12000

tcagatgggg attgtttcga tatattaccc taatgatgga taataagagt agttcacagt  12060

tatgttttga tcctgccaca tagtttgagt tttgtgatca gatttagttt tacttatttg  12120

tgcttagttc ggatgggatt gttctgatat tgttccaata gatgaatagc tcgttaggtt  12180

aaaatcttta ggttgagtta ggcgacacat agtttatttc ctctggattt ggattggaat  12240

tgtgttctta gttttttcc cctggatttg gattggaatt gtgtggagct gggttagaga  12300

attacatctg tatcgtgtac acctacttga actgtagagc ttgggttcta aggtcaattt  12360

aatctgtatt gtatctggct ctttgcctag ttgaactgta gtgctgatgt tgtactgtgt  12420

tttttaccc gttttatttg ctttactcgt gcaaatcaaa tctgtcagat gctagaacta  12480

ggtggcttta ttctgtgttc ttacatagat ctgttgtcct gtagttactt atgtcagttt  12540

tgttattatc tgaagatatt tttggttgtt gcttgttgat gtggtgtgag ctgtgagcag  12600

cgctcttatg attaatgatg ctgtccaatt gtagtgtagt atgatgtgat tgatatgttc  12660

atctattttg agctgacagt accgatatcg taggatctgg tgccaactta ttctccagct  12720

gcttttttt acctatgtta attccaatcc tttcttgcct cttccag               12767


<210> SEQ ID NO 24
<211> LENGTH: 39
<212> TYPE: DNA
<213> ORGANISM: Oryza sativa

<400> SEQUENCE: 24

tggaattttt gtttggatta ggttcatggc tacaaggca                          39


<210> SEQ ID NO 25
<211> LENGTH: 39
<212> TYPE: DNA
<213> ORGANISM: Sorghum bicolor

<400> SEQUENCE: 25

tggacttttt gtttggatta ggttcatggc taccaggca                          39


<210> SEQ ID NO 26
<211> LENGTH: 38
<212> TYPE: DNA
<213> ORGANISM: Zea mays
<220> FEATURE:
<221> NAME/KEY: misc_feature
<222> LOCATION: (1)..(19)
<223> OTHER INFORMATION: n, any nucleotide

<400> SEQUENCE: 26

nnnnnnnnnn nnnnnnnnng attcatggct accaggca                           38


<210> SEQ ID NO 27
<211> LENGTH: 39
<212> TYPE: DNA
<213> ORGANISM: solanum lycopersicon

<400> SEQUENCE: 27

tggaattctt gtatggatga ggttcatggc tacaaggca                          39


<210> SEQ ID NO 28
<211> LENGTH: 42
<212> TYPE: DNA
<213> ORGANISM: Oryza sativa
```

<400> SEQUENCE: 28
agagcgtcta ttgagctatg atcgaccgat tcattcagag cc 42

<210> SEQ ID NO 29
<211> LENGTH: 42
<212> TYPE: DNA
<213> ORGANISM: Sorghum bicolor

<400> SEQUENCE: 29
agagcgtctc ttgagctatg atcgtgctat tcattcagaa cc 42

<210> SEQ ID NO 30
<211> LENGTH: 42
<212> TYPE: DNA
<213> ORGANISM: zea mays

<400> SEQUENCE: 30
agagcgtctc ttgagctatg atcgtgctat tcattcagaa cc 42

<210> SEQ ID NO 31
<211> LENGTH: 42
<212> TYPE: DNA
<213> ORGANISM: solanum lycopersicon

<400> SEQUENCE: 31
agagcgtctt ttgagttatg accgtgctat ccattctgaa cc 42

<210> SEQ ID NO 32
<211> LENGTH: 39
<212> TYPE: DNA
<213> ORGANISM: Artificial Sequence
<220> FEATURE:
<223> OTHER INFORMATION: Synthetic sequence, dgGWDup2
<220> FEATURE:
<221> NAME/KEY: misc_feature
<222> LOCATION: (8)..(8)
<223> OTHER INFORMATION: Y is C or T
<220> FEATURE:
<221> NAME/KEY: misc_feature
<222> LOCATION: (13)..(13)
<223> OTHER INFORMATION: W is A or T
<220> FEATURE:
<221> NAME/KEY: misc_feature
<222> LOCATION: (19)..(19)
<223> OTHER INFORMATION: K is G or T
<220> FEATURE:
<221> NAME/KEY: misc_feature
<222> LOCATION: (22)..(22)
<223> OTHER INFORMATION: R is A or G
<220> FEATURE:
<221> NAME/KEY: misc_feature
<222> LOCATION: (34)..(34)
<223> OTHER INFORMATION: M is A or C

<400> SEQUENCE: 32
tggaattytt gtwtggatka grttcatggc tacmaggca 39

<210> SEQ ID NO 33
<211> LENGTH: 42
<212> TYPE: DNA
<213> ORGANISM: Artificial Sequence
<220> FEATURE:
<223> OTHER INFORMATION: Synthetic sequence, dgGWDdown2
<220> FEATURE:
<221> NAME/KEY: misc_feature
<222> LOCATION: (3)..(3)
<223> OTHER INFORMATION: Y is C or T
<220> FEATURE:
<221> NAME/KEY: misc_feature

```
<222> LOCATION: (6)..(6)
<223> OTHER INFORMATION: W is A or T
<220> FEATURE:
<221> NAME/KEY: misc_feature
<222> LOCATION: (12)..(12)
<223> OTHER INFORMATION: R is A or G
<220> FEATURE:
<221> NAME/KEY: misc_feature
<222> LOCATION: (15)..(15)
<223> OTHER INFORMATION: M is A or C
<220> FEATURE:
<221> NAME/KEY: misc_feature
<222> LOCATION: (17)..(17)
<223> OTHER INFORMATION: S is G or C
<220> FEATURE:
<221> NAME/KEY: misc_feature
<222> LOCATION: (18)..(18)
<223> OTHER INFORMATION: W is A or T
<220> FEATURE:
<221> NAME/KEY: misc_feature
<222> LOCATION: (21)..(21)
<223> OTHER INFORMATION: R is A or G
<220> FEATURE:
<221> NAME/KEY: misc_feature
<222> LOCATION: (27)..(27)
<223> OTHER INFORMATION: R is A or G
<220> FEATURE:
<221> NAME/KEY: misc_feature
<222> LOCATION: (33)..(33)
<223> OTHER INFORMATION: D is A, G or T

<400> SEQUENCE: 33

ggytcwgaat gratmgswcg rtcatarctc aadagacgct ct                    42

<210> SEQ ID NO 34
<211> LENGTH: 1130
<212> TYPE: DNA
<213> ORGANISM: Panicum virgatum

<400> SEQUENCE: 34

tggaattctt gtttggatga gattcatggc taccaggcaa ctaacatgga ataagaacta    60

taatgtgaag ccccggtata tacctgtctt tatcatttac ttcagtgatg tttactctct   120

gcttaaaaat ttaaagaatc tgaagctgtc cttttctttt gtgcgggaac ataattgaga   180

aattggtgtt tttgccacta cttcatgatg caattgtaat ttttccctca tttttttcaa   240

ctttgtgatt ttgcccttta ctattcacaa gtcaacgcaa ttttgctcct gttttgaccg   300

ttgactgagg gaaaaatcgc gttaacttgt gaatagtaag tgcaaaattg caaagttgaa   360

aaaaacaagg acaaaatcac aattgcactg caaagtaggg gtggaaacac aaatgcccca   420

aaataatttg gctgtttgtc ctgatagaaa acaatacaat tcagtactca gagaatatta   480

tatttctata aatgaaaaac ataactcatg tcacattctt tggcatctca tatcgatcaa   540

taactatgca gtgagataag caaagcacaa gataggttta cagatgatct tgagaacatg   600

tacaaagctt atcctcagtg cagagagata ttaagaatga taatggctgc tgttggtcgt   660

ggaggtgaag gtgatgttgg tcaacgtatt cgtgatgaga tattagtaat acaggtaaaa   720

ttaatggtcc taggtgaata tacacttact tttattcatt gcttcaccga attatacggt   780

tggtagttct catccaaaag atagacattg tgaataataa taaatgctt gctgctttaa   840

tagagaaata atgactgcaa aggtggaatg atggaagaat ggcaccagaa attgcacaac   900

aatacaagcc cagatgatgt agtgatatgc caggtaatgg atattttgaa ttcttaatac   960

agtaagtatt taagcattga ggttttcatg gttatgtctc tccttgggca ggcactaatt  1020

gattatatca agagtgattt tgatataagt gtttactggg acaccttgaa caaaaatggc  1080
```

ataaccaaag agcgtctctt gagctatgat cgagctatcc attcagaacc 1130

<210> SEQ ID NO 35
<211> LENGTH: 1130
<212> TYPE: DNA
<213> ORGANISM: Panicum virgatum

<400> SEQUENCE: 35
tggaattctt gtttggatta ggttcatggc taccaggcaa ctaacatgga ataagaacta 60
taatgtgaag ccccggtata tacctgtctt tatcatttac ttcagtgatg tttactctct 120
gcttaaaaat ttaaagaatc tgaagctgtc cttttctttt gtgcgggaac atatttgaga 180
aattggtgtt tttgccacta cttcatgatg caattgtaat ttttccctca ttttttttcaa 240 ctttgtgatt ttgcccttta ctattcacaa gtcaacgcaa ttttgctcct gttttgaccg 300
ttgactgagg gaaaaatcgc gttaacttgt gaatagtaag tgcaaaattg caaagttgaa 360
aaaaacaagg acaaaatcac aattgcactg caaagtaggg gtggaaacac aaatgcccca 420
aaataatttg gctgtttgtc ctgatagaaa acaatacaat tcagtactaa gagaatatta 480
tatttctata aatgaaaaac ataactcatg tcacattctt tggcatctca tatcgatcaa 540
taactatgca gtgagataag caaagcacaa gataggttta cagatgatct tgagaacatg 600
tacaaagctt atcctcagtg cagagagata ttaagaatga taatggctgc tgttggtcgt 660
ggaggtgaag gtgatgttgg tcaacgtatt cgagatgaga tattagtaat acaggtaaaa 720
ttaatggtcc taggtgaata tacacttact tttattcatt gcttcactga attatacggt 780
tggtagttct catccaaaag atagacattg tgaataataa taaaatgctt gctgctttaa 840
tagagaaata atgactgcaa aggtggaatg atggaagaat ggcaccagaa attgcacaac 900
aatacaagcc cagatgatgt agtgatatgc caggtaatgg atattttgaa ttcttaatac 960
agtaagtatt taagcattga ggttttcatg gttatgtctc tccttgggca ggcactaatt 1020
gattatatca agagtgattt tgatataagt gtttactggg acaccttgaa caaaaatggc 1080
ataaccaaag agcgtctatt gagttatgac cgtccgatcc attccagacc 1130

<210> SEQ ID NO 36
<211> LENGTH: 1071
<212> TYPE: DNA
<213> ORGANISM: Panicum virgatum

<400> SEQUENCE: 36
tggaattttt gtttggatga gattcatggc tacaagacaa ctgacatgga ataagaacta 60
taatgtgaag ccacggtata tacctgtctt tattatttac ttcagtaatg tttactctct 120
gctttaaaag ttaaagaatc agaagttgtc cctttctttt gtgcgggaac ataattgaaa 180
agttggtgtt cttgccacta caagtcaacg cgattttacc cctcgtcaac ggtcaaaaca 240
gtagcaaaat cgcgttgact tgtgaatagt aagggcaaat cacaaagttg gaaaaaacaa 300
ggacaaaatc acaattgcac tgcaaagtag tcgcggaaac acaaatgccc caaaataatt 360
tggctgtttg tcctgataaa aacaatacaa attcagtact cagagaatat tatatttcta 420
taaatgaaaa acataactca tgtcgcattc tttcattctt tggcatctca tattgattaa 480
taactacgca gtgagataag caaagcacaa gataggttta cagatgatct tgagaacatg 540
tacaaagctt atcctcagta cagagagata ttaagaatga taatggctgc tgttggtcgt 600
ggaggtgaag gtgatgttgg tcaacgtatt cgtgatgaga tattagtaat acaggtaaaa 660
ttaatggtcc taggtgaata tacacctact tttattcatt gcttcactga attatacggt 720

```
tggtagttct gatccaaaag atagacattg tgaataataa taaaatgctt gctgctttta    780

tagagaaata atgactgcaa aggtggaatg atggaagaat ggcaccagaa attgcacaac    840

aatacaagcc cagatgatgt agtgatatgc caggtattgg atattttgaa ttcttaatac    900

tgtaagtatt taagcattga ggtttttatg gttatgtctc tccttgggca ggcattaatt    960

gattatatca agagtgattt tgatataagt gtttactggg acaccttgaa caaaaatggc   1020

ataaccaaag agcgtctttt gagctatgat cgttgctatc cattcagaac c            1071
```

<210> SEQ ID NO 37
<211> LENGTH: 265
<212> TYPE: DNA
<213> ORGANISM: Artificial Sequence
<220> FEATURE:
<223> OTHER INFORMATION: Synthetic sequence, PvGWDko2 RNAi driver sequence

<400> SEQUENCE: 37

```
ggctagcgag ataagcaaag cacaagatag gtttacagat gatcttgaga acatgtacaa     60

agcttatcct cagtacagag agatattaag aatgataatg gctgctgttg gtcgtggagg    120

tgaaggtgat gttggtcaac gtattcgtga tgagatatta gtaatacagg agaaataatg    180

actgcaaagg tggaatgatg gaagaatggc accagaaatt gcacaacaat acaagcccag    240

atgatgtagt gatatgcccg ggagg                                          265
```

<210> SEQ ID NO 38
<211> LENGTH: 12930
<212> TYPE: DNA
<213> ORGANISM: Artificial Sequence
<220> FEATURE:
<223> OTHER INFORMATION: Synthetic sequence, pAG2104

<400> SEQUENCE: 38

```
atccagataa tgcagaaact cattaactca gtgcaaaact atgcctgggg cagcaaaacg     60

gcgttgactg aactttatgg tatggaaaat ccgtccagcc agccgatggc cgagctgtgg    120

atgggcgcac atccgaaaag cagttcacga gtgcagaatg ccgccggaga tatcgtttca    180

ctgcgtgatg tgattgagag tgataaatcg actctgctcg gagaggccgt tgccaaacgc    240

tttggcgaac tgcctttcct gttcaaagta ttatgcgcag cacagccact ctccattcag    300

gttcatccaa acaaacacaa ttctgaaatc ggttttgcca aagaaaatgc cgcaggtatc    360

ccgatggatg ccgccgagcg taactataaa gatcctaacc acaagccgga gctggttttt    420

gcgctgacgc ctttccttgc gatgaacgcg tttcgtgaat tttccgagat tgtctcccta    480

ctccagccgg tcgcaggtgc acatccggcg attgctcact tttttacaaca gcctgatgcc   540

gaacgtttaa gcgaactgtt cgccagcctg ttgaatatgc agggtgaaga aaaatcccgc    600

gcgctggcga ttttaaaatc ggccctcgat agccagcagg gtgaaccgtg gcaaacgatt    660

cgtttaattt ctgaatttta cccggaagac agcggtctgt tctccccgct attgctgaat    720

gtggtgaaat tgaaccctgg cgaagcgatg ttcctgttcg ctgaaacacc gcacgcttac    780

ctgcaaggcg tggcgctgga agtgatggca aactccgata acgtgctgcg tgcgggtctg    840

acgcctaaat acattgatat tccggaactg gttgccaatg tgaaattcga agccaaaccg    900

gctaaccagt tgttgaccca gccggtgaaa caaggtgcag aactggactt cccgattcca    960

gtggatgatt ttgccttctc gctgcatgac cttagtgata aagaaaccac cattagccag   1020

cagagtgccg ccattttgtt ctgcgtcgaa ggcgatgcaa cgttgtggaa aggttctcag   1080
```

-continued

```
cagttacagc ttaaaccggg tgaatcagcg tttattgccg ccaacgaatc accggtgact   1140
gtcaaaggcc acggccgttt agcgcgtgtt tacaacaagc tgtaagagct tactgaaaaa   1200
attaacatct cttgctaagc tgggagctct agatccccga atttccccga tcgttcaaac   1260
atttggcaat aaagtttctt aagattgaat cctgttgccg gtcttgcgat gattatcata   1320
taatttctgt tgaattacgt taagcatgta ataattaaca tgtaatgcat gacgttattt   1380
atgagatggg tttttatgat tagagtcccg caattataca tttaatacgc gatagaaaac   1440
aaaatatagc gcgcaaacta ggataaatta tcgcgcgcgg tgtcatctat gttactagat   1500
cgggaattgg cgagctcgaa ttaattcagt acattaaaaa cgtccgcaat gtgttattaa   1560
gttgtctaag cgtcaatttg tttacaccac aatatatcct gccaccagcc agccaacagc   1620
tccccgaccg gcagctcggc acaaaatcac cactcgatac aggcagccca tcagtccggg   1680
acggcgtcag cgggagagcc gttgtaaggc ggcagacttt gctcatgtta ccgatgctat   1740
tcggaagaac ggcaactaag ctgccgggtt tgaaacacgg atgatctcgc ggagggtagc   1800
atgttgattg taacgatgac agagcgttgc tgcctgtgat caaatatcat ctccctcgca   1860
gagatccgaa ttatcagcct tcttattcat ttctcgctta accgtgacag gctgtcgatc   1920
ttgagaacta tgccgacata ataggaaatc gctggataaa gccgctgagg aagctgagtg   1980
gcgctatttc tttagaagtg aacgttgacg atcgtcgacc gtaccccgat gaattaattc   2040
ggacgtacgt tctgaacaca gctggatact tacttgggcg attgtcatac atgacatcaa   2100
caatgtaccc gtttgtgtaa ccgtctcttg gaggttcgta tgacactagt ggttcccctc   2160
agcttgcgac tagatgttga ggcctaacat tttattagag agcaggctag ttgcttagat   2220
acatgatctt caggccgtta tctgtcaggg caagcgaaaa ttggccattt atgacgacca   2280
atgccccgca gaagctccca tctttgccgc catagacgcc gcgccccccct tttggggtgt   2340
agaacatcct tttgccagat gtggaaaaga agttcgttgt cccattgttg gcaatgacgt   2400
agtagccggc gaaagtgcga gacccatttg cgctatatat aagcctacga tttccgttgc   2460
gactattgtc gtaattggat gaactattat cgtagttgct ctcagagttg tcgtaatttg   2520
atggactatt gtcgtaattg cttatggagt tgtcgtagtt gcttggagaa atgtcgtagt   2580
tggatgggga gtagtcatag ggaagacgag cttcatccac taaaacaatt ggcaggtcag   2640
caagtgcctg ccccgatgcc atcgcaagta cgaggcttag aaccaccttc aacagatcgc   2700
gcatagtctt ccccagctct ctaacgcttg agttaagccg cgccgcgaag cggcgtcggc   2760
ttgaacgaat tgttagacat tatttgccga ctaccttggt gatctcgcct ttcacgtagt   2820
gaacaaattc ttccaactga tctgcgcgcg aggccaagcg atcttcttgt ccaagataag   2880
cctgcctagc ttcaagtatg acgggctgat actgggccgg caggcgctcc attgcccagt   2940
cggcagcgac atccttcggc gcgattttgc cggttactgc gctgtaccaa atgcgggaca   3000
acgtaagcac tacatttcgc tcatcgccag cccagtcggg cggcgagttc catagcgtta   3060
aggtttcatt tagcgcctca aatagatcct gttcaggaac cggatcaaag agttcctccg   3120
ccgctggacc taccaaggca acgctatgtt ctcttgcttt tgtcagcaag atagccagat   3180
caatgtcgat cgtggctggc tcgaagatac ctgcaagaat gtcattgcgc tgccattctc   3240
caaattgcag ttcgcgctta gctggataac gccacggaat gatgtcgtcg tgcacaacaa   3300
tggtgacttc tacagcgcgg agaatctcgc tctctccagg ggaagccgaa gtttccaaaa   3360
ggtcgttgat caaagctcgc cgcgttgttt catcaagcct tacggtcacc gtaaccagca   3420
```

-continued

```
aatcaatatc actgtgtggc ttcaggccgc catccactgc ggagccgtac aaatgtacgg   3480
ccagcaacgt cggttcgaga tggcgctcga tgacgccaac tacctctgat agttgagtcg   3540
atacttcggc gatcaccgct tccctcatga tgtttaactc ctgaattaag ccgcgccgcg   3600
aagcggtgtc ggcttgaatg aattgttagg cgtcatcctg tgctcccgag aaccagtacc   3660
agtacatcgc tgtttcgttc gagacttgag gtctagtttt atacgtgaac aggtcaatgc   3720
cgccgagagt aaagccacat tttgcgtaca aattgcaggc aggtacattg ttcgtttgtg   3780
tctctaatcg tatgccaagg agctgtctgc ttagtgccca ctttttcgca aattcgatga   3840
gactgtgcgc gactcctttg cctcggtgcg tgtgcgacac aacaatgtgt tcgatagagg   3900
ctagatcgtt ccatgttgag ttgagttcaa tcttcccgac aagctcttgg tcgatgaatg   3960
cgccatagca agcagagtct tcatcagagt catcatccga gatgtaatcc ttccggtagg   4020
ggctcacact tctggtagat agttcaaagc cttggtcgga taggtgcaca tcgaacactt   4080
cacgaacaat gaaatggttc tcagcatcca atgtttccgc cacctgctca gggatcaccg   4140
aaatcttcat atgacgccta acgcctggca cagcggatcg caaacctggc gcggcttttg   4200
gcacaaaagg cgtgacaggt ttgcgaatcc gttgctgcca cttgttaacc cttttgccag   4260
atttggtaac tataatttat gttagaggcg aagtcttggg taaaaactgg cctaaaattg   4320
ctggggattt caggaaagta aacatcacct tccggctcga tgtctattgt agatatatgt   4380
agtgtatcta cttgatcggg ggatctgctg cctcgcgcgt ttcggtgatg acggtgaaaa   4440
cctctgacac atgcagctcc cggagacggt cacagcttgt ctgtaagcgg atgccgggag   4500
cagacaagcc cgtcagggcg cgtcagcggg tgttggcggg tgtcggggcg cagccatgac   4560
ccagtcacgt agcgatagcg gagtgtatac tggcttaact atgcggcatc agagcagatt   4620
gtactgagag tgcaccatat gcggtgtgaa ataccgcaca gatgcgtaag gagaaaatac   4680
cgcatcaggc gctcttccgc ttcctcgctc actgactcgc tgcgctcggt cgttcggctg   4740
cggcgagcgg tatcagctca ctcaaaggcg gtaatacggt tatccacaga atcaggggat   4800
aacgcaggaa agaacatgtg agcaaaaggc cagcaaaagg ccaggaaccg taaaaaggcc   4860
gcgttgctgg cgtttttcca taggctccgc ccccctgacg agcatcacaa aaatcgacgc   4920
tcaagtcaga ggtggcgaaa cccgacagga ctataaagat accaggcgtt tccccctgga   4980
agctccctcg tgcgctctcc tgttccgacc ctgccgctta ccggatacct gtccgccttt   5040
ctcccttcgg gaagcgtggc gctttctcat agctcacgct gtaggtatct cagttcggtg   5100
taggtcgttc gctccaagct gggctgtgtg cacgaacccc ccgttcagcc cgaccgctgc   5160
gccttatccg gtaactatcg tcttgagtcc aacccggtaa gacacgactt atcgccactg   5220
gcagcagcca ctggtaacag gattagcaga gcgaggtatg taggcggtgc tacagagttc   5280
ttgaagtggt ggcctaacta cggctacact agaaggacag tatttggtat ctgcgctctg   5340
ctgaagccag ttaccttcgg aaaaagagtt ggtagctctt gatccggcaa acaaaccacc   5400
gctggtagcg gtggtttttt tgtttgcaag cagcagatta cgcgcagaaa aaaaggatct   5460
caagaagatc ctttgatctt ttctacgggg tctgacgctc agtggaacga aaactcacgt   5520
taagggattt tggtcatgag attatcaaaa aggatcttca cctagatcct tttaaattaa   5580
aaatgaagtt ttaaatcaat ctaaagtata tatgagtaaa cttggtctga cagttaccaa   5640
tgcttaatca gtgaggcacc tatctcagcg atctgtctat ttcgttcatc catagttgcc   5700
tgactccccg tcgtgtagat aactacgata cgggagggct taccatctgg ccccagtgct   5760
gcaatgatac cgcgagaccc acgctcaccg gctccagatt tatcagcaat aaaccagcca   5820
```

-continued

```
gccggaaggg ccgagcgcag aagtggtcct gcaactttat ccgcctccat ccagtctatt   5880
aattgttgcc gggaagctag agtaagtagt tcgccagtta atagtttgcg caacgttgtt   5940
gccattgctg caggggggggg ggggggggggg ttccattgtt cattccacgg acaaaaacag   6000
agaaaggaaa cgacagaggc caaaaagctc gctttcagca cctgtcgttt cctttctttt   6060
cagagggtat tttaaataaa aacattaagt tatgacgaag aagaacggaa acgccttaaa   6120
ccggaaaatt ttcataaata gcgaaaaccc gcgaggtcgc cgccccgtaa cctgtcggat   6180
caccggaaag gacccgtaaa gtgataatga ttatcatcta catatcacaa cgtgcgtgga   6240
ggccatcaaa ccacgtcaaa taatcaatta tgacgcaggt atcgtattaa ttgatctgca   6300
tcaacttaac gtaaaaacaa cttcagacaa tacaaatcag cgacactgaa tacggggcaa   6360
cctcatgtcc cccccccccc ccccctgcag gcatcgtggt gtcacgctcg tcgtttggta   6420
tggcttcatt cagctccggt tcccaacgat caaggcgagt tacatgatcc cccatgttgt   6480
gcaaaaaagc ggttagctcc ttcggtcctc cgatcgttgt cagaagtaag ttggccgcag   6540
tgttatcact catggttatg gcagcactgc ataattctct tactgtcatg ccatccgtaa   6600
gatgcttttc tgtgactggt gagtactcaa ccaagtcatt ctgagaatag tgtatgcggc   6660
gaccgagttg ctcttgcccg gcgtcaacac gggataatac cgcgccacat agcagaactt   6720
taaaagtgct catcattgga aaacgttctt cggggcgaaa actctcaagg atcttaccgc   6780
tgttgagatc cagttcgatg taacccactc gtgcacccaa ctgatcttca gcatctttta   6840
ctttcaccag cgtttctggg tgagcaaaaa caggaaggca aaatgccgca aaaaagggaa   6900
taagggcgac acggaaatgt tgaatactca tactcttcct ttttcaatat tattgaagca   6960
tttatcaggg ttattgtctc atgagcggat acatatttga atgtatttag aaaaataaac   7020
aaataggggt tccgcgcaca tttccccgaa aagtgccacc tgacgtctaa gaaaccatta   7080
ttatcatgac attaacctat aaaaataggc gtatcacgag gccctttcgt cttcaagaat   7140
tggtcgacga tcttgctgcg ttcggatatt ttcgtggagt tcccgccaca gacccggatt   7200
gaaggcgaga tccagcaact cgcgccagat catcctgtga cggaactttg gcgcgtgatg   7260
actggccagg acgtcggccg aaagagcgac aagcagatca cgcttttcga cagcgtcgga   7320
tttgcgatcg aggatttttc ggcgctgcgc tacgtccgcg accgcgttga gggatcaagc   7380
cacagcagcc cactcgacct tctagccgac ccagacgagc caagggatct tttggaatg    7440
ctgctccgtc gtcaggcttt ccgacgtttg ggtggttgaa cagaagtcat tatcgcacgg   7500
aatgccaagc actcccgagg ggaaccctgt ggttggcatg cacatacaaa tggacgaacg   7560
gataaacctt ttcacgccct tttaaatatc cgattattct aataaacgct cttttctctt   7620
aggtttaccc gccaatatat cctgtcaaac actgatagtt taaactgaag gcgggaaacg   7680
acaacctgat catgagcgga gaattaaggg agtcacgtta tgacccccgc cgatgacgcg   7740
ggacaagccg ttttacgttt ggaactgaca gaaccgcaac gttgaaggag ccactcagct   7800
taattaacta atcgactcta gtaacggccg ccagtgtgct ggaattaatt cggcttgtcg   7860
accacccaac cccatatcga cagaggatgt gaagaacagg taaatcacgc agaagaaccc   7920
atctctgata gcagctatcg attagaacaa cgaatccata ttgggtccgt gggaaatact   7980
tactgcacag gaagggggcg atctgacgag gccccgccac cggcctcgac ccgaggccga   8040
ggccgacgaa gcgccggcga gtacggcgcc gcggcggcct ctgcccgtgc cctctgcgcg   8100
tgggagggag aggccgcggt ggtgggggcg cgcgcgcgcg cgcgcgcagc tggtgcggcg   8160
```

-continued

```
gcgcgggggt cagccgccga gccggcggcg acggaggagc agggcggcgt ggacgcgaac   8220
ttccgatcgg ttggtcagag tgcgcgagtt gggcttagcc aattaggtct caacaatcta   8280
ttgggccgta aaattcatgg gccctggttt gtctaggccc aatatcccgt tcatttcagc   8340
ccacaaatat ttccccagag gattattaag gcccacacgc agcttatagc agatcaagta   8400
cgatgtttcc tgatcgttgg atcggaaacg tacggtcttg atcaggcatg ccgacttcgt   8460
caaagagagg cggcatgacc tgacgcggag ttggttccgg gcaccgtctg gatggtcgta   8520
ccgggaccgg acacgtgtcg cgcctccaac tacatggaca cgtgtggtgc tgccattggg   8580
ccgtacgcgt ggcggtgacc gcaccggatg ctgcctcgca ccgccttgcc cacgctttat   8640
atagagaggt tttctctcca ttaatcgcat agcgagtcga atcgaccgaa ggggaggggg   8700
agcgagagct ttgcgttctc taatcgcctc gtcaagccta gatgcatgct cgagcggccg   8760
ccagtgtgat ggatatctgc agaattcgcc cttggctgcg agataagcaa agcacaagat   8820
aggtttacag atgatcttga gaacatgtac aaagcttatc ctcagtacag agagatatta   8880
agaatgataa tggctgctgt tggtcgtgga ggtgaaggtg atgttggtca acgtattcgt   8940
gatgagatat tagtaataca ggagaaataa tgactgcaaa ggtggaatga tggaagaatg   9000
gcaccagaaa ttgcacaaca atacaagccc agatgatgta gtgatatgcc cggagtcaag   9060
gtaactaatc aatcacctcg tcctaatcct cgaatctctc gtggtgcccg tctaatctcg   9120
cgattttgat gctcgtggtg gaaagcgtag gaggatcccg tgcgagttag tctcaatctc   9180
tcagggtttc gtgcgatttt agggtgatcc acctcttaat cgagttacgg tttcgtgcga   9240
ttttagggta atcctcttaa tctctcattg atttagggtt tcgtgagaat cgaggtaggg   9300
atctgtgtta tttatatcga tctaatagat ggattggttt tgagattgtt ctgtcagatg   9360
gggattgttt cgatatatta ccctaatgat gtgtcagatg gggattgttt cgatatatta   9420
ccctaatgat gtgtcagatg gggattgttt cgatatatta ccctaatgat ggataataag   9480
agtagttcac agttatgttt tgatcctgcc acatagtttg agttttgtga tcagatttag   9540
ttttacttat ttgtgcttag ttcggatggg attgttctga tattgttcca atagatgaat   9600
agctcgttag gttaaaatct ttaggttgag ttaggcgaca catagtttat ttcctctgga   9660
tttggattgg aattgtgttc ttagtttttt tcccctggat ttggattgga attgtgtgga   9720
gctgggttag agaattacat ctgtatcgtg tacacctact tgaactgtag agcttgggtt   9780
ctaaggtcaa tttaatctgt attgtatctg gctctttgcc tagttgaact gtagtgctga   9840
tgttgtactg tgttttttta cccgttttat ttgctttact cgtgcaaatc aaatctgtca   9900
gatgctagaa ctaggtggct ttattctgtg ttcttacata gatctgttgt cctgtagtta   9960
cttatgtcag ttttgttatt atctgaagat atttttggtt gttgcttgtt gatgtggtgt  10020
gagctgtgag cagcgctctt atgattaatg atgctgtcca attgtagtgt agtatgatgt  10080
gattgatatg ttcatctatt ttgagctgac agtaccgata tcgtaggatc tggtgccaac  10140
ttattctcca gctgcttttt tttacctatg ttaattccaa tcctttcttg cctcttccag  10200
ggatccaccg ggcatatcac tacatcatct gggcttgtat tgttgtgcaa tttctggtgc  10260
cattcttcca tcattccacc tttgcagtca ttatttctcc tgtattacta atatctcatc  10320
acgaatacgt tgaccaacat caccttcacc tccacgacca acagcagcca ttatcattct  10380
taatatctct ctgtactgag gataagcttt gtacatgttc tcaagatcat ctgtaaacct  10440
atcttgtgct ttgcttatct cgcagccaag ggcgaattct gcagatatcc atcacactgg  10500
cggccgctcg agcatgcatc tagctccccg aatttccccg atcgttcaaa catttggcaa  10560
```

taaagtttct taagattgaa tcctgttgcc ggtcttgcga tgattatcat ataatttctg 10620
ttgaattacg ttaagcatgt aataattaac atgtaatgca tgacgttatt tatgagatgg 10680
gtttttatga ttagagtccc gcaattatac atttaatacg cgatagaaaa caaaatatag 10740
cgcgcaaact aggataaatt atcgcgcgcg gtgtcatcta tgttactaga tcgggaattg 10800
gcgagctcgc ccgggtattc atcctaggta tccaagaatt catactaaag cttgcatgcc 10860
tgcaggtcga ctctagtaac ggccgccagt gtgctggaat taattcggct tgtcgaccac 10920
ccaaccccat atcgacagag gatgtgaaga acaggtaaat cacgcagaag aacccatctc 10980
tgatagcagc tatcgattag aacaacgaat ccatattggg tccgtgggaa atacttactg 11040
cacaggaagg gggcgatctg acgaggcccc gccaccggcc tcgacccgag gccgaggccg 11100
acgaagcgcc ggcgagtacg gcgccgcggc ggcctctgcc cgtgccctct gcgcgtggga 11160
gggagaggcc gcggtggtgg gggcgcgcgc gcgcgcgcgc gcagctggtg cggcggcgcg 11220
ggggtcagcc gccgagccgg cggcgacgga ggagcagggc ggcgtggacg cgaacttccg 11280
atcggttggt cagagtgcgc gagttgggct tagccaatta ggtctcaaca atctattggg 11340
ccgtaaaatt catgggccct ggtttgtcta ggcccaatat cccgttcatt tcagcccaca 11400
aatatttccc cagaggatta ttaaggccca cacgcagctt atagcagatc aagtacgatg 11460
tttcctgatc gttggatcgg aaacgtacgg tcttgatcag gcatgccgac ttcgtcaaag 11520
agaggcggca tgacctgacg cggagttggt tccgggcacc gtctggatgg tcgtaccggg 11580
accggacacg tgtcgcgcct ccaactacat ggacacgtgt ggtgctgcca ttgggccgta 11640
cgcgtggcgg tgaccgcacc ggatgctgcc tcgcaccgcc ttgcccacgc tttatataga 11700
gaggttttct ctccattaat cgcatagcga gtcgaatcga ccgaagggga gggggagcga 11760
agctttgcgt tctctaatcg cctcgtcaag gtaactaatc aatcacctcg tcctaatcct 11820
cgaatctctc gtggtgcccg tctaatctcg cgattttgat gctcgtggtg gaaagcgtag 11880
gaggatcccg tgcgagttag tctcaatctc tcagggtttc gtgcgatttt agggtgatcc 11940
acctcttaat cgagttacgg tttcgtgcga ttttagggta atcctcttaa tctctcattg 12000
atttagggtt tcgtgagaat cgaggtaggg atctgtgtta tttatatcga tctaatagat 12060
ggattggttt tgagattgtt ctgtcagatg ggattgttt cgatatatta ccctaatgat 12120
gtgtcagatg ggattgttt cgatatatta ccctaatgat gtgtcagatg ggattgttt 12180
cgatatatta ccctaatgat ggataataag agtagttcac agttatgttt tgatcctgcc 12240
acatagtttg agttttgtga tcagatttag ttttacttat ttgtgcttag ttcggatggg 12300
attgttctga tattgttcca atagatgaat agctcgttag gttaaaatct ttaggttgag 12360
ttaggcgaca catagtttat ttcctctgga tttggattgg aattgtgttc ttagtttttt 12420
tcccctggat ttggattgga attgtgtgga gctgggttag agaattacat ctgtatcgtg 12480
tacacctact tgaactgtag agcttgggtt ctaaggtcaa tttaatctgt attgtatctg 12540
gctctttgcc tagttgaact gtagtgctga tgttgtactg tgttttttta cccgttttat 12600
ttgctttact cgtgcaaatc aaatctgtca gatgctagaa ctaggtggct ttattctgtg 12660
ttcttacata gatctgttgt cctgtagtta cttatgtcag ttttgttatt atctgaagat 12720
atttttggtt gttgcttgtt gatgtggtgt gagctgtgag cagcgctctt atgattaatg 12780
atgctgtcca attgtagtgt agtatgatgt gattgatatg ttcatctatt ttgagctgac 12840
agtaccgata tcgtaggatc tggtgccaac ttattctcca gctgcttttt tttacctatg 12900

-continued ttaattccaa tcctttcttg cctcttccag 12930

<210> SEQ ID NO 39
<211> LENGTH: 30
<212> TYPE: DNA
<213> ORGANISM: Panicum virgatum

<400> SEQUENCE: 39
ccgtggcttc acattatagt tcttattcca 30

<210> SEQ ID NO 40
<211> LENGTH: 25
<212> TYPE: DNA
<213> ORGANISM: Panicum virgatum

<400> SEQUENCE: 40
gagataagca aagcacaaga taggt 25

<210> SEQ ID NO 41
<211> LENGTH: 25
<212> TYPE: DNA
<213> ORGANISM: Panicum virgatum

<400> SEQUENCE: 41
gcctgcccaa ggagagacat aacca 25

<210> SEQ ID NO 42
<211> LENGTH: 25
<212> TYPE: DNA
<213> ORGANISM: Panicum virgatum

<400> SEQUENCE: 42
gatataagtg tttactggga cacct 25

<210> SEQ ID NO 43
<211> LENGTH: 7635
<212> TYPE: DNA
<213> ORGANISM: Panicum virgatum
<220> FEATURE:
<221> NAME/KEY: misc_feature
<222> LOCATION: (1)..(7636)
<223> OTHER INFORMATION: n, is any nucleotide

<400> SEQUENCE: 43
ggaacgacag tgtacaagaa cagggctctt cggacgcctt ttctaaaggt cagtcttgtt 60
acattatgga tctctttgtt accacagaac agtctggtta gcagtaatgt ccataactgt 120
gcagtcagga ggtgataact ccacgcttag aattgagata gatgatcctg cggtgcaagc 180
tattgaattt ctcatctttg atgagacaca gaacaaatgg taacccagct gttttcgtta 240
ccatgtagca ctgtttgttt gtttgaatgc aaaaggtata taaactatgc aaaactctac 300
attgcacagg tttaaaaata atggccagaa ttttcaaatt cagctccaat cgagccacca 360
tcatggtagt ggcgcatctg gtgcctcatc ttctgctact tctgccttgg tgccagagga 420
tcttgtgcag atccaagctt acctacggtg ggaaagaaat ggaaagcagt catacacacc 480
ggagcaagaa aaggaaagct tttagttgtt ttttttatc ttcagtctgg aaggaactca 540
atgtactaag ttgattaaaa ataagaggtg gtgtattttt tctccaggag gagtatgaag 600
ctgcacgagc tgagttaata gaagaattaa atagaggtgt ttctttggag aagcttcgag 660
ctaaattgac aaaagcacct gaagtgcccg actcagatga aaatgattct cctgcatctc 720
aaattactgt tgataaaatt ccagaggacc ttgtacaagt ccaggcttat ataaggtggg 780

```
agaaagcagg caagccaaac tatcctcctg agaagcaact ggtaatgcat tgattcaata    840
gcgtaaaata ccttgttggc tttacacttt atggaggttc ttatctcaca attcgctagg    900
tcgagtttga ggaagcaagg aaggaactgc aggctgaggt ggacaaggga atctcgattg    960
atcagttgag gaagaagatt ttgaaaggaa acattgagag taaagtttcg aagcagctga   1020
agaataagaa gtacttctct gtagaaagga ttcagcgcaa aaagagagat atcatgcaga   1080
ttcttagtaa acataagcat actgtcatag aagagcaagc agaggttgca ccaaaacaac   1140
taactgttct tgatctcttc accaattcat tacagaagga tggctttgaa gttctaagca   1200
aaaaactgtt caagttcggt gataaacaga tcctggttag gatccttaag atattctttg   1260
tatctccaga tctttttcta ccatgctaat taagcttctc tcttcttaag gcaatctcca   1320
ccaaggttct aaacaaatca aaagtttact tggcaacaaa tcatacggag ccacttatcc   1380
ttcactggtc actagcgaaa aaggctggag agtggaaggt taaatttcaa aattgtttcc   1440
agtagttaaa gccacaaact cagcagcttt tttaaacact gctatcagta ccaatgcggt   1500
gttatttaac tgtgcaggca cctccttcaa acatattgcc atctggttca aaattgttag   1560
acatggcatg cgaaactgaa tttactaagt ctgaattgga tggtttgcat tatcaggtgg   1620
aaataacatc ttcaacctgt tattttattc ttatttttat tagccctcct gctatctcaa   1680
ggctcttaat ttccaggttg ttgagataga gcttgatgat ggaggatata aagggatgcc   1740
attcgttctt cggtctggtg aaatgtggat aaaaaataat ggctctgatt tttaccttga   1800
tctcagcacc cgtgatacca gaaatattaa ggcaagtgtt tctgtccatt ttacctttca   1860
aactttaaac tattgtcttt gttttgtcta tgcaactagt cgctaaattg tgaagtaacc   1920
gatctgttct taattgaagg acactggtga tgctggtaaa ggtactgcta aggcattgct   1980
ggaaagaata gcagagctgg aggaagatgc ccagcgatct cttatgcaca ggtcaggcac   2040
taaaatatcc ataataatat gactgaattt tacatggaaa attctcctaa actacttcta   2100
ctccttgaca gattcaacat tgcagcagat ctagttgacc aagccagaga tgctggacta   2160
ttgggtattg ttggactttt tgtttggatt agattcatgg ctacaagaca actgacatgg   2220
aataagaact ataatgtgaa gccacggtat atacctgtct ttattattta cttcagtaat   2280
gtttactctc tgctttaaaa gttaaagaat cagaagttgt ccctttcttt tgtgcgggaa   2340
cataattgaa aagttggtgt tcttgccact acaagtcaac gcgattttac ccctcgtcaa   2400
cggtcaaaac agtagcaaaa tcgcgttgac ttgtgaatag taagggcaaa tcacaaagtt   2460
ggaaaaaaca aggacaaaat cacaattgca ctgcaaagta gtcgcggaaa cacaaatgcc   2520
ccaaaataat ttggctgttt gtcctgataa aaaacaatac aattcagtac tcagagaata   2580
ttatatttct ataaatgaaa aacataactc atgtcgcatt ctttcattct ttggcatctc   2640
atattgatta ataactacgc agtgagataa gcaaagcaca agataggttt acagatgatc   2700
ttgagaacat gtacaaagct tatcctcagt acagagagat attaagaatg ataatggctg   2760
ctgttggtcg tggaggtgaa ggtgatgttg gtcaacgtat tcgtgatgag atattagtaa   2820
tacaggtaaa attaatggtc ctaggtgaat atacacctac ttttattcat tgcttcactg   2880
aattatacgg ttggtagttc tgatccaaaa gatagacatt gtgaataata ataaaatgct   2940
tgctgctttt atagagaaat aatgactgca aaggtggaat gatggaagaa tggcaccaga   3000
aattgcacaa caatacaagc ccagatgatg tagtgatatg ccaggtattg gatattttga   3060
attcttaata ctgtaagtat ttaagcattg aggtttttat ggttatgtct ctccttgggc   3120
```

-continued

```
aggcattaat tgattatatc aagagtgatt ttgatataag tgtttactgg gacaccttga   3180
acaaaaatgg cataaccaaa gagcatctct tgagctatga tcgtgcgatt cattcagaac   3240
caaatttcag aagtgaacag aaggagggtt tactccatga cctgggtaat tacatgagaa   3300
gcctgaaggt atgtaaaaca cttaatatgg atataaaaaa aggcatgcaa aaaaatctgt   3360
gcattatctt tgaaattgag tatggtattt tctaaagaaa acatagaaaa acacatattg   3420
ccctttcagt tccggaaaaa aatgatctgc cataaagagc atacagtcaa ctcatgtatt   3480
agcactcgcc ttttctgcta atggtatgtt gtgttgtgtt ctgttctatt caatatatgc   3540
tttcagtaat aatattctag tgttgacaac atcattgctc acaacataca gaaactgtag   3600
tatgcccggt acagtatgaa cttgtccttg agtctcctca tttttccctt attcacgtca   3660
cagctttata tccttccaat gaataatgat caacttggaa atcattggca tctacagtga   3720
accgtccatt gtattctgat tttgaacaac tttttttccc ctcagaacac acagtaatag   3780
ccaagtataa cgaccttaca tggccaaaac aacaacctta catggccaaa atagccaggt   3840
aagggacaga agaagagaga gggttgccct gcggcagatg tggacaatga ctgatgatgt   3900
ggctgtccca gttatcaaaa caggcaaatc cactgttcat gtggccnaag ccagtaatga   3960
gctggttttg ggaaaccctg ggggattgag taaacaatta gagggttatg tggatttggt   4020
catagttggg ggtaggaatt tggaaatttc ccttttgctt gataattatg ttagtcaaga   4080
gattagacaa gtattgttag gagtttgttt cagctggttg agattggatt tggtttctta   4140
ggtgattggt tagtgctacc cttgctctat aattggggat ttgcttttaa taaagaaagc   4200
agaaataaac ccaatccttc tccggttctc cctcttttgt ccgatgtttg cagatgcggc   4260
cactgataag gtccaggtcc atgtcctccc atcaaccaca cacacataca gcctaagatc   4320
taattcaccc caggacaccc aagctcgtga aaatatacca tgtcatccca ctattcatac   4380
tttttttaaa aaaatcccac taatcctgca aatgtcctaa tataagaaca acatcatttt   4440
cagtcatgtt gtaccttttc ttggtgacaa aaagaagaca tccatttcat ctctttttaa   4500
ggggcatttt ctcatcgttt ctgcaattga atattctttc cctgatgtaa tctttgaatg   4560
aatgctattg tgatttgctc attctgttag gctgtgcatt ctggtgctga tcttgagtct   4620
gctatagcaa cttgcatggg atacaaatcg gaggtatcat tctcattcct tttcattccg   4680
ctagaattct ttagatacct gtgctcatat ctaatgaact aacttttggg tacagggtga   4740
aggtttcatg gtcggtgttc agatcaatcc agtgaagggt ttgccatctg gatttcctgt   4800
aaaaatccct caccttcttt tctcaacaca tgtactttct aagtttctta tacttgtgac   4860
atttaccttt ataggaattg ctcaaatttg tgcttgacca tgttgaggac aagtcagcgg   4920
aaccacttct tgaggtcagt gatataatcg aagttcctgt ttgtaataaa acgaagagaa   4980
gaagctgggt ttttcatcac aactcaaata atcagatctc acatagctga ttgaattttt   5040
aaaccaccat tttttgcggn tactatgnga atcacttgtt gctaacaaaa tgctaccttg   5100
naggggnngg tggaagctcn agttgaactc cnccctnnnc ttcntgnttc accngnacgc   5160
atgaaagaan ntattttttt ggncattgcn cctgattcna cttttangac agctatngaa   5220
aggncatatg angagctccn ccatggannc cccgangntg ggcncccnaa tattgncccc   5280
atgatnngnn nnangnnnag nnccnnnann nnnnncnnnn nnnnnntnnn nnanannnng   5340
nntnnnnnan nnnnnnnnnn ngnnnnnnnn cnnnnnnnnn nnnnnnnnnn nnnnnnnnnn   5400
nnaannnnnn nnnnnnnnan nnccnnnnnn nnnnnnnnnn annnnnnnna nnnnnnnnnn   5460
nnnnnnnncn nnnnnaannn nnnnnnatnc nnnnnnnnnn nnnnnnnnnn nnnnnnnnnn   5520
```

```
annnnnnnnn nnnnncnncn nnnnnnnnnn nnntnnnnnn nnannnncaa cnnnnnnnnn   5580

nnnnnnnnnn ccnnnnnnnn ngnnnnnnnn nnnnnannnn nnnnnnnnnn nnnannnnnn   5640

nnannnnnnn nnnnnnnnnn nnnannnnnn nnnnnnnnnn nnnnnnnnnn nnnnnnnnnn   5700

nnnnnnnnnn nnnnnnnnnn nnnnnnnnnn nnnnnnnnnn nnnnnnnnnn nnnnnnnnnn   5760

ccnnnnnnnn nnnnnnnnnn nnnnnnannn nnnnnnnnnn gnnnnnnnnn nnnnnnnnnn   5820

nnnnnnnnnn ncnnnnnnnn nnnnnnnncn nnnnnnnnnn nnnnannnnn nnnnnnnnna   5880

nnnnnnnnnn nnnnnnnnnn nnnnnnnnnn nnnnnnnnnn nnnnnnnnnn annnnnnnnn   5940

nnnntnnann ncnnnnanta nncnnnnnnn nntnnnngnn nnnnnnnnnn nnnnnnnnnn   6000

nnnngannnn nnnnnnnnnn nnagnnntnn nannnnncnn nnnnnnnngn nntnnnnnnn   6060

nnnnnngnnn nnnnnnnnnn nnnnnnnnnn tnnnnnnnnn nnnnnnnngn nnnnntnnnn   6120

nnnngnnnnn nnncnnnnnn nnnnnnnnnn nnnnnnnnnn tnacnnnnnn nnnnnnntcn   6180

cnnnnnnnnn nnnnnnnnnn nnnnnnnnnn nnnnnnnggc ntnnnnnnnn nnnnnnnnnn   6240

nnnnnnnnnn nnnnnnnnan nnnncnnnnn nnnnncnnnn nnnnnnnnnt nnnnnncnnn   6300

nncnnnnnnn nnnnnnnnnn nnnnnnnnnn nnnnnnnnnt gnnnnnncnn nnnnnnnnnn   6360

cannncnnnn gnagatctcg gagagtgaac ttcagcaatc aagttctccg gatgcagaag   6420

ctggccatgc agtaccatct atttcattgg tcaataagaa gtttcttgga aaatatgcaa   6480

tatcagctga agaattctct gaggaaatgg ttagtaatat aaaattttgc attaggaaat   6540

ctgccattcg taaggaagtc ttgatgaaac caattgttat tatgctggtt tccttttctt   6600

ttggccttgt gcttctagta ctcactttta tgttttcagg ttggggctaa gtctcggaat   6660

atagcatacc tcaaaggaaa agtaccttcg tgggttggtg tcccaacatc agttgcgata   6720

ccatttggca cttttgagaa ggttttatca gatgggctta ataaggttgg ttggtggttt   6780

attttgatgt atatacttga ataatagaac tgcatggttc ttggagaagt cagattcttt   6840

aacatgtttg aaatacacta ctgggaaggt aacaacgtgc aatttaatgt ccaccaatat   6900

ctaaacagcc atttttggca ttcaattcac tatatatttt atttcatgag cctgctctat   6960

aagtagcgtc ttcagtagtt gtagctcata gcttcatagt ctcattctac catgaactaa   7020

ttttgctaac ttacatctac tcttgaaata agtaatactt gtatattatt atctttgatt   7080

gtaaaagaac ttcccttgct cgtttgtcaa ggtgtctttt agacaggaga tggaattgac   7140

tgttatcaaa gcaaatgata acaagaaacc tcttgttgat tggttgagca gtttcaacta   7200

atccattttt ttttcttttt ggcatgtgat ctttgtatta ttggcccaaa tgaaattcta   7260

tttctcccat taaccaccca caatggcagg tttgggtaca tataggccaa ccatgggtag   7320

gtggcttaaa agttgagtaa agcataattg gggataaggt gcacataggc acggaccacc   7380

cacagacaaa gtgcttgcag gcactactaa tacattattc tatcaccatc aggattcaat   7440

tctaacatgt actgtttctt ctttttcttc tttgtacagt tcctgtatag accctttttgt  7500

acagtttcct aacaaatgaa aaagatcagt aggagaccct cttctcctgt tccacaaaaa   7560

atgttaaaat ggtctttcta atatttgatt gttctttctt ttatggcagg aagagcgcaa   7620

aacatagaaa agctt                                                    7635
```

<210> SEQ ID NO 44
<211> LENGTH: 327
<212> TYPE: DNA
<213> ORGANISM: Artificial Sequence
<220> FEATURE:

<223> OTHER INFORMATION: Synthetic sequence, sbGWDko2a minus flanking sequence

<400> SEQUENCE: 44
gtgagataag caaagcacaa gataggttta cagatgatct tgagaatatg tacagaactt 60
atcctcagta cagagagata ctaagaatga taatggctgc tgttggtcgt ggaggtgaag 120
gtgacgttgg tcaacgcatt cgtgatgaga tattagtaat acaggtaaaa ctgatggtcc 180
ttggtgaata tacagttatt ttcgttcatt gctctgctga attgagcagt tggtagtgct 240
catccaaaac gtagacattg tcaacaataa aatgtttggt gtgttacaga gaaataccgg 300
tgcaaagcta gcatgatgga agaatgg 327

<210> SEQ ID NO 45
<211> LENGTH: 164
<212> TYPE: DNA
<213> ORGANISM: Artificial Sequence
<220> FEATURE:
<223> OTHER INFORMATION: Synthetic sequence, sbGWDko2b minus flanking sequence

<400> SEQUENCE: 45
gtgagataag caaagcacaa gataggttta cagatgatct tgagaatatg tacagaactt 60
atcctcagta cagagagata ctaagaatga taatggctgc tgttggtcgt ggaggtgaag 120
gtgacgttgg tcaacgcatt cgtgatgaga tattagtaat acag 164

<210> SEQ ID NO 46
<211> LENGTH: 164
<212> TYPE: DNA
<213> ORGANISM: Artificial Sequence
<220> FEATURE:
<223> OTHER INFORMATION: Synthetic sequence, antisense sbGWDko2b

<400> SEQUENCE: 46
ctgtattact aatatctcat cacgaatgcg ttgaccaacg tcaccttcac ctccacgacc 60
aacagcagcc attatcattc ttagtatctc tctgtactga ggataagttc tgtacatatt 120
ctcaagatca tctgtaaacc tatcttgtgc tttgcttatc tcac 164

<210> SEQ ID NO 47
<211> LENGTH: 5506
<212> TYPE: DNA
<213> ORGANISM: Artificial Sequence
<220> FEATURE:
<223> OTHER INFORMATION: Synthetic sequence, pAL409jSbGWDko2

<400> SEQUENCE: 47
tagtttattt cctctggatt tggattggaa ttgtgttctt agttttttc ccctggattt 60 ggattggaat tgtgtggagc tgggttagag aattacatct gtatcgtgta cacctacttg 120
aactgtagag cttgggttct aaggtcaatt taatctgtat tgtatctggc tctttgccta 180
gttgaactgt agtgctgatg ttgtactgtg tttttttacc cgttttattt gctttactcg 240
tgcaaatcaa atctgtcaga tgctagaact aggtggcttt attctgtgtt cttacataga 300
tctgttgtcc tgtagttact tatgtcagtt ttgttattat ctgaagatat ttttggttgt 360
tgcttgttga tgtggtgtga gctgtgagca gcgctcttat gattaatgat gctgtccaat 420
tgtagtgtag tatgatgtga ttgatatgtt catctatttt gagctgacag taccgatatc 480
gtaggatctg gtgccaactt attctccagc tgcttttttt tacctatgtt aattccaatc 540
ctttcttgcc tcttccaggg atccaccggg agtgagataa gcaaagcaca agataggttt 600

-continued

```
acagatgatc ttgagaatat gtacagaact tatcctcagt acagagagat actaagaatg    660
ataatggctg ctgttggtcg tggaggtgaa ggtgacgttg gtcaacgcat tcgtgatgag    720
atattagtaa tacaggtaaa actgatggtc cttggtgaat atacagttat tttcgttcat    780
tgctctgctg aattgagcag ttggtagtgc tcatccaaaa cgtagacatt gtcaacaata    840
aaatgtttgg tgtgttacag agaaataccg ggctgtatta ctaatatctc atcacgaatg    900
cgttgaccaa cgtcaccttc acctccacga ccaacagcag ccattatcat tcttagtatc    960
tctctgtact gaggataagt tctgtacata ttctcaagat catctgtaaa cctatcttgt   1020
gctttgctta tctcactgct agctccccga atttccccga tcgttcaaac atttggcaat   1080
aaagtttctt aagattgaat cctgttgccg gtcttgcgat gattatcata taatttctgt   1140
tgaattacgt taagcatgta ataattaaca tgtaatgcat gacgttattt atgagatggg   1200
tttttatgat tagagtcccg caattataca tttaatacgc gatagaaaac aaaatatagc   1260
gcgcaaacta ggataaatta tcgcgcgcgg tgtcatctat gttactagat cgggaattgg   1320
cgagctcgcc cgggcgggcg aagcttggcg taatcatggt catagctgtt tcctgtgtga   1380
aattgttatc cgctcacaat tccacacaac atacgagccg gaagcataaa gtgtaaagcc   1440
tggggtgcct aatgagtgag ctaactcaca ttaattgcgt tgcgctcact gcccgctttc   1500
cagtcgggaa acctgtcgtg ccagctgcat taatgaatcg gccaacgcgc ggggagaggc   1560
ggtttgcgta ttgggcgctc ttccgcttcc tcgctcactg actcgctgcg ctcggtcgtt   1620
cggctgcggc gagcggtatc agctcactca aaggcggtaa tacggttatc cacagaatca   1680
ggggataacg caggaaagaa catgtgagca aaaggccagc aaaaggccag gaaccgtaaa   1740
aaggccgcgt tgctggcgtt tttccatagg ctccgccccc ctgacgagca tcacaaaaat   1800
cgacgctcaa gtcagaggtg gcgaaacccg acaggactat aaagatacca ggcgtttccc   1860
cctggaagct ccctcgtgcg ctctcctgtt ccgaccctgc cgcttaccgg atacctgtcc   1920
gcctttctcc cttcgggaag cgtggcgctt tctcatagct cacgctgtag gtatctcagt   1980
tcggtgtagg tcgttcgctc caagctgggc tgtgtgcacg aaccccccgt tcagcccgac   2040
cgctgcgcct tatccggtaa ctatcgtctt gagtccaacc cggtaagaca cgacttatcg   2100
ccactggcag cagccactgg taacaggatt agcagagcga ggtatgtagg cggtgctaca   2160
gagttcttga agtggtggcc taactacggc tacactagaa ggacagtatt tggtatctgc   2220
gctctgctga agccagttac cttcggaaaa agagttggta gctcttgatc cggcaaacaa   2280
accaccgctg gtagcggtgg tttttttgtt tgcaagcagc agattacgcg cagaaaaaaa   2340
ggatctcaag aagatccttt gatcttttct acggggtctg acgctcagtg gaacgaaaac   2400
tcacgttaag ggattttggt catgagatta tcaaaaagga tcttcaccta gatcctttta   2460
aattaaaaat gaagttttaa atcaatctaa agtatatatg agtaaacttg gtctgacagt   2520
taccaatgct taatcagtga ggcacctatc tcagcgatct gtctatttcg ttcatccata   2580
gttgcctgac tccccgtcgt gtagataact acgatacggg agggcttacc atctggcccc   2640
agtgctgcaa tgataccgcg agacccacgc tcaccggctc cagatttatc agcaataaac   2700
cagccagccg gaagggccga gcgcagaagt ggtcctgcaa ctttatccgc ctccatccag   2760
tctattaatt gttgccggga agctagagta agtagttcgc cagttaatag tttgcgcaac   2820
gttgttgcca ttgctacagg catcgtggtg tcacgctcgt cgtttggtat ggcttcattc   2880
agctccggtt cccaacgatc aaggcgagtt acatgatccc ccatgttgtg caaaaaagcg   2940
```

-continued gttagctcct tcggtcctcc gatcgttgtc agaagtaagt tggccgcagt gttatcactc 3000
atggttatgg cagcactgca taattctctt actgtcatgc catccgtaag atgcttttct 3060
gtgactggtg agtactcaac caagtcattc tgagaatagt gtatgcggcg accgagttgc 3120
tcttgcccgg cgtcaatacg ggataatacc gcgccacata gcagaacttt aaaagtgctc 3180
atcattggaa aacgttcttc ggggcgaaaa ctctcaagga tcttaccgct gttgagatcc 3240
agttcgatgt aacccactcg tgcacccaac tgatcttcag catcttttac tttcaccagc 3300
gtttctgggt gagcaaaaac aggaaggcaa aatgccgcaa aaaagggaat aagggcgaca 3360
cggaaatgtt gaatactcat actcttcctt tttcaatatt attgaagcat ttatcagggt 3420
tattgtctca tgagcggata catatttgaa tgtatttaga aaaataaaca aataggggtt 3480
ccgcgcacat ttccccgaaa agtgccacct gacgtctaag aaaccattat tatcatgaca 3540
ttaacctata aaaataggcg tatcacgagg ccctttcgtc tcgcgcgttt cggtgatgac 3600
ggtgaaaacc tctgacacat gcagctcccg gagacggtca cagcttgtct gtaagcggat 3660
gccgggagca gacaagcccg tcagggcgcg tcagcgggtg ttggcgggtg tcggggctgg 3720
cttaactatg cggcatcaga gcagattgta ctgagagtgc accatatgcg gtgtgaaata 3780
ccgcacagat gcgtaaggag aaaataccgc atcaggcgcc attcgccatt caggctgcgc 3840
aactgttggg aagggcgatc ggtgcgggcc tcttcgctat tacgccagct ggcgaaaggg 3900
ggatgtgctg caaggcgatt aagttgggta acgccagggt tttcccagtc acgacgttgt 3960
aaaacgacgg ccagtgaatt cgggcggtta attaactaat cgactctagt aacggccgcc 4020
agtgtgctgg aattaattcg gcttgtcgac cacccaaccc catatcgaca gaggatgtga 4080
agaacaggta aatcacgcag aagaacccat ctctgatagc agctatcgat tagaacaacg 4140
aatccatatt gggtccgtgg gaaatactta ctgcacagga agggggcgat ctgacgaggc 4200
cccgccaccg gcctcgaccc gaggccgagg ccgacgaagc gccggcgagt acggcgccgc 4260
ggcggcctct gcccgtgccc tctgcgcgtg ggagggagag gccgcggtgg tgggggcgcg 4320
cgcgcgcgcg cgcgcagctg gtgcggcggc gcgggggtca gccgccgagc cggcggcgac 4380
ggaggagcag ggcggcgtgg acgcgaactt ccgatcggtt ggtcagagtg cgcgagttgg 4440
gcttagccaa ttaggtctca acaatctatt gggccgtaaa attcatgggc cctggtttgt 4500
ctaggcccaa tatcccgttc atttcagccc acaaatattt ccccagagga ttattaaggc 4560
ccacacgcag cttatagcag atcaagtacg atgtttcctg atcgttggat cggaaacgta 4620
cggtcttgat caggcatgcc gacttcgtca aagagaggcg gcatgacctg acgcggagtt 4680
ggttccgggc accgtctgga tggtcgtacc gggaccggac acgtgtcgcg cctccaacta 4740
catggacacg tgtggtgctg ccattgggcc gtacgcgtgg cggtgaccgc accggatgct 4800
gcctcgcacc gccttgccca cgctttatat agagaggttt tctctccatt aatcgcatag 4860
cgagtcgaat cgaccgaagg ggagggggag cgagagcttt gcgttctcta atcgcctcgt 4920
caaggtaact aatcaatcac ctcgtcctaa tcctcgaatc tctcgtggtg cccgtctaat 4980
ctcgcgattt tgatgctcgt ggtggaaagc gtaggaggat cccgtgcgag ttagtctcaa 5040
tctctcaggg tttcgtgcga ttttagggtg atccacctct taatcgagtt acggtttcgt 5100
gcgattttag ggtaatcctc ttaatctctc attgatttag ggtttcgtga gaatcgaggt 5160
agggatctgt gttatttata tcgatctaat agatggattg gttttgagat tgttctgtca 5220
gatggggatt gtttcgatat attaccctaa tgatgtgtca gatggggatt gtttcgatat 5280
attaccctaa tgatgtgtca gatggggatt gtttcgatat attaccctaa tgatggataa 5340

-continued

```
taagagtagt tcacagttat gttttgatcc tgccacatag tttgagtttt gtgatcagat   5400

ttagttttac ttatttgtgc ttagttcgga tgggattgtt ctgatattgt tccaatagat   5460

gaatagctcg ttaggttaaa atctttaggt tgagttaggc gacaca                  5506
```